US009364528B1

(12) United States Patent  
Giuliani et al.

(10) Patent No.: US 9,364,528 B1
(45) Date of Patent: Jun. 14, 2016

(54) COMBINATION NEISSERIAL COMPOSITIONS

(71) Applicant: GlaxoSmithKline Biologicals SA, Rixensart (BE)

(72) Inventors: Marzia Monica Giuliani, Siena (IT); Mariagrazia Pizza, Siena (IT); Rino Rappuoli, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 15/015,041

(22) Filed: Feb. 3, 2016

Related U.S. Application Data

(63) Continuation of application No. 14/284,326, filed on May 21, 2014, which is a continuation of application No. 13/921,087, filed on Jun. 18, 2013, now abandoned, which is a continuation of application No. 12/979,239, filed on Dec. 27, 2010, now abandoned, which is a continuation of application No. 10/982,703, filed on Nov. 5, 2004, now Pat. No. 7,862,827, which is a continuation of application No. 09/979,263, filed as application No. PCT/IB00/00828 on May 19, 2000, now abandoned.

(30) Foreign Application Priority Data

May 19, 1999  (GB) .................................. 9911692.3
Aug. 19, 1999 (GB) .................................. 9919705.5
Mar. 9, 2000   (GB) .................................. 0005730.7

(51) Int. Cl.
*A61K 39/095* (2006.01)
*A61K 39/02* (2006.01)
*A61K 39/00* (2006.01)
*A61K 39/39* (2006.01)

(52) U.S. Cl.
CPC ............... *A61K 39/095* (2013.01); *A61K 39/02* (2013.01); *A61K 39/39* (2013.01); *A61K 2039/70* (2013.01)

(58) Field of Classification Search
CPC ............... C07K 14/22; C07K 16/1217; C07K 2319/00; A61K 39/095; A61K 39/00; A61K 2039/53; A61K 2039/55505; A61K 38/00; A61K 2039/55577; A61K 2039/505; A61K 39/39; A61K 47/02
See application file for complete search history.

(56) References Cited

U.S. PATENT DOCUMENTS

| 4,239,749 | A  | * | 12/1980 | Buchanan ............ A61K 39/095 424/249.1 |
| 7,348,006 | B2 |   | 3/2008  | Contorni et al. |
| 7,534,444 | B2 |   | 5/2009  | Granoff et al. |
| 7,576,176 | B1 |   | 8/2009  | Fraser et al. |
| 7,785,608 | B2 |   | 8/2010  | Zlotnick et al. |
| 7,862,827 | B2 |   | 1/2011  | Giuliani et al. |
| 8,101,194 | B2 |   | 1/2012  | Zlotnick et al. |
| 8,226,960 | B2 |   | 7/2012  | Masignani et al. |
| 8,273,360 | B2 |   | 9/2012  | Pizza et al. |
| 8,293,251 | B2 |   | 10/2012 | Scarlato et al. |
| 8,394,390 | B2 |   | 3/2013  | Galeotti et al. |
| 8,398,988 | B2 |   | 3/2013  | Contorni et al. |
| 8,398,999 | B2 |   | 3/2013  | Masignani et al. |
| 8,470,340 | B2 |   | 6/2013  | Beernink et al. |
| 8,524,251 | B2 |   | 9/2013  | Fraser et al. |
| 8,563,007 | B1 |   | 10/2013 | Zlotnick et al. |
| 8,574,597 | B2 |   | 11/2013 | Zlotnick |
| 8,663,656 | B2 |   | 3/2014  | Pizza |
| 8,734,812 | B1 |   | 5/2014  | Galeotti et al. |
| 8,765,135 | B2 |   | 7/2014  | Contorni |
| 8,834,888 | B2 |   | 9/2014  | Contorni et al. |
| 8,840,907 | B2 |   | 9/2014  | Pizza |
| 8,968,748 | B2 |   | 3/2015  | Granoff et al. |
| 8,980,277 | B2 |   | 3/2015  | Pizza |
| 8,980,286 | B2 |   | 3/2015  | Comanducci |
| 9,011,869 | B2 |   | 4/2015  | Pizza |
| 9,056,075 | B2 |   | 6/2015  | Pizza |
| 9,067,987 | B2 |   | 6/2015  | Galeotti et al. |
| 9,150,898 | B2 |   | 10/2015 | Arico |
| 9,156,894 | B2 |   | 10/2015 | Masignani et al. |
| 9,249,196 | B2 |   | 2/2016  | Fraser et al. |
| 2003/0215469 | A1 | | 11/2003 | Robinson et al. |
| 2004/0092711 | A1 | | 5/2004  | Arico |
| 2004/0110670 | A1 | | 6/2004  | Arico et al. |
| 2004/0167068 | A1 | | 8/2004  | Zlotnick et al. |
| 2006/0051840 | A1 | | 3/2006  | Arico et al. |
| 2006/0171957 | A1 | | 8/2006  | Pizza |
| 2006/0240045 | A1 | | 10/2006 | Berthet et al. |
| 2006/0251670 | A1 | | 11/2006 | Comanducci et al. |
| 2007/0026021 | A1 | | 2/2007  | Fraser et al. |
| 2007/0082014 | A1 | | 4/2007  | Costantino |

(Continued)

FOREIGN PATENT DOCUMENTS

| EP | 0467714 A1 | 1/1992 |
| EP | 1645631 B1 | 10/2007 |
| EP | 2351767 A2 | 8/2011 |
| EP | 1790660 A2 | 6/2012 |
| WO | WO-95/03413 A1 | 2/1995 |
| WO | WO-96/29412 A1 | 9/1996 |
| WO | WO-98/17805 A2 | 4/1998 |
| WO | WO-99/57280 A2 | 11/1999 |
| WO | WO-00/22430 A2 | 4/2000 |
| WO | WO-00/66791 A1 | 11/2000 |

(Continued)

OTHER PUBLICATIONS

Artenstein Yale J Biol Med Jul. 1975;48(3): 197-200.*

(Continued)

*Primary Examiner* — Padma V Baskar
(74) *Attorney, Agent, or Firm* — Morrison & Foerster LLP

(57) ABSTRACT

Compositions comprising a first biological molecule from a *Neisseria* bacterium and a second biological molecule from a *Neisseria* bacterium. The term "biological molecule" includes proteins and nucleic acids. Preferred *Neisseria* species are *N. meningitidis* and *N. gonorrhoeae*.

24 Claims, 51 Drawing Sheets

(56) References Cited

U.S. PATENT DOCUMENTS

| | | |
|---|---|---|
| 2007/0253984 A1 | 11/2007 | Khandke et al. |
| 2009/0285845 A1 | 11/2009 | Masignani et al. |
| 2010/0267931 A1 | 10/2010 | Arico et al. |
| 2011/0020390 A1 | 1/2011 | Pizza et al. |
| 2012/0107339 A1 | 5/2012 | Granoff et al. |
| 2014/0037668 A1 | 2/2014 | Giuliani et al. |
| 2014/0363462 A1 | 12/2014 | Aric et al. |
| 2015/0079124 A1 | 3/2015 | Fraser et al. |
| 2015/0086582 A1 | 3/2015 | Fraser et al. |

FOREIGN PATENT DOCUMENTS

| | | |
|---|---|---|
| WO | WO-01/31019 A2 | 5/2001 |
| WO | WO-01/52885 A1 | 7/2001 |
| WO | WO-01/64920 A2 | 9/2001 |
| WO | WO-01/64922 A2 | 9/2001 |
| WO | WO-03/009869 A1 | 2/2003 |
| WO | WO-03/020756 A2 | 3/2003 |
| WO | WO-03/063766 A2 | 8/2003 |
| WO | WO-2004/032958 A1 | 4/2004 |
| WO | WO-2004/048404 A2 | 6/2004 |
| WO | WO-2004/065603 A2 | 8/2004 |
| WO | WO-2004/094596 A2 | 11/2004 |
| WO | WO-2006/024954 A2 | 3/2006 |
| WO | WO-2006/081259 A2 | 8/2006 |
| WO | WO-2007/060548 A2 | 5/2007 |
| WO | WO-2007/127665 A2 | 11/2007 |
| WO | WO-2008/125985 A2 | 10/2008 |
| WO | WO-2008/149238 A2 | 12/2008 |
| WO | WO-2009/038889 A1 | 3/2009 |
| WO | WO-2009/104097 A2 | 8/2009 |
| WO | WO-2010/028859 A1 | 3/2010 |
| WO | WO-2010/046715 A1 | 4/2010 |
| WO | WO-2011/110634 A1 | 9/2011 |
| WO | WO-2011/126863 A1 | 10/2011 |

OTHER PUBLICATIONS

Wetzler 1994 Annals of the New York Academy of Sciences , 730: 367-70.*

Poolman 1986 Dev Biol Stand.;63:147-52 (Abstract only).*

1997-11-17-NM_shotgun.dbs and 1997-12-15-NM.dbs, located at <ftp://ftp.sanger.ac.uk/pub/pathogens/nm/old data/> Generated Jul. 23, 2008. 2 pages.

Adams (1996). "Should Non-Peer-Reviewed Raw DNA Sequence Data Release Be Forced on the Scientific Community?," Science, 274: 534-536.

Aderson et al. (2010). "Effectiveness of a bivalent factor H binding protein vaccine across Neisseria meningitidis serogroups," 17th International Pathogenic Neisseria Conference 2010, p. 196.

Ala'Aldeen et al. (2010) "Human antibody response to the meningococcal factor H binding protein (LP2086) during invasive disease, colonization and carriage," Vaccine 28:7667-75.

Alignment of SEQ ID No. 19 of EP2327719 against SEQ ID Nos. 92, 94, 96, 98, 100, 102, 104, 106, and 108 of WO/2003/063766, filed in opposition against EP2327719, submitted May 20, 2015, 9 pages.

Alignment of SEQ ID No. 42 of EP2258716 against SEQ ID No. 41 of EP2258716, filed in opposition against EP2258716, submitted Apr. 16, 2015, 1 page.

Alignment of SEQ ID No. 42 of EP2258716 against SEQ ID Nos: 50, 52, 54, 56, 58, 60, 62, 64, 66, 68, 70, and 72 of WO/2003/063766, filed in opposition against EP2258716, submitted Apr. 16, 2015, 12 pages.

Ambrose et al. (2006). "Characterization of LP2086 expression in Neisseria meningitidis," 15th International Pathogenic Neisseria Conference 2006, p. 103.

Amended Defence and Counterclaim, Jul. 24, 2015, Claim No. HP-2015-000022, Glaxosmithkline UK LTD v. Wyeth Holdings LLC, 4 pages.

Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.

Anderson et al. (2009). "Development of a factor H binding protein vaccine for broad protection against invasive Neisseria meningitidis serogroup B (MnB) disease," 10th European Meningococcal Disease Society Congress 2009, p. 39.

Anderson et al. (2009). "Epidemiology of the serogroup B Neisseria meningitidis (MnB) factor H binding protein and implications for vaccine development," European Society for Paediatric Infectious Disease Symposium 2009, p. 505.

Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.

Anderson et al. (2013) "Potential impact of the bivalent rLP2086 vaccine on Neisseria meningitidis carriage and invasive serogroup B disease," Hum Vacc Immunotherap 9:471-9.

Annex 1 to the Amended Defence and Counterclaim, Jun. 24, 2015, Claim No. HP-2015-000022, Glaxosmithkline UK LTD v. Wyeth Holdings LLC, 40 pages.

Appendix I to Statement of Grounds of Appeal filed by df-mp on Sep. 28, 2012, in relation to EP1645631, 1 page.

Appendix II to Statement of Grounds of Appeal filed by df-mp on Sep. 28, 2012, in relation to EP1645631, 2 pages.

Beernink (Jul. 2010) "Impaired immunogenicity of a meningococcal factor H-binding protein vaccine engineered to eliminate factor h binding," Clin Vac Immunol 17(7):1074-1078.

Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.

Beernink et al. (2011). "A meningococcal factor H binding protein mutant that eliminates factor H binding enhances protective antibody responses to vaccination," J Immunol, 186(6):3606-14.

Beernink et al. (Jun. 2008). "Bactericidal antibody responses, induced by meningococcal recombinant chimeric factor H-binding protein vaccines," Infection and Immunity 76(6):2568-2575.

Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.

BenMohamed et al. (2002). "Lipopeptide vaccines-yesterday, today, and tomorrow," Lancet 2(7):425-431.

Bentley et al. (2004). Identification of two immunologically distinct domains on the LP2086 outer membrane lipoprotein of Neisseria meningitidis, 14th International Pathogenic Neisseria meningitidis 2004, p. 144.

Bernfield et al. (2002). "Identification of a novel vaccine candidate for group B Neisseria meningitidis," 13th International Pathogenic Neisseria Conference 2002, Abstract No. 116.

Bernfield et al. (2002). "Identification of a novel vaccine candidate for group B Neisseria meningitidis ," 13th International Pathogenic Neisseria Conference 2002, Poster, 20 pages.

Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116 and 124.

Biswas et al. (1995). "Characterization of IbpA, the structural gene for a lactoferrin receptor in Neisseria gonorrhoeae," Infection and Immunity, 63(8): 2958-2967.

Blattner et al. (1997). "The complete genome sequence of Escherichia coli K-12," Science 277 (5331): 1453-1474.

Boslego et al. (1991). "Gonorrhea Vaccines," Chapter 17 in Vaccines and Immunotherapy, Cryz S.J. (Ed.), Pergamon Press: New York, NY, pp. 211-223.

Bouvier et al. (1991). "A gene for a new lipoprotein in the dapA-purC interval of the Escherichia coli chromosome," J Bacteriol 173(17):5523-5531.

Brendish and Read. (2015). "Neisseria meningitidis serogroup B bivalent factor H binding protein vaccine," Expert Rev. Vaccines, 14(4):493-503.

(56) References Cited

OTHER PUBLICATIONS

Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2 (Suppl.):S1-S4.
Cantini et al. (Mar. 2006). "Solution Structure of the Immunodominant Domain of Protective Antigen GNA 1870 of *Neisseria meningitidis*," Journal of Biological Chemistry 281(11): 7220-7227.
CECMED (Dec. 2, 2011), "Resumen de las Caracteristicas del Producto: VA-MENGOC-BC," Ministerio de Salud Publica de Cuba, 4 pages. (3 page English translation included).
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Claassen et al. (1996). "Production, characterization and control of a *Neisseria meningitidis* hexavalent class 1 outer membrane protein containing vesicle vaccine," Vaccine 14(10): 1001-1008.
Claimant's Amended Grounds of Invalidity under CPR 17.1 (2)(a) on Jul. 16, 2015, in respect of European Patent (UK) No. 2,343,308. In the High Court of Justice Chancery Division Patents Court, between GlaxoSmithKline UK Limited and Wyeth Holdings LLC. 9 pages.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1> 3 pages.
Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1> 4 pages.
Cohn et al. (2010). "Potential Impact of Serogroup B Vaccines: Prevalence of candidate vaccine antigens among invasive *Neisseria meningitidis* isolates in the United States," 17th International Pathogenic Neisseria Conference 2010, p. 77.
Cole et al. (1998). "Deciphering the biology of *Mycobacterium tuberculosis* from the complete genome sequence," Nature 394:651-653.
Cordis, "Preparation of meningococcal antigens," posted online on Feb. 2, 2005, 2 pages.
Cruse et al. (2003). Illustrated Dictionary of Immunology, $2^{nd}$ Ed. CRC Press, pp. 46, 166, and 382.
Database accession No. NMB1994 (cf. XP2231040) (Tettelin et al.), uploaded Oct. 1, 2000. 337 pages.
Database UniProt ( Feb. 6, 2007). 'Submitted name: Putative lipoprotein, Uniprot accession No. A1IQ30, PIR No. G81977, retrieved Jan. 20, 2016 from <http://www.uniprot.org/uniprot/A1IQ30>, 7 pages.
Database UniProt (Oct. 1, 2000), "SubName: Full=Uncharacterized protein" retrieved from EBI, accession No. Q9JXV4 Database accession No. Q9JXV4, PIR No. D81032, 2 pages.
de Moraes JC, et al. (1992). Protective efficacy of a serogroup B meningococcal vaccine in Sao Paulo, Brazil. Lancet 340: 1074-1078.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Decision revoking EP1737486, filed in opposition against EP1737486, dated Oct. 28, 2015, 28 pages.
Decision revoking the European Patent, filed in opposition against EP1976990, dated Nov. 11, 2013, 15 pages.
Decision to refuse a patent application, filed in the Opposition against EP1645631, dated Apr. 28, 2009, 7 pages.
Declaration by Dr. Ellen Murphy, Ph.D., dated Sep. 14, 2011, submitted in opposition proceedings for EP1645631, 4 pages.
Declaration by Dr. Julian Parkhill dated Jun. 12, 2008, submitted in opposition proceedings for EP1645631, 2 pages.
Declaration by Dr. Julian Parkhill, filed in the Opposition against EP1645631, dated Jul. 10, 2014, 5 pages.
Declaration by E. Richard Moxon dated Feb. 16, 2013, submitted in opposition proceedings for EP1645631, 5 pages.
Declaration by Ellen Murphy, filed in the Opposition against EP1645631, dated May 12, 2014, 3 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from *Neisseria meningitidis* serogroup B as a novel vaccine candidate," Vaccine 25:8420-8431.
Dintilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.
Dlawer et al. (2010). "Human antibody responses to the meningococcal factor H binding protein LP2086 during invasive disease," 17th International Pathogenic Neisseria Conference 2010, p. 130.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowsk. et al. (2013). "The Genetic Codes, a compilation," Retrieved from http://www.bioinformatics.org/JaMBW/2/3/TranslationTables.html. 16 pages.
Experimental data: expression of NspA, fHBP and GNA2132 in *N. meningitidis*, filed in opposition against EP1534326, dated Aug. 4, 2010. 2 pages.
Experimental Report, Submitted on Mar. 23, 2015, filed in relation to EP2411048, 2 pages.
Facts and Submissions dated May 21, 2012, in relation to EP1645631, 30 pages.
Farley et al. (2002). "Characterization, cloning and expression of different subfamilies of the ORF 2086 gene from *Neisseria meningitidis*," 13th International Pathogenic Neisseria Conference 2002, Abstract No. 124.
Farley et al. (2002). "Characterization, cloning and expression of different subfamilies of the ORF 2086 gene from *Neisseria meningitidis*," 13th International Pathogenic Neisseria Conference 2002, Poster, 15 pages.
Farley J. et al. (Sep. 2002). "Characterization, cloning and expression of different subfamilies of the ORF 2086 gene from *Neisseria meningitidis*," Thirteenth International Pathogenic Neisseria Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-501.
Fletcher et al. (2004). "Vaccine Potential of the *Neisseria meningitidis* 2086 Lipoprotein," Infection and Immunity 72(4): 2088-2100.
Fontana et al. (2002). A genomic approach Abstract from the $13^{th}$ International Pathogenic Neisseria Conference, Oslo, Norway, Sep. 1-6, 2002. p. 248.
Fraser et al. (1997). "Genomic sequence of a lyme disease spirochaete, Borrelia burgdorferi," Nature 390:580-586.
Fraser et al. (1998). "Complete genome sequence of Treponema pallidum, the syphilis spirochete," Science 281:375-388.
Galeano et al. (1995). "Efectividad de una vacuna antimeningococcica en una cohorte de itagui, Colombia, 1995," Epidemiologico de Antioquia 20(2), 8 pages. (9 page English translation included).
Gene Browser, Nature Technology Corporation, filed in the Opposition against EP1645631, dated Jun. 26, 2013, 6 pages.
GenPept accession No. AAF42204, "hypothetical protein NMB1870 [*Neisseria meningitidis* MC58]," retrieved on Sep. 26, 2012, 2 pages.

(56) References Cited

OTHER PUBLICATIONS

Gil et al. (2009). "Proteomic study via a non-gel based approach of meningococcal outer membrane vesicle vaccine obtained from strain CU385," Human Vaccines 5(5):347-356.

Giuliani et al. (2006). "A universal vaccine for serogroup B meningococcus," PNAS 103(29):10834-10839.

Giuliani et al. (2010). "Measuring antigen-specific bactericidal responses to a multicomponent vaccine against serogroup B meningococcus," Vaccine 28:5023-5030.

Giuliani et al. (Feb. 2005). "The Region Comprising Amino Acids 100 to 255 of *Neisseria meningitidis* Lipoprotein GNA 1870 Elicits Bactericidal Antibodies," *Infection and Immunity* 73(2): 1151-1160.

Gold and Stormo (1987). "Translation Initiation", in *Escherichia* con and *Salmonella typhimurium*, Cellular and Molecular Biology, Ed. Neidhardt, pp. 1302-1307.

Gorringe et al. (2009). "16th International Pathogenic Neisseria Conference: recent progress towards effective meningococcal disease vaccines," Human Vaccines 5(2):53-56.

Grandi (2005). "Reverse vaccinology: a critical analysis," in Encyclopedia of Genetics, Genomics, Proteomics and Bioinformatics, pp. 1322-1326.

Granoff, DM. (2009). Relative importance of complement-mediated bactericidal and opsonic activity for protection against meningococcal disease. Vaccine 27(Supplement 2): B117-B125.

Greenspan et al. (1999). "Defining Epitopes: It's Not as Easy as It Seems," Nature Biotechnology 17:936-937.

Harris et al. (2008). "Development and qualification of serum bactericidal assays for *Neisseria meningitidis* serogroup B," 16th International Pathogenic Neisseria Conference 2008, p. 268-269.

Harris et al. (2010). "Robustness of the Serum Bactericidal Activity (SBA) Assay for *Neisseria meningitidis* serogroup B," 17th International Pathogenic Neisseria Conference 2010, p. 169.

Harris et al. (2011) "Preclinical evidence for the potential of a bivalent fHBP vaccine to prevent *Neisseria meningitidis* serogroup C disease," Human Vaccines 7:1 (suppl) 1-7.

Hayashi and Wu, "Identification and characterization of lipid-modified proteins in bacteria," Chapter 10 in Lipid Modifications of Proteins: A Practical Approach, Hooper and Turner (eds.), published in 1992, 27 pages.

Hem et al. (1995). "Structure and properties of aluminum-containing adjuvants," Vaccine Design. Subunit and Adjuvant Approach, pp. 249-276.

Hodge et al. (2006). "Development of a luminex-based meningococcal rLP2086-specific human IgG assay," 15th International Pathogenic Neisseria Conference 2006, p. 113.

Hoiseth et al. (2008). "LP2086 and MLST distribution in epidemiologically relevant strains of serogroup B *Neisseria meningitidis*," 16th International Pathogenic Neisseria Conference 2008, p. 205.

Holmes, E. (2001). "PSMA Specific Antibodies and their Diagnostic and Therapeutic Use," Expert Opinion on Investigational Drugs 10(3): 511-519.

Hoist et al. (2014). "Variability of genes encoding surface proteins used as vaccine antigens in meningococcal endemic and epidemic strain panels from Norway," Vaccine 32:2722-2731.

Hou et al. (2005) "Protective antibody responses elicited by a meningococcal outer membrane vesicle vaccine with overexpressed genome-derived neisserial antigen 1870," J Infect Dis 192(4):580-90.

Hung et al. (2011). "The *Neisseria meningitidis* macrophage infectivity potentiator protein induces cross-strain serum bactericidal activity and is a potential serogroup B vaccine candidate," Infect Immun 79(9):3784-3791.

Interlocutory decision in opposition proceedings, filed in the Opposition against EP1645631, dated May 21, 2012, 82 pages.

Jacobsson et al. (2009). "Prevalence and sequence variations of the genes encoding the five antigens included in the novel 5CVMB vaccine covering group B meningococcal disease" Vaccine. 27:1579-1584.

Jansen et al. (2008). "Bivalent recombinant LP2086 vaccine to provide broad protection against Neisseria meningitidis B disease: immunological correlates of protection and how to assess coverage against invasive MnB strains," 16th International Pathogenic Neisseria Conference 2008, p. 80-81.

Jansen et al. (2009). "Development of a bivalent factor H binding protein vaccine to broadly protect against invasive *Neisseria meningitidis* serogroup B (MnB) disease," European Society for Paediatric Infectious Disease Symposium 2009, p. 311.

Jansen et al. (2010). "Estimating effectiveness for *Neisseria meningitidis* serogroup B (MnB) vaccine candidates composed of non-serogroup specific antigens," 17th International Pathogenic Neisseria Conference 2010, p. 37.

Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.

JCVI-CMR website showing Z2491 Sanger sequence (http://cmr.jcvi.org/tigr-scripts/CMR/shared/Genomes.cgi and links). (2010) 8 pages.

Jiang et al. (2003). "Using rate of acid neutralization to characterize aluminum phosphate adjuvant," Pharma Dev Tech 8(4):349-356.

Jiang et al. (2006). "Serum IgG response induced by a bivalent recombinant LP2086 provides broad protection against serogroup B *Neisseria meningitidis*," 15th International Pathogenic Neisseria Conference 2006, p. 113.

Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.

Jiang et al., (2010) "Broad vaccine coverage predicted for a bivalent recombinant factor H binding protein based vaccine to prevent serogroup B meningococcal disease" Vaccine 28:6086-6093.

Johnson et al. (1999). "Analysis of the human Ig isotype response to lactoferrin binding protein A from *Neisseria meningitidis*," FEMS Immun. Med. Microbial. 25(4): 349-354.

Jones et al. (2009). "Generation of human serum complement lots that perform consistently for use in *Neisseria meningitidis* serogroup B (MnB) vaccine clinical trials," European Society for Paediatric Infectious Disease Symposium 2009, p. 566.

Juncker et al. (2003). "Prediction of lipoprotein signal peptides in gram-negative bacteria," Protein Sci 12:1652-1662.

Koeberling et al. (2007). "Improved immunogenicity of a H44/76 group B outer membrane vesicle vaccine with over-expressed genome-derived Neisserial antigen 1870," Vaccine 25(10):1912-1920.

Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.

Koeberling et al. (2009). "Meningococcal outer membrane vesicle vaccines derived from mutant strains engineered to express factor H binding proteins from antigenic variant groups 1 and 2," Clin Vac Immunol, 16(2):156-162.

Kovacs-Simon et al. (2011). "Lipoproteins of Bacterial Pathogens," Infect Immun 79(2):548-561.

Lewis et al. (2010). "The meningococcal vaccine candidate neisserial surface protein A (NspA) binds to factor H and enhances meningococcal resistance to complement," PLoS Pathogens 6(7):e1001027. 20 pages.

Liebl et al. (1997). "Properties and gene structure of the Thermotoga maritima alpha-amylase AmyA, a putative lipoprotein of a hyperthermophilic bacterium," J Bacteriol 179(3):941-948.

Liechti et al. (2012). "Outer membrane biogenesis in *Escherichia coli, Neisseria meningitidis*, and *Helicobacter pylori*: paradigm deviations in *H. pylori*," Front Cell and Infect Microbiol 2:article 29. 18 pages.

Lindblad, (2004). "Aluminium compounds for use in vaccines," Immunol Cell Biol.,82(5):497-505.

(56) References Cited

OTHER PUBLICATIONS

Lucidarme et al., (2010). "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.

Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.

Madico et al. (2006). "The meningococcal vaccine candidate GNA1870 binds the complement regulatory protein factor H and enhances serum resistance," J Immunol 177(1):501-510.

Marshall et al. (2008). "A randomized, placebo-controlled, double-blind, phase 1 trial of ascending doses of meningococcal group B rLP2086 vaccine in healthy adults," 16th International Pathogenic Neisseria Conference 2008, p. 271-272.

Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.

Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.

Marshall et al. (2013) "A phase 2 open-label safety and immunogenicity study of a meningococcal B bivalent rLP2086 vaccine in healthy adults," Vaccine 31:1569-75.

Mascioni et al. (2008). "Determination of the domain and solution structure of rLP2086, a meningococcal vaccine candidate and human factor H binding protein," 16th International Pathogenic Neisseria Conference 2008, p. 77-78.

Mascioni et al. (2009) "Structural basis for the immunogenic properties of the meningococcal vaccine candidate LP2086," J Biol Chem 284:8738-46.

Mascioni et al. (2010) "NMR dynamics and antibody recognition of the meningococcal lipidated outer membrane protein LP2086 in micellar solution," Biochim Biophys Acta 1798:87-93.

Masignani V. (Mar. 17. 2003). "Vaccination against *Neisseria meningitidis* using three variants of the lipoprotein GNA1870," J. Exp. Med. 197(6):789-799.

McGuinness et al. (1993). "Class 1 outer membrane protein of *Neisseria meningitidis* : epitope analysis of the antigenic diversity between strains, implications for subtype definition and molecular epidemiology," Mol Microbiol. 7:505-514.

McNeil et al. (2009) "Detection of LP2086 on the cell surface of *Neisseria meningitidis* and its accessibility in the presence of serogroup B capsular polysaccharide," Vaccine 27:3417-21.

McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.

McNeil et al. (2013) "Role of factor H binding protein in *Neisseria meningitidis* virulence and its potential as a vaccine candidate to broadly protect against meningococcal disease," Microbiol Mol Biol Rev 77:234.

Meyer et al. (1984). "Pilus genes of *Neisseria gonorrheae*: Chromosomal organization and DNA sequence," Proc. Natl. Acad. Sci. USA 81: 6110-6114.

Milagres et al. (1998). "Specificity of bactericidal antibody response to serogroup B meningococcal strains in Brazilian children after immunization with an outer membrane vaccine," Infection and Immun. 66(10): 4755-4781.

Minutes of the oral proceedings, filed in the Opposition against EP1645631, dated Feb. 11, 2014, 4 pages.

Morley, S. et al. (Dec. 12, 2001). "Vaccine prevention of meningococcal disease, coming soon?" *Vaccine* 20(5-6):666-687.

Munkley, et al. (1991). "Blocking of bactericidal killing of *Neisseria meningitidis* by antibodies directed against slacc 4 outer membrane proteins," Microbial Pathogenesis 11: 447-452.

Murphy et al. (2008). "Sequence diversity of vaccine candidate LP2086 in *Neisseria meningitidis* serogroup B strains causing invasive disease," 16th International Pathogenic Neisseria Conference 2008, p. 61.

Murphy et al. (2010). "Prevalence of Factor H Binding Protein (fHBP) Variants in *N. meningitidis* Carriage Isolates," 17th International Pathogenic Neisseria Conference 2010, p. 96.

Murphy et al., (2009) "Sequence diversity of the factor H binding protein vaccine candidate in epidemiologically relevant strains of serogroup B *Neisseria meningitidis*" J Infect Dis 200:379-389.

Nassif (2000). "A Furtive Pathogen Revealed," Science 287:1767-1768.

Notice of Opposition against EP 1562983, filed on Jul. 1, 2014, 23 pages.

Notice of Opposition against EP1645631, filed in the Opposition against EP1645631, dated Jul. 23, 2008, 25 pages.

Notice of opposition against EP2343308, filed in opposition against EP1562983, submitted Jan. 11, 2016, 21 pages.

Notice of Opposition filed May 24, 2012, filed in opposition against EP1976990, 19 pages.

Notice of opposition, filed in opposition against EP2258716, dated Apr. 16, 2015, 12 pages.

Notice of opposition, filed in opposition against EP2327719, dated May 20, 2015, 14 pages.

Novartis (Jan. 22, 2013) "Novartis receives EU approval for Bexsero®, first vaccine to prevent the leading cause of life-threatening meningitis across Europe," Media Release, 3 pages.

Novartis (Jun. 9, 2011). "Novartis candidate vaccine Bexsero® shows significant potential in providing broad coverage against meningococcal serogroup B infections." Media Release, 6 pages.

Novartis (Oct. 9, 2008) "New Phase II data show Novartis investigational Meningitis B vaccine may also protect infants six months and older," Media Release, 4 pages.

Novartis internal data, filed in relation to EP1902726, submitted on Apr. 13, 2015, 1 page.

Ochoa, Rolando (2008). "Main projects on research, development and manufacturing of human vaccines," excerpt from presentation at BioQatar Symposium 2008, 4 slides.

Opponent's Further Submission in Preparation of the Oral Proceedings, filed in the Opposition against EP1645631, dated Nov. 3, 2011, 6 pages.

Opponent's Response to the Patentee's Submission dated Feb. 18, 2013, filed in the Opposition against EP1645631, dated Jul. 24 2014, 34 pages.

Opponents Final Written Submission in Preparation of Oral Proceedings, filed in the Opposition against EP1645631, dated Sep. 14, 2011, 28 pages.

ORF Finder (2013). "Bacterial Code," Retrieved from http://www.ncbi.nlm.nih.gov/gorf/gorf.html, 3 pages.

Pajon et al. (2010). "Frequency of factor H-binding protein modular groups and susceptibility to cross-reactive bactericidal activity in invasive meningococcal isolates" Vaccine 28:2122-2129.

Pajon et al. (2012). "Design of meningococcal factor H binding protein mutant vaccines that do not bind human complement factor H," Infect Immun 80:2667-2677.

Parkhill et al. (2000). "Complete DNA Sequence of a Serogroup A Strain of Neisseria meningitides Z2491," Nature, 404(6777):502-506.

Parkhill, "Campylobacter jejuni genome sequence at the Sanger Centre," Post on BIOSCI/Bionet of May 8, 1998. 1 page.

Patentee's response to notice of opposition, filed in opposition against EP1562983, dated Feb. 16, 2015, 9 pages.

Patentee's Submissions under Rule 116 EPC, filed in the Opposition against EP1645631, dated Sep. 13, 2011, 13 pages.

Patentees' Response to Opposition, filed in opposition against European Patent EP1645631, dated May 8, 2009, 13 pages.

Perez et al. (2010). "Community acquired bacterial meningitis in Cuba: a follow up of a decade," BMC Infectious Diseases 10:130, 9 pages.

(56) References Cited

OTHER PUBLICATIONS

Pettersson, et al. (2006). "Vaccine potential of the *Neisseria meningitidis* lactoferrin-binding proteins LbpA and LbpB," Vaccine 24(17):3545-3557.
Pfizer observations, filed in oppostion against EP1562983, dated Apr. 27, 2012, 7 pages.
Pfizer observations, filed in oppostion against EP1562983, dated May 12, 2011, 7 pages.
Pillai et al. (2005) "Outer membrane protein (OMP) based vaccine for Neisseria meningitidis serogroup B," Vaccine 23(17-18):2206-2209.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:I46-8.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.
PSORT analysis of SEQ ID Nos. 4 and 6, and of 'Contig295' 300mer (May 8, 2009), 5 pages.
PSORT prediction result for SEQ ID No. 2 (Mar. 30, 2010), 1 page.
Pugsley (1993). "The complete general secretory pathway in gram-negative bacteria," Microbiological Rev 5(1):50-108.
Response by opponent, filed in opposition against EP1562983, dated Jan. 11, 2016, 12 pages.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161.5. Oct. 28, 2009. 2 pages.
Response to Notice of Opposition, filed in opposition against EP2258716, dated Dec. 3, 2015, 8 pages.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B *Neisseria meningitidis* (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Richmond et al. (Sep. 7-12, 2008). "A randomized, observer-blinded, active control, phase 1 trial of meningococcal serogroup B rLP2086 vaccine in healthy children and adolescents aged 8 to 14 years." 16th International Pathogenic Conference; Rotterdam, the Netherlands. P212. 2 pages.
Rinaudo et al. (2009). "Vaccinology in the genome era", The Journal of Clinical Investigation, 119(9):2515-2525.

Rodriguez et al. (1999). "The epidemiological impact of antimeningococal B vaccination in Cuba," Mem Inst Oswaldo Cruz 94(4):433-440.
Rouppe van der Voort et al.(1996). "Specificity of human bactericidal antibodies against PorA P1.7,16 induced with a hexavalent meningococcal outer membrane vesicle vaccine," Infect. Immun. 64:2745-2751.
Sandbu et al. (2007). "Immunogenicity and safety of a combination of two serogroup B meningococcal outer membrane vesicle vaccines," Clin Vaccine Immunol, 14(9):1062-9.
Sanger Centre's "Projects" website as of Dec. 10, 1997 as retrievable via http://web.archive.org. 1 page.
Scarselli et al. (Feb. 13, 2009). "Epitope Mapping of a Bactericidal Monoclonal Antibody against the Factor H Binding Protein of *Neisseria meningitides*," Journal of Molecular Biology 386(1):97-108.
Schneider et al. (Apr. 16, 2009) "*Neisseria meningitidis* recruits factor H using protein mimicry of host carbohydrates," Nature 458(7240):890-893.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the meningococcus in vitro and in ex vivo and in vivo models of infection," Vaccine 28(12):2416-2427.
Seib et al. (2011). "Characterization of Diverse Subvariants of the Meningococcal Factor H (fH) Binding Protein for Their Ability to Bind fH, to Mediate Serum Resistance, and to Induce Bactericidal Antibodies," Infect Immun, 79(2):970-81.
Sequence for "Putative Lipoprotein [*Neisseria meningitidis* Z2491]," NCBI Reference Sequence: YP_002342062.1, Mar. 30, 2000. 2 pages.
Serruto et al. (2009). "Genome-based approaches to develop vaccines against bacterial pathogens," Vaccine 27:3245-3250.
Sheldon et al. (2011). "Phase 1, Randomized, Open-Label, Study to Assess the Safety and Immunogenicity of Serogroup B *Neisseria meningitidis* (Mnb) rLP2086 Vaccine in Healthy Adults," 14th Annual Conference on Vaccine Research, 2011, p. 59-60.
Sheldon et al. (2012) "A phase 1, randomized, open-label, act ve-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of Erwinia chrysanthemi 3937," Mole Microbiol 19(3):455-466.
Sierra GV, et al. (1991). Vaccine against group B *Neisseria meningitidis*: protection trial and mass vaccination results in Cuba. NIPH Ann 14: 195-207.
Sprengart et al. (1997). "Functional importance of RNA interactions in selection of translation initiation codons," Molecular Microbiology, 24(1): 19-28.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Statement of Grounds of Appeal, dated Mar. 23, 2015, filed in relation to EP2411048, 8 pages.
Statement of grounds of appeal, filed in relation to EP1902726, dated Apr. 13, 2015, 9 pages.
Statement of Grounds of Appeal, filed in relation to EP2353608, dated Jul. 22, 2015, 8 pages.
Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
Submission of the Patentee of Jul. 6, 2012, filed Jun. 24, 2014, in the Opposition against EP1645631, 4 pages.
Summons to oral proceedings pursuant to Rule 115(1) EPC, filed in the Opposition against EP1645631, dated Nov. 11, 2013, 12 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.

(56) References Cited

OTHER PUBLICATIONS

Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Supplementary Submission to the Grounds of Appeal, filed in the Opposition against EP1645631, dated Sep. 28, 2012, 2 pages.
Sutcliffe and Russell (1995). "Lipoproteins of gram-positive bacteria," J Bacteriol 177(5):1123-1128.
Swaminathan (1996). "Molecular cloning of the three base restriction endonuclease R.CviJI from eukaryotic Chlorella virus IL-3A," Nucleic Acids Research, 24(13): 2463-2469.
Tan et al. (2010). "Advances in the development of vaccines against *Neisseria meningitidis*," NEJM 362(16):1511-1520.
Telford et al. (2003). "Genomic and Proteomics in Vaccine Design", in *New Bacterial Vaccines*, edited by Ellis et al. Kleweur Academic/Plenum Publishers, USA. pp. 1-11.
Tettelin et al. (Mar. 10, 2000). "Complete Genome Sequence of *Neisseria meningitidis* Serogroup B Strain MC58," Science 287(5459):1809-1815.
The printed output from the NCBI open reading frame finder (Oct. 20, 2008), 12 pages.
TIGR Microbial Database, filed in the Opposition against EP1645631, dated Jun. 20, 2012, 14 pages.
TIGR website as of 1998, 8 pages.
UniProt accession No. C0JF81, Murphy et al., Last modified on May 5, 2009. 4 pages.
United States Office Action mailed on Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998. 82 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
U.S. Appl. No. 60/647,911, "GNA 1870-based vesicle vaccines for broad spectrum protection against diseases caused by *Neisseria meningitidis*," filed Jan. 27, 2005. 99 pages.
U.S. Appl. No. 61/358,816, "Combinations of Meningococcal Factor H Binding Proteins," filed Jun. 25, 2010. 48 pages.
Van der Lay et al. (1995). "Construction of *Neisseria meningitidis* Strains Carrying Multiple Chromosomal Copies of the PorA Gene for Use in Production of a Multivalent Outer Membrane Vesicle Vaccine," Vaccine 13(4): 401-407.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
von Heijne (1989). "The structure of signal peptides from bacterial lipoproteins," Protein Engineering 2(7):531-534.
Voulhoux and Tommassen (2002). "Transport of lipoproteins to the cell surface in *Neisseria meningitidis*," 13th International Pathogenic Neisseria Conference 2002, p. 31.
Wang et al. (2010). "Prevalence and genetic diversity of candidate vaccine antigens among invasive *Neisseria meningitidis* isolates in the United States," 17th International Pathogenic Neisseria Conference 2010, p. 122.
Welsch et al. (2004). "Protective Activity of Monoclonal Antibodies to Genome-Derived Neisserial Antigen 1870, a *Neisseria meningitidis* Candidate Vaccine," *The Journal of Immunology* 172: 5606-5615.
Welsch et al. (2007) "A novel mechanism for complement-mediated killing of encapsulated *Neisseria meningitidis* elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Written Submission to Oral Proceedings, filed in opposition against EP1976990, dated Jul. 24, 2013, 11 pages.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B *Neisseria meningitidis* in a murine nasal challenge model," 14th International Pathogenic Neisseria Conference 2004, p. 199.
Zhu et al. (2005) "Evaluation of recombinant lipidated P2086 protein as a vaccine candidate for group B *Neisseria meningitidis* in a murine nasal challenge model," Infect Immun 73(10):6838-45.
Zhu et al. (2006) "Intranasal immunization of mice with recombinant lipidated P2086 protein reduces nasal colonization of group B *Neisseria meningitidis*," Vaccine 24:5420-5.
Zhu et al. (2006). "Effective immunization strategy against group B *Neisseria meningitidis* using purified recombinant lipidated P2086 protein," 15th International Pathogenic Neisseria Conference 2006, p. 47.
Zlotnick et al. (2009). "Epidemiology of the serogroup B *Neisseria meningitidis* (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of *N. meningitidis*," 17th International Pathogenic Neisseria Conference 2010, p. 38.
Zollinger et al. (2010). "Design and evaluation in mice of a broadly protective meningococcal group B native outer membrane vesicle vaccine," Vaccine, 28(31):5057-5067.
Preliminary Amendment, filed for U.S. Appl. No. 14/882,320, dated Nov. 9, 2015, 37 pages.
Preliminary Amendment, filed for U.S. Appl. No. 14/961,725, dated Dec. 8, 2015, 41 pages.
Preliminary Amendment, filed for U.S. Appl. No. 15/015,004, dated Feb. 4, 2016, 40 pages.
Decision of Technical Board of Appeal for EP942983, dated Nov. 14, 2013, filed in relation to EP1645631, 28 pages.
Further submissions by patentee, dated Feb. 3, 2016, filed in relation to EP1645631 appeal, 9 pages.
Response to Notice of Opposition by Novartis Vaccines and Diagnostics SRL for EP2327719, dated Jan. 6, 2016. 10 pages.
Second Sworn Statement in EP1645631 from Isabel Delany, signed Feb. 2, 2016, 2 pages.
Statement of grounds of appeal, dated Mar. 7, 2016, filed in relation to EP1737486, 9 pages.
Sworn Statement in EP1645631 from Isabel Delany, signed Jan. 2, 2016. 2 pages.
Written Submissions from the Patentee, Glaxosmithkline Biologicals SA for EP1645631, dated Feb. 3, 2016. 10 pages.

\* cited by examiner

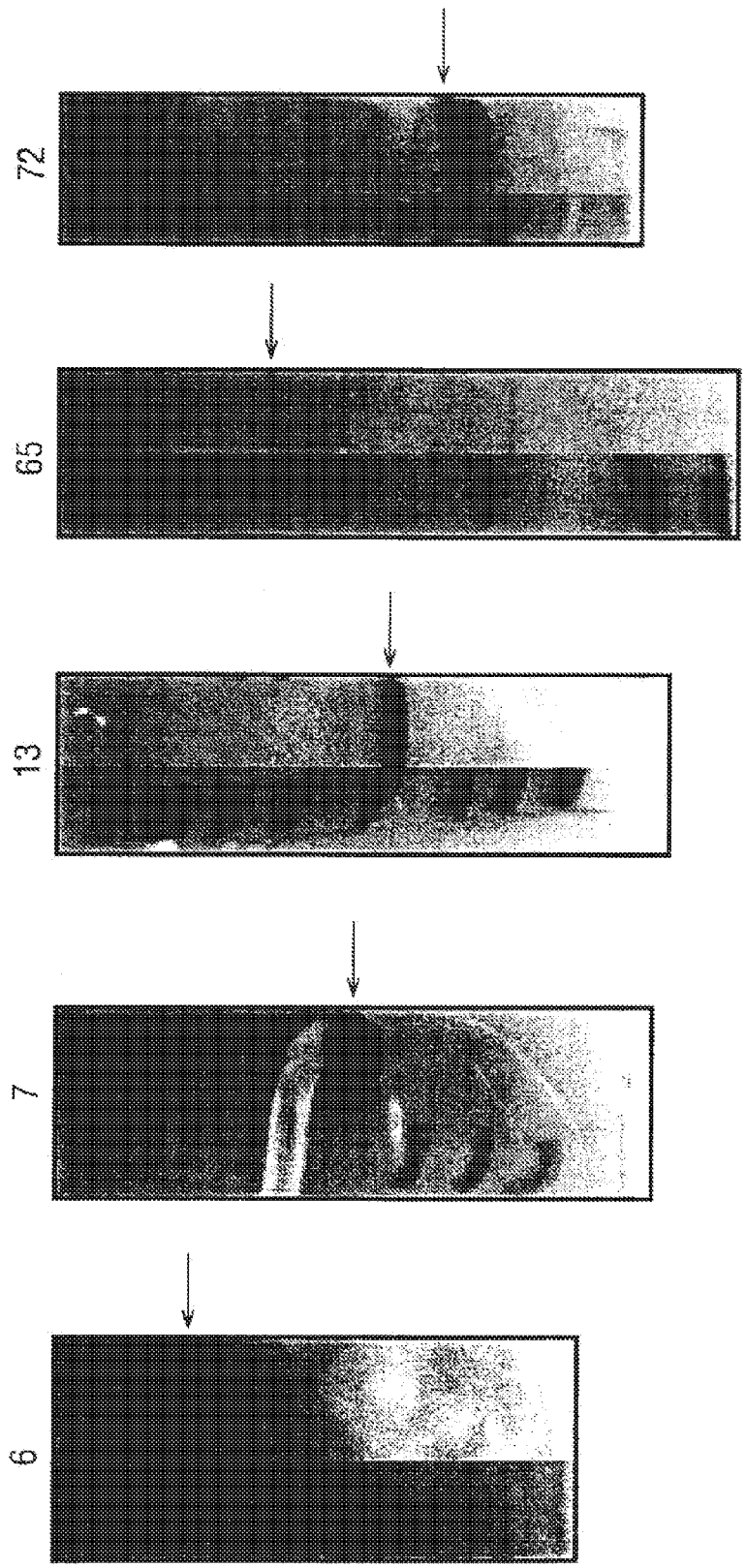

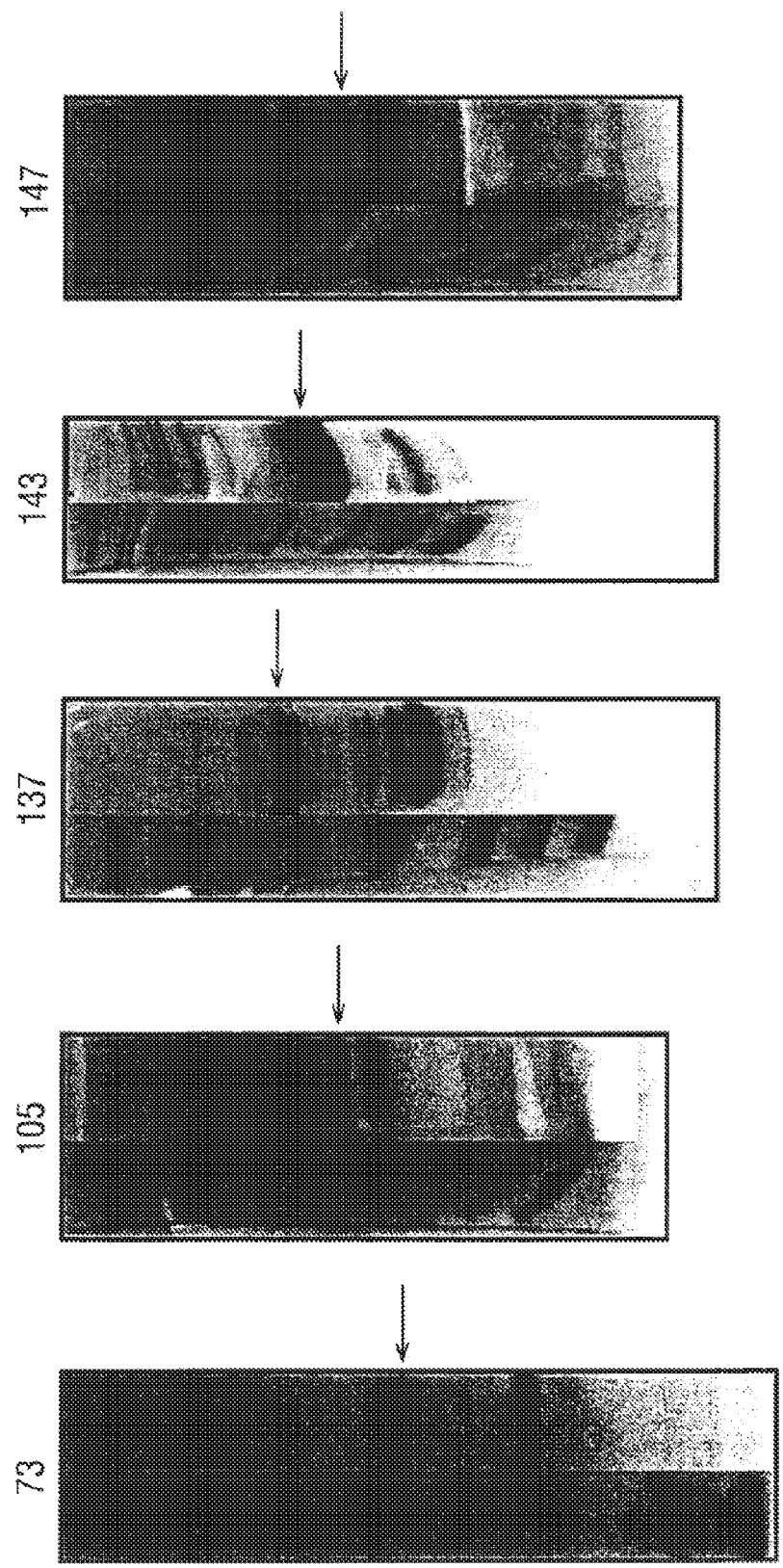

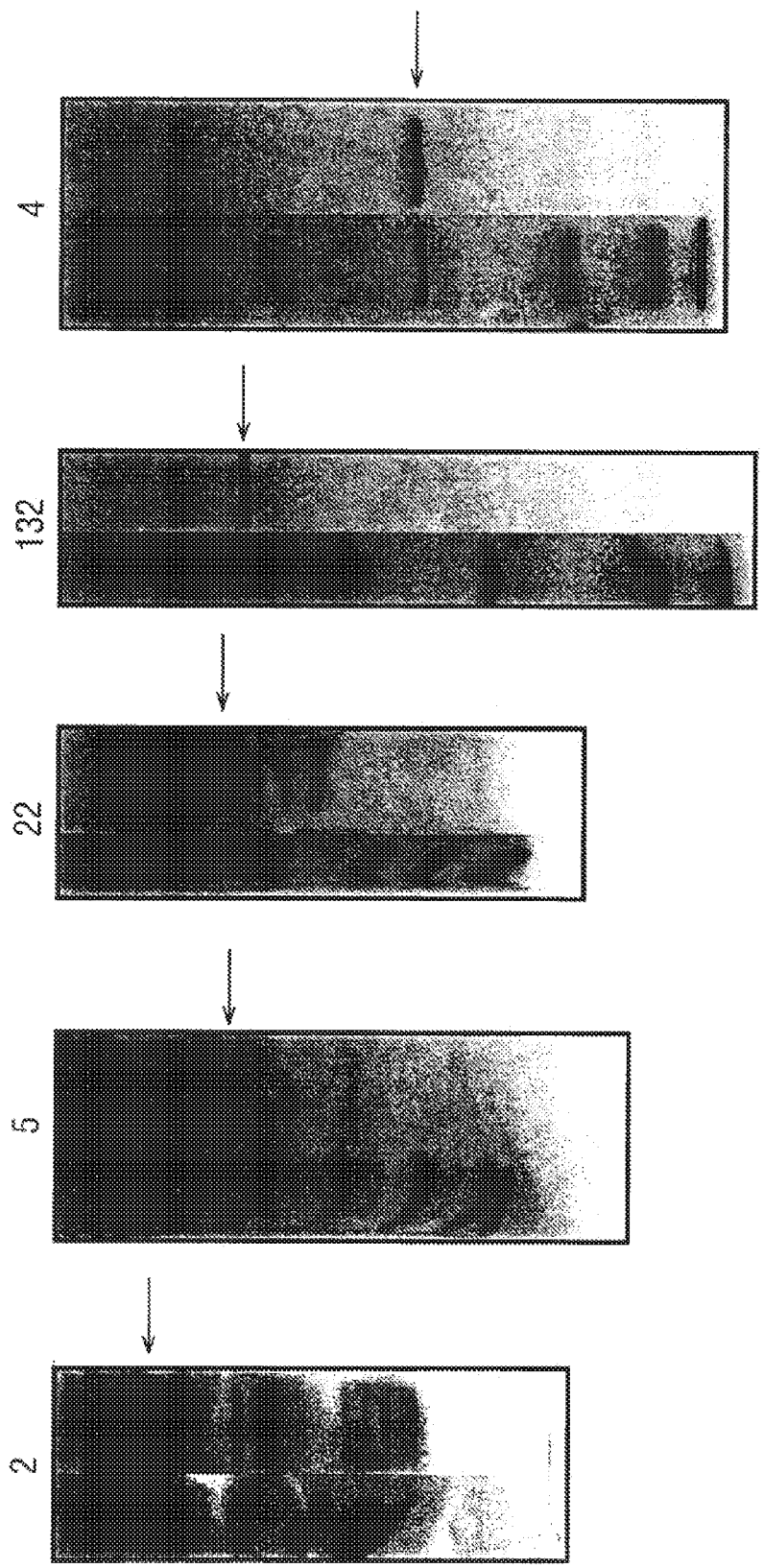

ORF2

ORF5

ORF6a

ORF7

FIG. 8 ORF9

ORF15

ORF23

ORF27

ORF28

ORF32

ORF65

ORF72

ORF73

ORF76

FIG. 20 ORF79

ORF89

ORF105

ORF106

ORF132

ORF137

ORF138

ORF143

ORF147

NspA sequences

FIG. 29B
NspA sequences

|  | 50 | Loop 2 60 | 70 | 80 | 90 | Loop 3 100 |
|---|---|---|---|---|---|---|
|  | RFAVDYTRYK | NYKAPSTDFK LYSIGASAIY | DFDTQSPVKP | YLGARLSLNR | ASVDLGGSDS |
| NM 608B | ---------- | ---------- ---------- | ---------- | ---------- | ---------- |
| NM NG6/88+ | ---------- | ---------- ---------- | ---------- | ---------- | ---------- |
| NM CU385+ | ---------- | ---------- ---------- | ---------- | ---------- | ---------- |
| NM 8047+ | ---------- | ---------- ---------- | ---------- | ---------- | ---------- |
| NM NGP165- | ---------- | ---------- ---------- | ---------- | ---------- | ---------- |
| NM MC58- | ---------- | ---------- ---------- | ---------- | ---------- | ---------- |
| NM M986- | ---------- | ---------- ---------- | ---------- | ---------- | ---------- |
| NM BZ232- | ---------- | ---------- ---------- | ---------- | ---------- | ---------- |
| NM M136- | ---------- | ---------- ---------- | ---------- | ---------- | ---------- |
| NM NG3/88- | ---------- | ---------- ---------- | ---------- | ---------- | ---------- |
| NG FA1090 | ---------- | --Q------- ---------V | ---------- | --F------- | --AH------ |
| NG B2 | ---------- | ---------- ---------V | ---------- | --F------- | --AH------ |

|              | 110        | 120        | 130        | 140        | 150        |
|--------------|------------|------------|------------|------------|------------|
|              | FSQTSIGLGV | LTIGVSYAVTP | NVDLDAGYRY | NYIGKVNTVK | NVRSGELSVG VRVKF |
| NM 6088      |            |            |            |            |            |
| NM NG6/88+   |            | --T-       |            |            |            |
| NM 8047+     |            | --A-       |            |            | --A        |
| NM CU385+    |            |            |            |            |            |
| NM NGP165-   |            |            |            |            |            |
| NM MC58-     |            |            |            |            | --A        |
| NM M986-     |            |            |            |            |            |
| NM BZ232-    |            | --A-       |            |            | --A        |
| NM M136-     |            | --T-       |            |            |            |
| NM NG3/88-   |            | --T-A-     |            |            |            |
| NG FA1090    | --K-       | --A-       |            | ---V-      | --A        |
| NG B2        | --K-       | --A-       |            | ---V-      | --A        |

Loop 4

FIG. 29C
NspA sequences

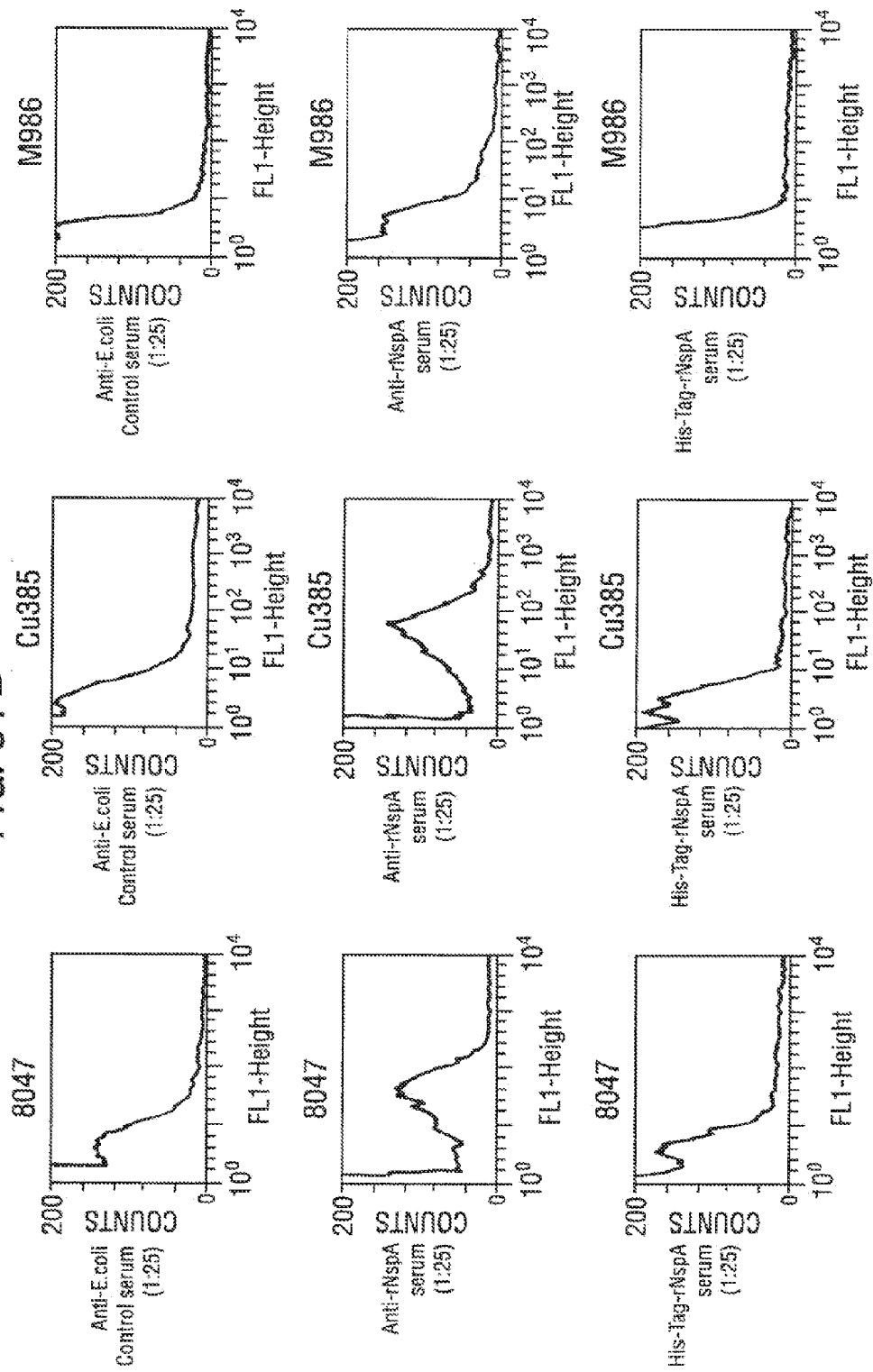

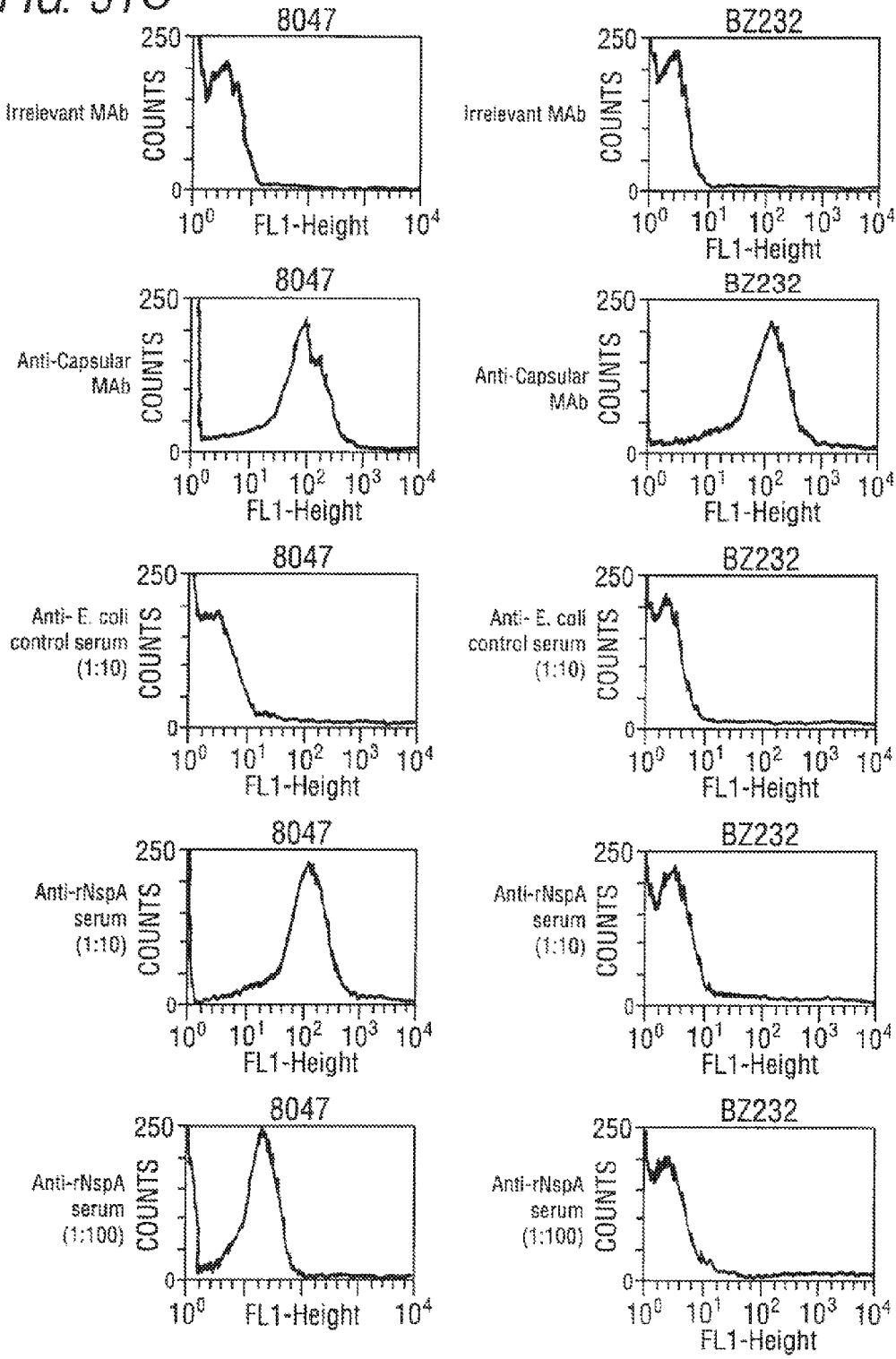

FIG. 33A
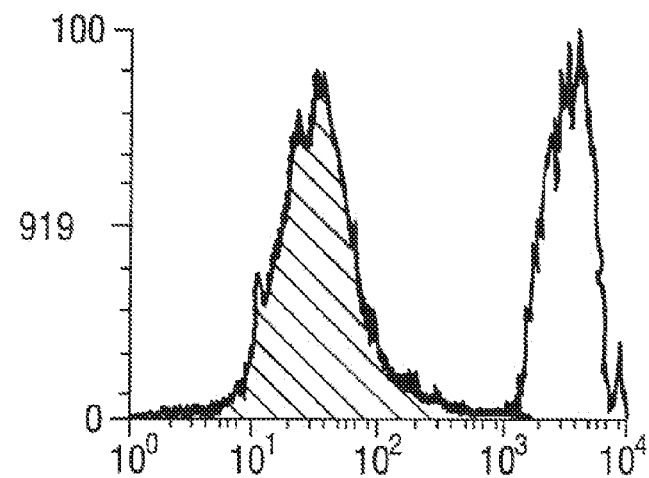
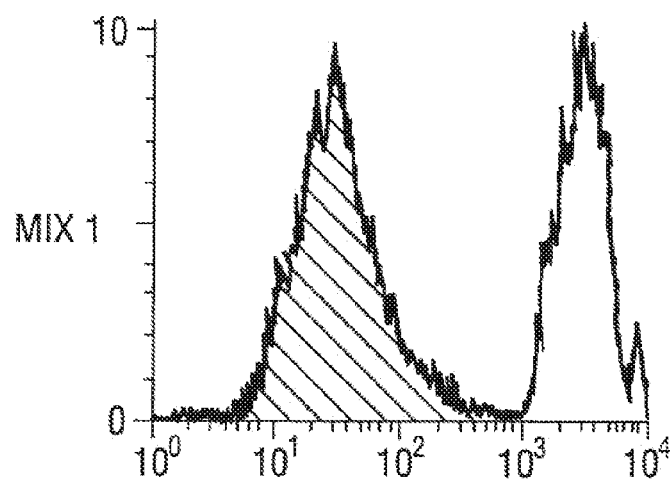
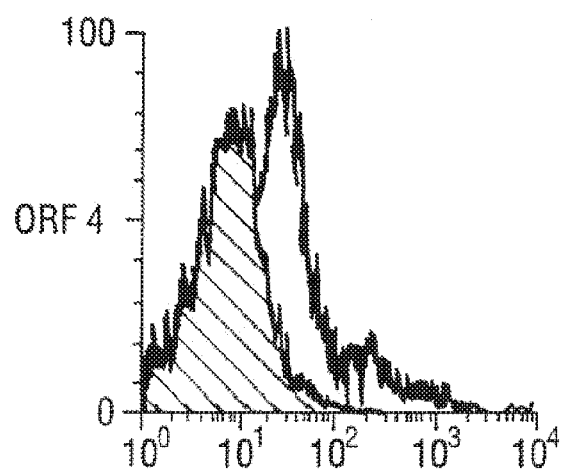

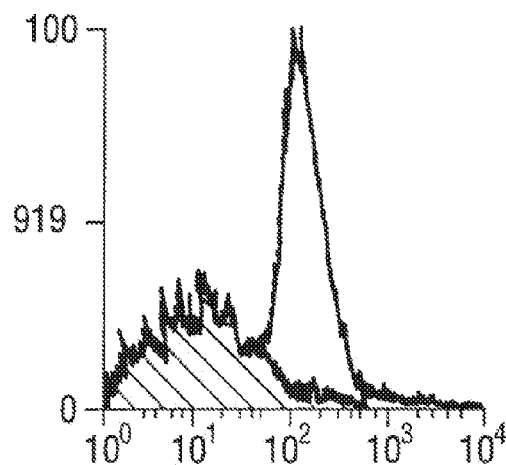
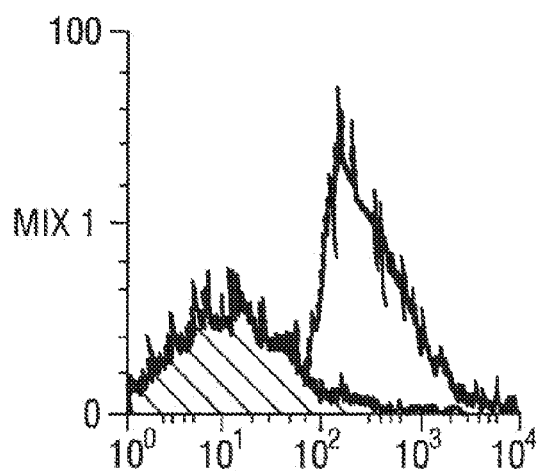
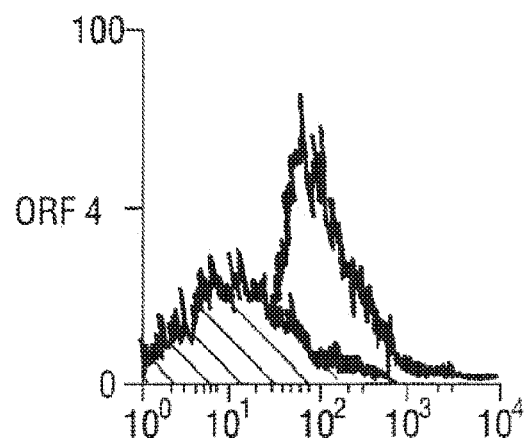
FIG. 33B

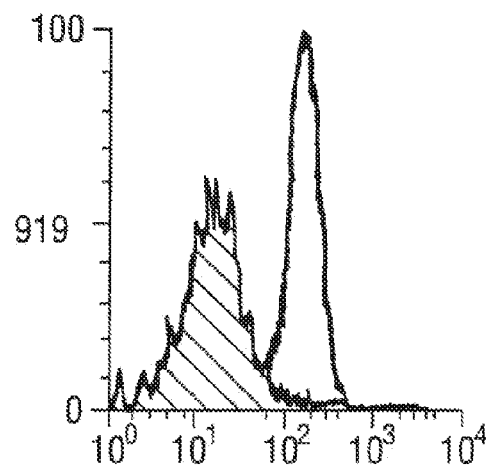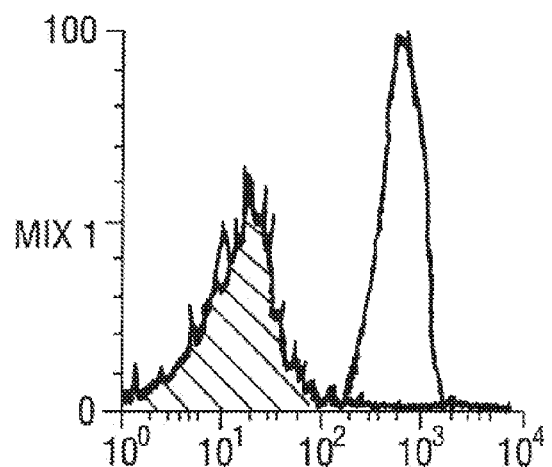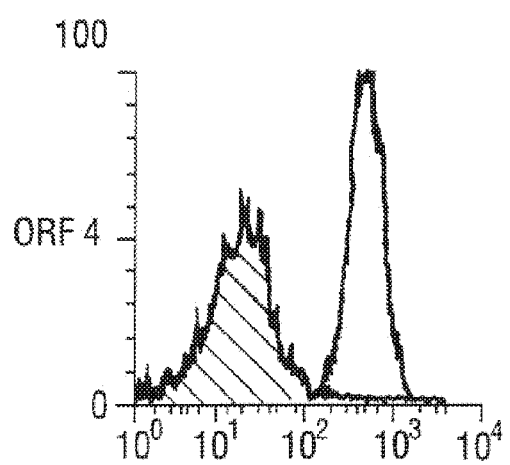
FIG. 33C
H44776

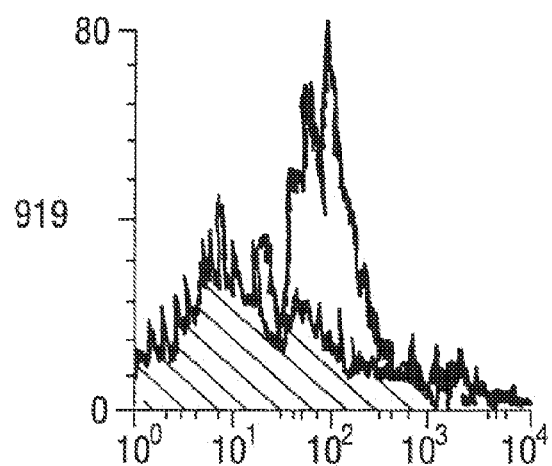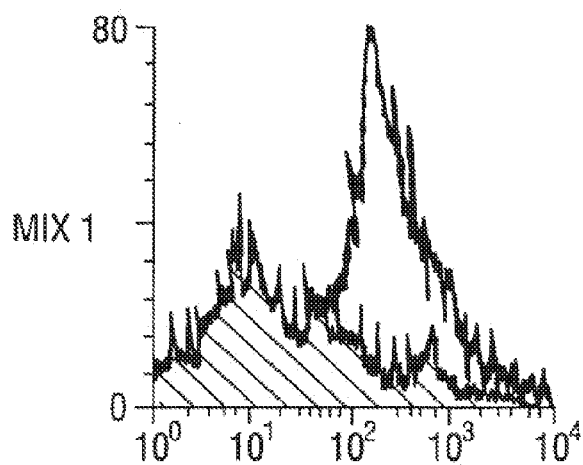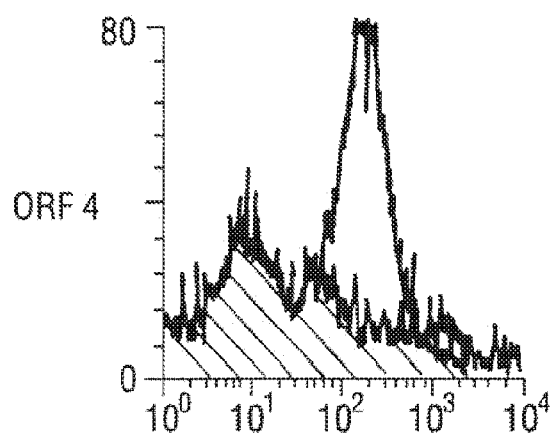
FIG. 33D

FIG. 33E
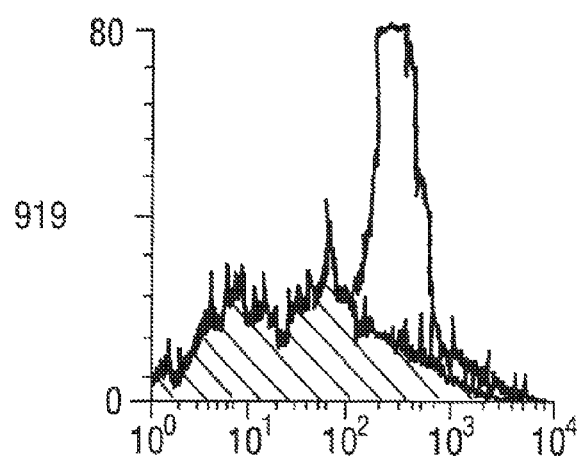
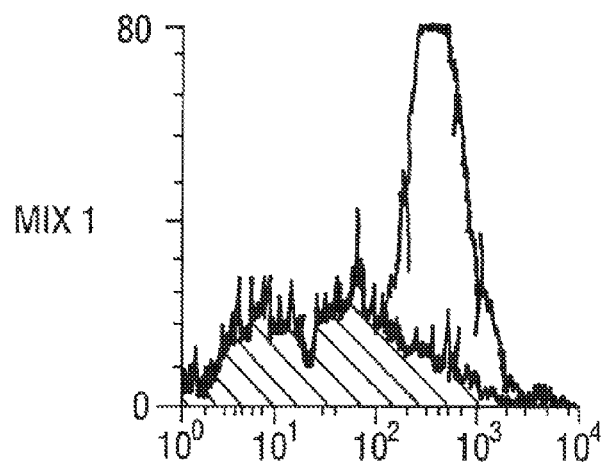
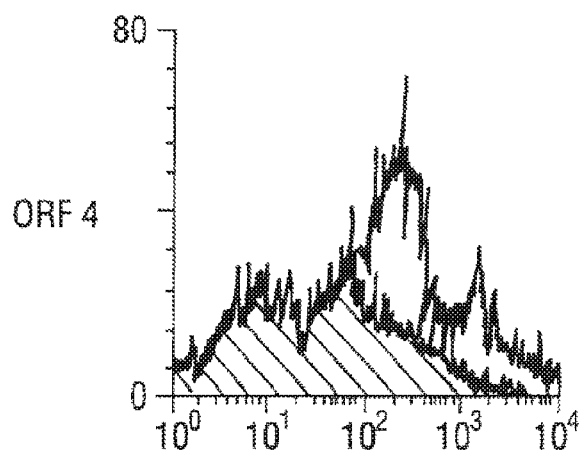

FIG. 33F
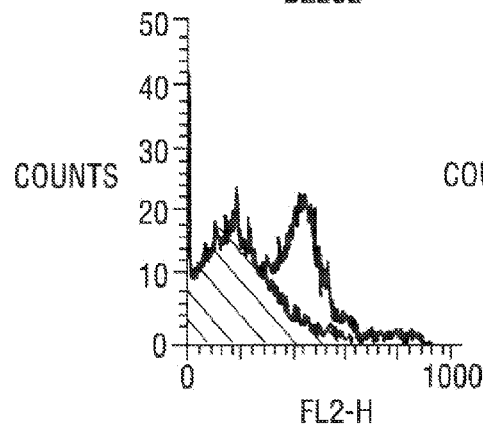
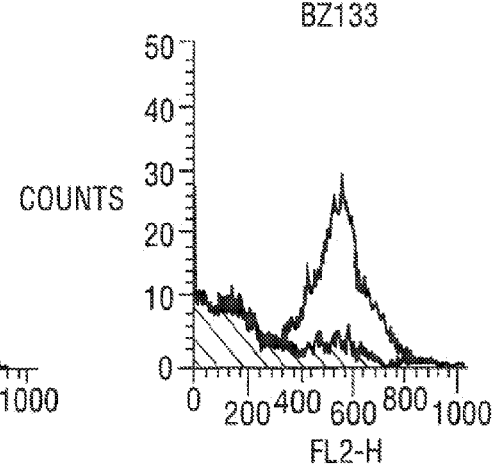
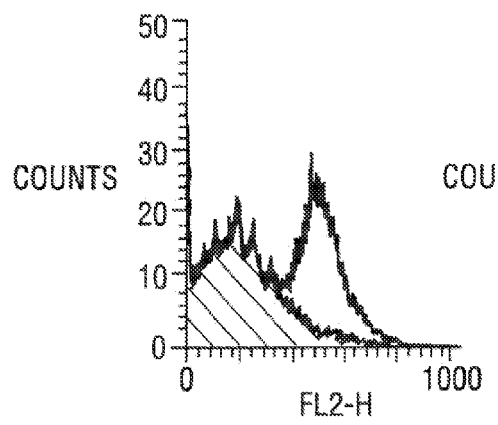
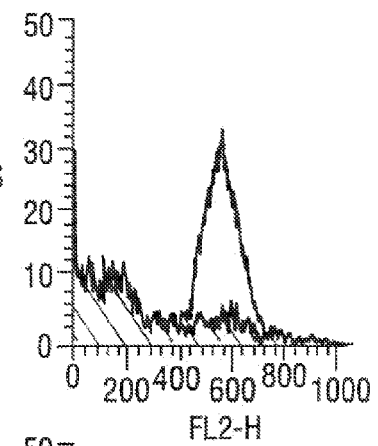
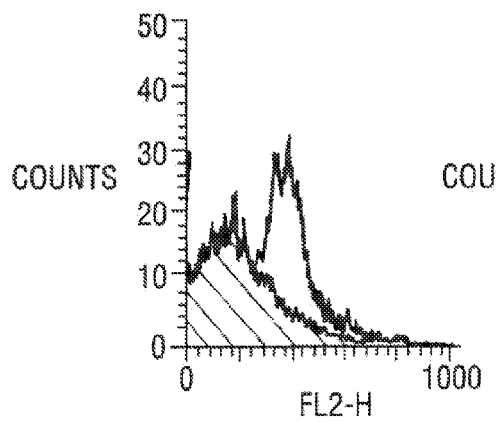
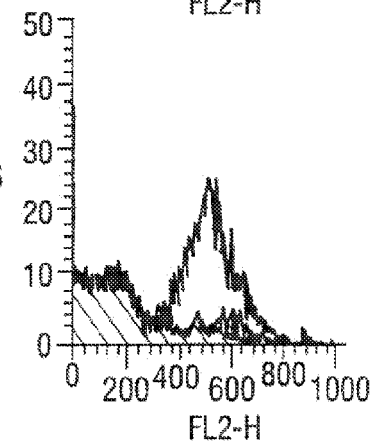

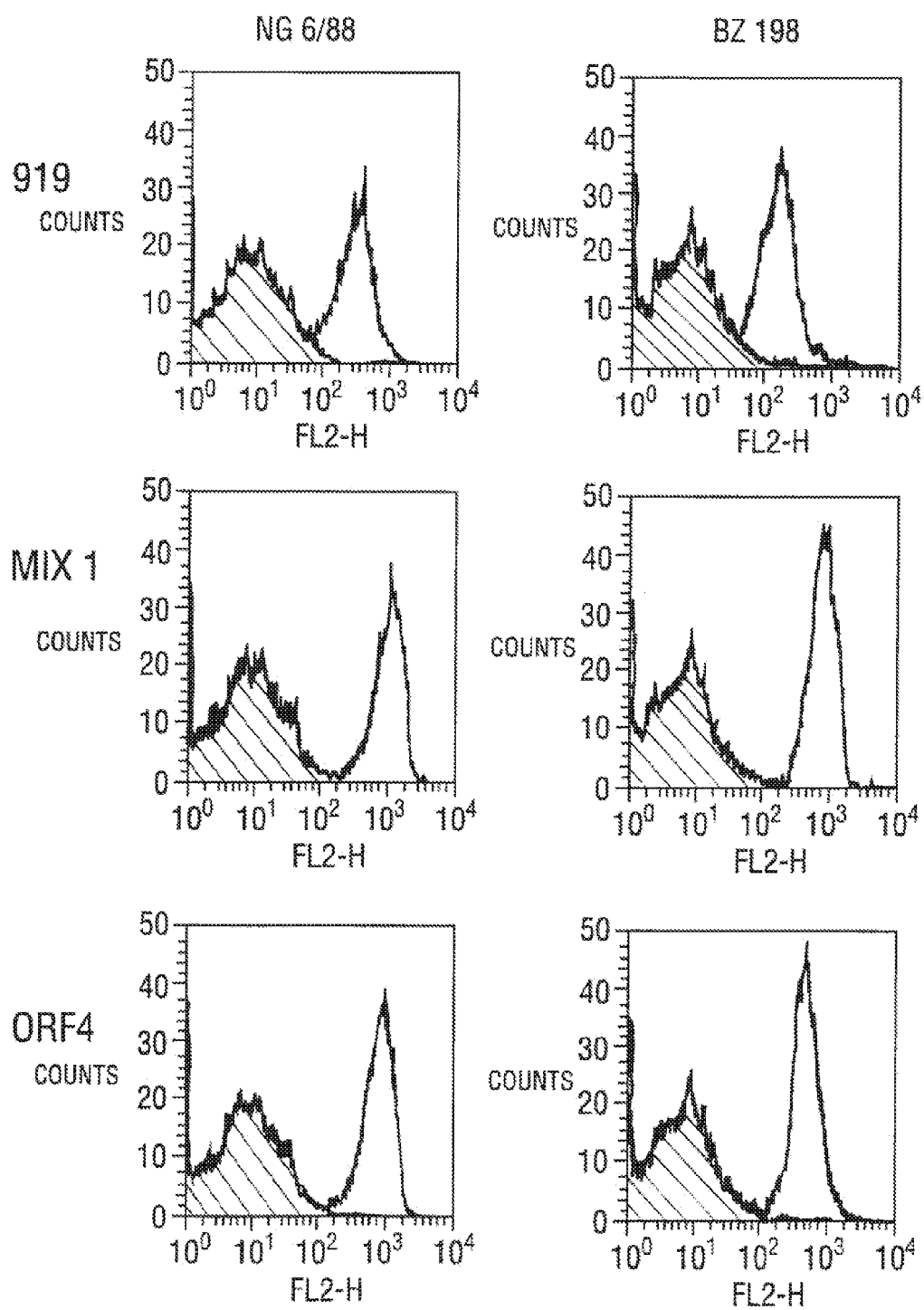

COMBINATION NEISSERIAL COMPOSITIONS

CROSS REFERENCE TO RELATED APPLICATIONS

This application is a Continuation of U.S. patent application Ser. No. 14/284,326, filed May 21, 2014, which is a Continuation of U.S. patent application Ser. No. 13/921,087, filed Jun. 18, 2013, (now Abandoned), which is a Continuation of U.S. patent application Ser. No. 12/979,239, filed Dec. 27, 2010, (now Abandoned), which is a Continuation of U.S. patent application Ser. No. 10/982,703, filed Nov. 5, 2004, (now U.S. Pat. No. 7,862,827), which is a Continuation of U.S. patent application Ser. No. 09/979,263, which claims an international filing date of May 19, 2000, (now Abandoned), which is the National Stage of International Patent Application of PCT/IB2000/000828, filed May 19, 2000, which claims the benefit of United Kingdom Patent Application No. 9911692.3, filed May 19, 1999, United Kingdom Patent Application No. 9919705.5, filed Aug. 19, 1999, and United Kingdom Patent Application No. 0005730.7, filed Mar. 9, 2000, each of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 303822001.207SeqList.txt, date recorded: Feb. 2, 2016, size: 11,264 KB).

FIELD OF THE INVENTION

This invention relates to compositions comprising combinations of biological molecules from *Neisseria* bacteria, particularly *N. meningitidis* and *N. gonorrhoeae*.

BACKGROUND ART

*Neisseria meningitidis* and *Neisseria gonorrhoeae* are non-motile. Grain negative diplococci that are pathogenic in humans.

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries.

The meningococcal vaccine currently in use is a tetravalent polysaccharide vaccine composed of serogroups A, C, Y and W135. Meningococcus B remains a problem, however. The polysaccharide approach cannot be used because the menB capsular polysaccharide is a polymer of α(2-8)-linked N-acetyl neuraminic acid that is also present in mammalian tissue. One approach to a menB vaccine uses mixtures of outer membrane proteins (OMPs). To overcome the antigenic variability, multivalent vaccines containing up to nine different porins have been constructed [eg. Poolman J T (1992) Development of a meningococcal vaccine. *Infect. Agents Dis.* 4:13-28). Additional proteins to be used in outer membrane vaccines have been the opa and opc proteins, but none of these approaches have been able to overcome the antigenic variability [eg. Ala'Aldeen & Boniello (1996) The meningococcal transferrin-binding proteins 1 and 2 are both surface exposed and generate bactericidal antibodies capable of killing homologous and heterologous strains. *Vaccine* 14(1):49-53].

Given the propensity for meningococcal disease during non-epidemic periods to be caused by multiple strains or strain variants [Russel et al. (1998) *Abstracts of 11th International pathogenic Neisseria conference*, page 281] together with frequent temporal shifts in the predominant strains in a community, it seems that a universal meningococcal B vaccine will require more than one antigenic species.

DESCRIPTION OF THE INVENTION

Neisserial protein and nucleotide sequences are disclosed in the following documents:
  WO 99/24578
  WO 99/36544
  WO 99/57280
  WO 97/28273
  WO 96/29412
  WO 95/03413
  Tettelin et al. (2000) *Science* 287:1809-1815

For ease of reference, the sequences disclosed in these documents are referred to in the present application according to the following table:

| Document | Original sequence numbering | Sequence numbering in this application |
| --- | --- | --- |
| WO 99/24578 | SEQ IDs 1-892 | SEQ IDs 1-892 |
| WO 99/36544 | SEQ IDs 1-90 | SEQ IDs 893-982 |
| WO 99/57280 | SEQ IDs 1-3020 | SEQ IDs 983-4002 |
| WO 97/28273 | FIG. 4 coding DNA | SEQ ID 4003 |
| | FIG. 4 protein | SEQ ID 4004 |
| | FIG. 9 coding DNA | SEQ ID 4005 |
| | FIG. 13 DNA | SEQ ID 4006 |
| | FIG. 13 protein | SEQ ID 4007 |
| WO 96/29412 | SEQ IDs 1-26 | SEQ IDs 4008-4033 |
| WO 95/03413 | SEQ IDs 1-23 | SEQ IDs 4034-4056 |
| Tettelin et al. (2000) *Science* 287: 1809-15 | NMB0001-2160 (DNA) | SEQ IDs 4057-6216 |
| | NMB0001-2160 (encoded proteins) | SEQ IDs 6217-8376 |

The present invention provides compositions comprising a first biological molecule from a *Neisseria* bacterium and a second biological molecule from a *Neisseria* bacterium. The term "biological molecule" includes proteins and nucleic acids.

The compositions may also comprise further biological molecules, preferably also from *Neisseria*, that is to say the compositions may comprise two or more biological molecules (eg. 3, 4, 5, 6, 7, 8 etc.), at least two of which are from a *Neisseria* bacterium (eg. 3, 4, 5, 6, 7, 8 etc.). Such compositions include those comprising (i) two or more different Neisserial proteins.

(ii) two or more different Neisserial nucleic acids, or mixtures of one or more Neisserial protein and one or more Neisserial nucleic acid.

In one preferred embodiment, the first and second biological molecules are from different *Neisseria* species (eg. one is from *N. meningitidis* and one is from *N. gonorrhoeae*), but they may be from the same species. The biological molecules in the compositions may be from different serogroups or strains of the same species.

The first biological molecule is preferably selected from the group consisting of SEQ IDs 1-8376. More preferably, it is selected from the group consisting, of SEQ IDs 1-4002 and/or SEQ IDs 4057-8376. It is preferably a purified or isolated biological molecule.

The second biological molecule is preferably selected from the group consisting of SEQ IDs 1-8376. More preferably, it is selected from the group consisting of SEQ IDs 1-4002 and/or SEQ IDs 4057-8376. It is preferably a purified or isolated biological molecule.

One or both of the first and second biological molecules may be a Neisserial biological molecule which is not specifically disclosed herein, and which may not have been identified, discovered, made available to the public or purified before this patent application was filed.

In particular, the invention provides a composition comprising one or more of the following pairs of first and second biological molecules (listed by SEQ ID):

| First | Second |
|---|---|
| 1 | 2-8376 |
| 2 | 1 and 3-8376 |
| 3 | 1-2 and 4-8376 |
| 4 | 1-3 and 5-8376 |
| 5 | 1-4 and 6-8376 |
| 6 | 1-5 and 7-8376 |
| 7 | 1-6 and 8-8376 |
| 8 | 1-7 and 9-8376 |
| 9 | 1-8 and 10-8376 |
| 10 | 1-9 and 11-8376 |
| 11 | 1-10 and 12-8376 |
| 12 | 1-11 and 13-8376 |
| 13 | 1-12 and 14-8376 |
| 14 | 1-13 and 15-8376 |
| 15 | 1-14 and 16-8376 |
| 16 | 1-15 and 17-8376 |
| 17 | 1-16 and 18-8376 |
| 18 | 1-17 and 19-8376 |
| 19 | 1-18 and 20-8376 |
| 20 | 1-19 and 21-8376 |
| 21 | 1-20 and 22-8376 |
| 22 | 1-21 and 23-8376 |
| 23 | 1-22 and 24-8376 |
| 24 | 1-23 and 25-8376 |
| 25 | 1-24 and 26-8376 |
| 26 | 1-25 and 27-8376 |
| 27 | 1-26 and 28-8376 |
| 28 | 1-27 and 29-8376 |
| 29 | 1-28 and 30-8376 |
| 30 | 1-29 and 31-8376 |
| 31 | 1-30 and 32-8376 |
| 32 | 1-31 and 33-8376 |
| 33 | 1-32 and 34-8376 |
| 34 | 1-33 and 35-8376 |
| 35 | 1-34 and 36-8376 |
| 36 | 1-35 and 37-8376 |
| 37 | 1-36 and 38-8376 |
| 38 | 1-37 and 39-8376 |
| 39 | 1-38 and 40-8376 |
| 40 | 1-39 and 41-8376 |
| 41 | 1-40 and 42-8376 |
| 42 | 1-41 and 43-8376 |
| 43 | 1-42 and 44-8376 |
| 44 | 1-43 and 45-8376 |
| 45 | 1-44 and 46-8376 |
| 46 | 1-45 and 47-8376 |
| 47 | 1-46 and 48-8376 |
| 48 | 1-47 and 49-8376 |
| 49 | 1-48 and 50-8376 |
| 50 | 1-49 and 51-8376 |
| 51 | 1-50 and 52-8376 |
| 52 | 1-51 and 53-8376 |
| 53 | 1-52 and 54-8376 |
| 54 | 1-53 and 55-8376 |
| 55 | 1-54 and 56-8376 |
| 56 | 1-55 and 57-8376 |
| 57 | 1-56 and 58-8376 |
| 58 | 1-57 and 59-8376 |
| 59 | 1-58 and 60-8376 |
| 60 | 1-59 and 61-8376 |
| 61 | 1-60 and 62-8376 |
| 62 | 1-61 and 63-8376 |
| 63 | 1-62 and 64-8376 |
| 64 | 1-63 and 65-8376 |
| 65 | 1-64 and 66-8376 |
| 66 | 1-65 and 67-8376 |
| 67 | 1-66 and 68-8376 |
| 68 | 1-67 and 69-8376 |
| 69 | 1-68 and 70-8376 |
| 70 | 1-69 and 71-8376 |
| 71 | 1-70 and 72-8376 |
| 72 | 1-71 and 73-8376 |
| 73 | 1-72 and 74-8376 |
| 74 | 1-73 and 75-8376 |
| 75 | 1-74 and 76-8376 |
| 76 | 1-75 and 77-8376 |
| 77 | 1-76 and 78-8376 |
| 78 | 1-77 and 79-8376 |
| 79 | 1-78 and 80-8376 |
| 80 | 1-79 and 81-8376 |
| 81 | 1-80 and 82-8376 |
| 82 | 1-81 and 83-8376 |
| 83 | 1-82 and 84-8376 |
| 84 | 1-83 and 85-8376 |
| 85 | 1-84 and 86-8376 |
| 86 | 1-85 and 87-8376 |
| 87 | 1-86 and 88-8376 |
| 88 | 1-87 and 89-8376 |
| 89 | 1-88 and 90-8376 |
| 90 | 1-89 and 91-8376 |
| 91 | 1-90 and 92-8376 |
| 92 | 1-91 and 93-8376 |
| 93 | 1-92 and 94-8376 |
| 94 | 1-93 and 95-8376 |
| 95 | 1-94 and 96-8376 |
| 96 | 1-95 and 97-8376 |
| 97 | 1-96 and 98-8376 |
| 98 | 1-97 and 99-8376 |
| 99 | 1-98 and 100-8376 |
| 100 | 1-99 and 101-8376 |
| 101 | 1-100 and 102-8376 |
| 102 | 1-101 and 103-8376 |
| 103 | 1-102 and 104-8376 |
| 104 | 1-103 and 105-8376 |
| 105 | 1-104 and 106-8376 |
| 106 | 1-105 and 107-8376 |
| 107 | 1-106 and 108-8376 |
| 108 | 1-107 and 109-8376 |
| 109 | 1-108 and 110-8376 |
| 110 | 1-109 and 111-8376 |
| 111 | 1-110 and 112-8376 |
| 112 | 1-111 and 113-8376 |
| 113 | 1-112 and 114-8376 |
| 114 | 1-113 and 115-8376 |
| 115 | 1-114 and 116-8376 |
| 116 | 1-115 and 117-8376 |
| 117 | 1-116 and 118-8376 |
| 118 | 1-117 and 119-8376 |
| 119 | 1-118 and 120-8376 |
| 120 | 1-119 and 121-8376 |
| 121 | 1-120 and 122-8376 |
| 122 | 1-121 and 123-8376 |
| 123 | 1-122 and 124-8376 |
| 124 | 1-123 and 125-8376 |
| 125 | 1-124 and 126-8376 |
| 126 | 1-125 and 127-8376 |
| 127 | 1-126 and 128-8376 |
| 128 | 1-127 and 129-8376 |
| 129 | 1-128 and 130-8376 |
| 130 | 1-129 and 131-8376 |
| 131 | 1-130 and 132-8376 |
| 132 | 1-131 and 133-8376 |
| 133 | 1-132 and 134-8376 |
| 134 | 1-133 and 135-8376 |
| 135 | 1-134 and 136-8376 |

| First | Second |
|---|---|
| 136 | 1-135 and 137-8376 |
| 137 | 1-136 and 138-8376 |
| 138 | 1-137 and 139-8376 |
| 139 | 1-138 and 140-8376 |
| 140 | 1-139 and 141-8376 |
| 141 | 1-140 and 142-8376 |
| 142 | 1-141 and 143-8376 |
| 143 | 1-142 and 144-8376 |
| 144 | 1-143 and 145-8376 |
| 145 | 1-144 and 146-8376 |
| 146 | 1-145 and 147-8376 |
| 147 | 1-146 and 148-8376 |
| 148 | 1-147 and 149-8376 |
| 149 | 1-148 and 150-8376 |
| 150 | 1-149 and 151-8376 |
| 151 | 1-150 and 152-8376 |
| 152 | 1-151 and 153-8376 |
| 153 | 1-152 and 154-8376 |
| 154 | 1-153 and 155-8376 |
| 155 | 1-154 and 156-8376 |
| 156 | 1-155 and 157-8376 |
| 157 | 1-156 and 158-8376 |
| 158 | 1-157 and 159-8376 |
| 159 | 1-158 and 160-8376 |
| 160 | 1-159 and 161-8376 |
| 161 | 1-160 and 162-8376 |
| 162 | 1-161 and 163-8376 |
| 163 | 1-162 and 164-8376 |
| 164 | 1-163 and 165-8376 |
| 165 | 1-164 and 166-8376 |
| 166 | 1-165 and 167-8376 |
| 167 | 1-166 and 168-8376 |
| 168 | 1-167 and 169-8376 |
| 169 | 1-168 and 170-8376 |
| 170 | 1-169 and 171-8376 |
| 171 | 1-170 and 172-8376 |
| 172 | 1-171 and 173-8376 |
| 173 | 1-172 and 174-8376 |
| 174 | 1-173 and 175-8376 |
| 175 | 1-174 and 176-8376 |
| 176 | 1-175 and 177-8376 |
| 177 | 1-176 and 178-8376 |
| 178 | 1-177 and 179-8376 |
| 179 | 1-178 and 180-8376 |
| 180 | 1-179 and 181-8376 |
| 181 | 1-180 and 182-8376 |
| 182 | 1-181 and 183-8376 |
| 183 | 1-182 and 184-8376 |
| 184 | 1-183 and 185-8376 |
| 185 | 1-184 and 186-8376 |
| 186 | 1-185 and 187-8376 |
| 187 | 1-186 and 188-8376 |
| 188 | 1-187 and 189-8376 |
| 189 | 1-188 and 190-8376 |
| 190 | 1-189 and 191-8376 |
| 191 | 1-190 and 192-8376 |
| 192 | 1-191 and 193-8376 |
| 193 | 1-192 and 194-8376 |
| 194 | 1-193 and 195-8376 |
| 195 | 1-194 and 196-8376 |
| 196 | 1-195 and 197-8376 |
| 197 | 1-196 and 198-8376 |
| 198 | 1-197 and 199-8376 |
| 199 | 1-198 and 200-8376 |
| 200 | 1-199 and 201-8376 |
| 201 | 1-200 and 202-8376 |
| 202 | 1-201 and 203-8376 |
| 203 | 1-202 and 204-8376 |
| 204 | 1-203 and 205-8376 |
| 205 | 1-204 and 206-8376 |
| 206 | 1-205 and 207-8376 |
| 207 | 1-206 and 208-8376 |
| 208 | 1-207 and 209-8376 |
| 209 | 1-208 and 210-8376 |
| 210 | 1-209 and 211-8376 |
| 211 | 1-210 and 212-8376 |
| 212 | 1-211 and 213-8376 |
| 213 | 1-212 and 214-8376 |
| 214 | 1-213 and 215-8376 |
| 215 | 1-214 and 216-8376 |
| 216 | 1-215 and 217-8376 |
| 217 | 1-216 and 218-8376 |
| 218 | 1-217 and 219-8376 |
| 219 | 1-218 and 220-8376 |
| 220 | 1-219 and 221-8376 |
| 221 | 1-220 and 222-8376 |
| 222 | 1-221 and 223-8376 |
| 223 | 1-222 and 224-8376 |
| 224 | 1-223 and 225-8376 |
| 225 | 1-224 and 226-8376 |
| 226 | 1-225 and 227-8376 |
| 227 | 1-226 and 228-8376 |
| 228 | 1-227 and 229-8376 |
| 229 | 1-228 and 230-8376 |
| 230 | 1-229 and 231-8376 |
| 231 | 1-230 and 232-8376 |
| 232 | 1-231 and 233-8376 |
| 233 | 1-232 and 234-8376 |
| 234 | 1-233 and 235-8376 |
| 235 | 1-234 and 236-8376 |
| 236 | 1-235 and 237-8376 |
| 237 | 1-236 and 238-8376 |
| 238 | 1-237 and 239-8376 |
| 239 | 1-238 and 240-8376 |
| 240 | 1-239 and 241-8376 |
| 241 | 1-240 and 242-8376 |
| 242 | 1-241 and 243-8376 |
| 243 | 1-242 and 244-8376 |
| 244 | 1-243 and 245-8376 |
| 245 | 1-244 and 246-8376 |
| 246 | 1-245 and 247-8376 |
| 247 | 1-246 and 248-8376 |
| 248 | 1-247 and 249-8376 |
| 249 | 1-248 and 250-8376 |
| 250 | 1-249 and 251-8376 |
| 251 | 1-250 and 252-8376 |
| 252 | 1-251 and 253-8376 |
| 253 | 1-252 and 254-8376 |
| 254 | 1-253 and 255-8376 |
| 255 | 1-254 and 256-8376 |
| 256 | 1-255 and 257-8376 |
| 257 | 1-256 and 258-8376 |
| 258 | 1-257 and 259-8376 |
| 259 | 1-258 and 260-8376 |
| 260 | 1-259 and 261-8376 |
| 261 | 1-260 and 262-8376 |
| 262 | 1-261 and 263-8376 |
| 263 | 1-262 and 264-8376 |
| 264 | 1-263 and 265-8376 |
| 265 | 1-264 and 266-8376 |
| 266 | 1-265 and 267-8376 |
| 267 | 1-266 and 268-8376 |
| 268 | 1-267 and 269-8376 |
| 269 | 1-268 and 270-8376 |
| 270 | 1-269 and 271-8376 |
| 271 | 1-270 and 272-8376 |
| 272 | 1-271 and 273-8376 |
| 273 | 1-272 and 274-8376 |
| 274 | 1-273 and 275-8376 |
| 275 | 1-274 and 276-8376 |
| 276 | 1-275 and 277-8376 |
| 277 | 1-276 and 278-8376 |
| 278 | 1-277 and 279-8376 |
| 279 | 1-278 and 280-8376 |
| 280 | 1-279 and 281-8376 |
| 281 | 1-280 and 282-8376 |
| 282 | 1-281 and 283-8376 |
| 283 | 1-282 and 284-8376 |
| 284 | 1-283 and 285-8376 |
| 285 | 1-284 and 286-8376 |
| 286 | 1-285 and 287-8376 |
| 287 | 1-286 and 288-8376 |
| 288 | 1-287 and 289-8376 |
| 289 | 1-288 and 290-8376 |

| First | Second |
|---|---|
| 290 | 1-289 and 291-8376 |
| 291 | 1-290 and 292-8376 |
| 292 | 1-291 and 293-8376 |
| 293 | 1-292 and 294-8376 |
| 294 | 1-293 and 295-8376 |
| 295 | 1-294 and 296-8376 |
| 296 | 1-295 and 297-8376 |
| 297 | 1-296 and 298-8376 |
| 298 | 1-297 and 299-8376 |
| 299 | 1-298 and 300-8376 |
| 300 | 1-299 and 301-8376 |
| 301 | 1-300 and 302-8376 |
| 302 | 1-301 and 303-8376 |
| 303 | 1-302 and 304-8376 |
| 304 | 1-303 and 305-8376 |
| 305 | 1-304 and 306-8376 |
| 306 | 1-305 and 307-8376 |
| 307 | 1-306 and 308-8376 |
| 308 | 1-307 and 309-8376 |
| 309 | 1-308 and 310-8376 |
| 310 | 1-309 and 311-8376 |
| 311 | 1-310 and 312-8376 |
| 312 | 1-311 and 313-8376 |
| 313 | 1-312 and 314-8376 |
| 314 | 1-313 and 315-8376 |
| 315 | 1-314 and 316-8376 |
| 316 | 1-315 and 317-8376 |
| 317 | 1-316 and 318-8376 |
| 318 | 1-317 and 319-8376 |
| 319 | 1-318 and 320-8376 |
| 320 | 1-319 and 321-8376 |
| 321 | 1-320 and 322-8376 |
| 322 | 1-321 and 323-8376 |
| 323 | 1-322 and 324-8376 |
| 324 | 1-323 and 325-8376 |
| 325 | 1-324 and 326-8376 |
| 326 | 1-325 and 327-8376 |
| 327 | 1-326 and 328-8376 |
| 328 | 1-327 and 329-8376 |
| 329 | 1-328 and 330-8376 |
| 330 | 1-329 and 331-8376 |
| 331 | 1-330 and 332-8376 |
| 332 | 1-331 and 333-8376 |
| 333 | 1-332 and 334-8376 |
| 334 | 1-333 and 335-8376 |
| 335 | 1-334 and 336-8376 |
| 336 | 1-335 and 337-8376 |
| 337 | 1-336 and 338-8376 |
| 338 | 1-337 and 339-8376 |
| 339 | 1-338 and 340-8376 |
| 340 | 1-339 and 341-8376 |
| 341 | 1-340 and 342-8376 |
| 342 | 1-341 and 343-8376 |
| 343 | 1-342 and 344-8376 |
| 344 | 1-343 and 345-8376 |
| 345 | 1-344 and 346-8376 |
| 346 | 1-345 and 347-8376 |
| 347 | 1-346 and 348-8376 |
| 348 | 1-347 and 349-8376 |
| 349 | 1-348 and 350-8376 |
| 350 | 1-349 and 351-8376 |
| 351 | 1-350 and 352-8376 |
| 352 | 1-351 and 353-8376 |
| 353 | 1-352 and 354-8376 |
| 354 | 1-353 and 355-8376 |
| 355 | 1-354 and 356-8376 |
| 356 | 1-355 and 357-8376 |
| 357 | 1-356 and 358-8376 |
| 358 | 1-357 and 359-8376 |
| 359 | 1-358 and 360-8376 |
| 360 | 1-359 and 361-8376 |
| 361 | 1-360 and 362-8376 |
| 362 | 1-361 and 363-8376 |
| 363 | 1-362 and 364-8376 |
| 364 | 1-363 and 365-8376 |
| 365 | 1-364 and 366-8376 |
| 366 | 1-365 and 367-8376 |
| 367 | 1-366 and 368-8376 |
| 368 | 1-367 and 369-8376 |
| 369 | 1-368 and 370-8376 |
| 370 | 1-369 and 371-8376 |
| 371 | 1-370 and 372-8376 |
| 372 | 1-371 and 373-8376 |
| 373 | 1-372 and 374-8376 |
| 374 | 1-373 and 375-8376 |
| 375 | 1-374 and 376-8376 |
| 376 | 1-375 and 377-8376 |
| 377 | 1-376 and 378-8376 |
| 378 | 1-377 and 379-8376 |
| 379 | 1-378 and 380-8376 |
| 380 | 1-379 and 381-8376 |
| 381 | 1-380 and 382-8376 |
| 382 | 1-381 and 383-8376 |
| 383 | 1-382 and 384-8376 |
| 384 | 1-383 and 385-8376 |
| 385 | 1-384 and 386-8376 |
| 386 | 1-385 and 387-8376 |
| 387 | 1-386 and 388-8376 |
| 388 | 1-387 and 389-8376 |
| 389 | 1-388 and 390-8376 |
| 390 | 1-389 and 391-8376 |
| 391 | 1-390 and 392-8376 |
| 392 | 1-391 and 393-8376 |
| 393 | 1-392 and 394-8376 |
| 394 | 1-393 and 395-8376 |
| 395 | 1-394 and 396-8376 |
| 396 | 1-395 and 397-8376 |
| 397 | 1-396 and 398-8376 |
| 398 | 1-397 and 399-8376 |
| 399 | 1-398 and 400-8376 |
| 400 | 1-399 and 401-8376 |
| 401 | 1-400 and 402-8376 |
| 402 | 1-401 and 403-8376 |
| 403 | 1-402 and 404-8376 |
| 404 | 1-403 and 405-8376 |
| 405 | 1-404 and 406-8376 |
| 406 | 1-405 and 407-8376 |
| 407 | 1-406 and 408-8376 |
| 408 | 1-407 and 409-8376 |
| 409 | 1-408 and 410-8376 |
| 410 | 1-409 and 411-8376 |
| 411 | 1-410 and 412-8376 |
| 412 | 1-411 and 413-8376 |
| 413 | 1-412 and 414-8376 |
| 414 | 1-413 and 415-8376 |
| 415 | 1-414 and 416-8376 |
| 416 | 1-415 and 417-8376 |
| 417 | 1-416 and 418-8376 |
| 418 | 1-417 and 419-8376 |
| 419 | 1-418 and 420-8376 |
| 420 | 1-419 and 421-8376 |
| 421 | 1-420 and 422-8376 |
| 422 | 1-421 and 423-8376 |
| 423 | 1-422 and 424-8376 |
| 424 | 1-423 and 425-8376 |
| 425 | 1-424 and 426-8376 |
| 426 | 1-425 and 427-8376 |
| 427 | 1-426 and 428-8376 |
| 428 | 1-427 and 429-8376 |
| 429 | 1-428 and 430-8376 |
| 430 | 1-429 and 431-8376 |
| 431 | 1-430 and 432-8376 |
| 432 | 1-431 and 433-8376 |
| 433 | 1-432 and 434-8376 |
| 434 | 1-433 and 435-8376 |
| 435 | 1-434 and 436-8376 |
| 436 | 1-435 and 437-8376 |
| 437 | 1-436 and 438-8376 |
| 438 | 1-437 and 439-8376 |
| 439 | 1-438 and 440-8376 |
| 440 | 1-439 and 441-8376 |
| 441 | 1-440 and 442-8376 |
| 442 | 1-441 and 443-8376 |
| 443 | 1-442 and 444-8376 |

-continued

| First | Second |
|---|---|
| 444 | 1-443 and 445-8376 |
| 445 | 1-444 and 446-8376 |
| 446 | 1-445 and 447-8376 |
| 447 | 1-446 and 448-8376 |
| 448 | 1-447 and 449-8376 |
| 449 | 1-448 and 450-8376 |
| 450 | 1-449 and 451-8376 |
| 451 | 1-450 and 452-8376 |
| 452 | 1-451 and 453-8376 |
| 453 | 1-452 and 454-8376 |
| 454 | 1-453 and 455-8376 |
| 455 | 1-454 and 456-8376 |
| 456 | 1-455 and 457-8376 |
| 457 | 1-456 and 458-8376 |
| 458 | 1-457 and 459-8376 |
| 459 | 1-458 and 460-8376 |
| 460 | 1-459 and 461-8376 |
| 461 | 1-460 and 462-8376 |
| 462 | 1-461 and 463-8376 |
| 463 | 1-462 and 464-8376 |
| 464 | 1-463 and 465-8376 |
| 465 | 1-464 and 466-8376 |
| 466 | 1-465 and 467-8376 |
| 467 | 1-466 and 468-8376 |
| 468 | 1-467 and 469-8376 |
| 469 | 1-468 and 470-8376 |
| 470 | 1-469 and 471-8376 |
| 471 | 1-470 and 472-8376 |
| 472 | 1-471 and 473-8376 |
| 473 | 1-472 and 474-8376 |
| 474 | 1-473 and 475-8376 |
| 475 | 1-474 and 476-8376 |
| 476 | 1-475 and 477-8376 |
| 477 | 1-476 and 478-8376 |
| 478 | 1-477 and 479-8376 |
| 479 | 1-478 and 480-8376 |
| 480 | 1-479 and 481-8376 |
| 481 | 1-480 and 482-8376 |
| 482 | 1-481 and 483-8376 |
| 483 | 1-482 and 484-8376 |
| 484 | 1-483 and 485-8376 |
| 485 | 1-484 and 486-8376 |
| 486 | 1-485 and 487-8376 |
| 487 | 1-486 and 488-8376 |
| 488 | 1-487 and 489-8376 |
| 489 | 1-488 and 490-8376 |
| 490 | 1-489 and 491-8376 |
| 491 | 1-490 and 492-8376 |
| 492 | 1-491 and 493-8376 |
| 493 | 1-492 and 494-8376 |
| 494 | 1-493 and 495-8376 |
| 495 | 1-494 and 496-8376 |
| 496 | 1-495 and 497-8376 |
| 497 | 1-496 and 498-8376 |
| 498 | 1-497 and 499-8376 |
| 499 | 1-498 and 500-8376 |
| 500 | 1-499 and 501-8376 |
| 501 | 1-500 and 502-8376 |
| 502 | 1-501 and 503-8376 |
| 503 | 1-502 and 504-8376 |
| 504 | 1-503 and 505-8376 |
| 505 | 1-504 and 506-8376 |
| 506 | 1-505 and 507-8376 |
| 507 | 1-506 and 508-8376 |
| 508 | 1-507 and 509-8376 |
| 509 | 1-508 and 510-8376 |
| 510 | 1-509 and 511-8376 |
| 511 | 1-510 and 512-8376 |
| 512 | 1-511 and 513-8376 |
| 513 | 1-512 and 514-8376 |
| 514 | 1-513 and 515-8376 |
| 515 | 1-514 and 516-8376 |
| 516 | 1-515 and 517-8376 |
| 517 | 1-516 and 518-8376 |
| 518 | 1-517 and 519-8376 |
| 519 | 1-518 and 520-8376 |
| 520 | 1-519 and 521-8376 |
| 521 | 1-520 and 522-8376 |
| 522 | 1-521 and 523-8376 |
| 523 | 1-522 and 524-8376 |
| 524 | 1-523 and 525-8376 |
| 525 | 1-524 and 526-8376 |
| 526 | 1-525 and 527-8376 |
| 527 | 1-526 and 528-8376 |
| 528 | 1-527 and 529-8376 |
| 529 | 1-528 and 530-8376 |
| 530 | 1-529 and 531-8376 |
| 531 | 1-530 and 532-8376 |
| 532 | 1-531 and 533-8376 |
| 533 | 1-532 and 534-8376 |
| 534 | 1-533 and 535-8376 |
| 535 | 1-534 and 536-8376 |
| 536 | 1-535 and 537-8376 |
| 537 | 1-536 and 538-8376 |
| 538 | 1-537 and 539-8376 |
| 539 | 1-538 and 540-8376 |
| 540 | 1-539 and 541-8376 |
| 541 | 1-540 and 542-8376 |
| 542 | 1-541 and 543-8376 |
| 543 | 1-542 and 544-8376 |
| 544 | 1-543 and 545-8376 |
| 545 | 1-544 and 546-8376 |
| 546 | 1-545 and 547-8376 |
| 547 | 1-546 and 548-8376 |
| 548 | 1-547 and 549-8376 |
| 549 | 1-548 and 550-8376 |
| 550 | 1-549 and 551-8376 |
| 551 | 1-550 and 552-8376 |
| 552 | 1-551 and 553-8376 |
| 553 | 1-552 and 554-8376 |
| 554 | 1-553 and 555-8376 |
| 555 | 1-554 and 556-8376 |
| 556 | 1-555 and 557-8376 |
| 557 | 1-556 and 558-8376 |
| 558 | 1-557 and 559-8376 |
| 559 | 1-558 and 560-8376 |
| 560 | 1-559 and 561-8376 |
| 561 | 1-560 and 562-8376 |
| 562 | 1-561 and 563-8376 |
| 563 | 1-562 and 564-8376 |
| 564 | 1-563 and 565-8376 |
| 565 | 1-564 and 566-8376 |
| 566 | 1-565 and 567-8376 |
| 567 | 1-566 and 568-8376 |
| 568 | 1-567 and 569-8376 |
| 569 | 1-568 and 570-8376 |
| 570 | 1-569 and 571-8376 |
| 571 | 1-570 and 572-8376 |
| 572 | 1-571 and 573-8376 |
| 573 | 1-572 and 574-8376 |
| 574 | 1-573 and 575-8376 |
| 575 | 1-574 and 576-8376 |
| 576 | 1-575 and 577-8376 |
| 577 | 1-576 and 578-8376 |
| 578 | 1-577 and 579-8376 |
| 579 | 1-578 and 580-8376 |
| 580 | 1-579 and 581-8376 |
| 581 | 1-580 and 582-8376 |
| 582 | 1-581 and 583-8376 |
| 583 | 1-582 and 584-8376 |
| 584 | 1-583 and 585-8376 |
| 585 | 1-584 and 586-8376 |
| 586 | 1-585 and 587-8376 |
| 587 | 1-586 and 588-8376 |
| 588 | 1-587 and 589-8376 |
| 589 | 1-588 and 590-8376 |
| 590 | 1-589 and 591-8376 |
| 591 | 1-590 and 592-8376 |
| 592 | 1-591 and 593-8376 |
| 593 | 1-592 and 594-8376 |
| 594 | 1-593 and 595-8376 |
| 595 | 1-594 and 596-8376 |
| 596 | 1-595 and 597-8376 |
| 597 | 1-596 and 598-8376 |

| First | Second |
|---|---|
| 598 | 1-597 and 599-8376 |
| 599 | 1-598 and 600-8376 |
| 600 | 1-599 and 601-8376 |
| 601 | 1-600 and 602-8376 |
| 602 | 1-601 and 603-8376 |
| 603 | 1-602 and 604-8376 |
| 604 | 1-603 and 605-8376 |
| 605 | 1-604 and 606-8376 |
| 606 | 1-605 and 607-8376 |
| 607 | 1-606 and 608-8376 |
| 608 | 1-607 and 609-8376 |
| 609 | 1-608 and 610-8376 |
| 610 | 1-609 and 611-8376 |
| 611 | 1-610 and 612-8376 |
| 612 | 1-611 and 613-8376 |
| 613 | 1-612 and 614-8376 |
| 614 | 1-613 and 615-8376 |
| 615 | 1-614 and 616-8376 |
| 616 | 1-615 and 617-8376 |
| 617 | 1-616 and 618-8376 |
| 618 | 1-617 and 619-8376 |
| 619 | 1-618 and 620-8376 |
| 620 | 1-619 and 621-8376 |
| 621 | 1-620 and 622-8376 |
| 622 | 1-621 and 623-8376 |
| 623 | 1-622 and 624-8376 |
| 624 | 1-623 and 625-8376 |
| 625 | 1-624 and 626-8376 |
| 626 | 1-625 and 627-8376 |
| 627 | 1-626 and 628-8376 |
| 628 | 1-627 and 629-8376 |
| 629 | 1-628 and 630-8376 |
| 630 | 1-629 and 631-8376 |
| 631 | 1-630 and 632-8376 |
| 632 | 1-631 and 633-8376 |
| 633 | 1-632 and 634-8376 |
| 634 | 1-633 and 635-8376 |
| 635 | 1-634 and 636-8376 |
| 636 | 1-635 and 637-8376 |
| 637 | 1-636 and 638-8376 |
| 638 | 1-637 and 639-8376 |
| 639 | 1-638 and 640-8376 |
| 640 | 1-639 and 641-8376 |
| 641 | 1-640 and 642-8376 |
| 642 | 1-641 and 643-8376 |
| 643 | 1-642 and 644-8376 |
| 644 | 1-643 and 645-8376 |
| 645 | 1-644 and 646-8376 |
| 646 | 1-645 and 647-8376 |
| 647 | 1-646 and 648-8376 |
| 648 | 1-647 and 649-8376 |
| 649 | 1-648 and 650-8376 |
| 650 | 1-649 and 651-8376 |
| 651 | 1-650 and 652-8376 |
| 652 | 1-651 and 653-8376 |
| 653 | 1-652 and 654-8376 |
| 654 | 1-653 and 655-8376 |
| 655 | 1-654 and 656-8376 |
| 656 | 1-655 and 657-8376 |
| 657 | 1-656 and 658-8376 |
| 658 | 1-657 and 659-8376 |
| 659 | 1-658 and 660-8376 |
| 660 | 1-659 and 661-8376 |
| 661 | 1-660 and 662-8376 |
| 662 | 1-661 and 663-8376 |
| 663 | 1-662 and 664-8376 |
| 664 | 1-663 and 665-8376 |
| 665 | 1-664 and 666-8376 |
| 666 | 1-665 and 667-8376 |
| 667 | 1-666 and 668-8376 |
| 668 | 1-667 and 669-8376 |
| 669 | 1-668 and 670-8376 |
| 670 | 1-669 and 671-8376 |
| 671 | 1-670 and 672-8376 |
| 672 | 1-671 and 673-8376 |
| 673 | 1-672 and 674-8376 |
| 674 | 1-673 and 675-8376 |
| 675 | 1-674 and 676-8376 |
| 676 | 1-675 and 677-8376 |
| 677 | 1-676 and 678-8376 |
| 678 | 1-677 and 679-8376 |
| 679 | 1-678 and 680-8376 |
| 680 | 1-679 and 681-8376 |
| 681 | 1-680 and 682-8376 |
| 682 | 1-681 and 683-8376 |
| 683 | 1-682 and 684-8376 |
| 684 | 1-683 and 685-8376 |
| 685 | 1-684 and 686-8376 |
| 686 | 1-685 and 687-8376 |
| 687 | 1-686 and 688-8376 |
| 688 | 1-687 and 689-8376 |
| 689 | 1-688 and 690-8376 |
| 690 | 1-689 and 691-8376 |
| 691 | 1-690 and 692-8376 |
| 692 | 1-691 and 693-8376 |
| 693 | 1-692 and 694-8376 |
| 694 | 1-693 and 695-8376 |
| 695 | 1-694 and 696-8376 |
| 696 | 1-695 and 697-8376 |
| 697 | 1-696 and 698-8376 |
| 698 | 1-697 and 699-8376 |
| 699 | 1-698 and 700-8376 |
| 700 | 1-699 and 701-8376 |
| 701 | 1-700 and 702-8376 |
| 702 | 1-701 and 703-8376 |
| 703 | 1-702 and 704-8376 |
| 704 | 1-703 and 705-8376 |
| 705 | 1-704 and 706-8376 |
| 706 | 1-705 and 707-8376 |
| 707 | 1-706 and 708-8376 |
| 708 | 1-707 and 709-8376 |
| 709 | 1-708 and 710-8376 |
| 710 | 1-709 and 711-8376 |
| 711 | 1-710 and 712-8376 |
| 712 | 1-711 and 713-8376 |
| 713 | 1-712 and 714-8376 |
| 714 | 1-713 and 715-8376 |
| 715 | 1-714 and 716-8376 |
| 716 | 1-715 and 717-8376 |
| 717 | 1-716 and 718-8376 |
| 718 | 1-717 and 719-8376 |
| 719 | 1-718 and 720-8376 |
| 720 | 1-719 and 721-8376 |
| 721 | 1-720 and 722-8376 |
| 722 | 1-721 and 723-8376 |
| 723 | 1-722 and 724-8376 |
| 724 | 1-723 and 725-8376 |
| 725 | 1-724 and 726-8376 |
| 726 | 1-725 and 727-8376 |
| 727 | 1-726 and 728-8376 |
| 728 | 1-727 and 729-8376 |
| 729 | 1-728 and 730-8376 |
| 730 | 1-729 and 731-8376 |
| 731 | 1-730 and 732-8376 |
| 732 | 1-731 and 733-8376 |
| 733 | 1-732 and 734-8376 |
| 734 | 1-733 and 735-8376 |
| 735 | 1-734 and 736-8376 |
| 736 | 1-735 and 737-8376 |
| 737 | 1-736 and 738-8376 |
| 738 | 1-737 and 739-8376 |
| 739 | 1-738 and 740-8376 |
| 740 | 1-739 and 741-8376 |
| 741 | 1-740 and 742-8376 |
| 742 | 1-741 and 743-8376 |
| 743 | 1-742 and 744-8376 |
| 744 | 1-743 and 745-8376 |
| 745 | 1-744 and 746-8376 |
| 746 | 1-745 and 747-8376 |
| 747 | 1-746 and 748-8376 |
| 748 | 1-747 and 749-8376 |
| 749 | 1-748 and 750-8376 |
| 750 | 1-749 and 751-8376 |
| 751 | 1-750 and 752-8376 |

| First | Second |
|---|---|
| 752 | 1-751 and 753-8376 |
| 753 | 1-752 and 754-8376 |
| 754 | 1-753 and 755-8376 |
| 755 | 1-754 and 756-8376 |
| 756 | 1-755 and 757-8376 |
| 757 | 1-756 and 758-8376 |
| 758 | 1-757 and 759-8376 |
| 759 | 1-758 and 760-8376 |
| 760 | 1-759 and 761-8376 |
| 761 | 1-760 and 762-8376 |
| 762 | 1-761 and 763-8376 |
| 763 | 1-762 and 764-8376 |
| 764 | 1-763 and 765-8376 |
| 765 | 1-764 and 766-8376 |
| 766 | 1-765 and 767-8376 |
| 767 | 1-766 and 768-8376 |
| 768 | 1-767 and 769-8376 |
| 769 | 1-768 and 770-8376 |
| 770 | 1-769 and 771-8376 |
| 771 | 1-770 and 772-8376 |
| 772 | 1-771 and 773-8376 |
| 773 | 1-772 and 774-8376 |
| 774 | 1-773 and 775-8376 |
| 775 | 1-774 and 776-8376 |
| 776 | 1-775 and 777-8376 |
| 777 | 1-776 and 778-8376 |
| 778 | 1-777 and 779-8376 |
| 779 | 1-778 and 780-8376 |
| 780 | 1-779 and 781-8376 |
| 781 | 1-780 and 782-8376 |
| 782 | 1-781 and 783-8376 |
| 783 | 1-782 and 784-8376 |
| 784 | 1-783 and 785-8376 |
| 785 | 1-784 and 786-8376 |
| 786 | 1-785 and 787-8376 |
| 787 | 1-786 and 788-8376 |
| 788 | 1-787 and 789-8376 |
| 789 | 1-788 and 790-8376 |
| 790 | 1-789 and 791-8376 |
| 791 | 1-790 and 792-8376 |
| 792 | 1-791 and 793-8376 |
| 793 | 1-792 and 794-8376 |
| 794 | 1-793 and 795-8376 |
| 795 | 1-794 and 796-8376 |
| 796 | 1-795 and 797-8376 |
| 797 | 1-796 and 798-8376 |
| 798 | 1-797 and 799-8376 |
| 799 | 1-798 and 800-8376 |
| 800 | 1-799 and 801-8376 |
| 801 | 1-800 and 802-8376 |
| 802 | 1-801 and 803-8376 |
| 803 | 1-802 and 804-8376 |
| 804 | 1-803 and 805-8376 |
| 805 | 1-804 and 806-8376 |
| 806 | 1-805 and 807-8376 |
| 807 | 1-806 and 808-8376 |
| 808 | 1-807 and 809-8376 |
| 809 | 1-808 and 810-8376 |
| 810 | 1-809 and 811-8376 |
| 811 | 1-810 and 812-8376 |
| 812 | 1-811 and 813-8376 |
| 813 | 1-812 and 814-8376 |
| 814 | 1-813 and 815-8376 |
| 815 | 1-814 and 816-8376 |
| 816 | 1-815 and 817-8376 |
| 817 | 1-816 and 818-8376 |
| 818 | 1-817 and 819-8376 |
| 819 | 1-818 and 820-8376 |
| 820 | 1-819 and 821-8376 |
| 821 | 1-820 and 822-8376 |
| 822 | 1-821 and 823-8376 |
| 823 | 1-822 and 824-8376 |
| 824 | 1-823 and 825-8376 |
| 825 | 1-824 and 826-8376 |
| 826 | 1-825 and 827-8376 |
| 827 | 1-826 and 828-8376 |
| 828 | 1-827 and 829-8376 |
| 829 | 1-828 and 830-8376 |
| 830 | 1-829 and 831-8376 |
| 831 | 1-830 and 832-8376 |
| 832 | 1-831 and 833-8376 |
| 833 | 1-832 and 834-8376 |
| 834 | 1-833 and 835-8376 |
| 835 | 1-834 and 836-8376 |
| 836 | 1-835 and 837-8376 |
| 837 | 1-836 and 838-8376 |
| 838 | 1-837 and 839-8376 |
| 839 | 1-838 and 840-8376 |
| 840 | 1-839 and 841-8376 |
| 841 | 1-840 and 842-8376 |
| 842 | 1-841 and 843-8376 |
| 843 | 1-842 and 844-8376 |
| 844 | 1-843 and 845-8376 |
| 845 | 1-844 and 846-8376 |
| 846 | 1-845 and 847-8376 |
| 847 | 1-846 and 848-8376 |
| 848 | 1-847 and 849-8376 |
| 849 | 1-848 and 850-8376 |
| 850 | 1-849 and 851-8376 |
| 851 | 1-850 and 852-8376 |
| 852 | 1-851 and 853-8376 |
| 853 | 1-852 and 854-8376 |
| 854 | 1-853 and 855-8376 |
| 855 | 1-854 and 856-8376 |
| 856 | 1-855 and 857-8376 |
| 857 | 1-856 and 858-8376 |
| 858 | 1-857 and 859-8376 |
| 859 | 1-858 and 860-8376 |
| 860 | 1-859 and 861-8376 |
| 861 | 1-860 and 862-8376 |
| 862 | 1-861 and 863-8376 |
| 863 | 1-862 and 864-8376 |
| 864 | 1-863 and 865-8376 |
| 865 | 1-864 and 866-8376 |
| 866 | 1-865 and 867-8376 |
| 867 | 1-866 and 868-8376 |
| 868 | 1-867 and 869-8376 |
| 869 | 1-868 and 870-8376 |
| 870 | 1-869 and 871-8376 |
| 871 | 1-870 and 872-8376 |
| 872 | 1-871 and 873-8376 |
| 873 | 1-872 and 874-8376 |
| 874 | 1-873 and 875-8376 |
| 875 | 1-874 and 876-8376 |
| 876 | 1-875 and 877-8376 |
| 877 | 1-876 and 878-8376 |
| 878 | 1-877 and 879-8376 |
| 879 | 1-878 and 880-8376 |
| 880 | 1-879 and 881-8376 |
| 881 | 1-880 and 882-8376 |
| 882 | 1-881 and 883-8376 |
| 883 | 1-882 and 884-8376 |
| 884 | 1-883 and 885-8376 |
| 885 | 1-884 and 886-8376 |
| 886 | 1-885 and 887-8376 |
| 887 | 1-886 and 888-8376 |
| 888 | 1-887 and 889-8376 |
| 889 | 1-888 and 890-8376 |
| 890 | 1-889 and 891-8376 |
| 891 | 1-890 and 892-8376 |
| 892 | 1-891 and 893-8376 |
| 893 | 1-892 and 894-8376 |
| 894 | 1-893 and 895-8376 |
| 895 | 1-894 and 896-8376 |
| 896 | 1-895 and 897-8376 |
| 897 | 1-896 and 898-8376 |
| 898 | 1-897 and 899-8376 |
| 899 | 1-898 and 900-8376 |
| 900 | 1-899 and 901-8376 |
| 901 | 1-900 and 902-8376 |
| 902 | 1-901 and 903-8376 |
| 903 | 1-902 and 904-8376 |
| 904 | 1-903 and 905-8376 |
| 905 | 1-904 and 906-8376 |

| First | Second |
|---|---|
| 906 | 1-905 and 907-8376 |
| 907 | 1-906 and 908-8376 |
| 908 | 1-907 and 909-8376 |
| 909 | 1-908 and 910-8376 |
| 910 | 1-909 and 911-8376 |
| 911 | 1-910 and 912-8376 |
| 912 | 1-911 and 913-8376 |
| 913 | 1-912 and 914-8376 |
| 914 | 1-913 and 915-8376 |
| 915 | 1-914 and 916-8376 |
| 916 | 1-915 and 917-8376 |
| 917 | 1-916 and 918-8376 |
| 918 | 1-917 and 919-8376 |
| 919 | 1-918 and 920-8376 |
| 920 | 1-919 and 921-8376 |
| 921 | 1-920 and 922-8376 |
| 922 | 1-921 and 923-8376 |
| 923 | 1-922 and 924-8376 |
| 924 | 1-923 and 925-8376 |
| 925 | 1-924 and 926-8376 |
| 926 | 1-925 and 927-8376 |
| 927 | 1-926 and 928-8376 |
| 928 | 1-927 and 929-8376 |
| 929 | 1-928 and 930-8376 |
| 930 | 1-929 and 931-8376 |
| 931 | 1-930 and 932-8376 |
| 932 | 1-931 and 933-8376 |
| 933 | 1-932 and 934-8376 |
| 934 | 1-933 and 935-8376 |
| 935 | 1-934 and 936-8376 |
| 936 | 1-935 and 937-8376 |
| 937 | 1-936 and 938-8376 |
| 938 | 1-937 and 939-8376 |
| 939 | 1-938 and 940-8376 |
| 940 | 1-939 and 941-8376 |
| 941 | 1-940 and 942-8376 |
| 942 | 1-941 and 943-8376 |
| 943 | 1-942 and 944-8376 |
| 944 | 1-943 and 945-8376 |
| 945 | 1-944 and 946-8376 |
| 946 | 1-945 and 947-8376 |
| 947 | 1-946 and 948-8376 |
| 948 | 1-947 and 949-8376 |
| 949 | 1-948 and 950-8376 |
| 950 | 1-949 and 951-8376 |
| 951 | 1-950 and 952-8376 |
| 952 | 1-951 and 953-8376 |
| 953 | 1-952 and 954-8376 |
| 954 | 1-953 and 955-8376 |
| 955 | 1-954 and 956-8376 |
| 956 | 1-955 and 957-8376 |
| 957 | 1-956 and 958-8376 |
| 958 | 1-957 and 959-8376 |
| 959 | 1-958 and 960-8376 |
| 960 | 1-959 and 961-8376 |
| 961 | 1-960 and 962-8376 |
| 962 | 1-961 and 963-8376 |
| 963 | 1-962 and 964-8376 |
| 964 | 1-963 and 965-8376 |
| 965 | 1-964 and 966-8376 |
| 966 | 1-965 and 967-8376 |
| 967 | 1-966 and 968-8376 |
| 968 | 1-967 and 969-8376 |
| 969 | 1-968 and 970-8376 |
| 970 | 1-969 and 971-8376 |
| 971 | 1-970 and 972-8376 |
| 972 | 1-971 and 973-8376 |
| 973 | 1-972 and 974-8376 |
| 974 | 1-973 and 975-8376 |
| 975 | 1-974 and 976-8376 |
| 976 | 1-975 and 977-8376 |
| 977 | 1-976 and 978-8376 |
| 978 | 1-977 and 979-8376 |
| 979 | 1-978 and 980-8376 |
| 980 | 1-979 and 981-8376 |
| 981 | 1-980 and 982-8376 |
| 982 | 1-981 and 983-8376 |
| 983 | 1-982 and 984-8376 |
| 984 | 1-983 and 985-8376 |
| 985 | 1-984 and 986-8376 |
| 986 | 1-985 and 987-8376 |
| 987 | 1-986 and 988-8376 |
| 988 | 1-987 and 989-8376 |
| 989 | 1-988 and 990-8376 |
| 990 | 1-989 and 991-8376 |
| 991 | 1-990 and 992-8376 |
| 992 | 1-991 and 993-8376 |
| 993 | 1-992 and 994-8376 |
| 994 | 1-993 and 995-8376 |
| 995 | 1-994 and 996-8376 |
| 996 | 1-995 and 997-8376 |
| 997 | 1-996 and 998-8376 |
| 998 | 1-997 and 999-8376 |
| 999 | 1-998 and 1000-8376 |
| 1000 | 1-999 and 1001-8376 |
| 1001 | 1-1000 and 1002-8376 |
| 1002 | 1-1001 and 1003-8376 |
| 1003 | 1-1002 and 1004-8376 |
| 1004 | 1-1003 and 1005-8376 |
| 1005 | 1-1004 and 1006-8376 |
| 1006 | 1-1005 and 1007-8376 |
| 1007 | 1-1006 and 1008-8376 |
| 1008 | 1-1007 and 1009-8376 |
| 1009 | 1-1008 and 1010-8376 |
| 1010 | 1-1009 and 1011-8376 |
| 1011 | 1-1010 and 1012-8376 |
| 1012 | 1-1011 and 1013-8376 |
| 1013 | 1-1012 and 1014-8376 |
| 1014 | 1-1013 and 1015-8376 |
| 1015 | 1-1014 and 1016-8376 |
| 1016 | 1-1015 and 1017-8376 |
| 1017 | 1-1016 and 1018-8376 |
| 1018 | 1-1017 and 1019-8376 |
| 1019 | 1-1018 and 1020-8376 |
| 1020 | 1-1019 and 1021-8376 |
| 1021 | 1-1020 and 1022-8376 |
| 1022 | 1-1021 and 1023-8376 |
| 1023 | 1-1022 and 1024-8376 |
| 1024 | 1-1023 and 1025-8376 |
| 1025 | 1-1024 and 1026-8376 |
| 1026 | 1-1025 and 1027-8376 |
| 1027 | 1-1026 and 1028-8376 |
| 1028 | 1-1027 and 1029-8376 |
| 1029 | 1-1028 and 1030-8376 |
| 1030 | 1-1029 and 1031-8376 |
| 1031 | 1-1030 and 1032-8376 |
| 1032 | 1-1031 and 1033-8376 |
| 1033 | 1-1032 and 1034-8376 |
| 1034 | 1-1033 and 1035-8376 |
| 1035 | 1-1034 and 1036-8376 |
| 1036 | 1-1035 and 1037-8376 |
| 1037 | 1-1036 and 1038-8376 |
| 1038 | 1-1037 and 1039-8376 |
| 1039 | 1-1038 and 1040-8376 |
| 1040 | 1-1039 and 1041-8376 |
| 1041 | 1-1040 and 1042-8376 |
| 1042 | 1-1041 and 1043-8376 |
| 1043 | 1-1042 and 1044-8376 |
| 1044 | 1-1043 and 1045-8376 |
| 1045 | 1-1044 and 1046-8376 |
| 1046 | 1-1045 and 1047-8376 |
| 1047 | 1-1046 and 1048-8376 |
| 1048 | 1-1047 and 1049-8376 |
| 1049 | 1-1048 and 1050-8376 |
| 1050 | 1-1049 and 1051-8376 |
| 1051 | 1-1050 and 1052-8376 |
| 1052 | 1-1051 and 1053-8376 |
| 1053 | 1-1052 and 1054-8376 |
| 1054 | 1-1053 and 1055-8376 |
| 1055 | 1-1054 and 1056-8376 |
| 1056 | 1-1055 and 1057-8376 |
| 1057 | 1-1056 and 1058-8376 |
| 1058 | 1-1057 and 1059-8376 |
| 1059 | 1-1058 and 1060-8376 |

| First | Second |
|---|---|
| 1060 | 1-1059 and 1061-8376 |
| 1061 | 1-1060 and 1062-8376 |
| 1062 | 1-1061 and 1063-8376 |
| 1063 | 1-1062 and 1064-8376 |
| 1064 | 1-1063 and 1065-8376 |
| 1065 | 1-1064 and 1066-8376 |
| 1066 | 1-1065 and 1067-8376 |
| 1067 | 1-1066 and 1068-8376 |
| 1068 | 1-1067 and 1069-8376 |
| 1069 | 1-1068 and 1070-8376 |
| 1070 | 1-1069 and 1071-8376 |
| 1071 | 1-1070 and 1072-8376 |
| 1072 | 1-1071 and 1073-8376 |
| 1073 | 1-1072 and 1074-8376 |
| 1074 | 1-1073 and 1075-8376 |
| 1075 | 1-1074 and 1076-8376 |
| 1076 | 1-1075 and 1077-8376 |
| 1077 | 1-1076 and 1078-8376 |
| 1078 | 1-1077 and 1079-8376 |
| 1079 | 1-1078 and 1080-8376 |
| 1080 | 1-1079 and 1081-8376 |
| 1081 | 1-1080 and 1082-8376 |
| 1082 | 1-1081 and 1083-8376 |
| 1083 | 1-1082 and 1084-8376 |
| 1084 | 1-1083 and 1085-8376 |
| 1085 | 1-1084 and 1086-8376 |
| 1086 | 1-1085 and 1087-8376 |
| 1087 | 1-1086 and 1088-8376 |
| 1088 | 1-1087 and 1089-8376 |
| 1089 | 1-1088 and 1090-8376 |
| 1090 | 1-1089 and 1091-8376 |
| 1091 | 1-1090 and 1092-8376 |
| 1092 | 1-1091 and 1093-8376 |
| 1093 | 1-1092 and 1094-8376 |
| 1094 | 1-1093 and 1095-8376 |
| 1095 | 1-1094 and 1096-8376 |
| 1096 | 1-1095 and 1097-8376 |
| 1097 | 1-1096 and 1098-8376 |
| 1098 | 1-1097 and 1099-8376 |
| 1099 | 1-1098 and 1100-8376 |
| 1100 | 1-1099 and 1101-8376 |
| 1101 | 1-1100 and 1102-8376 |
| 1102 | 1-1101 and 1103-8376 |
| 1103 | 1-1102 and 1104-8376 |
| 1104 | 1-1103 and 1105-8376 |
| 1105 | 1-1104 and 1106-8376 |
| 1106 | 1-1105 and 1107-8376 |
| 1107 | 1-1106 and 1108-8376 |
| 1108 | 1-1107 and 1109-8376 |
| 1109 | 1-1108 and 1110-8376 |
| 1110 | 1-1109 and 1111-8376 |
| 1111 | 1-1110 and 1112-8376 |
| 1112 | 1-1111 and 1113-8376 |
| 1113 | 1-1112 and 1114-8376 |
| 1114 | 1-1113 and 1115-8376 |
| 1115 | 1-1114 and 1116-8376 |
| 1116 | 1-1115 and 1117-8376 |
| 1117 | 1-1116 and 1118-8376 |
| 1118 | 1-1117 and 1119-8376 |
| 1119 | 1-1118 and 1120-8376 |
| 1120 | 1-1119 and 1121-8376 |
| 1121 | 1-1120 and 1122-8376 |
| 1122 | 1-1121 and 1123-8376 |
| 1123 | 1-1122 and 1124-8376 |
| 1124 | 1-1123 and 1125-8376 |
| 1125 | 1-1124 and 1126-8376 |
| 1126 | 1-1125 and 1127-8376 |
| 1127 | 1-1126 and 1128-8376 |
| 1128 | 1-1127 and 1129-8376 |
| 1129 | 1-1128 and 1130-8376 |
| 1130 | 1-1129 and 1131-8376 |
| 1131 | 1-1130 and 1132-8376 |
| 1132 | 1-1131 and 1133-8376 |
| 1133 | 1-1132 and 1134-8376 |
| 1134 | 1-1133 and 1135-8376 |
| 1135 | 1-1134 and 1136-8376 |
| 1136 | 1-1135 and 1137-8376 |
| 1137 | 1-1136 and 1138-8376 |
| 1138 | 1-1137 and 1139-8376 |
| 1139 | 1-1138 and 1140-8376 |
| 1140 | 1-1139 and 1141-8376 |
| 1141 | 1-1140 and 1142-8376 |
| 1142 | 1-1141 and 1143-8376 |
| 1143 | 1-1142 and 1144-8376 |
| 1144 | 1-1143 and 1145-8376 |
| 1145 | 1-1144 and 1146-8376 |
| 1146 | 1-1145 and 1147-8376 |
| 1147 | 1-1146 and 1148-8376 |
| 1148 | 1-1147 and 1149-8376 |
| 1149 | 1-1148 and 1150-8376 |
| 1150 | 1-1149 and 1151-8376 |
| 1151 | 1-1150 and 1152-8376 |
| 1152 | 1-1151 and 1153-8376 |
| 1153 | 1-1152 and 1154-8376 |
| 1154 | 1-1153 and 1155-8376 |
| 1155 | 1-1154 and 1156-8376 |
| 1156 | 1-1155 and 1157-8376 |
| 1157 | 1-1156 and 1158-8376 |
| 1158 | 1-1157 and 1159-8376 |
| 1159 | 1-1158 and 1160-8376 |
| 1160 | 1-1159 and 1161-8376 |
| 1161 | 1-1160 and 1162-8376 |
| 1162 | 1-1161 and 1163-8376 |
| 1163 | 1-1162 and 1164-8376 |
| 1164 | 1-1163 and 1165-8376 |
| 1165 | 1-1164 and 1166-8376 |
| 1166 | 1-1165 and 1167-8376 |
| 1167 | 1-1166 and 1168-8376 |
| 1168 | 1-1167 and 1169-8376 |
| 1169 | 1-1168 and 1170-8376 |
| 1170 | 1-1169 and 1171-8376 |
| 1171 | 1-1170 and 1172-8376 |
| 1172 | 1-1171 and 1173-8376 |
| 1173 | 1-1172 and 1174-8376 |
| 1174 | 1-1173 and 1175-8376 |
| 1175 | 1-1174 and 1176-8376 |
| 1176 | 1-1175 and 1177-8376 |
| 1177 | 1-1176 and 1178-8376 |
| 1178 | 1-1177 and 1179-8376 |
| 1179 | 1-1178 and 1180-8376 |
| 1180 | 1-1179 and 1181-8376 |
| 1181 | 1-1180 and 1182-8376 |
| 1182 | 1-1181 and 1183-8376 |
| 1183 | 1-1182 and 1184-8376 |
| 1184 | 1-1183 and 1185-8376 |
| 1185 | 1-1184 and 1186-8376 |
| 1186 | 1-1185 and 1187-8376 |
| 1187 | 1-1186 and 1188-8376 |
| 1188 | 1-1187 and 1189-8376 |
| 1189 | 1-1188 and 1190-8376 |
| 1190 | 1-1189 and 1191-8376 |
| 1191 | 1-1190 and 1192-8376 |
| 1192 | 1-1191 and 1193-8376 |
| 1193 | 1-1192 and 1194-8376 |
| 1194 | 1-1193 and 1195-8376 |
| 1195 | 1-1194 and 1196-8376 |
| 1196 | 1-1195 and 1197-8376 |
| 1197 | 1-1196 and 1198-8376 |
| 1198 | 1-1197 and 1199-8376 |
| 1199 | 1-1198 and 1200-8376 |
| 1200 | 1-1199 and 1201-8376 |
| 1201 | 1-1200 and 1202-8376 |
| 1202 | 1-1201 and 1203-8376 |
| 1203 | 1-1202 and 1204-8376 |
| 1204 | 1-1203 and 1205-8376 |
| 1205 | 1-1204 and 1206-8376 |
| 1206 | 1-1205 and 1207-8376 |
| 1207 | 1-1206 and 1208-8376 |
| 1208 | 1-1207 and 1209-8376 |
| 1209 | 1-1208 and 1210-8376 |
| 1210 | 1-1209 and 1211-8376 |
| 1211 | 1-1210 and 1212-8376 |
| 1212 | 1-1211 and 1213-8376 |
| 1213 | 1-1212 and 1214-8376 |

-continued

| First | Second |
|---|---|
| 1214 | 1-1213 and 1215-8376 |
| 1215 | 1-1214 and 1216-8376 |
| 1216 | 1-1215 and 1217-8376 |
| 1217 | 1-1216 and 1218-8376 |
| 1218 | 1-1217 and 1219-8376 |
| 1219 | 1-1218 and 1220-8376 |
| 1220 | 1-1219 and 1221-8376 |
| 1221 | 1-1220 and 1222-8376 |
| 1222 | 1-1221 and 1223-8376 |
| 1223 | 1-1222 and 1224-8376 |
| 1224 | 1-1223 and 1225-8376 |
| 1225 | 1-1224 and 1226-8376 |
| 1226 | 1-1225 and 1227-8376 |
| 1227 | 1-1226 and 1228-8376 |
| 1228 | 1-1227 and 1229-8376 |
| 1229 | 1-1228 and 1230-8376 |
| 1230 | 1-1229 and 1231-8376 |
| 1231 | 1-1230 and 1232-8376 |
| 1232 | 1-1231 and 1233-8376 |
| 1233 | 1-1232 and 1234-8376 |
| 1234 | 1-1233 and 1235-8376 |
| 1235 | 1-1234 and 1236-8376 |
| 1236 | 1-1235 and 1237-8376 |
| 1237 | 1-1236 and 1238-8376 |
| 1238 | 1-1237 and 1239-8376 |
| 1239 | 1-1238 and 1240-8376 |
| 1240 | 1-1239 and 1241-8376 |
| 1241 | 1-1240 and 1242-8376 |
| 1242 | 1-1241 and 1243-8376 |
| 1243 | 1-1242 and 1244-8376 |
| 1244 | 1-1243 and 1245-8376 |
| 1245 | 1-1244 and 1246-8376 |
| 1246 | 1-1245 and 1247-8376 |
| 1247 | 1-1246 and 1248-8376 |
| 1248 | 1-1247 and 1249-8376 |
| 1249 | 1-1248 and 1250-8376 |
| 1250 | 1-1249 and 1251-8376 |
| 1251 | 1-1250 and 1252-8376 |
| 1252 | 1-1251 and 1253-8376 |
| 1253 | 1-1252 and 1254-8376 |
| 1254 | 1-1253 and 1255-8376 |
| 1255 | 1-1254 and 1256-8376 |
| 1256 | 1-1255 and 1257-8376 |
| 1257 | 1-1256 and 1258-8376 |
| 1258 | 1-1257 and 1259-8376 |
| 1259 | 1-1258 and 1260-8376 |
| 1260 | 1-1259 and 1261-8376 |
| 1261 | 1-1260 and 1262-8376 |
| 1262 | 1-1261 and 1263-8376 |
| 1263 | 1-1262 and 1264-8376 |
| 1264 | 1-1263 and 1265-8376 |
| 1265 | 1-1264 and 1266-8376 |
| 1266 | 1-1265 and 1267-8376 |
| 1267 | 1-1266 and 1268-8376 |
| 1268 | 1-1267 and 1269-8376 |
| 1269 | 1-1268 and 1270-8376 |
| 1270 | 1-1269 and 1271-8376 |
| 1271 | 1-1270 and 1272-8376 |
| 1272 | 1-1271 and 1273-8376 |
| 1273 | 1-1272 and 1274-8376 |
| 1274 | 1-1273 and 1275-8376 |
| 1275 | 1-1274 and 1276-8376 |
| 1276 | 1-1275 and 1277-8376 |
| 1277 | 1-1276 and 1278-8376 |
| 1278 | 1-1277 and 1279-8376 |
| 1279 | 1-1278 and 1280-8376 |
| 1280 | 1-1279 and 1281-8376 |
| 1281 | 1-1280 and 1282-8376 |
| 1282 | 1-1281 and 1283-8376 |
| 1283 | 1-1282 and 1284-8376 |
| 1284 | 1-1283 and 1285-8376 |
| 1285 | 1-1284 and 1286-8376 |
| 1286 | 1-1285 and 1287-8376 |
| 1287 | 1-1286 and 1288-8376 |
| 1288 | 1-1287 and 1289-8376 |
| 1289 | 1-1288 and 1290-8376 |
| 1290 | 1-1289 and 1291-8376 |

-continued

| First | Second |
|---|---|
| 1291 | 1-1290 and 1292-8376 |
| 1292 | 1-1291 and 1293-8376 |
| 1293 | 1-1292 and 1294-8376 |
| 1294 | 1-1293 and 1295-8376 |
| 1295 | 1-1294 and 1296-8376 |
| 1296 | 1-1295 and 1297-8376 |
| 1297 | 1-1296 and 1298-8376 |
| 1298 | 1-1297 and 1299-8376 |
| 1299 | 1-1298 and 1300-8376 |
| 1300 | 1-1299 and 1301-8376 |
| 1301 | 1-1300 and 1302-8376 |
| 1302 | 1-1301 and 1303-8376 |
| 1303 | 1-1302 and 1304-8376 |
| 1304 | 1-1303 and 1305-8376 |
| 1305 | 1-1304 and 1306-8376 |
| 1306 | 1-1305 and 1307-8376 |
| 1307 | 1-1306 and 1308-8376 |
| 1308 | 1-1307 and 1309-8376 |
| 1309 | 1-1308 and 1310-8376 |
| 1310 | 1-1309 and 1311-8376 |
| 1311 | 1-1310 and 1312-8376 |
| 1312 | 1-1311 and 1313-8376 |
| 1313 | 1-1312 and 1314-8376 |
| 1314 | 1-1313 and 1315-8376 |
| 1315 | 1-1314 and 1316-8376 |
| 1316 | 1-1315 and 1317-8376 |
| 1317 | 1-1316 and 1318-8376 |
| 1318 | 1-1317 and 1319-8376 |
| 1319 | 1-1318 and 1320-8376 |
| 1320 | 1-1319 and 1321-8376 |
| 1321 | 1-1320 and 1322-8376 |
| 1322 | 1-1321 and 1323-8376 |
| 1323 | 1-1322 and 1324-8376 |
| 1324 | 1-1323 and 1325-8376 |
| 1325 | 1-1324 and 1326-8376 |
| 1326 | 1-1325 and 1327-8376 |
| 1327 | 1-1326 and 1328-8376 |
| 1328 | 1-1327 and 1329-8376 |
| 1329 | 1-1328 and 1330-8376 |
| 1330 | 1-1329 and 1331-8376 |
| 1331 | 1-1330 and 1332-8376 |
| 1332 | 1-1331 and 1333-8376 |
| 1333 | 1-1332 and 1334-8376 |
| 1334 | 1-1333 and 1335-8376 |
| 1335 | 1-1334 and 1336-8376 |
| 1336 | 1-1335 and 1337-8376 |
| 1337 | 1-1336 and 1338-8376 |
| 1338 | 1-1337 and 1339-8376 |
| 1339 | 1-1338 and 1340-8376 |
| 1340 | 1-1339 and 1341-8376 |
| 1341 | 1-1340 and 1342-8376 |
| 1342 | 1-1341 and 1343-8376 |
| 1343 | 1-1342 and 1344-8376 |
| 1344 | 1-1343 and 1345-8376 |
| 1345 | 1-1344 and 1346-8376 |
| 1346 | 1-1345 and 1347-8376 |
| 1347 | 1-1346 and 1348-8376 |
| 1348 | 1-1347 and 1349-8376 |
| 1349 | 1-1348 and 1350-8376 |
| 1350 | 1-1349 and 1351-8376 |
| 1351 | 1-1350 and 1352-8376 |
| 1352 | 1-1351 and 1353-8376 |
| 1353 | 1-1352 and 1354-8376 |
| 1354 | 1-1353 and 1355-8376 |
| 1355 | 1-1354 and 1356-8376 |
| 1356 | 1-1355 and 1357-8376 |
| 1357 | 1-1356 and 1358-8376 |
| 1358 | 1-1357 and 1359-8376 |
| 1359 | 1-1358 and 1360-8376 |
| 1360 | 1-1359 and 1361-8376 |
| 1361 | 1-1360 and 1362-8376 |
| 1362 | 1-1361 and 1363-8376 |
| 1363 | 1-1362 and 1364-8376 |
| 1364 | 1-1363 and 1365-8376 |
| 1365 | 1-1364 and 1366-8376 |
| 1366 | 1-1365 and 1367-8376 |
| 1367 | 1-1366 and 1368-8376 |

| First | Second |
|---|---|
| 1368 | 1-1367 and 1369-8376 |
| 1369 | 1-1368 and 1370-8376 |
| 1370 | 1-1369 and 1371-8376 |
| 1371 | 1-1370 and 1372-8376 |
| 1372 | 1-1371 and 1373-8376 |
| 1373 | 1-1372 and 1374-8376 |
| 1374 | 1-1373 and 1375-8376 |
| 1375 | 1-1374 and 1376-8376 |
| 1376 | 1-1375 and 1377-8376 |
| 1377 | 1-1376 and 1378-8376 |
| 1378 | 1-1377 and 1379-8376 |
| 1379 | 1-1378 and 1380-8376 |
| 1380 | 1-1379 and 1381-8376 |
| 1381 | 1-1380 and 1382-8376 |
| 1382 | 1-1381 and 1383-8376 |
| 1383 | 1-1382 and 1384-8376 |
| 1384 | 1-1383 and 1385-8376 |
| 1385 | 1-1384 and 1386-8376 |
| 1386 | 1-1385 and 1387-8376 |
| 1387 | 1-1386 and 1388-8376 |
| 1388 | 1-1387 and 1389-8376 |
| 1389 | 1-1388 and 1390-8376 |
| 1390 | 1-1389 and 1391-8376 |
| 1391 | 1-1390 and 1392-8376 |
| 1392 | 1-1391 and 1393-8376 |
| 1393 | 1-1392 and 1394-8376 |
| 1394 | 1-1393 and 1395-8376 |
| 1395 | 1-1394 and 1396-8376 |
| 1396 | 1-1395 and 1397-8376 |
| 1397 | 1-1396 and 1398-8376 |
| 1398 | 1-1397 and 1399-8376 |
| 1399 | 1-1398 and 1400-8376 |
| 1400 | 1-1399 and 1401-8376 |
| 1401 | 1-1400 and 1402-8376 |
| 1402 | 1-1401 and 1403-8376 |
| 1403 | 1-1402 and 1404-8376 |
| 1404 | 1-1403 and 1405-8376 |
| 1405 | 1-1404 and 1406-8376 |
| 1406 | 1-1405 and 1407-8376 |
| 1407 | 1-1406 and 1408-8376 |
| 1408 | 1-1407 and 1409-8376 |
| 1409 | 1-1408 and 1410-8376 |
| 1410 | 1-1409 and 1411-8376 |
| 1411 | 1-1410 and 1412-8376 |
| 1412 | 1-1411 and 1413-8376 |
| 1413 | 1-1412 and 1414-8376 |
| 1414 | 1-1413 and 1415-8376 |
| 1415 | 1-1414 and 1416-8376 |
| 1416 | 1-1415 and 1417-8376 |
| 1417 | 1-1416 and 1418-8376 |
| 1418 | 1-1417 and 1419-8376 |
| 1419 | 1-1418 and 1420-8376 |
| 1420 | 1-1419 and 1421-8376 |
| 1421 | 1-1420 and 1422-8376 |
| 1422 | 1-1421 and 1423-8376 |
| 1423 | 1-1422 and 1424-8376 |
| 1424 | 1-1423 and 1425-8376 |
| 1425 | 1-1424 and 1426-8376 |
| 1426 | 1-1425 and 1427-8376 |
| 1427 | 1-1426 and 1428-8376 |
| 1428 | 1-1427 and 1429-8376 |
| 1429 | 1-1428 and 1430-8376 |
| 1430 | 1-1429 and 1431-8376 |
| 1431 | 1-1430 and 1432-8376 |
| 1432 | 1-1431 and 1433-8376 |
| 1433 | 1-1432 and 1434-8376 |
| 1434 | 1-1433 and 1435-8376 |
| 1435 | 1-1434 and 1436-8376 |
| 1436 | 1-1435 and 1437-8376 |
| 1437 | 1-1436 and 1438-8376 |
| 1438 | 1-1437 and 1439-8376 |
| 1439 | 1-1438 and 1440-8376 |
| 1440 | 1-1439 and 1441-8376 |
| 1441 | 1-1440 and 1442-8376 |
| 1442 | 1-1441 and 1443-8376 |
| 1443 | 1-1442 and 1444-8376 |
| 1444 | 1-1443 and 1445-8376 |
| 1445 | 1-1444 and 1446-8376 |
| 1446 | 1-1445 and 1447-8376 |
| 1447 | 1-1446 and 1448-8376 |
| 1448 | 1-1447 and 1449-8376 |
| 1449 | 1-1448 and 1450-8376 |
| 1450 | 1-1449 and 1451-8376 |
| 1451 | 1-1450 and 1452-8376 |
| 1452 | 1-1451 and 1453-8376 |
| 1453 | 1-1452 and 1454-8376 |
| 1454 | 1-1453 and 1455-8376 |
| 1455 | 1-1454 and 1456-8376 |
| 1456 | 1-1455 and 1457-8376 |
| 1457 | 1-1456 and 1458-8376 |
| 1458 | 1-1457 and 1459-8376 |
| 1459 | 1-1458 and 1460-8376 |
| 1460 | 1-1459 and 1461-8376 |
| 1461 | 1-1460 and 1462-8376 |
| 1462 | 1-1461 and 1463-8376 |
| 1463 | 1-1462 and 1464-8376 |
| 1464 | 1-1463 and 1465-8376 |
| 1465 | 1-1464 and 1466-8376 |
| 1466 | 1-1465 and 1467-8376 |
| 1467 | 1-1466 and 1468-8376 |
| 1468 | 1-1467 and 1469-8376 |
| 1469 | 1-1468 and 1470-8376 |
| 1470 | 1-1469 and 1471-8376 |
| 1471 | 1-1470 and 1472-8376 |
| 1472 | 1-1471 and 1473-8376 |
| 1473 | 1-1472 and 1474-8376 |
| 1474 | 1-1473 and 1475-8376 |
| 1475 | 1-1474 and 1476-8376 |
| 1476 | 1-1475 and 1477-8376 |
| 1477 | 1-1476 and 1478-8376 |
| 1478 | 1-1477 and 1479-8376 |
| 1479 | 1-1478 and 1480-8376 |
| 1480 | 1-1479 and 1481-8376 |
| 1481 | 1-1480 and 1482-8376 |
| 1482 | 1-1481 and 1483-8376 |
| 1483 | 1-1482 and 1484-8376 |
| 1484 | 1-1483 and 1485-8376 |
| 1485 | 1-1484 and 1486-8376 |
| 1486 | 1-1485 and 1487-8376 |
| 1487 | 1-1486 and 1488-8376 |
| 1488 | 1-1487 and 1489-8376 |
| 1489 | 1-1488 and 1490-8376 |
| 1490 | 1-1489 and 1491-8376 |
| 1491 | 1-1490 and 1492-8376 |
| 1492 | 1-1491 and 1493-8376 |
| 1493 | 1-1492 and 1494-8376 |
| 1494 | 1-1493 and 1495-8376 |
| 1495 | 1-1494 and 1496-8376 |
| 1496 | 1-1495 and 1497-8376 |
| 1497 | 1-1496 and 1498-8376 |
| 1498 | 1-1497 and 1499-8376 |
| 1499 | 1-1498 and 1500-8376 |
| 1500 | 1-1499 and 1501-8376 |
| 1501 | 1-1500 and 1502-8376 |
| 1502 | 1-1501 and 1503-8376 |
| 1503 | 1-1502 and 1504-8376 |
| 1504 | 1-1503 and 1505-8376 |
| 1505 | 1-1504 and 1506-8376 |
| 1506 | 1-1505 and 1507-8376 |
| 1507 | 1-1506 and 1508-8376 |
| 1508 | 1-1507 and 1509-8376 |
| 1509 | 1-1508 and 1510-8376 |
| 1510 | 1-1509 and 1511-8376 |
| 1511 | 1-1510 and 1512-8376 |
| 1512 | 1-1511 and 1513-8376 |
| 1513 | 1-1512 and 1514-8376 |
| 1514 | 1-1513 and 1515-8376 |
| 1515 | 1-1514 and 1516-8376 |
| 1516 | 1-1515 and 1517-8376 |
| 1517 | 1-1516 and 1518-8376 |
| 1518 | 1-1517 and 1519-8376 |
| 1519 | 1-1518 and 1520-8376 |
| 1520 | 1-1519 and 1521-8376 |
| 1521 | 1-1520 and 1522-8376 |

| First | Second |
|---|---|
| 1522 | 1-1521 and 1523-8376 |
| 1523 | 1-1522 and 1524-8376 |
| 1524 | 1-1523 and 1525-8376 |
| 1525 | 1-1524 and 1526-8376 |
| 1526 | 1-1525 and 1527-8376 |
| 1527 | 1-1526 and 1528-8376 |
| 1528 | 1-1527 and 1529-8376 |
| 1529 | 1-1528 and 1530-8376 |
| 1530 | 1-1529 and 1531-8376 |
| 1531 | 1-1530 and 1532-8376 |
| 1532 | 1-1531 and 1533-8376 |
| 1533 | 1-1532 and 1534-8376 |
| 1534 | 1-1533 and 1535-8376 |
| 1535 | 1-1534 and 1536-8376 |
| 1536 | 1-1535 and 1537-8376 |
| 1537 | 1-1536 and 1538-8376 |
| 1538 | 1-1537 and 1539-8376 |
| 1539 | 1-1538 and 1540-8376 |
| 1540 | 1-1539 and 1541-8376 |
| 1541 | 1-1540 and 1542-8376 |
| 1542 | 1-1541 and 1543-8376 |
| 1543 | 1-1542 and 1544-8376 |
| 1544 | 1-1543 and 1545-8376 |
| 1545 | 1-1544 and 1546-8376 |
| 1546 | 1-1545 and 1547-8376 |
| 1547 | 1-1546 and 1548-8376 |
| 1548 | 1-1547 and 1549-8376 |
| 1549 | 1-1548 and 1550-8376 |
| 1550 | 1-1549 and 1551-8376 |
| 1551 | 1-1550 and 1552-8376 |
| 1552 | 1-1551 and 1553-8376 |
| 1553 | 1-1552 and 1554-8376 |
| 1554 | 1-1553 and 1555-8376 |
| 1555 | 1-1554 and 1556-8376 |
| 1556 | 1-1555 and 1557-8376 |
| 1557 | 1-1556 and 1558-8376 |
| 1558 | 1-1557 and 1559-8376 |
| 1559 | 1-1558 and 1560-8376 |
| 1560 | 1-1559 and 1561-8376 |
| 1561 | 1-1560 and 1562-8376 |
| 1562 | 1-1561 and 1563-8376 |
| 1563 | 1-1562 and 1564-8376 |
| 1564 | 1-1563 and 1565-8376 |
| 1565 | 1-1564 and 1566-8376 |
| 1566 | 1-1565 and 1567-8376 |
| 1567 | 1-1566 and 1568-8376 |
| 1568 | 1-1567 and 1569-8376 |
| 1569 | 1-1568 and 1570-8376 |
| 1570 | 1-1569 and 1571-8376 |
| 1571 | 1-1570 and 1572-8376 |
| 1572 | 1-1571 and 1573-8376 |
| 1573 | 1-1572 and 1574-8376 |
| 1574 | 1-1573 and 1575-8376 |
| 1575 | 1-1574 and 1576-8376 |
| 1576 | 1-1575 and 1577-8376 |
| 1577 | 1-1576 and 1578-8376 |
| 1578 | 1-1577 and 1579-8376 |
| 1579 | 1-1578 and 1580-8376 |
| 1580 | 1-1579 and 1581-8376 |
| 1581 | 1-1580 and 1582-8376 |
| 1582 | 1-1581 and 1583-8376 |
| 1583 | 1-1582 and 1584-8376 |
| 1584 | 1-1583 and 1585-8376 |
| 1585 | 1-1584 and 1586-8376 |
| 1586 | 1-1585 and 1587-8376 |
| 1587 | 1-1586 and 1588-8376 |
| 1588 | 1-1587 and 1589-8376 |
| 1589 | 1-1588 and 1590-8376 |
| 1590 | 1-1589 and 1591-8376 |
| 1591 | 1-1590 and 1592-8376 |
| 1592 | 1-1591 and 1593-8376 |
| 1593 | 1-1592 and 1594-8376 |
| 1594 | 1-1593 and 1595-8376 |
| 1595 | 1-1594 and 1596-8376 |
| 1596 | 1-1595 and 1597-8376 |
| 1597 | 1-1596 and 1598-8376 |
| 1598 | 1-1597 and 1599-8376 |
| 1599 | 1-1598 and 1600-8376 |
| 1600 | 1-1599 and 1601-8376 |
| 1601 | 1-1600 and 1602-8376 |
| 1602 | 1-1601 and 1603-8376 |
| 1603 | 1-1602 and 1604-8376 |
| 1604 | 1-1603 and 1605-8376 |
| 1605 | 1-1604 and 1606-8376 |
| 1606 | 1-1605 and 1607-8376 |
| 1607 | 1-1606 and 1608-8376 |
| 1608 | 1-1607 and 1609-8376 |
| 1609 | 1-1608 and 1610-8376 |
| 1610 | 1-1609 and 1611-8376 |
| 1611 | 1-1610 and 1612-8376 |
| 1612 | 1-1611 and 1613-8376 |
| 1613 | 1-1612 and 1614-8376 |
| 1614 | 1-1613 and 1615-8376 |
| 1615 | 1-1614 and 1616-8376 |
| 1616 | 1-1615 and 1617-8376 |
| 1617 | 1-1616 and 1618-8376 |
| 1618 | 1-1617 and 1619-8376 |
| 1619 | 1-1618 and 1620-8376 |
| 1620 | 1-1619 and 1621-8376 |
| 1621 | 1-1620 and 1622-8376 |
| 1622 | 1-1621 and 1623-8376 |
| 1623 | 1-1622 and 1624-8376 |
| 1624 | 1-1623 and 1625-8376 |
| 1625 | 1-1624 and 1626-8376 |
| 1626 | 1-1625 and 1627-8376 |
| 1627 | 1-1626 and 1628-8376 |
| 1628 | 1-1627 and 1629-8376 |
| 1629 | 1-1628 and 1630-8376 |
| 1630 | 1-1629 and 1631-8376 |
| 1631 | 1-1630 and 1632-8376 |
| 1632 | 1-1631 and 1633-8376 |
| 1633 | 1-1632 and 1634-8376 |
| 1634 | 1-1633 and 1635-8376 |
| 1635 | 1-1634 and 1636-8376 |
| 1636 | 1-1635 and 1637-8376 |
| 1637 | 1-1636 and 1638-8376 |
| 1638 | 1-1637 and 1639-8376 |
| 1639 | 1-1638 and 1640-8376 |
| 1640 | 1-1639 and 1641-8376 |
| 1641 | 1-1640 and 1642-8376 |
| 1642 | 1-1641 and 1643-8376 |
| 1643 | 1-1642 and 1644-8376 |
| 1644 | 1-1643 and 1645-8376 |
| 1645 | 1-1644 and 1646-8376 |
| 1646 | 1-1645 and 1647-8376 |
| 1647 | 1-1646 and 1648-8376 |
| 1648 | 1-1647 and 1649-8376 |
| 1649 | 1-1648 and 1650-8376 |
| 1650 | 1-1649 and 1651-8376 |
| 1651 | 1-1650 and 1652-8376 |
| 1652 | 1-1651 and 1653-8376 |
| 1653 | 1-1652 and 1654-8376 |
| 1654 | 1-1653 and 1655-8376 |
| 1655 | 1-1654 and 1656-8376 |
| 1656 | 1-1655 and 1657-8376 |
| 1657 | 1-1656 and 1658-8376 |
| 1658 | 1-1657 and 1659-8376 |
| 1659 | 1-1658 and 1660-8376 |
| 1660 | 1-1659 and 1661-8376 |
| 1661 | 1-1660 and 1662-8376 |
| 1662 | 1-1661 and 1663-8376 |
| 1663 | 1-1662 and 1664-8376 |
| 1664 | 1-1663 and 1665-8376 |
| 1665 | 1-1664 and 1666-8376 |
| 1666 | 1-1665 and 1667-8376 |
| 1667 | 1-1666 and 1668-8376 |
| 1668 | 1-1667 and 1669-8376 |
| 1669 | 1-1668 and 1670-8376 |
| 1670 | 1-1669 and 1671-8376 |
| 1671 | 1-1670 and 1672-8376 |
| 1672 | 1-1671 and 1673-8376 |
| 1673 | 1-1672 and 1674-8376 |
| 1674 | 1-1673 and 1675-8376 |
| 1675 | 1-1674 and 1676-8376 |

| First | Second |
|---|---|
| 1676 | 1-1675 and 1677-8376 |
| 1677 | 1-1676 and 1678-8376 |
| 1678 | 1-1677 and 1679-8376 |
| 1679 | 1-1678 and 1680-8376 |
| 1680 | 1-1679 and 1681-8376 |
| 1681 | 1-1680 and 1682-8376 |
| 1682 | 1-1681 and 1683-8376 |
| 1683 | 1-1682 and 1684-8376 |
| 1684 | 1-1683 and 1685-8376 |
| 1685 | 1-1684 and 1686-8376 |
| 1686 | 1-1685 and 1687-8376 |
| 1687 | 1-1686 and 1688-8376 |
| 1688 | 1-1687 and 1689-8376 |
| 1689 | 1-1688 and 1690-8376 |
| 1690 | 1-1689 and 1691-8376 |
| 1691 | 1-1690 and 1692-8376 |
| 1692 | 1-1691 and 1693-8376 |
| 1693 | 1-1692 and 1694-8376 |
| 1694 | 1-1693 and 1695-8376 |
| 1695 | 1-1694 and 1696-8376 |
| 1696 | 1-1695 and 1697-8376 |
| 1697 | 1-1696 and 1698-8376 |
| 1698 | 1-1697 and 1699-8376 |
| 1699 | 1-1698 and 1700-8376 |
| 1700 | 1-1699 and 1701-8376 |
| 1701 | 1-1700 and 1702-8376 |
| 1702 | 1-1701 and 1703-8376 |
| 1703 | 1-1702 and 1704-8376 |
| 1704 | 1-1703 and 1705-8376 |
| 1705 | 1-1704 and 1706-8376 |
| 1706 | 1-1705 and 1707-8376 |
| 1707 | 1-1706 and 1708-8376 |
| 1708 | 1-1707 and 1709-8376 |
| 1709 | 1-1708 and 1710-8376 |
| 1710 | 1-1709 and 1711-8376 |
| 1711 | 1-1710 and 1712-8376 |
| 1712 | 1-1711 and 1713-8376 |
| 1713 | 1-1712 and 1714-8376 |
| 1714 | 1-1713 and 1715-8376 |
| 1715 | 1-1714 and 1716-8376 |
| 1716 | 1-1715 and 1717-8376 |
| 1717 | 1-1716 and 1718-8376 |
| 1718 | 1-1717 and 1719-8376 |
| 1719 | 1-1718 and 1720-8376 |
| 1720 | 1-1719 and 1721-8376 |
| 1721 | 1-1720 and 1722-8376 |
| 1722 | 1-1721 and 1723-8376 |
| 1723 | 1-1722 and 1724-8376 |
| 1724 | 1-1723 and 1725-8376 |
| 1725 | 1-1724 and 1726-8376 |
| 1726 | 1-1725 and 1727-8376 |
| 1727 | 1-1726 and 1728-8376 |
| 1728 | 1-1727 and 1729-8376 |
| 1729 | 1-1728 and 1730-8376 |
| 1730 | 1-1729 and 1731-8376 |
| 1731 | 1-1730 and 1732-8376 |
| 1732 | 1-1731 and 1733-8376 |
| 1733 | 1-1732 and 1734-8376 |
| 1734 | 1-1733 and 1735-8376 |
| 1735 | 1-1734 and 1736-8376 |
| 1736 | 1-1735 and 1737-8376 |
| 1737 | 1-1736 and 1738-8376 |
| 1738 | 1-1737 and 1739-8376 |
| 1739 | 1-1738 and 1740-8376 |
| 1740 | 1-1739 and 1741-8376 |
| 1741 | 1-1740 and 1742-8376 |
| 1742 | 1-1741 and 1743-8376 |
| 1743 | 1-1742 and 1744-8376 |
| 1744 | 1-1743 and 1745-8376 |
| 1745 | 1-1744 and 1746-8376 |
| 1746 | 1-1745 and 1747-8376 |
| 1747 | 1-1746 and 1748-8376 |
| 1748 | 1-1747 and 1749-8376 |
| 1749 | 1-1748 and 1750-8376 |
| 1750 | 1-1749 and 1751-8376 |
| 1751 | 1-1750 and 1752-8376 |
| 1752 | 1-1751 and 1753-8376 |
| 1753 | 1-1752 and 1754-8376 |
| 1754 | 1-1753 and 1755-8376 |
| 1755 | 1-1754 and 1756-8376 |
| 1756 | 1-1755 and 1757-8376 |
| 1757 | 1-1756 and 1758-8376 |
| 1758 | 1-1757 and 1759-8376 |
| 1759 | 1-1758 and 1760-8376 |
| 1760 | 1-1759 and 1761-8376 |
| 1761 | 1-1760 and 1762-8376 |
| 1762 | 1-1761 and 1763-8376 |
| 1763 | 1-1762 and 1764-8376 |
| 1764 | 1-1763 and 1765-8376 |
| 1765 | 1-1764 and 1766-8376 |
| 1766 | 1-1765 and 1767-8376 |
| 1767 | 1-1766 and 1768-8376 |
| 1768 | 1-1767 and 1769-8376 |
| 1769 | 1-1768 and 1770-8376 |
| 1770 | 1-1769 and 1771-8376 |
| 1771 | 1-1770 and 1772-8376 |
| 1772 | 1-1771 and 1773-8376 |
| 1773 | 1-1772 and 1774-8376 |
| 1774 | 1-1773 and 1775-8376 |
| 1775 | 1-1774 and 1776-8376 |
| 1776 | 1-1775 and 1777-8376 |
| 1777 | 1-1776 and 1778-8376 |
| 1778 | 1-1777 and 1779-8376 |
| 1779 | 1-1778 and 1780-8376 |
| 1780 | 1-1779 and 1781-8376 |
| 1781 | 1-1780 and 1782-8376 |
| 1782 | 1-1781 and 1783-8376 |
| 1783 | 1-1782 and 1784-8376 |
| 1784 | 1-1783 and 1785-8376 |
| 1785 | 1-1784 and 1786-8376 |
| 1786 | 1-1785 and 1787-8376 |
| 1787 | 1-1786 and 1788-8376 |
| 1788 | 1-1787 and 1789-8376 |
| 1789 | 1-1788 and 1790-8376 |
| 1790 | 1-1789 and 1791-8376 |
| 1791 | 1-1790 and 1792-8376 |
| 1792 | 1-1791 and 1793-8376 |
| 1793 | 1-1792 and 1794-8376 |
| 1794 | 1-1793 and 1795-8376 |
| 1795 | 1-1794 and 1796-8376 |
| 1796 | 1-1795 and 1797-8376 |
| 1797 | 1-1796 and 1798-8376 |
| 1798 | 1-1797 and 1799-8376 |
| 1799 | 1-1798 and 1800-8376 |
| 1800 | 1-1799 and 1801-8376 |
| 1801 | 1-1800 and 1802-8376 |
| 1802 | 1-1801 and 1803-8376 |
| 1803 | 1-1802 and 1804-8376 |
| 1804 | 1-1803 and 1805-8376 |
| 1805 | 1-1804 and 1806-8376 |
| 1806 | 1-1805 and 1807-8376 |
| 1807 | 1-1806 and 1808-8376 |
| 1808 | 1-1807 and 1809-8376 |
| 1809 | 1-1808 and 1810-8376 |
| 1810 | 1-1809 and 1811-8376 |
| 1811 | 1-1810 and 1812-8376 |
| 1812 | 1-1811 and 1813-8376 |
| 1813 | 1-1812 and 1814-8376 |
| 1814 | 1-1813 and 1815-8376 |
| 1815 | 1-1814 and 1816-8376 |
| 1816 | 1-1815 and 1817-8376 |
| 1817 | 1-1816 and 1818-8376 |
| 1818 | 1-1817 and 1819-8376 |
| 1819 | 1-1818 and 1820-8376 |
| 1820 | 1-1819 and 1821-8376 |
| 1821 | 1-1820 and 1822-8376 |
| 1822 | 1-1821 and 1823-8376 |
| 1823 | 1-1822 and 1824-8376 |
| 1824 | 1-1823 and 1825-8376 |
| 1825 | 1-1824 and 1826-8376 |
| 1826 | 1-1825 and 1827-8376 |
| 1827 | 1-1826 and 1828-8376 |
| 1828 | 1-1827 and 1829-8376 |
| 1829 | 1-1828 and 1830-8376 |

| First | Second |
|---|---|
| 1830 | 1-1829 and 1831-8376 |
| 1831 | 1-1830 and 1832-8376 |
| 1832 | 1-1831 and 1833-8376 |
| 1833 | 1-1832 and 1834-8376 |
| 1834 | 1-1833 and 1835-8376 |
| 1835 | 1-1834 and 1836-8376 |
| 1836 | 1-1835 and 1837-8376 |
| 1837 | 1-1836 and 1838-8376 |
| 1838 | 1-1837 and 1839-8376 |
| 1839 | 1-1838 and 1840-8376 |
| 1840 | 1-1839 and 1841-8376 |
| 1841 | 1-1840 and 1842-8376 |
| 1842 | 1-1841 and 1843-8376 |
| 1843 | 1-1842 and 1844-8376 |
| 1844 | 1-1843 and 1845-8376 |
| 1845 | 1-1844 and 1846-8376 |
| 1846 | 1-1845 and 1847-8376 |
| 1847 | 1-1846 and 1848-8376 |
| 1848 | 1-1847 and 1849-8376 |
| 1849 | 1-1848 and 1850-8376 |
| 1850 | 1-1849 and 1851-8376 |
| 1851 | 1-1850 and 1852-8376 |
| 1852 | 1-1851 and 1853-8376 |
| 1853 | 1-1852 and 1854-8376 |
| 1854 | 1-1853 and 1855-8376 |
| 1855 | 1-1854 and 1856-8376 |
| 1856 | 1-1855 and 1857-8376 |
| 1857 | 1-1856 and 1858-8376 |
| 1858 | 1-1857 and 1859-8376 |
| 1859 | 1-1858 and 1860-8376 |
| 1860 | 1-1859 and 1861-8376 |
| 1861 | 1-1860 and 1862-8376 |
| 1862 | 1-1861 and 1863-8376 |
| 1863 | 1-1862 and 1864-8376 |
| 1864 | 1-1863 and 1865-8376 |
| 1865 | 1-1864 and 1866-8376 |
| 1866 | 1-1865 and 1867-8376 |
| 1867 | 1-1866 and 1868-8376 |
| 1868 | 1-1867 and 1869-8376 |
| 1869 | 1-1868 and 1870-8376 |
| 1870 | 1-1869 and 1871-8376 |
| 1871 | 1-1870 and 1872-8376 |
| 1872 | 1-1871 and 1873-8376 |
| 1873 | 1-1872 and 1874-8376 |
| 1874 | 1-1873 and 1875-8376 |
| 1875 | 1-1874 and 1876-8376 |
| 1876 | 1-1875 and 1877-8376 |
| 1877 | 1-1876 and 1878-8376 |
| 1878 | 1-1877 and 1879-8376 |
| 1879 | 1-1878 and 1880-8376 |
| 1880 | 1-1879 and 1881-8376 |
| 1881 | 1-1880 and 1882-8376 |
| 1882 | 1-1881 and 1883-8376 |
| 1883 | 1-1882 and 1884-8376 |
| 1884 | 1-1883 and 1885-8376 |
| 1885 | 1-1884 and 1886-8376 |
| 1886 | 1-1885 and 1887-8376 |
| 1887 | 1-1886 and 1888-8376 |
| 1888 | 1-1887 and 1889-8376 |
| 1889 | 1-1888 and 1890-8376 |
| 1890 | 1-1889 and 1891-8376 |
| 1891 | 1-1890 and 1892-8376 |
| 1892 | 1-1891 and 1893-8376 |
| 1893 | 1-1892 and 1894-8376 |
| 1894 | 1-1893 and 1895-8376 |
| 1895 | 1-1894 and 1896-8376 |
| 1896 | 1-1895 and 1897-8376 |
| 1897 | 1-1896 and 1898-8376 |
| 1898 | 1-1897 and 1899-8376 |
| 1899 | 1-1898 and 1900-8376 |
| 1900 | 1-1899 and 1901-8376 |
| 1901 | 1-1900 and 1902-8376 |
| 1902 | 1-1901 and 1903-8376 |
| 1903 | 1-1902 and 1904-8376 |
| 1904 | 1-1903 and 1905-8376 |
| 1905 | 1-1904 and 1906-8376 |
| 1906 | 1-1905 and 1907-8376 |
| 1907 | 1-1906 and 1908-8376 |
| 1908 | 1-1907 and 1909-8376 |
| 1909 | 1-1908 and 1910-8376 |
| 1910 | 1-1909 and 1911-8376 |
| 1911 | 1-1910 and 1912-8376 |
| 1912 | 1-1911 and 1913-8376 |
| 1913 | 1-1912 and 1914-8376 |
| 1914 | 1-1913 and 1915-8376 |
| 1915 | 1-1914 and 1916-8376 |
| 1916 | 1-1915 and 1917-8376 |
| 1917 | 1-1916 and 1918-8376 |
| 1918 | 1-1917 and 1919-8376 |
| 1919 | 1-1918 and 1920-8376 |
| 1920 | 1-1919 and 1921-8376 |
| 1921 | 1-1920 and 1922-8376 |
| 1922 | 1-1921 and 1923-8376 |
| 1923 | 1-1922 and 1924-8376 |
| 1924 | 1-1923 and 1925-8376 |
| 1925 | 1-1924 and 1926-8376 |
| 1926 | 1-1925 and 1927-8376 |
| 1927 | 1-1926 and 1928-8376 |
| 1928 | 1-1927 and 1929-8376 |
| 1929 | 1-1928 and 1930-8376 |
| 1930 | 1-1929 and 1931-8376 |
| 1931 | 1-1930 and 1932-8376 |
| 1932 | 1-1931 and 1933-8376 |
| 1933 | 1-1932 and 1934-8376 |
| 1934 | 1-1933 and 1935-8376 |
| 1935 | 1-1934 and 1936-8376 |
| 1936 | 1-1935 and 1937-8376 |
| 1937 | 1-1936 and 1938-8376 |
| 1938 | 1-1937 and 1939-8376 |
| 1939 | 1-1938 and 1940-8376 |
| 1940 | 1-1939 and 1941-8376 |
| 1941 | 1-1940 and 1942-8376 |
| 1942 | 1-1941 and 1943-8376 |
| 1943 | 1-1942 and 1944-8376 |
| 1944 | 1-1943 and 1945-8376 |
| 1945 | 1-1944 and 1946-8376 |
| 1946 | 1-1945 and 1947-8376 |
| 1947 | 1-1946 and 1948-8376 |
| 1948 | 1-1947 and 1949-8376 |
| 1949 | 1-1948 and 1950-8376 |
| 1950 | 1-1949 and 1951-8376 |
| 1951 | 1-1950 and 1952-8376 |
| 1952 | 1-1951 and 1953-8376 |
| 1953 | 1-1952 and 1954-8376 |
| 1954 | 1-1953 and 1955-8376 |
| 1955 | 1-1954 and 1956-8376 |
| 1956 | 1-1955 and 1957-8376 |
| 1957 | 1-1956 and 1958-8376 |
| 1958 | 1-1957 and 1959-8376 |
| 1959 | 1-1958 and 1960-8376 |
| 1960 | 1-1959 and 1961-8376 |
| 1961 | 1-1960 and 1962-8376 |
| 1962 | 1-1961 and 1963-8376 |
| 1963 | 1-1962 and 1964-8376 |
| 1964 | 1-1963 and 1965-8376 |
| 1965 | 1-1964 and 1966-8376 |
| 1966 | 1-1965 and 1967-8376 |
| 1967 | 1-1966 and 1968-8376 |
| 1968 | 1-1967 and 1969-8376 |
| 1969 | 1-1968 and 1970-8376 |
| 1970 | 1-1969 and 1971-8376 |
| 1971 | 1-1970 and 1972-8376 |
| 1972 | 1-1971 and 1973-8376 |
| 1973 | 1-1972 and 1974-8376 |
| 1974 | 1-1973 and 1975-8376 |
| 1975 | 1-1974 and 1976-8376 |
| 1976 | 1-1975 and 1977-8376 |
| 1977 | 1-1976 and 1978-8376 |
| 1978 | 1-1977 and 1979-8376 |
| 1979 | 1-1978 and 1980-8376 |
| 1980 | 1-1979 and 1981-8376 |
| 1981 | 1-1980 and 1982-8376 |
| 1982 | 1-1981 and 1983-8376 |
| 1983 | 1-1982 and 1984-8376 |

| First | Second |
|---|---|
| 1984 | 1-1983 and 1985-8376 |
| 1985 | 1-1984 and 1986-8376 |
| 1986 | 1-1985 and 1987-8376 |
| 1987 | 1-1986 and 1988-8376 |
| 1988 | 1-1987 and 1989-8376 |
| 1989 | 1-1988 and 1990-8376 |
| 1990 | 1-1989 and 1991-8376 |
| 1991 | 1-1990 and 1992-8376 |
| 1992 | 1-1991 and 1993-8376 |
| 1993 | 1-1992 and 1994-8376 |
| 1994 | 1-1993 and 1995-8376 |
| 1995 | 1-1994 and 1996-8376 |
| 1996 | 1-1995 and 1997-8376 |
| 1997 | 1-1996 and 1998-8376 |
| 1998 | 1-1997 and 1999-8376 |
| 1999 | 1-1998 and 2000-8376 |
| 2000 | 1-1999 and 2001-8376 |
| 2001 | 1-2000 and 2002-8376 |
| 2002 | 1-2001 and 2003-8376 |
| 2003 | 1-2002 and 2004-8376 |
| 2004 | 1-2003 and 2005-8376 |
| 2005 | 1-2004 and 2006-8376 |
| 2006 | 1-2005 and 2007-8376 |
| 2007 | 1-2006 and 2008-8376 |
| 2008 | 1-2007 and 2009-8376 |
| 2009 | 1-2008 and 2010-8376 |
| 2010 | 1-2009 and 2011-8376 |
| 2011 | 1-2010 and 2012-8376 |
| 2012 | 1-2011 and 2013-8376 |
| 2013 | 1-2012 and 2014-8376 |
| 2014 | 1-2013 and 2015-8376 |
| 2015 | 1-2014 and 2016-8376 |
| 2016 | 1-2015 and 2017-8376 |
| 2017 | 1-2016 and 2018-8376 |
| 2018 | 1-2017 and 2019-8376 |
| 2019 | 1-2018 and 2020-8376 |
| 2020 | 1-2019 and 2021-8376 |
| 2021 | 1-2020 and 2022-8376 |
| 2022 | 1-2021 and 2023-8376 |
| 2023 | 1-2022 and 2024-8376 |
| 2024 | 1-2023 and 2025-8376 |
| 2025 | 1-2024 and 2026-8376 |
| 2026 | 1-2025 and 2027-8376 |
| 2027 | 1-2026 and 2028-8376 |
| 2028 | 1-2027 and 2029-8376 |
| 2029 | 1-2028 and 2030-8376 |
| 2030 | 1-2029 and 2031-8376 |
| 2031 | 1-2030 and 2032-8376 |
| 2032 | 1-2031 and 2033-8376 |
| 2033 | 1-2032 and 2034-8376 |
| 2034 | 1-2033 and 2035-8376 |
| 2035 | 1-2034 and 2036-8376 |
| 2036 | 1-2035 and 2037-8376 |
| 2037 | 1-2036 and 2038-8376 |
| 2038 | 1-2037 and 2039-8376 |
| 2039 | 1-2038 and 2040-8376 |
| 2040 | 1-2039 and 2041-8376 |
| 2041 | 1-2040 and 2042-8376 |
| 2042 | 1-2041 and 2043-8376 |
| 2043 | 1-2042 and 2044-8376 |
| 2044 | 1-2043 and 2045-8376 |
| 2045 | 1-2044 and 2046-8376 |
| 2046 | 1-2045 and 2047-8376 |
| 2047 | 1-2046 and 2048-8376 |
| 2048 | 1-2047 and 2049-8376 |
| 2049 | 1-2048 and 2050-8376 |
| 2050 | 1-2049 and 2051-8376 |
| 2051 | 1-2050 and 2052-8376 |
| 2052 | 1-2051 and 2053-8376 |
| 2053 | 1-2052 and 2054-8376 |
| 2054 | 1-2053 and 2055-8376 |
| 2055 | 1-2054 and 2056-8376 |
| 2056 | 1-2055 and 2057-8376 |
| 2057 | 1-2056 and 2058-8376 |
| 2058 | 1-2057 and 2059-8376 |
| 2059 | 1-2058 and 2060-8376 |
| 2060 | 1-2059 and 2061-8376 |
| 2061 | 1-2060 and 2062-8376 |
| 2062 | 1-2061 and 2063-8376 |
| 2063 | 1-2062 and 2064-8376 |
| 2064 | 1-2063 and 2065-8376 |
| 2065 | 1-2064 and 2066-8376 |
| 2066 | 1-2065 and 2067-8376 |
| 2067 | 1-2066 and 2068-8376 |
| 2068 | 1-2067 and 2069-8376 |
| 2069 | 1-2068 and 2070-8376 |
| 2070 | 1-2069 and 2071-8376 |
| 2071 | 1-2070 and 2072-8376 |
| 2072 | 1-2071 and 2073-8376 |
| 2073 | 1-2072 and 2074-8376 |
| 2074 | 1-2073 and 2075-8376 |
| 2075 | 1-2074 and 2076-8376 |
| 2076 | 1-2075 and 2077-8376 |
| 2077 | 1-2076 and 2078-8376 |
| 2078 | 1-2077 and 2079-8376 |
| 2079 | 1-2078 and 2080-8376 |
| 2080 | 1-2079 and 2081-8376 |
| 2081 | 1-2080 and 2082-8376 |
| 2082 | 1-2081 and 2083-8376 |
| 2083 | 1-2082 and 2084-8376 |
| 2084 | 1-2083 and 2085-8376 |
| 2085 | 1-2084 and 2086-8376 |
| 2086 | 1-2085 and 2087-8376 |
| 2087 | 1-2086 and 2088-8376 |
| 2088 | 1-2087 and 2089-8376 |
| 2089 | 1-2088 and 2090-8376 |
| 2090 | 1-2089 and 2091-8376 |
| 2091 | 1-2090 and 2092-8376 |
| 2092 | 1-2091 and 2093-8376 |
| 2093 | 1-2092 and 2094-8376 |
| 2094 | 1-2093 and 2095-8376 |
| 2095 | 1-2094 and 2096-8376 |
| 2096 | 1-2095 and 2097-8376 |
| 2097 | 1-2096 and 2098-8376 |
| 2098 | 1-2097 and 2099-8376 |
| 2099 | 1-2098 and 2100-8376 |
| 2100 | 1-2099 and 2101-8376 |
| 2101 | 1-2100 and 2102-8376 |
| 2102 | 1-2101 and 2103-8376 |
| 2103 | 1-2102 and 2104-8376 |
| 2104 | 1-2103 and 2105-8376 |
| 2105 | 1-2104 and 2106-8376 |
| 2106 | 1-2105 and 2107-8376 |
| 2107 | 1-2106 and 2108-8376 |
| 2108 | 1-2107 and 2109-8376 |
| 2109 | 1-2108 and 2110-8376 |
| 2110 | 1-2109 and 2111-8376 |
| 2111 | 1-2110 and 2112-8376 |
| 2112 | 1-2111 and 2113-8376 |
| 2113 | 1-2112 and 2114-8376 |
| 2114 | 1-2113 and 2115-8376 |
| 2115 | 1-2114 and 2116-8376 |
| 2116 | 1-2115 and 2117-8376 |
| 2117 | 1-2116 and 2118-8376 |
| 2118 | 1-2117 and 2119-8376 |
| 2119 | 1-2118 and 2120-8376 |
| 2120 | 1-2119 and 2121-8376 |
| 2121 | 1-2120 and 2122-8376 |
| 2122 | 1-2121 and 2123-8376 |
| 2123 | 1-2122 and 2124-8376 |
| 2124 | 1-2123 and 2125-8376 |
| 2125 | 1-2124 and 2126-8376 |
| 2126 | 1-2125 and 2127-8376 |
| 2127 | 1-2126 and 2128-8376 |
| 2128 | 1-2127 and 2129-8376 |
| 2129 | 1-2128 and 2130-8376 |
| 2130 | 1-2129 and 2131-8376 |
| 2131 | 1-2130 and 2132-8376 |
| 2132 | 1-2131 and 2133-8376 |
| 2133 | 1-2132 and 2134-8376 |
| 2134 | 1-2133 and 2135-8376 |
| 2135 | 1-2134 and 2136-8376 |
| 2136 | 1-2135 and 2137-8376 |
| 2137 | 1-2136 and 2138-8376 |

-continued

| First | Second |
|---|---|
| 2138 | 1-2137 and 2139-8376 |
| 2139 | 1-2138 and 2140-8376 |
| 2140 | 1-2139 and 2141-8376 |
| 2141 | 1-2140 and 2142-8376 |
| 2142 | 1-2141 and 2143-8376 |
| 2143 | 1-2142 and 2144-8376 |
| 2144 | 1-2143 and 2145-8376 |
| 2145 | 1-2144 and 2146-8376 |
| 2146 | 1-2145 and 2147-8376 |
| 2147 | 1-2146 and 2148-8376 |
| 2148 | 1-2147 and 2149-8376 |
| 2149 | 1-2148 and 2150-8376 |
| 2150 | 1-2149 and 2151-8376 |
| 2151 | 1-2150 and 2152-8376 |
| 2152 | 1-2151 and 2153-8376 |
| 2153 | 1-2152 and 2154-8376 |
| 2154 | 1-2153 and 2155-8376 |
| 2155 | 1-2154 and 2156-8376 |
| 2156 | 1-2155 and 2157-8376 |
| 2157 | 1-2156 and 2158-8376 |
| 2158 | 1-2157 and 2159-8376 |
| 2159 | 1-2158 and 2160-8376 |
| 2160 | 1-2159 and 2161-8376 |
| 2161 | 1-2160 and 2162-8376 |
| 2162 | 1-2161 and 2163-8376 |
| 2163 | 1-2162 and 2164-8376 |
| 2164 | 1-2163 and 2165-8376 |
| 2165 | 1-2164 and 2166-8376 |
| 2166 | 1-2165 and 2167-8376 |
| 2167 | 1-2166 and 2168-8376 |
| 2168 | 1-2167 and 2169-8376 |
| 2169 | 1-2168 and 2170-8376 |
| 2170 | 1-2169 and 2171-8376 |
| 2171 | 1-2170 and 2172-8376 |
| 2172 | 1-2171 and 2173-8376 |
| 2173 | 1-2172 and 2174-8376 |
| 2174 | 1-2173 and 2175-8376 |
| 2175 | 1-2174 and 2176-8376 |
| 2176 | 1-2175 and 2177-8376 |
| 2177 | 1-2176 and 2178-8376 |
| 2178 | 1-2177 and 2179-8376 |
| 2179 | 1-2178 and 2180-8376 |
| 2180 | 1-2179 and 2181-8376 |
| 2181 | 1-2180 and 2182-8376 |
| 2182 | 1-2181 and 2183-8376 |
| 2183 | 1-2182 and 2184-8376 |
| 2184 | 1-2183 and 2185-8376 |
| 2185 | 1-2184 and 2186-8376 |
| 2186 | 1-2185 and 2187-8376 |
| 2187 | 1-2186 and 2188-8376 |
| 2188 | 1-2187 and 2189-8376 |
| 2189 | 1-2188 and 2190-8376 |
| 2190 | 1-2189 and 2191-8376 |
| 2191 | 1-2190 and 2192-8376 |
| 2192 | 1-2191 and 2193-8376 |
| 2193 | 1-2192 and 2194-8376 |
| 2194 | 1-2193 and 2195-8376 |
| 2195 | 1-2194 and 2196-8376 |
| 2196 | 1-2195 and 2197-8376 |
| 2197 | 1-2196 and 2198-8376 |
| 2198 | 1-2197 and 2199-8376 |
| 2199 | 1-2198 and 2200-8376 |
| 2200 | 1-2199 and 2201-8376 |
| 2201 | 1-2200 and 2202-8376 |
| 2202 | 1-2201 and 2203-8376 |
| 2203 | 1-2202 and 2204-8376 |
| 2204 | 1-2203 and 2205-8376 |
| 2205 | 1-2204 and 2206-8376 |
| 2206 | 1-2205 and 2207-8376 |
| 2207 | 1-2206 and 2208-8376 |
| 2208 | 1-2207 and 2209-8376 |
| 2209 | 1-2208 and 2210-8376 |
| 2210 | 1-2209 and 2211-8376 |
| 2211 | 1-2210 and 2212-8376 |
| 2212 | 1-2211 and 2213-8376 |
| 2213 | 1-2212 and 2214-8376 |
| 2214 | 1-2213 and 2215-8376 |
| 2215 | 1-2214 and 2216-8376 |
| 2216 | 1-2215 and 2217-8376 |
| 2217 | 1-2216 and 2218-8376 |
| 2218 | 1-2217 and 2219-8376 |
| 2219 | 1-2218 and 2220-8376 |
| 2220 | 1-2219 and 2221-8376 |
| 2221 | 1-2220 and 2222-8376 |
| 2222 | 1-2221 and 2223-8376 |
| 2223 | 1-2222 and 2224-8376 |
| 2224 | 1-2223 and 2225-8376 |
| 2225 | 1-2224 and 2226-8376 |
| 2226 | 1-2225 and 2227-8376 |
| 2227 | 1-2226 and 2228-8376 |
| 2228 | 1-2227 and 2229-8376 |
| 2229 | 1-2228 and 2230-8376 |
| 2230 | 1-2229 and 2231-8376 |
| 2231 | 1-2230 and 2232-8376 |
| 2232 | 1-2231 and 2233-8376 |
| 2233 | 1-2232 and 2234-8376 |
| 2234 | 1-2233 and 2235-8376 |
| 2235 | 1-2234 and 2236-8376 |
| 2236 | 1-2235 and 2237-8376 |
| 2237 | 1-2236 and 2238-8376 |
| 2238 | 1-2237 and 2239-8376 |
| 2239 | 1-2238 and 2240-8376 |
| 2240 | 1-2239 and 2241-8376 |
| 2241 | 1-2240 and 2242-8376 |
| 2242 | 1-2241 and 2243-8376 |
| 2243 | 1-2242 and 2244-8376 |
| 2244 | 1-2243 and 2245-8376 |
| 2245 | 1-2244 and 2246-8376 |
| 2246 | 1-2245 and 2247-8376 |
| 2247 | 1-2246 and 2248-8376 |
| 2248 | 1-2247 and 2249-8376 |
| 2249 | 1-2248 and 2250-8376 |
| 2250 | 1-2249 and 2251-8376 |
| 2251 | 1-2250 and 2252-8376 |
| 2252 | 1-2251 and 2253-8376 |
| 2253 | 1-2252 and 2254-8376 |
| 2254 | 1-2253 and 2255-8376 |
| 2255 | 1-2254 and 2256-8376 |
| 2256 | 1-2255 and 2257-8376 |
| 2257 | 1-2256 and 2258-8376 |
| 2258 | 1-2257 and 2259-8376 |
| 2259 | 1-2258 and 2260-8376 |
| 2260 | 1-2259 and 2261-8376 |
| 2261 | 1-2260 and 2262-8376 |
| 2262 | 1-2261 and 2263-8376 |
| 2263 | 1-2262 and 2264-8376 |
| 2264 | 1-2263 and 2265-8376 |
| 2265 | 1-2264 and 2266-8376 |
| 2266 | 1-2265 and 2267-8376 |
| 2267 | 1-2266 and 2268-8376 |
| 2268 | 1-2267 and 2269-8376 |
| 2269 | 1-2268 and 2270-8376 |
| 2270 | 1-2269 and 2271-8376 |
| 2271 | 1-2270 and 2272-8376 |
| 2272 | 1-2271 and 2273-8376 |
| 2273 | 1-2272 and 2274-8376 |
| 2274 | 1-2273 and 2275-8376 |
| 2275 | 1-2274 and 2276-8376 |
| 2276 | 1-2275 and 2277-8376 |
| 2277 | 1-2276 and 2278-8376 |
| 2278 | 1-2277 and 2279-8376 |
| 2279 | 1-2278 and 2280-8376 |
| 2280 | 1-2279 and 2281-8376 |
| 2281 | 1-2280 and 2282-8376 |
| 2282 | 1-2281 and 2283-8376 |
| 2283 | 1-2282 and 2284-8376 |
| 2284 | 1-2283 and 2285-8376 |
| 2285 | 1-2284 and 2286-8376 |
| 2286 | 1-2285 and 2287-8376 |
| 2287 | 1-2286 and 2288-8376 |
| 2288 | 1-2287 and 2289-8376 |
| 2289 | 1-2288 and 2290-8376 |
| 2290 | 1-2289 and 2291-8376 |
| 2291 | 1-2290 and 2292-8376 |

| First | Second |
|---|---|
| 2292 | 1-2291 and 2293-8376 |
| 2293 | 1-2292 and 2294-8376 |
| 2294 | 1-2293 and 2295-8376 |
| 2295 | 1-2294 and 2296-8376 |
| 2296 | 1-2295 and 2297-8376 |
| 2297 | 1-2296 and 2298-8376 |
| 2298 | 1-2297 and 2299-8376 |
| 2299 | 1-2298 and 2300-8376 |
| 2300 | 1-2299 and 2301-8376 |
| 2301 | 1-2300 and 2302-8376 |
| 2302 | 1-2301 and 2303-8376 |
| 2303 | 1-2302 and 2304-8376 |
| 2304 | 1-2303 and 2305-8376 |
| 2305 | 1-2304 and 2306-8376 |
| 2306 | 1-2305 and 2307-8376 |
| 2307 | 1-2306 and 2308-8376 |
| 2308 | 1-2307 and 2309-8376 |
| 2309 | 1-2308 and 2310-8376 |
| 2310 | 1-2309 and 2311-8376 |
| 2311 | 1-2310 and 2312-8376 |
| 2312 | 1-2311 and 2313-8376 |
| 2313 | 1-2312 and 2314-8376 |
| 2314 | 1-2313 and 2315-8376 |
| 2315 | 1-2314 and 2316-8376 |
| 2316 | 1-2315 and 2317-8376 |
| 2317 | 1-2316 and 2318-8376 |
| 2318 | 1-2317 and 2319-8376 |
| 2319 | 1-2318 and 2320-8376 |
| 2320 | 1-2319 and 2321-8376 |
| 2321 | 1-2320 and 2322-8376 |
| 2322 | 1-2321 and 2323-8376 |
| 2323 | 1-2322 and 2324-8376 |
| 2324 | 1-2323 and 2325-8376 |
| 2325 | 1-2324 and 2326-8376 |
| 2326 | 1-2325 and 2327-8376 |
| 2327 | 1-2326 and 2328-8376 |
| 2328 | 1-2327 and 2329-8376 |
| 2329 | 1-2328 and 2330-8376 |
| 2330 | 1-2329 and 2331-8376 |
| 2331 | 1-2330 and 2332-8376 |
| 2332 | 1-2331 and 2333-8376 |
| 2333 | 1-2332 and 2334-8376 |
| 2334 | 1-2333 and 2335-8376 |
| 2335 | 1-2334 and 2336-8376 |
| 2336 | 1-2335 and 2337-8376 |
| 2337 | 1-2336 and 2338-8376 |
| 2338 | 1-2337 and 2339-8376 |
| 2339 | 1-2338 and 2340-8376 |
| 2340 | 1-2339 and 2341-8376 |
| 2341 | 1-2340 and 2342-8376 |
| 2342 | 1-2341 and 2343-8376 |
| 2343 | 1-2342 and 2344-8376 |
| 2344 | 1-2343 and 2345-8376 |
| 2345 | 1-2344 and 2346-8376 |
| 2346 | 1-2345 and 2347-8376 |
| 2347 | 1-2346 and 2348-8376 |
| 2348 | 1-2347 and 2349-8376 |
| 2349 | 1-2348 and 2350-8376 |
| 2350 | 1-2349 and 2351-8376 |
| 2351 | 1-2350 and 2352-8376 |
| 2352 | 1-2351 and 2353-8376 |
| 2353 | 1-2352 and 2354-8376 |
| 2354 | 1-2353 and 2355-8376 |
| 2355 | 1-2354 and 2356-8376 |
| 2356 | 1-2355 and 2357-8376 |
| 2357 | 1-2356 and 2358-8376 |
| 2358 | 1-2357 and 2359-8376 |
| 2359 | 1-2358 and 2360-8376 |
| 2360 | 1-2359 and 2361-8376 |
| 2361 | 1-2360 and 2362-8376 |
| 2362 | 1-2361 and 2363-8376 |
| 2363 | 1-2362 and 2364-8376 |
| 2364 | 1-2363 and 2365-8376 |
| 2365 | 1-2364 and 2366-8376 |
| 2366 | 1-2365 and 2367-8376 |
| 2367 | 1-2366 and 2368-8376 |
| 2368 | 1-2367 and 2369-8376 |
| 2369 | 1-2368 and 2370-8376 |
| 2370 | 1-2369 and 2371-8376 |
| 2371 | 1-2370 and 2372-8376 |
| 2372 | 1-2371 and 2373-8376 |
| 2373 | 1-2372 and 2374-8376 |
| 2374 | 1-2373 and 2375-8376 |
| 2375 | 1-2374 and 2376-8376 |
| 2376 | 1-2375 and 2377-8376 |
| 2377 | 1-2376 and 2378-8376 |
| 2378 | 1-2377 and 2379-8376 |
| 2379 | 1-2378 and 2380-8376 |
| 2380 | 1-2379 and 2381-8376 |
| 2381 | 1-2380 and 2382-8376 |
| 2382 | 1-2381 and 2383-8376 |
| 2383 | 1-2382 and 2384-8376 |
| 2384 | 1-2383 and 2385-8376 |
| 2385 | 1-2384 and 2386-8376 |
| 2386 | 1-2385 and 2387-8376 |
| 2387 | 1-2386 and 2388-8376 |
| 2388 | 1-2387 and 2389-8376 |
| 2389 | 1-2388 and 2390-8376 |
| 2390 | 1-2389 and 2391-8376 |
| 2391 | 1-2390 and 2392-8376 |
| 2392 | 1-2391 and 2393-8376 |
| 2393 | 1-2392 and 2394-8376 |
| 2394 | 1-2393 and 2395-8376 |
| 2395 | 1-2394 and 2396-8376 |
| 2396 | 1-2395 and 2397-8376 |
| 2397 | 1-2396 and 2398-8376 |
| 2398 | 1-2397 and 2399-8376 |
| 2399 | 1-2398 and 2400-8376 |
| 2400 | 1-2399 and 2401-8376 |
| 2401 | 1-2400 and 2402-8376 |
| 2402 | 1-2401 and 2403-8376 |
| 2403 | 1-2402 and 2404-8376 |
| 2404 | 1-2403 and 2405-8376 |
| 2405 | 1-2404 and 2406-8376 |
| 2406 | 1-2405 and 2407-8376 |
| 2407 | 1-2406 and 2408-8376 |
| 2408 | 1-2407 and 2409-8376 |
| 2409 | 1-2408 and 2410-8376 |
| 2410 | 1-2409 and 2411-8376 |
| 2411 | 1-2410 and 2412-8376 |
| 2412 | 1-2411 and 2413-8376 |
| 2413 | 1-2412 and 2414-8376 |
| 2414 | 1-2413 and 2415-8376 |
| 2415 | 1-2414 and 2416-8376 |
| 2416 | 1-2415 and 2417-8376 |
| 2417 | 1-2416 and 2418-8376 |
| 2418 | 1-2417 and 2419-8376 |
| 2419 | 1-2418 and 2420-8376 |
| 2420 | 1-2419 and 2421-8376 |
| 2421 | 1-2420 and 2422-8376 |
| 2422 | 1-2421 and 2423-8376 |
| 2423 | 1-2422 and 2424-8376 |
| 2424 | 1-2423 and 2425-8376 |
| 2425 | 1-2424 and 2426-8376 |
| 2426 | 1-2425 and 2427-8376 |
| 2427 | 1-2426 and 2428-8376 |
| 2428 | 1-2427 and 2429-8376 |
| 2429 | 1-2428 and 2430-8376 |
| 2430 | 1-2429 and 2431-8376 |
| 2431 | 1-2430 and 2432-8376 |
| 2432 | 1-2431 and 2433-8376 |
| 2433 | 1-2432 and 2434-8376 |
| 2434 | 1-2433 and 2435-8376 |
| 2435 | 1-2434 and 2436-8376 |
| 2436 | 1-2435 and 2437-8376 |
| 2437 | 1-2436 and 2438-8376 |
| 2438 | 1-2437 and 2439-8376 |
| 2439 | 1-2438 and 2440-8376 |
| 2440 | 1-2439 and 2441-8376 |
| 2441 | 1-2440 and 2442-8376 |
| 2442 | 1-2441 and 2443-8376 |
| 2443 | 1-2442 and 2444-8376 |
| 2444 | 1-2443 and 2445-8376 |
| 2445 | 1-2444 and 2446-8376 |

| First | Second |
|---|---|
| 2446 | 1-2445 and 2447-8376 |
| 2447 | 1-2446 and 2448-8376 |
| 2448 | 1-2447 and 2449-8376 |
| 2449 | 1-2448 and 2450-8376 |
| 2450 | 1-2449 and 2451-8376 |
| 2451 | 1-2450 and 2452-8376 |
| 2452 | 1-2451 and 2453-8376 |
| 2453 | 1-2452 and 2454-8376 |
| 2454 | 1-2453 and 2455-8376 |
| 2455 | 1-2454 and 2456-8376 |
| 2456 | 1-2455 and 2457-8376 |
| 2457 | 1-2456 and 2458-8376 |
| 2458 | 1-2457 and 2459-8376 |
| 2459 | 1-2458 and 2460-8376 |
| 2460 | 1-2459 and 2461-8376 |
| 2461 | 1-2460 and 2462-8376 |
| 2462 | 1-2461 and 2463-8376 |
| 2463 | 1-2462 and 2464-8376 |
| 2464 | 1-2463 and 2465-8376 |
| 2465 | 1-2464 and 2466-8376 |
| 2466 | 1-2465 and 2467-8376 |
| 2467 | 1-2466 and 2468-8376 |
| 2468 | 1-2467 and 2469-8376 |
| 2469 | 1-2468 and 2470-8376 |
| 2470 | 1-2469 and 2471-8376 |
| 2471 | 1-2470 and 2472-8376 |
| 2472 | 1-2471 and 2473-8376 |
| 2473 | 1-2472 and 2474-8376 |
| 2474 | 1-2473 and 2475-8376 |
| 2475 | 1-2474 and 2476-8376 |
| 2476 | 1-2475 and 2477-8376 |
| 2477 | 1-2476 and 2478-8376 |
| 2478 | 1-2477 and 2479-8376 |
| 2479 | 1-2478 and 2480-8376 |
| 2480 | 1-2479 and 2481-8376 |
| 2481 | 1-2480 and 2482-8376 |
| 2482 | 1-2481 and 2483-8376 |
| 2483 | 1-2482 and 2484-8376 |
| 2484 | 1-2483 and 2485-8376 |
| 2485 | 1-2484 and 2486-8376 |
| 2486 | 1-2485 and 2487-8376 |
| 2487 | 1-2486 and 2488-8376 |
| 2488 | 1-2487 and 2489-8376 |
| 2489 | 1-2488 and 2490-8376 |
| 2490 | 1-2489 and 2491-8376 |
| 2491 | 1-2490 and 2492-8376 |
| 2492 | 1-2491 and 2493-8376 |
| 2493 | 1-2492 and 2494-8376 |
| 2494 | 1-2493 and 2495-8376 |
| 2495 | 1-2494 and 2496-8376 |
| 2496 | 1-2495 and 2497-8376 |
| 2497 | 1-2496 and 2498-8376 |
| 2498 | 1-2497 and 2499-8376 |
| 2499 | 1-2498 and 2500-8376 |
| 2500 | 1-2499 and 2501-8376 |
| 2501 | 1-2500 and 2502-8376 |
| 2502 | 1-2501 and 2503-8376 |
| 2503 | 1-2502 and 2504-8376 |
| 2504 | 1-2503 and 2505-8376 |
| 2505 | 1-2504 and 2506-8376 |
| 2506 | 1-2505 and 2507-8376 |
| 2507 | 1-2506 and 2508-8376 |
| 2508 | 1-2507 and 2509-8376 |
| 2509 | 1-2508 and 2510-8376 |
| 2510 | 1-2509 and 2511-8376 |
| 2511 | 1-2510 and 2512-8376 |
| 2512 | 1-2511 and 2513-8376 |
| 2513 | 1-2512 and 2514-8376 |
| 2514 | 1-2513 and 2515-8376 |
| 2515 | 1-2514 and 2516-8376 |
| 2516 | 1-2515 and 2517-8376 |
| 2517 | 1-2516 and 2518-8376 |
| 2518 | 1-2517 and 2519-8376 |
| 2519 | 1-2518 and 2520-8376 |
| 2520 | 1-2519 and 2521-8376 |
| 2521 | 1-2520 and 2522-8376 |
| 2522 | 1-2521 and 2523-8376 |
| 2523 | 1-2522 and 2524-8376 |
| 2524 | 1-2523 and 2525-8376 |
| 2525 | 1-2524 and 2526-8376 |
| 2526 | 1-2525 and 2527-8376 |
| 2527 | 1-2526 and 2528-8376 |
| 2528 | 1-2527 and 2529-8376 |
| 2529 | 1-2528 and 2530-8376 |
| 2530 | 1-2529 and 2531-8376 |
| 2531 | 1-2530 and 2532-8376 |
| 2532 | 1-2531 and 2533-8376 |
| 2533 | 1-2532 and 2534-8376 |
| 2534 | 1-2533 and 2535-8376 |
| 2535 | 1-2534 and 2536-8376 |
| 2536 | 1-2535 and 2537-8376 |
| 2537 | 1-2536 and 2538-8376 |
| 2538 | 1-2537 and 2539-8376 |
| 2539 | 1-2538 and 2540-8376 |
| 2540 | 1-2539 and 2541-8376 |
| 2541 | 1-2540 and 2542-8376 |
| 2542 | 1-2541 and 2543-8376 |
| 2543 | 1-2542 and 2544-8376 |
| 2544 | 1-2543 and 2545-8376 |
| 2545 | 1-2544 and 2546-8376 |
| 2546 | 1-2545 and 2547-8376 |
| 2547 | 1-2546 and 2548-8376 |
| 2548 | 1-2547 and 2549-8376 |
| 2549 | 1-2548 and 2550-8376 |
| 2550 | 1-2549 and 2551-8376 |
| 2551 | 1-2550 and 2552-8376 |
| 2552 | 1-2551 and 2553-8376 |
| 2553 | 1-2552 and 2554-8376 |
| 2554 | 1-2553 and 2555-8376 |
| 2555 | 1-2554 and 2556-8376 |
| 2556 | 1-2555 and 2557-8376 |
| 2557 | 1-2556 and 2558-8376 |
| 2558 | 1-2557 and 2559-8376 |
| 2559 | 1-2558 and 2560-8376 |
| 2560 | 1-2559 and 2561-8376 |
| 2561 | 1-2560 and 2562-8376 |
| 2562 | 1-2561 and 2563-8376 |
| 2563 | 1-2562 and 2564-8376 |
| 2564 | 1-2563 and 2565-8376 |
| 2565 | 1-2564 and 2566-8376 |
| 2566 | 1-2565 and 2567-8376 |
| 2567 | 1-2566 and 2568-8376 |
| 2568 | 1-2567 and 2569-8376 |
| 2569 | 1-2568 and 2570-8376 |
| 2570 | 1-2569 and 2571-8376 |
| 2571 | 1-2570 and 2572-8376 |
| 2572 | 1-2571 and 2573-8376 |
| 2573 | 1-2572 and 2574-8376 |
| 2574 | 1-2573 and 2575-8376 |
| 2575 | 1-2574 and 2576-8376 |
| 2576 | 1-2575 and 2577-8376 |
| 2577 | 1-2576 and 2578-8376 |
| 2578 | 1-2577 and 2579-8376 |
| 2579 | 1-2578 and 2580-8376 |
| 2580 | 1-2579 and 2581-8376 |
| 2581 | 1-2580 and 2582-8376 |
| 2582 | 1-2581 and 2583-8376 |
| 2583 | 1-2582 and 2584-8376 |
| 2584 | 1-2583 and 2585-8376 |
| 2585 | 1-2584 and 2586-8376 |
| 2586 | 1-2585 and 2587-8376 |
| 2587 | 1-2586 and 2588-8376 |
| 2588 | 1-2587 and 2589-8376 |
| 2589 | 1-2588 and 2590-8376 |
| 2590 | 1-2589 and 2591-8376 |
| 2591 | 1-2590 and 2592-8376 |
| 2592 | 1-2591 and 2593-8376 |
| 2593 | 1-2592 and 2594-8376 |
| 2594 | 1-2593 and 2595-8376 |
| 2595 | 1-2594 and 2596-8376 |
| 2596 | 1-2595 and 2597-8376 |
| 2597 | 1-2596 and 2598-8376 |
| 2598 | 1-2597 and 2599-8376 |
| 2599 | 1-2598 and 2600-8376 |

| First | Second |
|---|---|
| 2600 | 1-2599 and 2601-8376 |
| 2601 | 1-2600 and 2602-8376 |
| 2602 | 1-2601 and 2603-8376 |
| 2603 | 1-2602 and 2604-8376 |
| 2604 | 1-2603 and 2605-8376 |
| 2605 | 1-2604 and 2606-8376 |
| 2606 | 1-2605 and 2607-8376 |
| 2607 | 1-2606 and 2608-8376 |
| 2608 | 1-2607 and 2609-8376 |
| 2609 | 1-2608 and 2610-8376 |
| 2610 | 1-2609 and 2611-8376 |
| 2611 | 1-2610 and 2612-8376 |
| 2612 | 1-2611 and 2613-8376 |
| 2613 | 1-2612 and 2614-8376 |
| 2614 | 1-2613 and 2615-8376 |
| 2615 | 1-2614 and 2616-8376 |
| 2616 | 1-2615 and 2617-8376 |
| 2617 | 1-2616 and 2618-8376 |
| 2618 | 1-2617 and 2619-8376 |
| 2619 | 1-2618 and 2620-8376 |
| 2620 | 1-2619 and 2621-8376 |
| 2621 | 1-2620 and 2622-8376 |
| 2622 | 1-2621 and 2623-8376 |
| 2623 | 1-2622 and 2624-8376 |
| 2624 | 1-2623 and 2625-8376 |
| 2625 | 1-2624 and 2626-8376 |
| 2626 | 1-2625 and 2627-8376 |
| 2627 | 1-2626 and 2628-8376 |
| 2628 | 1-2627 and 2629-8376 |
| 2629 | 1-2628 and 2630-8376 |
| 2630 | 1-2629 and 2631-8376 |
| 2631 | 1-2630 and 2632-8376 |
| 2632 | 1-2631 and 2633-8376 |
| 2633 | 1-2632 and 2634-8376 |
| 2634 | 1-2633 and 2635-8376 |
| 2635 | 1-2634 and 2636-8376 |
| 2636 | 1-2635 and 2637-8376 |
| 2637 | 1-2636 and 2638-8376 |
| 2638 | 1-2637 and 2639-8376 |
| 2639 | 1-2638 and 2640-8376 |
| 2640 | 1-2639 and 2641-8376 |
| 2641 | 1-2640 and 2642-8376 |
| 2642 | 1-2641 and 2643-8376 |
| 2643 | 1-2642 and 2644-8376 |
| 2644 | 1-2643 and 2645-8376 |
| 2645 | 1-2644 and 2646-8376 |
| 2646 | 1-2645 and 2647-8376 |
| 2647 | 1-2646 and 2648-8376 |
| 2648 | 1-2647 and 2649-8376 |
| 2649 | 1-2648 and 2650-8376 |
| 2650 | 1-2649 and 2651-8376 |
| 2651 | 1-2650 and 2652-8376 |
| 2652 | 1-2651 and 2653-8376 |
| 2653 | 1-2652 and 2654-8376 |
| 2654 | 1-2653 and 2655-8376 |
| 2655 | 1-2654 and 2656-8376 |
| 2656 | 1-2655 and 2657-8376 |
| 2657 | 1-2656 and 2658-8376 |
| 2658 | 1-2657 and 2659-8376 |
| 2659 | 1-2658 and 2660-8376 |
| 2660 | 1-2659 and 2661-8376 |
| 2661 | 1-2660 and 2662-8376 |
| 2662 | 1-2661 and 2663-8376 |
| 2663 | 1-2662 and 2664-8376 |
| 2664 | 1-2663 and 2665-8376 |
| 2665 | 1-2664 and 2666-8376 |
| 2666 | 1-2665 and 2667-8376 |
| 2667 | 1-2666 and 2668-8376 |
| 2668 | 1-2667 and 2669-8376 |
| 2669 | 1-2668 and 2670-8376 |
| 2670 | 1-2669 and 2671-8376 |
| 2671 | 1-2670 and 2672-8376 |
| 2672 | 1-2671 and 2673-8376 |
| 2673 | 1-2672 and 2674-8376 |
| 2674 | 1-2673 and 2675-8376 |
| 2675 | 1-2674 and 2676-8376 |
| 2676 | 1-2675 and 2677-8376 |
| 2677 | 1-2676 and 2678-8376 |
| 2678 | 1-2677 and 2679-8376 |
| 2679 | 1-2678 and 2680-8376 |
| 2680 | 1-2679 and 2681-8376 |
| 2681 | 1-2680 and 2682-8376 |
| 2682 | 1-2681 and 2683-8376 |
| 2683 | 1-2682 and 2684-8376 |
| 2684 | 1-2683 and 2685-8376 |
| 2685 | 1-2684 and 2686-8376 |
| 2686 | 1-2685 and 2687-8376 |
| 2687 | 1-2686 and 2688-8376 |
| 2688 | 1-2687 and 2689-8376 |
| 2689 | 1-2688 and 2690-8376 |
| 2690 | 1-2689 and 2691-8376 |
| 2691 | 1-2690 and 2692-8376 |
| 2692 | 1-2691 and 2693-8376 |
| 2693 | 1-2692 and 2694-8376 |
| 2694 | 1-2693 and 2695-8376 |
| 2695 | 1-2694 and 2696-8376 |
| 2696 | 1-2695 and 2697-8376 |
| 2697 | 1-2696 and 2698-8376 |
| 2698 | 1-2697 and 2699-8376 |
| 2699 | 1-2698 and 2700-8376 |
| 2700 | 1-2699 and 2701-8376 |
| 2701 | 1-2700 and 2702-8376 |
| 2702 | 1-2701 and 2703-8376 |
| 2703 | 1-2702 and 2704-8376 |
| 2704 | 1-2703 and 2705-8376 |
| 2705 | 1-2704 and 2706-8376 |
| 2706 | 1-2705 and 2707-8376 |
| 2707 | 1-2706 and 2708-8376 |
| 2708 | 1-2707 and 2709-8376 |
| 2709 | 1-2708 and 2710-8376 |
| 2710 | 1-2709 and 2711-8376 |
| 2711 | 1-2710 and 2712-8376 |
| 2712 | 1-2711 and 2713-8376 |
| 2713 | 1-2712 and 2714-8376 |
| 2714 | 1-2713 and 2715-8376 |
| 2715 | 1-2714 and 2716-8376 |
| 2716 | 1-2715 and 2717-8376 |
| 2717 | 1-2716 and 2718-8376 |
| 2718 | 1-2717 and 2719-8376 |
| 2719 | 1-2718 and 2720-8376 |
| 2720 | 1-2719 and 2721-8376 |
| 2721 | 1-2720 and 2722-8376 |
| 2722 | 1-2721 and 2723-8376 |
| 2723 | 1-2722 and 2724-8376 |
| 2724 | 1-2723 and 2725-8376 |
| 2725 | 1-2724 and 2726-8376 |
| 2726 | 1-2725 and 2727-8376 |
| 2727 | 1-2726 and 2728-8376 |
| 2728 | 1-2727 and 2729-8376 |
| 2729 | 1-2728 and 2730-8376 |
| 2730 | 1-2729 and 2731-8376 |
| 2731 | 1-2730 and 2732-8376 |
| 2732 | 1-2731 and 2733-8376 |
| 2733 | 1-2732 and 2734-8376 |
| 2734 | 1-2733 and 2735-8376 |
| 2735 | 1-2734 and 2736-8376 |
| 2736 | 1-2735 and 2737-8376 |
| 2737 | 1-2736 and 2738-8376 |
| 2738 | 1-2737 and 2739-8376 |
| 2739 | 1-2738 and 2740-8376 |
| 2740 | 1-2739 and 2741-8376 |
| 2741 | 1-2740 and 2742-8376 |
| 2742 | 1-2741 and 2743-8376 |
| 2743 | 1-2742 and 2744-8376 |
| 2744 | 1-2743 and 2745-8376 |
| 2745 | 1-2744 and 2746-8376 |
| 2746 | 1-2745 and 2747-8376 |
| 2747 | 1-2746 and 2748-8376 |
| 2748 | 1-2747 and 2749-8376 |
| 2749 | 1-2748 and 2750-8376 |
| 2750 | 1-2749 and 2751-8376 |
| 2751 | 1-2750 and 2752-8376 |
| 2752 | 1-2751 and 2753-8376 |
| 2753 | 1-2752 and 2754-8376 |

| First | Second |
|---|---|
| 2754 | 1-2753 and 2755-8376 |
| 2755 | 1-2754 and 2756-8376 |
| 2756 | 1-2755 and 2757-8376 |
| 2757 | 1-2756 and 2758-8376 |
| 2758 | 1-2757 and 2759-8376 |
| 2759 | 1-2758 and 2760-8376 |
| 2760 | 1-2759 and 2761-8376 |
| 2761 | 1-2760 and 2762-8376 |
| 2762 | 1-2761 and 2763-8376 |
| 2763 | 1-2762 and 2764-8376 |
| 2764 | 1-2763 and 2765-8376 |
| 2765 | 1-2764 and 2766-8376 |
| 2766 | 1-2765 and 2767-8376 |
| 2767 | 1-2766 and 2768-8376 |
| 2768 | 1-2767 and 2769-8376 |
| 2769 | 1-2768 and 2770-8376 |
| 2770 | 1-2769 and 2771-8376 |
| 2771 | 1-2770 and 2772-8376 |
| 2772 | 1-2771 and 2773-8376 |
| 2773 | 1-2772 and 2774-8376 |
| 2774 | 1-2773 and 2775-8376 |
| 2775 | 1-2774 and 2776-8376 |
| 2776 | 1-2775 and 2777-8376 |
| 2777 | 1-2776 and 2778-8376 |
| 2778 | 1-2777 and 2779-8376 |
| 2779 | 1-2778 and 2780-8376 |
| 2780 | 1-2779 and 2781-8376 |
| 2781 | 1-2780 and 2782-8376 |
| 2782 | 1-2781 and 2783-8376 |
| 2783 | 1-2782 and 2784-8376 |
| 2784 | 1-2783 and 2785-8376 |
| 2785 | 1-2784 and 2786-8376 |
| 2786 | 1-2785 and 2787-8376 |
| 2787 | 1-2786 and 2788-8376 |
| 2788 | 1-2787 and 2789-8376 |
| 2789 | 1-2788 and 2790-8376 |
| 2790 | 1-2789 and 2791-8376 |
| 2791 | 1-2790 and 2792-8376 |
| 2792 | 1-2791 and 2793-8376 |
| 2793 | 1-2792 and 2794-8376 |
| 2794 | 1-2793 and 2795-8376 |
| 2795 | 1-2794 and 2796-8376 |
| 2796 | 1-2795 and 2797-8376 |
| 2797 | 1-2796 and 2798-8376 |
| 2798 | 1-2797 and 2799-8376 |
| 2799 | 1-2798 and 2800-8376 |
| 2800 | 1-2799 and 2801-8376 |
| 2801 | 1-2800 and 2802-8376 |
| 2802 | 1-2801 and 2803-8376 |
| 2803 | 1-2802 and 2804-8376 |
| 2804 | 1-2803 and 2805-8376 |
| 2805 | 1-2804 and 2806-8376 |
| 2806 | 1-2805 and 2807-8376 |
| 2807 | 1-2806 and 2808-8376 |
| 2808 | 1-2807 and 2809-8376 |
| 2809 | 1-2808 and 2810-8376 |
| 2810 | 1-2809 and 2811-8376 |
| 2811 | 1-2810 and 2812-8376 |
| 2812 | 1-2811 and 2813-8376 |
| 2813 | 1-2812 and 2814-8376 |
| 2814 | 1-2813 and 2815-8376 |
| 2815 | 1-2814 and 2816-8376 |
| 2816 | 1-2815 and 2817-8376 |
| 2817 | 1-2816 and 2818-8376 |
| 2818 | 1-2817 and 2819-8376 |
| 2819 | 1-2818 and 2820-8376 |
| 2820 | 1-2819 and 2821-8376 |
| 2821 | 1-2820 and 2822-8376 |
| 2822 | 1-2821 and 2823-8376 |
| 2823 | 1-2822 and 2824-8376 |
| 2824 | 1-2823 and 2825-8376 |
| 2825 | 1-2824 and 2826-8376 |
| 2826 | 1-2825 and 2827-8376 |
| 2827 | 1-2826 and 2828-8376 |
| 2828 | 1-2827 and 2829-8376 |
| 2829 | 1-2828 and 2830-8376 |
| 2830 | 1-2829 and 2831-8376 |
| 2831 | 1-2830 and 2832-8376 |
| 2832 | 1-2831 and 2833-8376 |
| 2833 | 1-2832 and 2834-8376 |
| 2834 | 1-2833 and 2835-8376 |
| 2835 | 1-2834 and 2836-8376 |
| 2836 | 1-2835 and 2837-8376 |
| 2837 | 1-2836 and 2838-8376 |
| 2838 | 1-2837 and 2839-8376 |
| 2839 | 1-2838 and 2840-8376 |
| 2840 | 1-2839 and 2841-8376 |
| 2841 | 1-2840 and 2842-8376 |
| 2842 | 1-2841 and 2843-8376 |
| 2843 | 1-2842 and 2844-8376 |
| 2844 | 1-2843 and 2845-8376 |
| 2845 | 1-2844 and 2846-8376 |
| 2846 | 1-2845 and 2847-8376 |
| 2847 | 1-2846 and 2848-8376 |
| 2848 | 1-2847 and 2849-8376 |
| 2849 | 1-2848 and 2850-8376 |
| 2850 | 1-2849 and 2851-8376 |
| 2851 | 1-2850 and 2852-8376 |
| 2852 | 1-2851 and 2853-8376 |
| 2853 | 1-2852 and 2854-8376 |
| 2854 | 1-2853 and 2855-8376 |
| 2855 | 1-2854 and 2856-8376 |
| 2856 | 1-2855 and 2857-8376 |
| 2857 | 1-2856 and 2858-8376 |
| 2858 | 1-2857 and 2859-8376 |
| 2859 | 1-2858 and 2860-8376 |
| 2860 | 1-2859 and 2861-8376 |
| 2861 | 1-2860 and 2862-8376 |
| 2862 | 1-2861 and 2863-8376 |
| 2863 | 1-2862 and 2864-8376 |
| 2864 | 1-2863 and 2865-8376 |
| 2865 | 1-2864 and 2866-8376 |
| 2866 | 1-2865 and 2867-8376 |
| 2867 | 1-2866 and 2868-8376 |
| 2868 | 1-2867 and 2869-8376 |
| 2869 | 1-2868 and 2870-8376 |
| 2870 | 1-2869 and 2871-8376 |
| 2871 | 1-2870 and 2872-8376 |
| 2872 | 1-2871 and 2873-8376 |
| 2873 | 1-2872 and 2874-8376 |
| 2874 | 1-2873 and 2875-8376 |
| 2875 | 1-2874 and 2876-8376 |
| 2876 | 1-2875 and 2877-8376 |
| 2877 | 1-2876 and 2878-8376 |
| 2878 | 1-2877 and 2879-8376 |
| 2879 | 1-2878 and 2880-8376 |
| 2880 | 1-2879 and 2881-8376 |
| 2881 | 1-2880 and 2882-8376 |
| 2882 | 1-2881 and 2883-8376 |
| 2883 | 1-2882 and 2884-8376 |
| 2884 | 1-2883 and 2885-8376 |
| 2885 | 1-2884 and 2886-8376 |
| 2886 | 1-2885 and 2887-8376 |
| 2887 | 1-2886 and 2888-8376 |
| 2888 | 1-2887 and 2889-8376 |
| 2889 | 1-2888 and 2890-8376 |
| 2890 | 1-2889 and 2891-8376 |
| 2891 | 1-2890 and 2892-8376 |
| 2892 | 1-2891 and 2893-8376 |
| 2893 | 1-2892 and 2894-8376 |
| 2894 | 1-2893 and 2895-8376 |
| 2895 | 1-2894 and 2896-8376 |
| 2896 | 1-2895 and 2897-8376 |
| 2897 | 1-2896 and 2898-8376 |
| 2898 | 1-2897 and 2899-8376 |
| 2899 | 1-2898 and 2900-8376 |
| 2900 | 1-2899 and 2901-8376 |
| 2901 | 1-2900 and 2902-8376 |
| 2902 | 1-2901 and 2903-8376 |
| 2903 | 1-2902 and 2904-8376 |
| 2904 | 1-2903 and 2905-8376 |
| 2905 | 1-2904 and 2906-8376 |
| 2906 | 1-2905 and 2907-8376 |
| 2907 | 1-2906 and 2908-8376 |

| First | Second |
|---|---|
| 2908 | 1-2907 and 2909-8376 |
| 2909 | 1-2908 and 2910-8376 |
| 2910 | 1-2909 and 2911-8376 |
| 2911 | 1-2910 and 2912-8376 |
| 2912 | 1-2911 and 2913-8376 |
| 2913 | 1-2912 and 2914-8376 |
| 2914 | 1-2913 and 2915-8376 |
| 2915 | 1-2914 and 2916-8376 |
| 2916 | 1-2915 and 2917-8376 |
| 2917 | 1-2916 and 2918-8376 |
| 2918 | 1-2917 and 2919-8376 |
| 2919 | 1-2918 and 2920-8376 |
| 2920 | 1-2919 and 2921-8376 |
| 2921 | 1-2920 and 2922-8376 |
| 2922 | 1-2921 and 2923-8376 |
| 2923 | 1-2922 and 2924-8376 |
| 2924 | 1-2923 and 2925-8376 |
| 2925 | 1-2924 and 2926-8376 |
| 2926 | 1-2925 and 2927-8376 |
| 2927 | 1-2926 and 2928-8376 |
| 2928 | 1-2927 and 2929-8376 |
| 2929 | 1-2928 and 2930-8376 |
| 2930 | 1-2929 and 2931-8376 |
| 2931 | 1-2930 and 2932-8376 |
| 2932 | 1-2931 and 2933-8376 |
| 2933 | 1-2932 and 2934-8376 |
| 2934 | 1-2933 and 2935-8376 |
| 2935 | 1-2934 and 2936-8376 |
| 2936 | 1-2935 and 2937-8376 |
| 2937 | 1-2936 and 2938-8376 |
| 2938 | 1-2937 and 2939-8376 |
| 2939 | 1-2938 and 2940-8376 |
| 2940 | 1-2939 and 2941-8376 |
| 2941 | 1-2940 and 2942-8376 |
| 2942 | 1-2941 and 2943-8376 |
| 2943 | 1-2942 and 2944-8376 |
| 2944 | 1-2943 and 2945-8376 |
| 2945 | 1-2944 and 2946-8376 |
| 2946 | 1-2945 and 2947-8376 |
| 2947 | 1-2946 and 2948-8376 |
| 2948 | 1-2947 and 2949-8376 |
| 2949 | 1-2948 and 2950-8376 |
| 2950 | 1-2949 and 2951-8376 |
| 2951 | 1-2950 and 2952-8376 |
| 2952 | 1-2951 and 2953-8376 |
| 2953 | 1-2952 and 2954-8376 |
| 2954 | 1-2953 and 2955-8376 |
| 2955 | 1-2954 and 2956-8376 |
| 2956 | 1-2955 and 2957-8376 |
| 2957 | 1-2956 and 2958-8376 |
| 2958 | 1-2957 and 2959-8376 |
| 2959 | 1-2958 and 2960-8376 |
| 2960 | 1-2959 and 2961-8376 |
| 2961 | 1-2960 and 2962-8376 |
| 2962 | 1-2961 and 2963-8376 |
| 2963 | 1-2962 and 2964-8376 |
| 2964 | 1-2963 and 2965-8376 |
| 2965 | 1-2964 and 2966-8376 |
| 2966 | 1-2965 and 2967-8376 |
| 2967 | 1-2966 and 2968-8376 |
| 2968 | 1-2967 and 2969-8376 |
| 2969 | 1-2968 and 2970-8376 |
| 2970 | 1-2969 and 2971-8376 |
| 2971 | 1-2970 and 2972-8376 |
| 2972 | 1-2971 and 2973-8376 |
| 2973 | 1-2972 and 2974-8376 |
| 2974 | 1-2973 and 2975-8376 |
| 2975 | 1-2974 and 2976-8376 |
| 2976 | 1-2975 and 2977-8376 |
| 2977 | 1-2976 and 2978-8376 |
| 2978 | 1-2977 and 2979-8376 |
| 2979 | 1-2978 and 2980-8376 |
| 2980 | 1-2979 and 2981-8376 |
| 2981 | 1-2980 and 2982-8376 |
| 2982 | 1-2981 and 2983-8376 |
| 2983 | 1-2982 and 2984-8376 |
| 2984 | 1-2983 and 2985-8376 |
| 2985 | 1-2984 and 2986-8376 |
| 2986 | 1-2985 and 2987-8376 |
| 2987 | 1-2986 and 2988-8376 |
| 2988 | 1-2987 and 2989-8376 |
| 2989 | 1-2988 and 2990-8376 |
| 2990 | 1-2989 and 2991-8376 |
| 2991 | 1-2990 and 2992-8376 |
| 2992 | 1-2991 and 2993-8376 |
| 2993 | 1-2992 and 2994-8376 |
| 2994 | 1-2993 and 2995-8376 |
| 2995 | 1-2994 and 2996-8376 |
| 2996 | 1-2995 and 2997-8376 |
| 2997 | 1-2996 and 2998-8376 |
| 2998 | 1-2997 and 2999-8376 |
| 2999 | 1-2998 and 3000-8376 |
| 3000 | 1-2999 and 3001-8376 |
| 3001 | 1-3000 and 3002-8376 |
| 3002 | 1-3001 and 3003-8376 |
| 3003 | 1-3002 and 3004-8376 |
| 3004 | 1-3003 and 3005-8376 |
| 3005 | 1-3004 and 3006-8376 |
| 3006 | 1-3005 and 3007-8376 |
| 3007 | 1-3006 and 3008-8376 |
| 3008 | 1-3007 and 3009-8376 |
| 3009 | 1-3008 and 3010-8376 |
| 3010 | 1-3009 and 3011-8376 |
| 3011 | 1-3010 and 3012-8376 |
| 3012 | 1-3011 and 3013-8376 |
| 3013 | 1-3012 and 3014-8376 |
| 3014 | 1-3013 and 3015-8376 |
| 3015 | 1-3014 and 3016-8376 |
| 3016 | 1-3015 and 3017-8376 |
| 3017 | 1-3016 and 3018-8376 |
| 3018 | 1-3017 and 3019-8376 |
| 3019 | 1-3018 and 3020-8376 |
| 3020 | 1-3019 and 3021-8376 |
| 3021 | 1-3020 and 3022-8376 |
| 3022 | 1-3021 and 3023-8376 |
| 3023 | 1-3022 and 3024-8376 |
| 3024 | 1-3023 and 3025-8376 |
| 3025 | 1-3024 and 3026-8376 |
| 3026 | 1-3025 and 3027-8376 |
| 3027 | 1-3026 and 3028-8376 |
| 3028 | 1-3027 and 3029-8376 |
| 3029 | 1-3028 and 3030-8376 |
| 3030 | 1-3029 and 3031-8376 |
| 3031 | 1-3030 and 3032-8376 |
| 3032 | 1-3031 and 3033-8376 |
| 3033 | 1-3032 and 3034-8376 |
| 3034 | 1-3033 and 3035-8376 |
| 3035 | 1-3034 and 3036-8376 |
| 3036 | 1-3035 and 3037-8376 |
| 3037 | 1-3036 and 3038-8376 |
| 3038 | 1-3037 and 3039-8376 |
| 3039 | 1-3038 and 3040-8376 |
| 3040 | 1-3039 and 3041-8376 |
| 3041 | 1-3040 and 3042-8376 |
| 3042 | 1-3041 and 3043-8376 |
| 3043 | 1-3042 and 3044-8376 |
| 3044 | 1-3043 and 3045-8376 |
| 3045 | 1-3044 and 3046-8376 |
| 3046 | 1-3045 and 3047-8376 |
| 3047 | 1-3046 and 3048-8376 |
| 3048 | 1-3047 and 3049-8376 |
| 3049 | 1-3048 and 3050-8376 |
| 3050 | 1-3049 and 3051-8376 |
| 3051 | 1-3050 and 3052-8376 |
| 3052 | 1-3051 and 3053-8376 |
| 3053 | 1-3052 and 3054-8376 |
| 3054 | 1-3053 and 3055-8376 |
| 3055 | 1-3054 and 3056-8376 |
| 3056 | 1-3055 and 3057-8376 |
| 3057 | 1-3056 and 3058-8376 |
| 3058 | 1-3057 and 3059-8376 |
| 3059 | 1-3058 and 3060-8376 |
| 3060 | 1-3059 and 3061-8376 |
| 3061 | 1-3060 and 3062-8376 |

| First | Second |
|---|---|
| 3062 | 1-3061 and 3063-8376 |
| 3063 | 1-3062 and 3064-8376 |
| 3064 | 1-3063 and 3065-8376 |
| 3065 | 1-3064 and 3066-8376 |
| 3066 | 1-3065 and 3067-8376 |
| 3067 | 1-3066 and 3068-8376 |
| 3068 | 1-3067 and 3069-8376 |
| 3069 | 1-3068 and 3070-8376 |
| 3070 | 1-3069 and 3071-8376 |
| 3071 | 1-3070 and 3072-8376 |
| 3072 | 1-3071 and 3073-8376 |
| 3073 | 1-3072 and 3074-8376 |
| 3074 | 1-3073 and 3075-8376 |
| 3075 | 1-3074 and 3076-8376 |
| 3076 | 1-3075 and 3077-8376 |
| 3077 | 1-3076 and 3078-8376 |
| 3078 | 1-3077 and 3079-8376 |
| 3079 | 1-3078 and 3080-8376 |
| 3080 | 1-3079 and 3081-8376 |
| 3081 | 1-3080 and 3082-8376 |
| 3082 | 1-3081 and 3083-8376 |
| 3083 | 1-3082 and 3084-8376 |
| 3084 | 1-3083 and 3085-8376 |
| 3085 | 1-3084 and 3086-8376 |
| 3086 | 1-3085 and 3087-8376 |
| 3087 | 1-3086 and 3088-8376 |
| 3088 | 1-3087 and 3089-8376 |
| 3089 | 1-3088 and 3090-8376 |
| 3090 | 1-3089 and 3091-8376 |
| 3091 | 1-3090 and 3092-8376 |
| 3092 | 1-3091 and 3093-8376 |
| 3093 | 1-3092 and 3094-8376 |
| 3094 | 1-3093 and 3095-8376 |
| 3095 | 1-3094 and 3096-8376 |
| 3096 | 1-3095 and 3097-8376 |
| 3097 | 1-3096 and 3098-8376 |
| 3098 | 1-3097 and 3099-8376 |
| 3099 | 1-3098 and 3100-8376 |
| 3100 | 1-3099 and 3101-8376 |
| 3101 | 1-3100 and 3102-8376 |
| 3102 | 1-3101 and 3103-8376 |
| 3103 | 1-3102 and 3104-8376 |
| 3104 | 1-3103 and 3105-8376 |
| 3105 | 1-3104 and 3106-8376 |
| 3106 | 1-3105 and 3107-8376 |
| 3107 | 1-3106 and 3108-8376 |
| 3108 | 1-3107 and 3109-8376 |
| 3109 | 1-3108 and 3110-8376 |
| 3110 | 1-3109 and 3111-8376 |
| 3111 | 1-3110 and 3112-8376 |
| 3112 | 1-3111 and 3113-8376 |
| 3113 | 1-3112 and 3114-8376 |
| 3114 | 1-3113 and 3115-8376 |
| 3115 | 1-3114 and 3116-8376 |
| 3116 | 1-3115 and 3117-8376 |
| 3117 | 1-3116 and 3118-8376 |
| 3118 | 1-3117 and 3119-8376 |
| 3119 | 1-3118 and 3120-8376 |
| 3120 | 1-3119 and 3121-8376 |
| 3121 | 1-3120 and 3122-8376 |
| 3122 | 1-3121 and 3123-8376 |
| 3123 | 1-3122 and 3124-8376 |
| 3124 | 1-3123 and 3125-8376 |
| 3125 | 1-3124 and 3126-8376 |
| 3126 | 1-3125 and 3127-8376 |
| 3127 | 1-3126 and 3128-8376 |
| 3128 | 1-3127 and 3129-8376 |
| 3129 | 1-3128 and 3130-8376 |
| 3130 | 1-3129 and 3131-8376 |
| 3131 | 1-3130 and 3132-8376 |
| 3132 | 1-3131 and 3133-8376 |
| 3133 | 1-3132 and 3134-8376 |
| 3134 | 1-3133 and 3135-8376 |
| 3135 | 1-3134 and 3136-8376 |
| 3136 | 1-3135 and 3137-8376 |
| 3137 | 1-3136 and 3138-8376 |
| 3138 | 1-3137 and 3139-8376 |
| 3139 | 1-3138 and 3140-8376 |
| 3140 | 1-3139 and 3141-8376 |
| 3141 | 1-3140 and 3142-8376 |
| 3142 | 1-3141 and 3143-8376 |
| 3143 | 1-3142 and 3144-8376 |
| 3144 | 1-3143 and 3145-8376 |
| 3145 | 1-3144 and 3146-8376 |
| 3146 | 1-3145 and 3147-8376 |
| 3147 | 1-3146 and 3148-8376 |
| 3148 | 1-3147 and 3149-8376 |
| 3149 | 1-3148 and 3150-8376 |
| 3150 | 1-3149 and 3151-8376 |
| 3151 | 1-3150 and 3152-8376 |
| 3152 | 1-3151 and 3153-8376 |
| 3153 | 1-3152 and 3154-8376 |
| 3154 | 1-3153 and 3155-8376 |
| 3155 | 1-3154 and 3156-8376 |
| 3156 | 1-3155 and 3157-8376 |
| 3157 | 1-3156 and 3158-8376 |
| 3158 | 1-3157 and 3159-8376 |
| 3159 | 1-3158 and 3160-8376 |
| 3160 | 1-3159 and 3161-8376 |
| 3161 | 1-3160 and 3162-8376 |
| 3162 | 1-3161 and 3163-8376 |
| 3163 | 1-3162 and 3164-8376 |
| 3164 | 1-3163 and 3165-8376 |
| 3165 | 1-3164 and 3166-8376 |
| 3166 | 1-3165 and 3167-8376 |
| 3167 | 1-3166 and 3168-8376 |
| 3168 | 1-3167 and 3169-8376 |
| 3169 | 1-3168 and 3170-8376 |
| 3170 | 1-3169 and 3171-8376 |
| 3171 | 1-3170 and 3172-8376 |
| 3172 | 1-3171 and 3173-8376 |
| 3173 | 1-3172 and 3174-8376 |
| 3174 | 1-3173 and 3175-8376 |
| 3175 | 1-3174 and 3176-8376 |
| 3176 | 1-3175 and 3177-8376 |
| 3177 | 1-3176 and 3178-8376 |
| 3178 | 1-3177 and 3179-8376 |
| 3179 | 1-3178 and 3180-8376 |
| 3180 | 1-3179 and 3181-8376 |
| 3181 | 1-3180 and 3182-8376 |
| 3182 | 1-3181 and 3183-8376 |
| 3183 | 1-3182 and 3184-8376 |
| 3184 | 1-3183 and 3185-8376 |
| 3185 | 1-3184 and 3186-8376 |
| 3186 | 1-3185 and 3187-8376 |
| 3187 | 1-3186 and 3188-8376 |
| 3188 | 1-3187 and 3189-8376 |
| 3189 | 1-3188 and 3190-8376 |
| 3190 | 1-3189 and 3191-8376 |
| 3191 | 1-3190 and 3192-8376 |
| 3192 | 1-3191 and 3193-8376 |
| 3193 | 1-3192 and 3194-8376 |
| 3194 | 1-3193 and 3195-8376 |
| 3195 | 1-3194 and 3196-8376 |
| 3196 | 1-3195 and 3197-8376 |
| 3197 | 1-3196 and 3198-8376 |
| 3198 | 1-3197 and 3199-8376 |
| 3199 | 1-3198 and 3200-8376 |
| 3200 | 1-3199 and 3201-8376 |
| 3201 | 1-3200 and 3202-8376 |
| 3202 | 1-3201 and 3203-8376 |
| 3203 | 1-3202 and 3204-8376 |
| 3204 | 1-3203 and 3205-8376 |
| 3205 | 1-3204 and 3206-8376 |
| 3206 | 1-3205 and 3207-8376 |
| 3207 | 1-3206 and 3208-8376 |
| 3208 | 1-3207 and 3209-8376 |
| 3209 | 1-3208 and 3210-8376 |
| 3210 | 1-3209 and 3211-8376 |
| 3211 | 1-3210 and 3212-8376 |
| 3212 | 1-3211 and 3213-8376 |
| 3213 | 1-3212 and 3214-8376 |
| 3214 | 1-3213 and 3215-8376 |
| 3215 | 1-3214 and 3216-8376 |

| First | Second |
|---|---|
| 3216 | 1-3215 and 3217-8376 |
| 3217 | 1-3216 and 3218-8376 |
| 3218 | 1-3217 and 3219-8376 |
| 3219 | 1-3218 and 3220-8376 |
| 3220 | 1-3219 and 3221-8376 |
| 3221 | 1-3220 and 3222-8376 |
| 3222 | 1-3221 and 3223-8376 |
| 3223 | 1-3222 and 3224-8376 |
| 3224 | 1-3223 and 3225-8376 |
| 3225 | 1-3224 and 3226-8376 |
| 3226 | 1-3225 and 3227-8376 |
| 3227 | 1-3226 and 3228-8376 |
| 3228 | 1-3227 and 3229-8376 |
| 3229 | 1-3228 and 3230-8376 |
| 3230 | 1-3229 and 3231-8376 |
| 3231 | 1-3230 and 3232-8376 |
| 3232 | 1-3231 and 3233-8376 |
| 3233 | 1-3232 and 3234-8376 |
| 3234 | 1-3233 and 3235-8376 |
| 3235 | 1-3234 and 3236-8376 |
| 3236 | 1-3235 and 3237-8376 |
| 3237 | 1-3236 and 3238-8376 |
| 3238 | 1-3237 and 3239-8376 |
| 3239 | 1-3238 and 3240-8376 |
| 3240 | 1-3239 and 3241-8376 |
| 3241 | 1-3240 and 3242-8376 |
| 3242 | 1-3241 and 3243-8376 |
| 3243 | 1-3242 and 3244-8376 |
| 3244 | 1-3243 and 3245-8376 |
| 3245 | 1-3244 and 3246-8376 |
| 3246 | 1-3245 and 3247-8376 |
| 3247 | 1-3246 and 3248-8376 |
| 3248 | 1-3247 and 3249-8376 |
| 3249 | 1-3248 and 3250-8376 |
| 3250 | 1-3249 and 3251-8376 |
| 3251 | 1-3250 and 3252-8376 |
| 3252 | 1-3251 and 3253-8376 |
| 3253 | 1-3252 and 3254-8376 |
| 3254 | 1-3253 and 3255-8376 |
| 3255 | 1-3254 and 3256-8376 |
| 3256 | 1-3255 and 3257-8376 |
| 3257 | 1-3256 and 3258-8376 |
| 3258 | 1-3257 and 3259-8376 |
| 3259 | 1-3258 and 3260-8376 |
| 3260 | 1-3259 and 3261-8376 |
| 3261 | 1-3260 and 3262-8376 |
| 3262 | 1-3261 and 3263-8376 |
| 3263 | 1-3262 and 3264-8376 |
| 3264 | 1-3263 and 3265-8376 |
| 3265 | 1-3264 and 3266-8376 |
| 3266 | 1-3265 and 3267-8376 |
| 3267 | 1-3266 and 3268-8376 |
| 3268 | 1-3267 and 3269-8376 |
| 3269 | 1-3268 and 3270-8376 |
| 3270 | 1-3269 and 3271-8376 |
| 3271 | 1-3270 and 3272-8376 |
| 3272 | 1-3271 and 3273-8376 |
| 3273 | 1-3272 and 3274-8376 |
| 3274 | 1-3273 and 3275-8376 |
| 3275 | 1-3274 and 3276-8376 |
| 3276 | 1-3275 and 3277-8376 |
| 3277 | 1-3276 and 3278-8376 |
| 3278 | 1-3277 and 3279-8376 |
| 3279 | 1-3278 and 3280-8376 |
| 3280 | 1-3279 and 3281-8376 |
| 3281 | 1-3280 and 3282-8376 |
| 3282 | 1-3281 and 3283-8376 |
| 3283 | 1-3282 and 3284-8376 |
| 3284 | 1-3283 and 3285-8376 |
| 3285 | 1-3284 and 3286-8376 |
| 3286 | 1-3285 and 3287-8376 |
| 3287 | 1-3286 and 3288-8376 |
| 3288 | 1-3287 and 3289-8376 |
| 3289 | 1-3288 and 3290-8376 |
| 3290 | 1-3289 and 3291-8376 |
| 3291 | 1-3290 and 3292-8376 |
| 3292 | 1-3291 and 3293-8376 |
| 3293 | 1-3292 and 3294-8376 |
| 3294 | 1-3293 and 3295-8376 |
| 3295 | 1-3294 and 3296-8376 |
| 3296 | 1-3295 and 3297-8376 |
| 3297 | 1-3296 and 3298-8376 |
| 3298 | 1-3297 and 3299-8376 |
| 3299 | 1-3298 and 3300-8376 |
| 3300 | 1-3299 and 3301-8376 |
| 3301 | 1-3300 and 3302-8376 |
| 3302 | 1-3301 and 3303-8376 |
| 3303 | 1-3302 and 3304-8376 |
| 3304 | 1-3303 and 3305-8376 |
| 3305 | 1-3304 and 3306-8376 |
| 3306 | 1-3305 and 3307-8376 |
| 3307 | 1-3306 and 3308-8376 |
| 3308 | 1-3307 and 3309-8376 |
| 3309 | 1-3308 and 3310-8376 |
| 3310 | 1-3309 and 3311-8376 |
| 3311 | 1-3310 and 3312-8376 |
| 3312 | 1-3311 and 3313-8376 |
| 3313 | 1-3312 and 3314-8376 |
| 3314 | 1-3313 and 3315-8376 |
| 3315 | 1-3314 and 3316-8376 |
| 3316 | 1-3315 and 3317-8376 |
| 3317 | 1-3316 and 3318-8376 |
| 3318 | 1-3317 and 3319-8376 |
| 3319 | 1-3318 and 3320-8376 |
| 3320 | 1-3319 and 3321-8376 |
| 3321 | 1-3320 and 3322-8376 |
| 3322 | 1-3321 and 3323-8376 |
| 3323 | 1-3322 and 3324-8376 |
| 3324 | 1-3323 and 3325-8376 |
| 3325 | 1-3324 and 3326-8376 |
| 3326 | 1-3325 and 3327-8376 |
| 3327 | 1-3326 and 3328-8376 |
| 3328 | 1-3327 and 3329-8376 |
| 3329 | 1-3328 and 3330-8376 |
| 3330 | 1-3329 and 3331-8376 |
| 3331 | 1-3330 and 3332-8376 |
| 3332 | 1-3331 and 3333-8376 |
| 3333 | 1-3332 and 3334-8376 |
| 3334 | 1-3333 and 3335-8376 |
| 3335 | 1-3334 and 3336-8376 |
| 3336 | 1-3335 and 3337-8376 |
| 3337 | 1-3336 and 3338-8376 |
| 3338 | 1-3337 and 3339-8376 |
| 3339 | 1-3338 and 3340-8376 |
| 3340 | 1-3339 and 3341-8376 |
| 3341 | 1-3340 and 3342-8376 |
| 3342 | 1-3341 and 3343-8376 |
| 3343 | 1-3342 and 3344-8376 |
| 3344 | 1-3343 and 3345-8376 |
| 3345 | 1-3344 and 3346-8376 |
| 3346 | 1-3345 and 3347-8376 |
| 3347 | 1-3346 and 3348-8376 |
| 3348 | 1-3347 and 3349-8376 |
| 3349 | 1-3348 and 3350-8376 |
| 3350 | 1-3349 and 3351-8376 |
| 3351 | 1-3350 and 3352-8376 |
| 3352 | 1-3351 and 3353-8376 |
| 3353 | 1-3352 and 3354-8376 |
| 3354 | 1-3353 and 3355-8376 |
| 3355 | 1-3354 and 3356-8376 |
| 3356 | 1-3355 and 3357-8376 |
| 3357 | 1-3356 and 3358-8376 |
| 3358 | 1-3357 and 3359-8376 |
| 3359 | 1-3358 and 3360-8376 |
| 3360 | 1-3359 and 3361-8376 |
| 3361 | 1-3360 and 3362-8376 |
| 3362 | 1-3361 and 3363-8376 |
| 3363 | 1-3362 and 3364-8376 |
| 3364 | 1-3363 and 3365-8376 |
| 3365 | 1-3364 and 3366-8376 |
| 3366 | 1-3365 and 3367-8376 |
| 3367 | 1-3366 and 3368-8376 |
| 3368 | 1-3367 and 3369-8376 |
| 3369 | 1-3368 and 3370-8376 |

| First | Second |
|---|---|
| 3370 | 1-3369 and 3371-8376 |
| 3371 | 1-3370 and 3372-8376 |
| 3372 | 1-3371 and 3373-8376 |
| 3373 | 1-3372 and 3374-8376 |
| 3374 | 1-3373 and 3375-8376 |
| 3375 | 1-3374 and 3376-8376 |
| 3376 | 1-3375 and 3377-8376 |
| 3377 | 1-3376 and 3378-8376 |
| 3378 | 1-3377 and 3379-8376 |
| 3379 | 1-3378 and 3380-8376 |
| 3380 | 1-3379 and 3381-8376 |
| 3381 | 1-3380 and 3382-8376 |
| 3382 | 1-3381 and 3383-8376 |
| 3383 | 1-3382 and 3384-8376 |
| 3384 | 1-3383 and 3385-8376 |
| 3385 | 1-3384 and 3386-8376 |
| 3386 | 1-3385 and 3387-8376 |
| 3387 | 1-3386 and 3388-8376 |
| 3388 | 1-3387 and 3389-8376 |
| 3389 | 1-3388 and 3390-8376 |
| 3390 | 1-3389 and 3391-8376 |
| 3391 | 1-3390 and 3392-8376 |
| 3392 | 1-3391 and 3393-8376 |
| 3393 | 1-3392 and 3394-8376 |
| 3394 | 1-3393 and 3395-8376 |
| 3395 | 1-3394 and 3396-8376 |
| 3396 | 1-3395 and 3397-8376 |
| 3397 | 1-3396 and 3398-8376 |
| 3398 | 1-3397 and 3399-8376 |
| 3399 | 1-3398 and 3400-8376 |
| 3400 | 1-3399 and 3401-8376 |
| 3401 | 1-3400 and 3402-8376 |
| 3402 | 1-3401 and 3403-8376 |
| 3403 | 1-3402 and 3404-8376 |
| 3404 | 1-3403 and 3405-8376 |
| 3405 | 1-3404 and 3406-8376 |
| 3406 | 1-3405 and 3407-8376 |
| 3407 | 1-3406 and 3408-8376 |
| 3408 | 1-3407 and 3409-8376 |
| 3409 | 1-3408 and 3410-8376 |
| 3410 | 1-3409 and 3411-8376 |
| 3411 | 1-3410 and 3412-8376 |
| 3412 | 1-3411 and 3413-8376 |
| 3413 | 1-3412 and 3414-8376 |
| 3414 | 1-3413 and 3415-8376 |
| 3415 | 1-3414 and 3416-8376 |
| 3416 | 1-3415 and 3417-8376 |
| 3417 | 1-3416 and 3418-8376 |
| 3418 | 1-3417 and 3419-8376 |
| 3419 | 1-3418 and 3420-8376 |
| 3420 | 1-3419 and 3421-8376 |
| 3421 | 1-3420 and 3422-8376 |
| 3422 | 1-3421 and 3423-8376 |
| 3423 | 1-3422 and 3424-8376 |
| 3424 | 1-3423 and 3425-8376 |
| 3425 | 1-3424 and 3426-8376 |
| 3426 | 1-3425 and 3427-8376 |
| 3427 | 1-3426 and 3428-8376 |
| 3428 | 1-3427 and 3429-8376 |
| 3429 | 1-3428 and 3430-8376 |
| 3430 | 1-3429 and 3431-8376 |
| 3431 | 1-3430 and 3432-8376 |
| 3432 | 1-3431 and 3433-8376 |
| 3433 | 1-3432 and 3434-8376 |
| 3434 | 1-3433 and 3435-8376 |
| 3435 | 1-3434 and 3436-8376 |
| 3436 | 1-3435 and 3437-8376 |
| 3437 | 1-3436 and 3438-8376 |
| 3438 | 1-3437 and 3439-8376 |
| 3439 | 1-3438 and 3440-8376 |
| 3440 | 1-3439 and 3441-8376 |
| 3441 | 1-3440 and 3442-8376 |
| 3442 | 1-3441 and 3443-8376 |
| 3443 | 1-3442 and 3444-8376 |
| 3444 | 1-3443 and 3445-8376 |
| 3445 | 1-3444 and 3446-8376 |
| 3446 | 1-3445 and 3447-8376 |
| 3447 | 1-3446 and 3448-8376 |
| 3448 | 1-3447 and 3449-8376 |
| 3449 | 1-3448 and 3450-8376 |
| 3450 | 1-3449 and 3451-8376 |
| 3451 | 1-3450 and 3452-8376 |
| 3452 | 1-3451 and 3453-8376 |
| 3453 | 1-3452 and 3454-8376 |
| 3454 | 1-3453 and 3455-8376 |
| 3455 | 1-3454 and 3456-8376 |
| 3456 | 1-3455 and 3457-8376 |
| 3457 | 1-3456 and 3458-8376 |
| 3458 | 1-3457 and 3459-8376 |
| 3459 | 1-3458 and 3460-8376 |
| 3460 | 1-3459 and 3461-8376 |
| 3461 | 1-3460 and 3462-8376 |
| 3462 | 1-3461 and 3463-8376 |
| 3463 | 1-3462 and 3464-8376 |
| 3464 | 1-3463 and 3465-8376 |
| 3465 | 1-3464 and 3466-8376 |
| 3466 | 1-3465 and 3467-8376 |
| 3467 | 1-3466 and 3468-8376 |
| 3468 | 1-3467 and 3469-8376 |
| 3469 | 1-3468 and 3470-8376 |
| 3470 | 1-3469 and 3471-8376 |
| 3471 | 1-3470 and 3472-8376 |
| 3472 | 1-3471 and 3473-8376 |
| 3473 | 1-3472 and 3474-8376 |
| 3474 | 1-3473 and 3475-8376 |
| 3475 | 1-3474 and 3476-8376 |
| 3476 | 1-3475 and 3477-8376 |
| 3477 | 1-3476 and 3478-8376 |
| 3478 | 1-3477 and 3479-8376 |
| 3479 | 1-3478 and 3480-8376 |
| 3480 | 1-3479 and 3481-8376 |
| 3481 | 1-3480 and 3482-8376 |
| 3482 | 1-3481 and 3483-8376 |
| 3483 | 1-3482 and 3484-8376 |
| 3484 | 1-3483 and 3485-8376 |
| 3485 | 1-3484 and 3486-8376 |
| 3486 | 1-3485 and 3487-8376 |
| 3487 | 1-3486 and 3488-8376 |
| 3488 | 1-3487 and 3489-8376 |
| 3489 | 1-3488 and 3490-8376 |
| 3490 | 1-3489 and 3491-8376 |
| 3491 | 1-3490 and 3492-8376 |
| 3492 | 1-3491 and 3493-8376 |
| 3493 | 1-3492 and 3494-8376 |
| 3494 | 1-3493 and 3495-8376 |
| 3495 | 1-3494 and 3496-8376 |
| 3496 | 1-3495 and 3497-8376 |
| 3497 | 1-3496 and 3498-8376 |
| 3498 | 1-3497 and 3499-8376 |
| 3499 | 1-3498 and 3500-8376 |
| 3500 | 1-3499 and 3501-8376 |
| 3501 | 1-3500 and 3502-8376 |
| 3502 | 1-3501 and 3503-8376 |
| 3503 | 1-3502 and 3504-8376 |
| 3504 | 1-3503 and 3505-8376 |
| 3505 | 1-3504 and 3506-8376 |
| 3506 | 1-3505 and 3507-8376 |
| 3507 | 1-3506 and 3508-8376 |
| 3508 | 1-3507 and 3509-8376 |
| 3509 | 1-3508 and 3510-8376 |
| 3510 | 1-3509 and 3511-8376 |
| 3511 | 1-3510 and 3512-8376 |
| 3512 | 1-3511 and 3513-8376 |
| 3513 | 1-3512 and 3514-8376 |
| 3514 | 1-3513 and 3515-8376 |
| 3515 | 1-3514 and 3516-8376 |
| 3516 | 1-3515 and 3517-8376 |
| 3517 | 1-3516 and 3518-8376 |
| 3518 | 1-3517 and 3519-8376 |
| 3519 | 1-3518 and 3520-8376 |
| 3520 | 1-3519 and 3521-8376 |
| 3521 | 1-3520 and 3522-8376 |
| 3522 | 1-3521 and 3523-8376 |
| 3523 | 1-3522 and 3524-8376 |

| First | Second |
|---|---|
| 3524 | 1-3523 and 3525-8376 |
| 3525 | 1-3524 and 3526-8376 |
| 3526 | 1-3525 and 3527-8376 |
| 3527 | 1-3526 and 3528-8376 |
| 3528 | 1-3527 and 3529-8376 |
| 3529 | 1-3528 and 3530-8376 |
| 3530 | 1-3529 and 3531-8376 |
| 3531 | 1-3530 and 3532-8376 |
| 3532 | 1-3531 and 3533-8376 |
| 3533 | 1-3532 and 3534-8376 |
| 3534 | 1-3533 and 3535-8376 |
| 3535 | 1-3534 and 3536-8376 |
| 3536 | 1-3535 and 3537-8376 |
| 3537 | 1-3536 and 3538-8376 |
| 3538 | 1-3537 and 3539-8376 |
| 3539 | 1-3538 and 3540-8376 |
| 3540 | 1-3539 and 3541-8376 |
| 3541 | 1-3540 and 3542-8376 |
| 3542 | 1-3541 and 3543-8376 |
| 3543 | 1-3542 and 3544-8376 |
| 3544 | 1-3543 and 3545-8376 |
| 3545 | 1-3544 and 3546-8376 |
| 3546 | 1-3545 and 3547-8376 |
| 3547 | 1-3546 and 3548-8376 |
| 3548 | 1-3547 and 3549-8376 |
| 3549 | 1-3548 and 3550-8376 |
| 3550 | 1-3549 and 3551-8376 |
| 3551 | 1-3550 and 3552-8376 |
| 3552 | 1-3551 and 3553-8376 |
| 3553 | 1-3552 and 3554-8376 |
| 3554 | 1-3553 and 3555-8376 |
| 3555 | 1-3554 and 3556-8376 |
| 3556 | 1-3555 and 3557-8376 |
| 3557 | 1-3556 and 3558-8376 |
| 3558 | 1-3557 and 3559-8376 |
| 3559 | 1-3558 and 3560-8376 |
| 3560 | 1-3559 and 3561-8376 |
| 3561 | 1-3560 and 3562-8376 |
| 3562 | 1-3561 and 3563-8376 |
| 3563 | 1-3562 and 3564-8376 |
| 3564 | 1-3563 and 3565-8376 |
| 3565 | 1-3564 and 3566-8376 |
| 3566 | 1-3565 and 3567-8376 |
| 3567 | 1-3566 and 3568-8376 |
| 3568 | 1-3567 and 3569-8376 |
| 3569 | 1-3568 and 3570-8376 |
| 3570 | 1-3569 and 3571-8376 |
| 3571 | 1-3570 and 3572-8376 |
| 3572 | 1-3571 and 3573-8376 |
| 3573 | 1-3572 and 3574-8376 |
| 3574 | 1-3573 and 3575-8376 |
| 3575 | 1-3574 and 3576-8376 |
| 3576 | 1-3575 and 3577-8376 |
| 3577 | 1-3576 and 3578-8376 |
| 3578 | 1-3577 and 3579-8376 |
| 3579 | 1-3578 and 3580-8376 |
| 3580 | 1-3579 and 3581-8376 |
| 3581 | 1-3580 and 3582-8376 |
| 3582 | 1-3581 and 3583-8376 |
| 3583 | 1-3582 and 3584-8376 |
| 3584 | 1-3583 and 3585-8376 |
| 3585 | 1-3584 and 3586-8376 |
| 3586 | 1-3585 and 3587-8376 |
| 3587 | 1-3586 and 3588-8376 |
| 3588 | 1-3587 and 3589-8376 |
| 3589 | 1-3588 and 3590-8376 |
| 3590 | 1-3589 and 3591-8376 |
| 3591 | 1-3590 and 3592-8376 |
| 3592 | 1-3591 and 3593-8376 |
| 3593 | 1-3592 and 3594-8376 |
| 3594 | 1-3593 and 3595-8376 |
| 3595 | 1-3594 and 3596-8376 |
| 3596 | 1-3595 and 3597-8376 |
| 3597 | 1-3596 and 3598-8376 |
| 3598 | 1-3597 and 3599-8376 |
| 3599 | 1-3598 and 3600-8376 |
| 3600 | 1-3599 and 3601-8376 |
| 3601 | 1-3600 and 3602-8376 |
| 3602 | 1-3601 and 3603-8376 |
| 3603 | 1-3602 and 3604-8376 |
| 3604 | 1-3603 and 3605-8376 |
| 3605 | 1-3604 and 3606-8376 |
| 3606 | 1-3605 and 3607-8376 |
| 3607 | 1-3606 and 3608-8376 |
| 3608 | 1-3607 and 3609-8376 |
| 3609 | 1-3608 and 3610-8376 |
| 3610 | 1-3609 and 3611-8376 |
| 3611 | 1-3610 and 3612-8376 |
| 3612 | 1-3611 and 3613-8376 |
| 3613 | 1-3612 and 3614-8376 |
| 3614 | 1-3613 and 3615-8376 |
| 3615 | 1-3614 and 3616-8376 |
| 3616 | 1-3615 and 3617-8376 |
| 3617 | 1-3616 and 3618-8376 |
| 3618 | 1-3617 and 3619-8376 |
| 3619 | 1-3618 and 3620-8376 |
| 3620 | 1-3619 and 3621-8376 |
| 3621 | 1-3620 and 3622-8376 |
| 3622 | 1-3621 and 3623-8376 |
| 3623 | 1-3622 and 3624-8376 |
| 3624 | 1-3623 and 3625-8376 |
| 3625 | 1-3624 and 3626-8376 |
| 3626 | 1-3625 and 3627-8376 |
| 3627 | 1-3626 and 3628-8376 |
| 3628 | 1-3627 and 3629-8376 |
| 3629 | 1-3628 and 3630-8376 |
| 3630 | 1-3629 and 3631-8376 |
| 3631 | 1-3630 and 3632-8376 |
| 3632 | 1-3631 and 3633-8376 |
| 3633 | 1-3632 and 3634-8376 |
| 3634 | 1-3633 and 3635-8376 |
| 3635 | 1-3634 and 3636-8376 |
| 3636 | 1-3635 and 3637-8376 |
| 3637 | 1-3636 and 3638-8376 |
| 3638 | 1-3637 and 3639-8376 |
| 3639 | 1-3638 and 3640-8376 |
| 3640 | 1-3639 and 3641-8376 |
| 3641 | 1-3640 and 3642-8376 |
| 3642 | 1-3641 and 3643-8376 |
| 3643 | 1-3642 and 3644-8376 |
| 3644 | 1-3643 and 3645-8376 |
| 3645 | 1-3644 and 3646-8376 |
| 3646 | 1-3645 and 3647-8376 |
| 3647 | 1-3646 and 3648-8376 |
| 3648 | 1-3647 and 3649-8376 |
| 3649 | 1-3648 and 3650-8376 |
| 3650 | 1-3649 and 3651-8376 |
| 3651 | 1-3650 and 3652-8376 |
| 3652 | 1-3651 and 3653-8376 |
| 3653 | 1-3652 and 3654-8376 |
| 3654 | 1-3653 and 3655-8376 |
| 3655 | 1-3654 and 3656-8376 |
| 3656 | 1-3655 and 3657-8376 |
| 3657 | 1-3656 and 3658-8376 |
| 3658 | 1-3657 and 3659-8376 |
| 3659 | 1-3658 and 3660-8376 |
| 3660 | 1-3659 and 3661-8376 |
| 3661 | 1-3660 and 3662-8376 |
| 3662 | 1-3661 and 3663-8376 |
| 3663 | 1-3662 and 3664-8376 |
| 3664 | 1-3663 and 3665-8376 |
| 3665 | 1-3664 and 3666-8376 |
| 3666 | 1-3665 and 3667-8376 |
| 3667 | 1-3666 and 3668-8376 |
| 3668 | 1-3667 and 3669-8376 |
| 3669 | 1-3668 and 3670-8376 |
| 3670 | 1-3669 and 3671-8376 |
| 3671 | 1-3670 and 3672-8376 |
| 3672 | 1-3671 and 3673-8376 |
| 3673 | 1-3672 and 3674-8376 |
| 3674 | 1-3673 and 3675-8376 |
| 3675 | 1-3674 and 3676-8376 |
| 3676 | 1-3675 and 3677-8376 |
| 3677 | 1-3676 and 3678-8376 |

| First | Second |
|---|---|
| 3678 | 1-3677 and 3679-8376 |
| 3679 | 1-3678 and 3680-8376 |
| 3680 | 1-3679 and 3681-8376 |
| 3681 | 1-3680 and 3682-8376 |
| 3682 | 1-3681 and 3683-8376 |
| 3683 | 1-3682 and 3684-8376 |
| 3684 | 1-3683 and 3685-8376 |
| 3685 | 1-3684 and 3686-8376 |
| 3686 | 1-3685 and 3687-8376 |
| 3687 | 1-3686 and 3688-8376 |
| 3688 | 1-3687 and 3689-8376 |
| 3689 | 1-3688 and 3690-8376 |
| 3690 | 1-3689 and 3691-8376 |
| 3691 | 1-3690 and 3692-8376 |
| 3692 | 1-3691 and 3693-8376 |
| 3693 | 1-3692 and 3694-8376 |
| 3694 | 1-3693 and 3695-8376 |
| 3695 | 1-3694 and 3696-8376 |
| 3696 | 1-3695 and 3697-8376 |
| 3697 | 1-3696 and 3698-8376 |
| 3698 | 1-3697 and 3699-8376 |
| 3699 | 1-3698 and 3700-8376 |
| 3700 | 1-3699 and 3701-8376 |
| 3701 | 1-3700 and 3702-8376 |
| 3702 | 1-3701 and 3703-8376 |
| 3703 | 1-3702 and 3704-8376 |
| 3704 | 1-3703 and 3705-8376 |
| 3705 | 1-3704 and 3706-8376 |
| 3706 | 1-3705 and 3707-8376 |
| 3707 | 1-3706 and 3708-8376 |
| 3708 | 1-3707 and 3709-8376 |
| 3709 | 1-3708 and 3710-8376 |
| 3710 | 1-3709 and 3711-8376 |
| 3711 | 1-3710 and 3712-8376 |
| 3712 | 1-3711 and 3713-8376 |
| 3713 | 1-3712 and 3714-8376 |
| 3714 | 1-3713 and 3715-8376 |
| 3715 | 1-3714 and 3716-8376 |
| 3716 | 1-3715 and 3717-8376 |
| 3717 | 1-3716 and 3718-8376 |
| 3718 | 1-3717 and 3719-8376 |
| 3719 | 1-3718 and 3720-8376 |
| 3720 | 1-3719 and 3721-8376 |
| 3721 | 1-3720 and 3722-8376 |
| 3722 | 1-3721 and 3723-8376 |
| 3723 | 1-3722 and 3724-8376 |
| 3724 | 1-3723 and 3725-8376 |
| 3725 | 1-3724 and 3726-8376 |
| 3726 | 1-3725 and 3727-8376 |
| 3727 | 1-3726 and 3728-8376 |
| 3728 | 1-3727 and 3729-8376 |
| 3729 | 1-3728 and 3730-8376 |
| 3730 | 1-3729 and 3731-8376 |
| 3731 | 1-3730 and 3732-8376 |
| 3732 | 1-3731 and 3733-8376 |
| 3733 | 1-3732 and 3734-8376 |
| 3734 | 1-3733 and 3735-8376 |
| 3735 | 1-3734 and 3736-8376 |
| 3736 | 1-3735 and 3737-8376 |
| 3737 | 1-3736 and 3738-8376 |
| 3738 | 1-3737 and 3739-8376 |
| 3739 | 1-3738 and 3740-8376 |
| 3740 | 1-3739 and 3741-8376 |
| 3741 | 1-3740 and 3742-8376 |
| 3742 | 1-3741 and 3743-8376 |
| 3743 | 1-3742 and 3744-8376 |
| 3744 | 1-3743 and 3745-8376 |
| 3745 | 1-3744 and 3746-8376 |
| 3746 | 1-3745 and 3747-8376 |
| 3747 | 1-3746 and 3748-8376 |
| 3748 | 1-3747 and 3749-8376 |
| 3749 | 1-3748 and 3750-8376 |
| 3750 | 1-3749 and 3751-8376 |
| 3751 | 1-3750 and 3752-8376 |
| 3752 | 1-3751 and 3753-8376 |
| 3753 | 1-3752 and 3754-8376 |
| 3754 | 1-3753 and 3755-8376 |
| 3755 | 1-3754 and 3756-8376 |
| 3756 | 1-3755 and 3757-8376 |
| 3757 | 1-3756 and 3758-8376 |
| 3758 | 1-3757 and 3759-8376 |
| 3759 | 1-3758 and 3760-8376 |
| 3760 | 1-3759 and 3761-8376 |
| 3761 | 1-3760 and 3762-8376 |
| 3762 | 1-3761 and 3763-8376 |
| 3763 | 1-3762 and 3764-8376 |
| 3764 | 1-3763 and 3765-8376 |
| 3765 | 1-3764 and 3766-8376 |
| 3766 | 1-3765 and 3767-8376 |
| 3767 | 1-3766 and 3768-8376 |
| 3768 | 1-3767 and 3769-8376 |
| 3769 | 1-3768 and 3770-8376 |
| 3770 | 1-3769 and 3771-8376 |
| 3771 | 1-3770 and 3772-8376 |
| 3772 | 1-3771 and 3773-8376 |
| 3773 | 1-3772 and 3774-8376 |
| 3774 | 1-3773 and 3775-8376 |
| 3775 | 1-3774 and 3776-8376 |
| 3776 | 1-3775 and 3777-8376 |
| 3777 | 1-3776 and 3778-8376 |
| 3778 | 1-3777 and 3779-8376 |
| 3779 | 1-3778 and 3780-8376 |
| 3780 | 1-3779 and 3781-8376 |
| 3781 | 1-3780 and 3782-8376 |
| 3782 | 1-3781 and 3783-8376 |
| 3783 | 1-3782 and 3784-8376 |
| 3784 | 1-3783 and 3785-8376 |
| 3785 | 1-3784 and 3786-8376 |
| 3786 | 1-3785 and 3787-8376 |
| 3787 | 1-3786 and 3788-8376 |
| 3788 | 1-3787 and 3789-8376 |
| 3789 | 1-3788 and 3790-8376 |
| 3790 | 1-3789 and 3791-8376 |
| 3791 | 1-3790 and 3792-8376 |
| 3792 | 1-3791 and 3793-8376 |
| 3793 | 1-3792 and 3794-8376 |
| 3794 | 1-3793 and 3795-8376 |
| 3795 | 1-3794 and 3796-8376 |
| 3796 | 1-3795 and 3797-8376 |
| 3797 | 1-3796 and 3798-8376 |
| 3798 | 1-3797 and 3799-8376 |
| 3799 | 1-3798 and 3800-8376 |
| 3800 | 1-3799 and 3801-8376 |
| 3801 | 1-3800 and 3802-8376 |
| 3802 | 1-3801 and 3803-8376 |
| 3803 | 1-3802 and 3804-8376 |
| 3804 | 1-3803 and 3805-8376 |
| 3805 | 1-3804 and 3806-8376 |
| 3806 | 1-3805 and 3807-8376 |
| 3807 | 1-3806 and 3808-8376 |
| 3808 | 1-3807 and 3809-8376 |
| 3809 | 1-3808 and 3810-8376 |
| 3810 | 1-3809 and 3811-8376 |
| 3811 | 1-3810 and 3812-8376 |
| 3812 | 1-3811 and 3813-8376 |
| 3813 | 1-3812 and 3814-8376 |
| 3814 | 1-3813 and 3815-8376 |
| 3815 | 1-3814 and 3816-8376 |
| 3816 | 1-3815 and 3817-8376 |
| 3817 | 1-3816 and 3818-8376 |
| 3818 | 1-3817 and 3819-8376 |
| 3819 | 1-3818 and 3820-8376 |
| 3820 | 1-3819 and 3821-8376 |
| 3821 | 1-3820 and 3822-8376 |
| 3822 | 1-3821 and 3823-8376 |
| 3823 | 1-3822 and 3824-8376 |
| 3824 | 1-3823 and 3825-8376 |
| 3825 | 1-3824 and 3826-8376 |
| 3826 | 1-3825 and 3827-8376 |
| 3827 | 1-3826 and 3828-8376 |
| 3828 | 1-3827 and 3829-8376 |
| 3829 | 1-3828 and 3830-8376 |
| 3830 | 1-3829 and 3831-8376 |
| 3831 | 1-3830 and 3832-8376 |

-continued

| First | Second |
|---|---|
| 3832 | 1-3831 and 3833-8376 |
| 3833 | 1-3832 and 3834-8376 |
| 3834 | 1-3833 and 3835-8376 |
| 3835 | 1-3834 and 3836-8376 |
| 3836 | 1-3835 and 3837-8376 |
| 3837 | 1-3836 and 3838-8376 |
| 3838 | 1-3837 and 3839-8376 |
| 3839 | 1-3838 and 3840-8376 |
| 3840 | 1-3839 and 3841-8376 |
| 3841 | 1-3840 and 3842-8376 |
| 3842 | 1-3841 and 3843-8376 |
| 3843 | 1-3842 and 3844-8376 |
| 3844 | 1-3843 and 3845-8376 |
| 3845 | 1-3844 and 3846-8376 |
| 3846 | 1-3845 and 3847-8376 |
| 3847 | 1-3846 and 3848-8376 |
| 3848 | 1-3847 and 3849-8376 |
| 3849 | 1-3848 and 3850-8376 |
| 3850 | 1-3849 and 3851-8376 |
| 3851 | 1-3850 and 3852-8376 |
| 3852 | 1-3851 and 3853-8376 |
| 3853 | 1-3852 and 3854-8376 |
| 3854 | 1-3853 and 3855-8376 |
| 3855 | 1-3854 and 3856-8376 |
| 3856 | 1-3855 and 3857-8376 |
| 3857 | 1-3856 and 3858-8376 |
| 3858 | 1-3857 and 3859-8376 |
| 3859 | 1-3858 and 3860-8376 |
| 3860 | 1-3859 and 3861-8376 |
| 3861 | 1-3860 and 3862-8376 |
| 3862 | 1-3861 and 3863-8376 |
| 3863 | 1-3862 and 3864-8376 |
| 3864 | 1-3863 and 3865-8376 |
| 3865 | 1-3864 and 3866-8376 |
| 3866 | 1-3865 and 3867-8376 |
| 3867 | 1-3866 and 3868-8376 |
| 3868 | 1-3867 and 3869-8376 |
| 3869 | 1-3868 and 3870-8376 |
| 3870 | 1-3869 and 3871-8376 |
| 3871 | 1-3870 and 3872-8376 |
| 3872 | 1-3871 and 3873-8376 |
| 3873 | 1-3872 and 3874-8376 |
| 3874 | 1-3873 and 3875-8376 |
| 3875 | 1-3874 and 3876-8376 |
| 3876 | 1-3875 and 3877-8376 |
| 3877 | 1-3876 and 3878-8376 |
| 3878 | 1-3877 and 3879-8376 |
| 3879 | 1-3878 and 3880-8376 |
| 3880 | 1-3879 and 3881-8376 |
| 3881 | 1-3880 and 3882-8376 |
| 3882 | 1-3881 and 3883-8376 |
| 3883 | 1-3882 and 3884-8376 |
| 3884 | 1-3883 and 3885-8376 |
| 3885 | 1-3884 and 3886-8376 |
| 3886 | 1-3885 and 3887-8376 |
| 3887 | 1-3886 and 3888-8376 |
| 3888 | 1-3887 and 3889-8376 |
| 3889 | 1-3888 and 3890-8376 |
| 3890 | 1-3889 and 3891-8376 |
| 3891 | 1-3890 and 3892-8376 |
| 3892 | 1-3891 and 3893-8376 |
| 3893 | 1-3892 and 3894-8376 |
| 3894 | 1-3893 and 3895-8376 |
| 3895 | 1-3894 and 3896-8376 |
| 3896 | 1-3895 and 3897-8376 |
| 3897 | 1-3896 and 3898-8376 |
| 3898 | 1-3897 and 3899-8376 |
| 3899 | 1-3898 and 3900-8376 |
| 3900 | 1-3899 and 3901-8376 |
| 3901 | 1-3900 and 3902-8376 |
| 3902 | 1-3901 and 3903-8376 |
| 3903 | 1-3902 and 3904-8376 |
| 3904 | 1-3903 and 3905-8376 |
| 3905 | 1-3904 and 3906-8376 |
| 3906 | 1-3905 and 3907-8376 |
| 3907 | 1-3906 and 3908-8376 |
| 3908 | 1-3907 and 3909-8376 |

-continued

| First | Second |
|---|---|
| 3909 | 1-3908 and 3910-8376 |
| 3910 | 1-3909 and 3911-8376 |
| 3911 | 1-3910 and 3912-8376 |
| 3912 | 1-3911 and 3913-8376 |
| 3913 | 1-3912 and 3914-8376 |
| 3914 | 1-3913 and 3915-8376 |
| 3915 | 1-3914 and 3916-8376 |
| 3916 | 1-3915 and 3917-8376 |
| 3917 | 1-3916 and 3918-8376 |
| 3918 | 1-3917 and 3919-8376 |
| 3919 | 1-3918 and 3920-8376 |
| 3920 | 1-3919 and 3921-8376 |
| 3921 | 1-3920 and 3922-8376 |
| 3922 | 1-3921 and 3923-8376 |
| 3923 | 1-3922 and 3924-8376 |
| 3924 | 1-3923 and 3925-8376 |
| 3925 | 1-3924 and 3926-8376 |
| 3926 | 1-3925 and 3927-8376 |
| 3927 | 1-3926 and 3928-8376 |
| 3928 | 1-3927 and 3929-8376 |
| 3929 | 1-3928 and 3930-8376 |
| 3930 | 1-3929 and 3931-8376 |
| 3931 | 1-3930 and 3932-8376 |
| 3932 | 1-3931 and 3933-8376 |
| 3933 | 1-3932 and 3934-8376 |
| 3934 | 1-3933 and 3935-8376 |
| 3935 | 1-3934 and 3936-8376 |
| 3936 | 1-3935 and 3937-8376 |
| 3937 | 1-3936 and 3938-8376 |
| 3938 | 1-3937 and 3939-8376 |
| 3939 | 1-3938 and 3940-8376 |
| 3940 | 1-3939 and 3941-8376 |
| 3941 | 1-3940 and 3942-8376 |
| 3942 | 1-3941 and 3943-8376 |
| 3943 | 1-3942 and 3944-8376 |
| 3944 | 1-3943 and 3945-8376 |
| 3945 | 1-3944 and 3946-8376 |
| 3946 | 1-3945 and 3947-8376 |
| 3947 | 1-3946 and 3948-8376 |
| 3948 | 1-3947 and 3949-8376 |
| 3949 | 1-3948 and 3950-8376 |
| 3950 | 1-3949 and 3951-8376 |
| 3951 | 1-3950 and 3952-8376 |
| 3952 | 1-3951 and 3953-8376 |
| 3953 | 1-3952 and 3954-8376 |
| 3954 | 1-3953 and 3955-8376 |
| 3955 | 1-3954 and 3956-8376 |
| 3956 | 1-3955 and 3957-8376 |
| 3957 | 1-3956 and 3958-8376 |
| 3958 | 1-3957 and 3959-8376 |
| 3959 | 1-3958 and 3960-8376 |
| 3960 | 1-3959 and 3961-8376 |
| 3961 | 1-3960 and 3962-8376 |
| 3962 | 1-3961 and 3963-8376 |
| 3963 | 1-3962 and 3964-8376 |
| 3964 | 1-3963 and 3965-8376 |
| 3965 | 1-3964 and 3966-8376 |
| 3966 | 1-3965 and 3967-8376 |
| 3967 | 1-3966 and 3968-8376 |
| 3968 | 1-3967 and 3969-8376 |
| 3969 | 1-3968 and 3970-8376 |
| 3970 | 1-3969 and 3971-8376 |
| 3971 | 1-3970 and 3972-8376 |
| 3972 | 1-3971 and 3973-8376 |
| 3973 | 1-3972 and 3974-8376 |
| 3974 | 1-3973 and 3975-8376 |
| 3975 | 1-3974 and 3976-8376 |
| 3976 | 1-3975 and 3977-8376 |
| 3977 | 1-3976 and 3978-8376 |
| 3978 | 1-3977 and 3979-8376 |
| 3979 | 1-3978 and 3980-8376 |
| 3980 | 1-3979 and 3981-8376 |
| 3981 | 1-3980 and 3982-8376 |
| 3982 | 1-3981 and 3983-8376 |
| 3983 | 1-3982 and 3984-8376 |
| 3984 | 1-3983 and 3985-8376 |
| 3985 | 1-3984 and 3986-8376 |

| First | Second |
|---|---|
| 3986 | 1-3985 and 3987-8376 |
| 3987 | 1-3986 and 3988-8376 |
| 3988 | 1-3987 and 3989-8376 |
| 3989 | 1-3988 and 3990-8376 |
| 3990 | 1-3989 and 3991-8376 |
| 3991 | 1-3990 and 3992-8376 |
| 3992 | 1-3991 and 3993-8376 |
| 3993 | 1-3992 and 3994-8376 |
| 3994 | 1-3993 and 3995-8376 |
| 3995 | 1-3994 and 3996-8376 |
| 3996 | 1-3995 and 3997-8376 |
| 3997 | 1-3996 and 3998-8376 |
| 3998 | 1-3997 and 3999-8376 |
| 3999 | 1-3998 and 4000-8376 |
| 4000 | 1-3999 and 4001-8376 |
| 4001 | 1-4000 and 4002-8376 |
| 4002 | 1-4001 and 4003-8376 |
| 4003 | 1-4002 and 4004-8376 |
| 4004 | 1-4003 and 4005-8376 |
| 4005 | 1-4004 and 4006-8376 |
| 4006 | 1-4005 and 4007-8376 |
| 4007 | 1-4006 and 4008-8376 |
| 4008 | 1-4007 and 4009-8376 |
| 4009 | 1-4008 and 4010-8376 |
| 4010 | 1-4009 and 4011-8376 |
| 4011 | 1-4010 and 4012-8376 |
| 4012 | 1-4011 and 4013-8376 |
| 4013 | 1-4012 and 4014-8376 |
| 4014 | 1-4013 and 4015-8376 |
| 4015 | 1-4014 and 4016-8376 |
| 4016 | 1-4015 and 4017-8376 |
| 4017 | 1-4016 and 4018-8376 |
| 4018 | 1-4017 and 4019-8376 |
| 4019 | 1-4018 and 4020-8376 |
| 4020 | 1-4019 and 4021-8376 |
| 4021 | 1-4020 and 4022-8376 |
| 4022 | 1-4021 and 4023-8376 |
| 4023 | 1-4022 and 4024-8376 |
| 4024 | 1-4023 and 4025-8376 |
| 4025 | 1-4024 and 4026-8376 |
| 4026 | 1-4025 and 4027-8376 |
| 4027 | 1-4026 and 4028-8376 |
| 4028 | 1-4027 and 4029-8376 |
| 4029 | 1-4028 and 4030-8376 |
| 4030 | 1-4029 and 4031-8376 |
| 4031 | 1-4030 and 4032-8376 |
| 4032 | 1-4031 and 4033-8376 |
| 4033 | 1-4032 and 4034-8376 |
| 4034 | 1-4033 and 4035-8376 |
| 4035 | 1-4034 and 4036-8376 |
| 4036 | 1-4035 and 4037-8376 |
| 4037 | 1-4036 and 4038-8376 |
| 4038 | 1-4037 and 4039-8376 |
| 4039 | 1-4038 and 4040-8376 |
| 4040 | 1-4039 and 4041-8376 |
| 4041 | 1-4040 and 4042-8376 |
| 4042 | 1-4041 and 4043-8376 |
| 4043 | 1-4042 and 4044-8376 |
| 4044 | 1-4043 and 4045-8376 |
| 4045 | 1-4044 and 4046-8376 |
| 4046 | 1-4045 and 4047-8376 |
| 4047 | 1-4046 and 4048-8376 |
| 4048 | 1-4047 and 4049-8376 |
| 4049 | 1-4048 and 4050-8376 |
| 4050 | 1-4049 and 4051-8376 |
| 4051 | 1-4050 and 4052-8376 |
| 4052 | 1-4051 and 4053-8376 |
| 4053 | 1-4052 and 4054-8376 |
| 4054 | 1-4053 and 4055-8376 |
| 4055 | 1-4054 and 4056-8376 |
| 4056 | 1-4055 and 4057-8376 |
| 4057 | 1-4056 and 4058-8376 |
| 4058 | 1-4057 and 4059-8376 |
| 4059 | 1-4058 and 4060-8376 |
| 4060 | 1-4059 and 4061-8376 |
| 4061 | 1-4060 and 4062-8376 |
| 4062 | 1-4061 and 4063-8376 |
| 4063 | 1-4062 and 4064-8376 |
| 4064 | 1-4063 and 4065-8376 |
| 4065 | 1-4064 and 4066-8376 |
| 4066 | 1-4065 and 4067-8376 |
| 4067 | 1-4066 and 4068-8376 |
| 4068 | 1-4067 and 4069-8376 |
| 4069 | 1-4068 and 4070-8376 |
| 4070 | 1-4069 and 4071-8376 |
| 4071 | 1-4070 and 4072-8376 |
| 4072 | 1-4071 and 4073-8376 |
| 4073 | 1-4072 and 4074-8376 |
| 4074 | 1-4073 and 4075-8376 |
| 4075 | 1-4074 and 4076-8376 |
| 4076 | 1-4075 and 4077-8376 |
| 4077 | 1-4076 and 4078-8376 |
| 4078 | 1-4077 and 4079-8376 |
| 4079 | 1-4078 and 4080-8376 |
| 4080 | 1-4079 and 4081-8376 |
| 4081 | 1-4080 and 4082-8376 |
| 4082 | 1-4081 and 4083-8376 |
| 4083 | 1-4082 and 4084-8376 |
| 4084 | 1-4083 and 4085-8376 |
| 4085 | 1-4084 and 4086-8376 |
| 4086 | 1-4085 and 4087-8376 |
| 4087 | 1-4086 and 4088-8376 |
| 4088 | 1-4087 and 4089-8376 |
| 4089 | 1-4088 and 4090-8376 |
| 4090 | 1-4089 and 4091-8376 |
| 4091 | 1-4090 and 4092-8376 |
| 4092 | 1-4091 and 4093-8376 |
| 4093 | 1-4092 and 4094-8376 |
| 4094 | 1-4093 and 4095-8376 |
| 4095 | 1-4094 and 4096-8376 |
| 4096 | 1-4095 and 4097-8376 |
| 4097 | 1-4096 and 4098-8376 |
| 4098 | 1-4097 and 4099-8376 |
| 4099 | 1-4098 and 4100-8376 |
| 4100 | 1-4099 and 4101-8376 |
| 4101 | 1-4100 and 4102-8376 |
| 4102 | 1-4101 and 4103-8376 |
| 4103 | 1-4102 and 4104-8376 |
| 4104 | 1-4103 and 4105-8376 |
| 4105 | 1-4104 and 4106-8376 |
| 4106 | 1-4105 and 4107-8376 |
| 4107 | 1-4106 and 4108-8376 |
| 4108 | 1-4107 and 4109-8376 |
| 4109 | 1-4108 and 4110-8376 |
| 4110 | 1-4109 and 4111-8376 |
| 4111 | 1-4110 and 4112-8376 |
| 4112 | 1-4111 and 4113-8376 |
| 4113 | 1-4112 and 4114-8376 |
| 4114 | 1-4113 and 4115-8376 |
| 4115 | 1-4114 and 4116-8376 |
| 4116 | 1-4115 and 4117-8376 |
| 4117 | 1-4116 and 4118-8376 |
| 4118 | 1-4117 and 4119-8376 |
| 4119 | 1-4118 and 4120-8376 |
| 4120 | 1-4119 and 4121-8376 |
| 4121 | 1-4120 and 4122-8376 |
| 4122 | 1-4121 and 4123-8376 |
| 4123 | 1-4122 and 4124-8376 |
| 4124 | 1-4123 and 4125-8376 |
| 4125 | 1-4124 and 4126-8376 |
| 4126 | 1-4125 and 4127-8376 |
| 4127 | 1-4126 and 4128-8376 |
| 4128 | 1-4127 and 4129-8376 |
| 4129 | 1-4128 and 4130-8376 |
| 4130 | 1-4129 and 4131-8376 |
| 4131 | 1-4130 and 4132-8376 |
| 4132 | 1-4131 and 4133-8376 |
| 4133 | 1-4132 and 4134-8376 |
| 4134 | 1-4133 and 4135-8376 |
| 4135 | 1-4134 and 4136-8376 |
| 4136 | 1-4135 and 4137-8376 |
| 4137 | 1-4136 and 4138-8376 |
| 4138 | 1-4137 and 4139-8376 |
| 4139 | 1-4138 and 4140-8376 |

| First | Second |
|---|---|
| 4140 | 1-4139 and 4141-8376 |
| 4141 | 1-4140 and 4142-8376 |
| 4142 | 1-4141 and 4143-8376 |
| 4143 | 1-4142 and 4144-8376 |
| 4144 | 1-4143 and 4145-8376 |
| 4145 | 1-4144 and 4146-8376 |
| 4146 | 1-4145 and 4147-8376 |
| 4147 | 1-4146 and 4148-8376 |
| 4148 | 1-4147 and 4149-8376 |
| 4149 | 1-4148 and 4150-8376 |
| 4150 | 1-4149 and 4151-8376 |
| 4151 | 1-4150 and 4152-8376 |
| 4152 | 1-4151 and 4153-8376 |
| 4153 | 1-4152 and 4154-8376 |
| 4154 | 1-4153 and 4155-8376 |
| 4155 | 1-4154 and 4156-8376 |
| 4156 | 1-4155 and 4157-8376 |
| 4157 | 1-4156 and 4158-8376 |
| 4158 | 1-4157 and 4159-8376 |
| 4159 | 1-4158 and 4160-8376 |
| 4160 | 1-4159 and 4161-8376 |
| 4161 | 1-4160 and 4162-8376 |
| 4162 | 1-4161 and 4163-8376 |
| 4163 | 1-4162 and 4164-8376 |
| 4164 | 1-4163 and 4165-8376 |
| 4165 | 1-4164 and 4166-8376 |
| 4166 | 1-4165 and 4167-8376 |
| 4167 | 1-4166 and 4168-8376 |
| 4168 | 1-4167 and 4169-8376 |
| 4169 | 1-4168 and 4170-8376 |
| 4170 | 1-4169 and 4171-8376 |
| 4171 | 1-4170 and 4172-8376 |
| 4172 | 1-4171 and 4173-8376 |
| 4173 | 1-4172 and 4174-8376 |
| 4174 | 1-4173 and 4175-8376 |
| 4175 | 1-4174 and 4176-8376 |
| 4176 | 1-4175 and 4177-8376 |
| 4177 | 1-4176 and 4178-8376 |
| 4178 | 1-4177 and 4179-8376 |
| 4179 | 1-4178 and 4180-8376 |
| 4180 | 1-4179 and 4181-8376 |
| 4181 | 1-4180 and 4182-8376 |
| 4182 | 1-4181 and 4183-8376 |
| 4183 | 1-4182 and 4184-8376 |
| 4184 | 1-4183 and 4185-8376 |
| 4185 | 1-4184 and 4186-8376 |
| 4186 | 1-4185 and 4187-8376 |
| 4187 | 1-4186 and 4188-8376 |
| 4188 | 1-4187 and 4189-8376 |
| 4189 | 1-4188 and 4190-8376 |
| 4190 | 1-4189 and 4191-8376 |
| 4191 | 1-4190 and 4192-8376 |
| 4192 | 1-4191 and 4193-8376 |
| 4193 | 1-4192 and 4194-8376 |
| 4194 | 1-4193 and 4195-8376 |
| 4195 | 1-4194 and 4196-8376 |
| 4196 | 1-4195 and 4197-8376 |
| 4197 | 1-4196 and 4198-8376 |
| 4198 | 1-4197 and 4199-8376 |
| 4199 | 1-4198 and 4200-8376 |
| 4200 | 1-4199 and 4201-8376 |
| 4201 | 1-4200 and 4202-8376 |
| 4202 | 1-4201 and 4203-8376 |
| 4203 | 1-4202 and 4204-8376 |
| 4204 | 1-4203 and 4205-8376 |
| 4205 | 1-4204 and 4206-8376 |
| 4206 | 1-4205 and 4207-8376 |
| 4207 | 1-4206 and 4208-8376 |
| 4208 | 1-4207 and 4209-8376 |
| 4209 | 1-4208 and 4210-8376 |
| 4210 | 1-4209 and 4211-8376 |
| 4211 | 1-4210 and 4212-8376 |
| 4212 | 1-4211 and 4213-8376 |
| 4213 | 1-4212 and 4214-8376 |
| 4214 | 1-4213 and 4215-8376 |
| 4215 | 1-4214 and 4216-8376 |
| 4216 | 1-4215 and 4217-8376 |
| 4217 | 1-4216 and 4218-8376 |
| 4218 | 1-4217 and 4219-8376 |
| 4219 | 1-4218 and 4220-8376 |
| 4220 | 1-4219 and 4221-8376 |
| 4221 | 1-4220 and 4222-8376 |
| 4222 | 1-4221 and 4223-8376 |
| 4223 | 1-4222 and 4224-8376 |
| 4224 | 1-4223 and 4225-8376 |
| 4225 | 1-4224 and 4226-8376 |
| 4226 | 1-4225 and 4227-8376 |
| 4227 | 1-4226 and 4228-8376 |
| 4228 | 1-4227 and 4229-8376 |
| 4229 | 1-4228 and 4230-8376 |
| 4230 | 1-4229 and 4231-8376 |
| 4231 | 1-4230 and 4232-8376 |
| 4232 | 1-4231 and 4233-8376 |
| 4233 | 1-4232 and 4234-8376 |
| 4234 | 1-4233 and 4235-8376 |
| 4235 | 1-4234 and 4236-8376 |
| 4236 | 1-4235 and 4237-8376 |
| 4237 | 1-4236 and 4238-8376 |
| 4238 | 1-4237 and 4239-8376 |
| 4239 | 1-4238 and 4240-8376 |
| 4240 | 1-4239 and 4241-8376 |
| 4241 | 1-4240 and 4242-8376 |
| 4242 | 1-4241 and 4243-8376 |
| 4243 | 1-4242 and 4244-8376 |
| 4244 | 1-4243 and 4245-8376 |
| 4245 | 1-4244 and 4246-8376 |
| 4246 | 1-4245 and 4247-8376 |
| 4247 | 1-4246 and 4248-8376 |
| 4248 | 1-4247 and 4249-8376 |
| 4249 | 1-4248 and 4250-8376 |
| 4250 | 1-4249 and 4251-8376 |
| 4251 | 1-4250 and 4252-8376 |
| 4252 | 1-4251 and 4253-8376 |
| 4253 | 1-4252 and 4254-8376 |
| 4254 | 1-4253 and 4255-8376 |
| 4255 | 1-4254 and 4256-8376 |
| 4256 | 1-4255 and 4257-8376 |
| 4257 | 1-4256 and 4258-8376 |
| 4258 | 1-4257 and 4259-8376 |
| 4259 | 1-4258 and 4260-8376 |
| 4260 | 1-4259 and 4261-8376 |
| 4261 | 1-4260 and 4262-8376 |
| 4262 | 1-4261 and 4263-8376 |
| 4263 | 1-4262 and 4264-8376 |
| 4264 | 1-4263 and 4265-8376 |
| 4265 | 1-4264 and 4266-8376 |
| 4266 | 1-4265 and 4267-8376 |
| 4267 | 1-4266 and 4268-8376 |
| 4268 | 1-4267 and 4269-8376 |
| 4269 | 1-4268 and 4270-8376 |
| 4270 | 1-4269 and 4271-8376 |
| 4271 | 1-4270 and 4272-8376 |
| 4272 | 1-4271 and 4273-8376 |
| 4273 | 1-4272 and 4274-8376 |
| 4274 | 1-4273 and 4275-8376 |
| 4275 | 1-4274 and 4276-8376 |
| 4276 | 1-4275 and 4277-8376 |
| 4277 | 1-4276 and 4278-8376 |
| 4278 | 1-4277 and 4279-8376 |
| 4279 | 1-4278 and 4280-8376 |
| 4280 | 1-4279 and 4281-8376 |
| 4281 | 1-4280 and 4282-8376 |
| 4282 | 1-4281 and 4283-8376 |
| 4283 | 1-4282 and 4284-8376 |
| 4284 | 1-4283 and 4285-8376 |
| 4285 | 1-4284 and 4286-8376 |
| 4286 | 1-4285 and 4287-8376 |
| 4287 | 1-4286 and 4288-8376 |
| 4288 | 1-4287 and 4289-8376 |
| 4289 | 1-4288 and 4290-8376 |
| 4290 | 1-4289 and 4291-8376 |
| 4291 | 1-4290 and 4292-8376 |
| 4292 | 1-4291 and 4293-8376 |
| 4293 | 1-4292 and 4294-8376 |

| First | Second |
|---|---|
| 4294 | 1-4293 and 4295-8376 |
| 4295 | 1-4294 and 4296-8376 |
| 4296 | 1-4295 and 4297-8376 |
| 4297 | 1-4296 and 4298-8376 |
| 4298 | 1-4297 and 4299-8376 |
| 4299 | 1-4298 and 4300-8376 |
| 4300 | 1-4299 and 4301-8376 |
| 4301 | 1-4300 and 4302-8376 |
| 4302 | 1-4301 and 4303-8376 |
| 4303 | 1-4302 and 4304-8376 |
| 4304 | 1-4303 and 4305-8376 |
| 4305 | 1-4304 and 4306-8376 |
| 4306 | 1-4305 and 4307-8376 |
| 4307 | 1-4306 and 4308-8376 |
| 4308 | 1-4307 and 4309-8376 |
| 4309 | 1-4308 and 4310-8376 |
| 4310 | 1-4309 and 4311-8376 |
| 4311 | 1-4310 and 4312-8376 |
| 4312 | 1-4311 and 4313-8376 |
| 4313 | 1-4312 and 4314-8376 |
| 4314 | 1-4313 and 4315-8376 |
| 4315 | 1-4314 and 4316-8376 |
| 4316 | 1-4315 and 4317-8376 |
| 4317 | 1-4316 and 4318-8376 |
| 4318 | 1-4317 and 4319-8376 |
| 4319 | 1-4318 and 4320-8376 |
| 4320 | 1-4319 and 4321-8376 |
| 4321 | 1-4320 and 4322-8376 |
| 4322 | 1-4321 and 4323-8376 |
| 4323 | 1-4322 and 4324-8376 |
| 4324 | 1-4323 and 4325-8376 |
| 4325 | 1-4324 and 4326-8376 |
| 4326 | 1-4325 and 4327-8376 |
| 4327 | 1-4326 and 4328-8376 |
| 4328 | 1-4327 and 4329-8376 |
| 4329 | 1-4328 and 4330-8376 |
| 4330 | 1-4329 and 4331-8376 |
| 4331 | 1-4330 and 4332-8376 |
| 4332 | 1-4331 and 4333-8376 |
| 4333 | 1-4332 and 4334-8376 |
| 4334 | 1-4333 and 4335-8376 |
| 4335 | 1-4334 and 4336-8376 |
| 4336 | 1-4335 and 4337-8376 |
| 4337 | 1-4336 and 4338-8376 |
| 4338 | 1-4337 and 4339-8376 |
| 4339 | 1-4338 and 4340-8376 |
| 4340 | 1-4339 and 4341-8376 |
| 4341 | 1-4340 and 4342-8376 |
| 4342 | 1-4341 and 4343-8376 |
| 4343 | 1-4342 and 4344-8376 |
| 4344 | 1-4343 and 4345-8376 |
| 4345 | 1-4344 and 4346-8376 |
| 4346 | 1-4345 and 4347-8376 |
| 4347 | 1-4346 and 4348-8376 |
| 4348 | 1-4347 and 4349-8376 |
| 4349 | 1-4348 and 4350-8376 |
| 4350 | 1-4349 and 4351-8376 |
| 4351 | 1-4350 and 4352-8376 |
| 4352 | 1-4351 and 4353-8376 |
| 4353 | 1-4352 and 4354-8376 |
| 4354 | 1-4353 and 4355-8376 |
| 4355 | 1-4354 and 4356-8376 |
| 4356 | 1-4355 and 4357-8376 |
| 4357 | 1-4356 and 4358-8376 |
| 4358 | 1-4357 and 4359-8376 |
| 4359 | 1-4358 and 4360-8376 |
| 4360 | 1-4359 and 4361-8376 |
| 4361 | 1-4360 and 4362-8376 |
| 4362 | 1-4361 and 4363-8376 |
| 4363 | 1-4362 and 4364-8376 |
| 4364 | 1-4363 and 4365-8376 |
| 4365 | 1-4364 and 4366-8376 |
| 4366 | 1-4365 and 4367-8376 |
| 4367 | 1-4366 and 4368-8376 |
| 4368 | 1-4367 and 4369-8376 |
| 4369 | 1-4368 and 4370-8376 |
| 4370 | 1-4369 and 4371-8376 |
| 4371 | 1-4370 and 4372-8376 |
| 4372 | 1-4371 and 4373-8376 |
| 4373 | 1-4372 and 4374-8376 |
| 4374 | 1-4373 and 4375-8376 |
| 4375 | 1-4374 and 4376-8376 |
| 4376 | 1-4375 and 4377-8376 |
| 4377 | 1-4376 and 4378-8376 |
| 4378 | 1-4377 and 4379-8376 |
| 4379 | 1-4378 and 4380-8376 |
| 4380 | 1-4379 and 4381-8376 |
| 4381 | 1-4380 and 4382-8376 |
| 4382 | 1-4381 and 4383-8376 |
| 4383 | 1-4382 and 4384-8376 |
| 4384 | 1-4383 and 4385-8376 |
| 4385 | 1-4384 and 4386-8376 |
| 4386 | 1-4385 and 4387-8376 |
| 4387 | 1-4386 and 4388-8376 |
| 4388 | 1-4387 and 4389-8376 |
| 4389 | 1-4388 and 4390-8376 |
| 4390 | 1-4389 and 4391-8376 |
| 4391 | 1-4390 and 4392-8376 |
| 4392 | 1-4391 and 4393-8376 |
| 4393 | 1-4392 and 4394-8376 |
| 4394 | 1-4393 and 4395-8376 |
| 4395 | 1-4394 and 4396-8376 |
| 4396 | 1-4395 and 4397-8376 |
| 4397 | 1-4396 and 4398-8376 |
| 4398 | 1-4397 and 4399-8376 |
| 4399 | 1-4398 and 4400-8376 |
| 4400 | 1-4399 and 4401-8376 |
| 4401 | 1-4400 and 4402-8376 |
| 4402 | 1-4401 and 4403-8376 |
| 4403 | 1-4402 and 4404-8376 |
| 4404 | 1-4403 and 4405-8376 |
| 4405 | 1-4404 and 4406-8376 |
| 4406 | 1-4405 and 4407-8376 |
| 4407 | 1-4406 and 4408-8376 |
| 4408 | 1-4407 and 4409-8376 |
| 4409 | 1-4408 and 4410-8376 |
| 4410 | 1-4409 and 4411-8376 |
| 4411 | 1-4410 and 4412-8376 |
| 4412 | 1-4411 and 4413-8376 |
| 4413 | 1-4412 and 4414-8376 |
| 4414 | 1-4413 and 4415-8376 |
| 4415 | 1-4414 and 4416-8376 |
| 4416 | 1-4415 and 4417-8376 |
| 4417 | 1-4416 and 4418-8376 |
| 4418 | 1-4417 and 4419-8376 |
| 4419 | 1-4418 and 4420-8376 |
| 4420 | 1-4419 and 4421-8376 |
| 4421 | 1-4420 and 4422-8376 |
| 4422 | 1-4421 and 4423-8376 |
| 4423 | 1-4422 and 4424-8376 |
| 4424 | 1-4423 and 4425-8376 |
| 4425 | 1-4424 and 4426-8376 |
| 4426 | 1-4425 and 4427-8376 |
| 4427 | 1-4426 and 4428-8376 |
| 4428 | 1-4427 and 4429-8376 |
| 4429 | 1-4428 and 4430-8376 |
| 4430 | 1-4429 and 4431-8376 |
| 4431 | 1-4430 and 4432-8376 |
| 4432 | 1-4431 and 4433-8376 |
| 4433 | 1-4432 and 4434-8376 |
| 4434 | 1-4433 and 4435-8376 |
| 4435 | 1-4434 and 4436-8376 |
| 4436 | 1-4435 and 4437-8376 |
| 4437 | 1-4436 and 4438-8376 |
| 4438 | 1-4437 and 4439-8376 |
| 4439 | 1-4438 and 4440-8376 |
| 4440 | 1-4439 and 4441-8376 |
| 4441 | 1-4440 and 4442-8376 |
| 4442 | 1-4441 and 4443-8376 |
| 4443 | 1-4442 and 4444-8376 |
| 4444 | 1-4443 and 4445-8376 |
| 4445 | 1-4444 and 4446-8376 |
| 4446 | 1-4445 and 4447-8376 |
| 4447 | 1-4446 and 4448-8376 |

| First | Second |
| --- | --- |
| 4448 | 1-4447 and 4449-8376 |
| 4449 | 1-4448 and 4450-8376 |
| 4450 | 1-4449 and 4451-8376 |
| 4451 | 1-4450 and 4452-8376 |
| 4452 | 1-4451 and 4453-8376 |
| 4453 | 1-4452 and 4454-8376 |
| 4454 | 1-4453 and 4455-8376 |
| 4455 | 1-4454 and 4456-8376 |
| 4456 | 1-4455 and 4457-8376 |
| 4457 | 1-4456 and 4458-8376 |
| 4458 | 1-4457 and 4459-8376 |
| 4459 | 1-4458 and 4460-8376 |
| 4460 | 1-4459 and 4461-8376 |
| 4461 | 1-4460 and 4462-8376 |
| 4462 | 1-4461 and 4463-8376 |
| 4463 | 1-4462 and 4464-8376 |
| 4464 | 1-4463 and 4465-8376 |
| 4465 | 1-4464 and 4466-8376 |
| 4466 | 1-4465 and 4467-8376 |
| 4467 | 1-4466 and 4468-8376 |
| 4468 | 1-4467 and 4469-8376 |
| 4469 | 1-4468 and 4470-8376 |
| 4470 | 1-4469 and 4471-8376 |
| 4471 | 1-4470 and 4472-8376 |
| 4472 | 1-4471 and 4473-8376 |
| 4473 | 1-4472 and 4474-8376 |
| 4474 | 1-4473 and 4475-8376 |
| 4475 | 1-4474 and 4476-8376 |
| 4476 | 1-4475 and 4477-8376 |
| 4477 | 1-4476 and 4478-8376 |
| 4478 | 1-4477 and 4479-8376 |
| 4479 | 1-4478 and 4480-8376 |
| 4480 | 1-4479 and 4481-8376 |
| 4481 | 1-4480 and 4482-8376 |
| 4482 | 1-4481 and 4483-8376 |
| 4483 | 1-4482 and 4484-8376 |
| 4484 | 1-4483 and 4485-8376 |
| 4485 | 1-4484 and 4486-8376 |
| 4486 | 1-4485 and 4487-8376 |
| 4487 | 1-4486 and 4488-8376 |
| 4488 | 1-4487 and 4489-8376 |
| 4489 | 1-4488 and 4490-8376 |
| 4490 | 1-4489 and 4491-8376 |
| 4491 | 1-4490 and 4492-8376 |
| 4492 | 1-4491 and 4493-8376 |
| 4493 | 1-4492 and 4494-8376 |
| 4494 | 1-4493 and 4495-8376 |
| 4495 | 1-4494 and 4496-8376 |
| 4496 | 1-4495 and 4497-8376 |
| 4497 | 1-4496 and 4498-8376 |
| 4498 | 1-4497 and 4499-8376 |
| 4499 | 1-4498 and 4500-8376 |
| 4500 | 1-4499 and 4501-8376 |
| 4501 | 1-4500 and 4502-8376 |
| 4502 | 1-4501 and 4503-8376 |
| 4503 | 1-4502 and 4504-8376 |
| 4504 | 1-4503 and 4505-8376 |
| 4505 | 1-4504 and 4506-8376 |
| 4506 | 1-4505 and 4507-8376 |
| 4507 | 1-4506 and 4508-8376 |
| 4508 | 1-4507 and 4509-8376 |
| 4509 | 1-4508 and 4510-8376 |
| 4510 | 1-4509 and 4511-8376 |
| 4511 | 1-4510 and 4512-8376 |
| 4512 | 1-4511 and 4513-8376 |
| 4513 | 1-4512 and 4514-8376 |
| 4514 | 1-4513 and 4515-8376 |
| 4515 | 1-4514 and 4516-8376 |
| 4516 | 1-4515 and 4517-8376 |
| 4517 | 1-4516 and 4518-8376 |
| 4518 | 1-4517 and 4519-8376 |
| 4519 | 1-4518 and 4520-8376 |
| 4520 | 1-4519 and 4521-8376 |
| 4521 | 1-4520 and 4522-8376 |
| 4522 | 1-4521 and 4523-8376 |
| 4523 | 1-4522 and 4524-8376 |
| 4524 | 1-4523 and 4525-8376 |
| 4525 | 1-4524 and 4526-8376 |
| 4526 | 1-4525 and 4527-8376 |
| 4527 | 1-4526 and 4528-8376 |
| 4528 | 1-4527 and 4529-8376 |
| 4529 | 1-4528 and 4530-8376 |
| 4530 | 1-4529 and 4531-8376 |
| 4531 | 1-4530 and 4532-8376 |
| 4532 | 1-4531 and 4533-8376 |
| 4533 | 1-4532 and 4534-8376 |
| 4534 | 1-4533 and 4535-8376 |
| 4535 | 1-4534 and 4536-8376 |
| 4536 | 1-4535 and 4537-8376 |
| 4537 | 1-4536 and 4538-8376 |
| 4538 | 1-4537 and 4539-8376 |
| 4539 | 1-4538 and 4540-8376 |
| 4540 | 1-4539 and 4541-8376 |
| 4541 | 1-4540 and 4542-8376 |
| 4542 | 1-4541 and 4543-8376 |
| 4543 | 1-4542 and 4544-8376 |
| 4544 | 1-4543 and 4545-8376 |
| 4545 | 1-4544 and 4546-8376 |
| 4546 | 1-4545 and 4547-8376 |
| 4547 | 1-4546 and 4548-8376 |
| 4548 | 1-4547 and 4549-8376 |
| 4549 | 1-4548 and 4550-8376 |
| 4550 | 1-4549 and 4551-8376 |
| 4551 | 1-4550 and 4552-8376 |
| 4552 | 1-4551 and 4553-8376 |
| 4553 | 1-4552 and 4554-8376 |
| 4554 | 1-4553 and 4555-8376 |
| 4555 | 1-4554 and 4556-8376 |
| 4556 | 1-4555 and 4557-8376 |
| 4557 | 1-4556 and 4558-8376 |
| 4558 | 1-4557 and 4559-8376 |
| 4559 | 1-4558 and 4560-8376 |
| 4560 | 1-4559 and 4561-8376 |
| 4561 | 1-4560 and 4562-8376 |
| 4562 | 1-4561 and 4563-8376 |
| 4563 | 1-4562 and 4564-8376 |
| 4564 | 1-4563 and 4565-8376 |
| 4565 | 1-4564 and 4566-8376 |
| 4566 | 1-4565 and 4567-8376 |
| 4567 | 1-4566 and 4568-8376 |
| 4568 | 1-4567 and 4569-8376 |
| 4569 | 1-4568 and 4570-8376 |
| 4570 | 1-4569 and 4571-8376 |
| 4571 | 1-4570 and 4572-8376 |
| 4572 | 1-4571 and 4573-8376 |
| 4573 | 1-4572 and 4574-8376 |
| 4574 | 1-4573 and 4575-8376 |
| 4575 | 1-4574 and 4576-8376 |
| 4576 | 1-4575 and 4577-8376 |
| 4577 | 1-4576 and 4578-8376 |
| 4578 | 1-4577 and 4579-8376 |
| 4579 | 1-4578 and 4580-8376 |
| 4580 | 1-4579 and 4581-8376 |
| 4581 | 1-4580 and 4582-8376 |
| 4582 | 1-4581 and 4583-8376 |
| 4583 | 1-4582 and 4584-8376 |
| 4584 | 1-4583 and 4585-8376 |
| 4585 | 1-4584 and 4586-8376 |
| 4586 | 1-4585 and 4587-8376 |
| 4587 | 1-4586 and 4588-8376 |
| 4588 | 1-4587 and 4589-8376 |
| 4589 | 1-4588 and 4590-8376 |
| 4590 | 1-4589 and 4591-8376 |
| 4591 | 1-4590 and 4592-8376 |
| 4592 | 1-4591 and 4593-8376 |
| 4593 | 1-4592 and 4594-8376 |
| 4594 | 1-4593 and 4595-8376 |
| 4595 | 1-4594 and 4596-8376 |
| 4596 | 1-4595 and 4597-8376 |
| 4597 | 1-4596 and 4598-8376 |
| 4598 | 1-4597 and 4599-8376 |
| 4599 | 1-4598 and 4600-8376 |
| 4600 | 1-4599 and 4601-8376 |
| 4601 | 1-4600 and 4602-8376 |

| First | Second |
|---|---|
| 4602 | 1-4601 and 4603-8376 |
| 4603 | 1-4602 and 4604-8376 |
| 4604 | 1-4603 and 4605-8376 |
| 4605 | 1-4604 and 4606-8376 |
| 4606 | 1-4605 and 4607-8376 |
| 4607 | 1-4606 and 4608-8376 |
| 4608 | 1-4607 and 4609-8376 |
| 4609 | 1-4608 and 4610-8376 |
| 4610 | 1-4609 and 4611-8376 |
| 4611 | 1-4610 and 4612-8376 |
| 4612 | 1-4611 and 4613-8376 |
| 4613 | 1-4612 and 4614-8376 |
| 4614 | 1-4613 and 4615-8376 |
| 4615 | 1-4614 and 4616-8376 |
| 4616 | 1-4615 and 4617-8376 |
| 4617 | 1-4616 and 4618-8376 |
| 4618 | 1-4617 and 4619-8376 |
| 4619 | 1-4618 and 4620-8376 |
| 4620 | 1-4619 and 4621-8376 |
| 4621 | 1-4620 and 4622-8376 |
| 4622 | 1-4621 and 4623-8376 |
| 4623 | 1-4622 and 4624-8376 |
| 4624 | 1-4623 and 4625-8376 |
| 4625 | 1-4624 and 4626-8376 |
| 4626 | 1-4625 and 4627-8376 |
| 4627 | 1-4626 and 4628-8376 |
| 4628 | 1-4627 and 4629-8376 |
| 4629 | 1-4628 and 4630-8376 |
| 4630 | 1-4629 and 4631-8376 |
| 4631 | 1-4630 and 4632-8376 |
| 4632 | 1-4631 and 4633-8376 |
| 4633 | 1-4632 and 4634-8376 |
| 4634 | 1-4633 and 4635-8376 |
| 4635 | 1-4634 and 4636-8376 |
| 4636 | 1-4635 and 4637-8376 |
| 4637 | 1-4636 and 4638-8376 |
| 4638 | 1-4637 and 4639-8376 |
| 4639 | 1-4638 and 4640-8376 |
| 4640 | 1-4639 and 4641-8376 |
| 4641 | 1-4640 and 4642-8376 |
| 4642 | 1-4641 and 4643-8376 |
| 4643 | 1-4642 and 4644-8376 |
| 4644 | 1-4643 and 4645-8376 |
| 4645 | 1-4644 and 4646-8376 |
| 4646 | 1-4645 and 4647-8376 |
| 4647 | 1-4646 and 4648-8376 |
| 4648 | 1-4647 and 4649-8376 |
| 4649 | 1-4648 and 4650-8376 |
| 4650 | 1-4649 and 4651-8376 |
| 4651 | 1-4650 and 4652-8376 |
| 4652 | 1-4651 and 4653-8376 |
| 4653 | 1-4652 and 4654-8376 |
| 4654 | 1-4653 and 4655-8376 |
| 4655 | 1-4654 and 4656-8376 |
| 4656 | 1-4655 and 4657-8376 |
| 4657 | 1-4656 and 4658-8376 |
| 4658 | 1-4657 and 4659-8376 |
| 4659 | 1-4658 and 4660-8376 |
| 4660 | 1-4659 and 4661-8376 |
| 4661 | 1-4660 and 4662-8376 |
| 4662 | 1-4661 and 4663-8376 |
| 4663 | 1-4662 and 4664-8376 |
| 4664 | 1-4663 and 4665-8376 |
| 4665 | 1-4664 and 4666-8376 |
| 4666 | 1-4665 and 4667-8376 |
| 4667 | 1-4666 and 4668-8376 |
| 4668 | 1-4667 and 4669-8376 |
| 4669 | 1-4668 and 4670-8376 |
| 4670 | 1-4669 and 4671-8376 |
| 4671 | 1-4670 and 4672-8376 |
| 4672 | 1-4671 and 4673-8376 |
| 4673 | 1-4672 and 4674-8376 |
| 4674 | 1-4673 and 4675-8376 |
| 4675 | 1-4674 and 4676-8376 |
| 4676 | 1-4675 and 4677-8376 |
| 4677 | 1-4676 and 4678-8376 |
| 4678 | 1-4677 and 4679-8376 |
| 4679 | 1-4678 and 4680-8376 |
| 4680 | 1-4679 and 4681-8376 |
| 4681 | 1-4680 and 4682-8376 |
| 4682 | 1-4681 and 4683-8376 |
| 4683 | 1-4682 and 4684-8376 |
| 4684 | 1-4683 and 4685-8376 |
| 4685 | 1-4684 and 4686-8376 |
| 4686 | 1-4685 and 4687-8376 |
| 4687 | 1-4686 and 4688-8376 |
| 4688 | 1-4687 and 4689-8376 |
| 4689 | 1-4688 and 4690-8376 |
| 4690 | 1-4689 and 4691-8376 |
| 4691 | 1-4690 and 4692-8376 |
| 4692 | 1-4691 and 4693-8376 |
| 4693 | 1-4692 and 4694-8376 |
| 4694 | 1-4693 and 4695-8376 |
| 4695 | 1-4694 and 4696-8376 |
| 4696 | 1-4695 and 4697-8376 |
| 4697 | 1-4696 and 4698-8376 |
| 4698 | 1-4697 and 4699-8376 |
| 4699 | 1-4698 and 4700-8376 |
| 4700 | 1-4699 and 4701-8376 |
| 4701 | 1-4700 and 4702-8376 |
| 4702 | 1-4701 and 4703-8376 |
| 4703 | 1-4702 and 4704-8376 |
| 4704 | 1-4703 and 4705-8376 |
| 4705 | 1-4704 and 4706-8376 |
| 4706 | 1-4705 and 4707-8376 |
| 4707 | 1-4706 and 4708-8376 |
| 4708 | 1-4707 and 4709-8376 |
| 4709 | 1-4708 and 4710-8376 |
| 4710 | 1-4709 and 4711-8376 |
| 4711 | 1-4710 and 4712-8376 |
| 4712 | 1-4711 and 4713-8376 |
| 4713 | 1-4712 and 4714-8376 |
| 4714 | 1-4713 and 4715-8376 |
| 4715 | 1-4714 and 4716-8376 |
| 4716 | 1-4715 and 4717-8376 |
| 4717 | 1-4716 and 4718-8376 |
| 4718 | 1-4717 and 4719-8376 |
| 4719 | 1-4718 and 4720-8376 |
| 4720 | 1-4719 and 4721-8376 |
| 4721 | 1-4720 and 4722-8376 |
| 4722 | 1-4721 and 4723-8376 |
| 4723 | 1-4722 and 4724-8376 |
| 4724 | 1-4723 and 4725-8376 |
| 4725 | 1-4724 and 4726-8376 |
| 4726 | 1-4725 and 4727-8376 |
| 4727 | 1-4726 and 4728-8376 |
| 4728 | 1-4727 and 4729-8376 |
| 4729 | 1-4728 and 4730-8376 |
| 4730 | 1-4729 and 4731-8376 |
| 4731 | 1-4730 and 4732-8376 |
| 4732 | 1-4731 and 4733-8376 |
| 4733 | 1-4732 and 4734-8376 |
| 4734 | 1-4733 and 4735-8376 |
| 4735 | 1-4734 and 4736-8376 |
| 4736 | 1-4735 and 4737-8376 |
| 4737 | 1-4736 and 4738-8376 |
| 4738 | 1-4737 and 4739-8376 |
| 4739 | 1-4738 and 4740-8376 |
| 4740 | 1-4739 and 4741-8376 |
| 4741 | 1-4740 and 4742-8376 |
| 4742 | 1-4741 and 4743-8376 |
| 4743 | 1-4742 and 4744-8376 |
| 4744 | 1-4743 and 4745-8376 |
| 4745 | 1-4744 and 4746-8376 |
| 4746 | 1-4745 and 4747-8376 |
| 4747 | 1-4746 and 4748-8376 |
| 4748 | 1-4747 and 4749-8376 |
| 4749 | 1-4748 and 4750-8376 |
| 4750 | 1-4749 and 4751-8376 |
| 4751 | 1-4750 and 4752-8376 |
| 4752 | 1-4751 and 4753-8376 |
| 4753 | 1-4752 and 4754-8376 |
| 4754 | 1-4753 and 4755-8376 |
| 4755 | 1-4754 and 4756-8376 |

| First | Second |
|---|---|
| 4756 | 1-4755 and 4757-8376 |
| 4757 | 1-4756 and 4758-8376 |
| 4758 | 1-4757 and 4759-8376 |
| 4759 | 1-4758 and 4760-8376 |
| 4760 | 1-4759 and 4761-8376 |
| 4761 | 1-4760 and 4762-8376 |
| 4762 | 1-4761 and 4763-8376 |
| 4763 | 1-4762 and 4764-8376 |
| 4764 | 1-4763 and 4765-8376 |
| 4765 | 1-4764 and 4766-8376 |
| 4766 | 1-4765 and 4767-8376 |
| 4767 | 1-4766 and 4768-8376 |
| 4768 | 1-4767 and 4769-8376 |
| 4769 | 1-4768 and 4770-8376 |
| 4770 | 1-4769 and 4771-8376 |
| 4771 | 1-4770 and 4772-8376 |
| 4772 | 1-4771 and 4773-8376 |
| 4773 | 1-4772 and 4774-8376 |
| 4774 | 1-4773 and 4775-8376 |
| 4775 | 1-4774 and 4776-8376 |
| 4776 | 1-4775 and 4777-8376 |
| 4777 | 1-4776 and 4778-8376 |
| 4778 | 1-4777 and 4779-8376 |
| 4779 | 1-4778 and 4780-8376 |
| 4780 | 1-4779 and 4781-8376 |
| 4781 | 1-4780 and 4782-8376 |
| 4782 | 1-4781 and 4783-8376 |
| 4783 | 1-4782 and 4784-8376 |
| 4784 | 1-4783 and 4785-8376 |
| 4785 | 1-4784 and 4786-8376 |
| 4786 | 1-4785 and 4787-8376 |
| 4787 | 1-4786 and 4788-8376 |
| 4788 | 1-4787 and 4789-8376 |
| 4789 | 1-4788 and 4790-8376 |
| 4790 | 1-4789 and 4791-8376 |
| 4791 | 1-4790 and 4792-8376 |
| 4792 | 1-4791 and 4793-8376 |
| 4793 | 1-4792 and 4794-8376 |
| 4794 | 1-4793 and 4795-8376 |
| 4795 | 1-4794 and 4796-8376 |
| 4796 | 1-4795 and 4797-8376 |
| 4797 | 1-4796 and 4798-8376 |
| 4798 | 1-4797 and 4799-8376 |
| 4799 | 1-4798 and 4800-8376 |
| 4800 | 1-4799 and 4801-8376 |
| 4801 | 1-4800 and 4802-8376 |
| 4802 | 1-4801 and 4803-8376 |
| 4803 | 1-4802 and 4804-8376 |
| 4804 | 1-4803 and 4805-8376 |
| 4805 | 1-4804 and 4806-8376 |
| 4806 | 1-4805 and 4807-8376 |
| 4807 | 1-4806 and 4808-8376 |
| 4808 | 1-4807 and 4809-8376 |
| 4809 | 1-4808 and 4810-8376 |
| 4810 | 1-4809 and 4811-8376 |
| 4811 | 1-4810 and 4812-8376 |
| 4812 | 1-4811 and 4813-8376 |
| 4813 | 1-4812 and 4814-8376 |
| 4814 | 1-4813 and 4815-8376 |
| 4815 | 1-4814 and 4816-8376 |
| 4816 | 1-4815 and 4817-8376 |
| 4817 | 1-4816 and 4818-8376 |
| 4818 | 1-4817 and 4819-8376 |
| 4819 | 1-4818 and 4820-8376 |
| 4820 | 1-4819 and 4821-8376 |
| 4821 | 1-4820 and 4822-8376 |
| 4822 | 1-4821 and 4823-8376 |
| 4823 | 1-4822 and 4824-8376 |
| 4824 | 1-4823 and 4825-8376 |
| 4825 | 1-4824 and 4826-8376 |
| 4826 | 1-4825 and 4827-8376 |
| 4827 | 1-4826 and 4828-8376 |
| 4828 | 1-4827 and 4829-8376 |
| 4829 | 1-4828 and 4830-8376 |
| 4830 | 1-4829 and 4831-8376 |
| 4831 | 1-4830 and 4832-8376 |
| 4832 | 1-4831 and 4833-8376 |
| 4833 | 1-4832 and 4834-8376 |
| 4834 | 1-4833 and 4835-8376 |
| 4835 | 1-4834 and 4836-8376 |
| 4836 | 1-4835 and 4837-8376 |
| 4837 | 1-4836 and 4838-8376 |
| 4838 | 1-4837 and 4839-8376 |
| 4839 | 1-4838 and 4840-8376 |
| 4840 | 1-4839 and 4841-8376 |
| 4841 | 1-4840 and 4842-8376 |
| 4842 | 1-4841 and 4843-8376 |
| 4843 | 1-4842 and 4844-8376 |
| 4844 | 1-4843 and 4845-8376 |
| 4845 | 1-4844 and 4846-8376 |
| 4846 | 1-4845 and 4847-8376 |
| 4847 | 1-4846 and 4848-8376 |
| 4848 | 1-4847 and 4849-8376 |
| 4849 | 1-4848 and 4850-8376 |
| 4850 | 1-4849 and 4851-8376 |
| 4851 | 1-4850 and 4852-8376 |
| 4852 | 1-4851 and 4853-8376 |
| 4853 | 1-4852 and 4854-8376 |
| 4854 | 1-4853 and 4855-8376 |
| 4855 | 1-4854 and 4856-8376 |
| 4856 | 1-4855 and 4857-8376 |
| 4857 | 1-4856 and 4858-8376 |
| 4858 | 1-4857 and 4859-8376 |
| 4859 | 1-4858 and 4860-8376 |
| 4860 | 1-4859 and 4861-8376 |
| 4861 | 1-4860 and 4862-8376 |
| 4862 | 1-4861 and 4863-8376 |
| 4863 | 1-4862 and 4864-8376 |
| 4864 | 1-4863 and 4865-8376 |
| 4865 | 1-4864 and 4866-8376 |
| 4866 | 1-4865 and 4867-8376 |
| 4867 | 1-4866 and 4868-8376 |
| 4868 | 1-4867 and 4869-8376 |
| 4869 | 1-4868 and 4870-8376 |
| 4870 | 1-4869 and 4871-8376 |
| 4871 | 1-4870 and 4872-8376 |
| 4872 | 1-4871 and 4873-8376 |
| 4873 | 1-4872 and 4874-8376 |
| 4874 | 1-4873 and 4875-8376 |
| 4875 | 1-4874 and 4876-8376 |
| 4876 | 1-4875 and 4877-8376 |
| 4877 | 1-4876 and 4878-8376 |
| 4878 | 1-4877 and 4879-8376 |
| 4879 | 1-4878 and 4880-8376 |
| 4880 | 1-4879 and 4881-8376 |
| 4881 | 1-4880 and 4882-8376 |
| 4882 | 1-4881 and 4883-8376 |
| 4883 | 1-4882 and 4884-8376 |
| 4884 | 1-4883 and 4885-8376 |
| 4885 | 1-4884 and 4886-8376 |
| 4886 | 1-4885 and 4887-8376 |
| 4887 | 1-4886 and 4888-8376 |
| 4888 | 1-4887 and 4889-8376 |
| 4889 | 1-4888 and 4890-8376 |
| 4890 | 1-4889 and 4891-8376 |
| 4891 | 1-4890 and 4892-8376 |
| 4892 | 1-4891 and 4893-8376 |
| 4893 | 1-4892 and 4894-8376 |
| 4894 | 1-4893 and 4895-8376 |
| 4895 | 1-4894 and 4896-8376 |
| 4896 | 1-4895 and 4897-8376 |
| 4897 | 1-4896 and 4898-8376 |
| 4898 | 1-4897 and 4899-8376 |
| 4899 | 1-4898 and 4900-8376 |
| 4900 | 1-4899 and 4901-8376 |
| 4901 | 1-4900 and 4902-8376 |
| 4902 | 1-4901 and 4903-8376 |
| 4903 | 1-4902 and 4904-8376 |
| 4904 | 1-4903 and 4905-8376 |
| 4905 | 1-4904 and 4906-8376 |
| 4906 | 1-4905 and 4907-8376 |
| 4907 | 1-4906 and 4908-8376 |
| 4908 | 1-4907 and 4909-8376 |
| 4909 | 1-4908 and 4910-8376 |

| First | Second |
|---|---|
| 4910 | 1-4909 and 4911-8376 |
| 4911 | 1-4910 and 4912-8376 |
| 4912 | 1-4911 and 4913-8376 |
| 4913 | 1-4912 and 4914-8376 |
| 4914 | 1-4913 and 4915-8376 |
| 4915 | 1-4914 and 4916-8376 |
| 4916 | 1-4915 and 4917-8376 |
| 4917 | 1-4916 and 4918-8376 |
| 4918 | 1-4917 and 4919-8376 |
| 4919 | 1-4918 and 4920-8376 |
| 4920 | 1-4919 and 4921-8376 |
| 4921 | 1-4920 and 4922-8376 |
| 4922 | 1-4921 and 4923-8376 |
| 4923 | 1-4922 and 4924-8376 |
| 4924 | 1-4923 and 4925-8376 |
| 4925 | 1-4924 and 4926-8376 |
| 4926 | 1-4925 and 4927-8376 |
| 4927 | 1-4926 and 4928-8376 |
| 4928 | 1-4927 and 4929-8376 |
| 4929 | 1-4928 and 4930-8376 |
| 4930 | 1-4929 and 4931-8376 |
| 4931 | 1-4930 and 4932-8376 |
| 4932 | 1-4931 and 4933-8376 |
| 4933 | 1-4932 and 4934-8376 |
| 4934 | 1-4933 and 4935-8376 |
| 4935 | 1-4934 and 4936-8376 |
| 4936 | 1-4935 and 4937-8376 |
| 4937 | 1-4936 and 4938-8376 |
| 4938 | 1-4937 and 4939-8376 |
| 4939 | 1-4938 and 4940-8376 |
| 4940 | 1-4939 and 4941-8376 |
| 4941 | 1-4940 and 4942-8376 |
| 4942 | 1-4941 and 4943-8376 |
| 4943 | 1-4942 and 4944-8376 |
| 4944 | 1-4943 and 4945-8376 |
| 4945 | 1-4944 and 4946-8376 |
| 4946 | 1-4945 and 4947-8376 |
| 4947 | 1-4946 and 4948-8376 |
| 4948 | 1-4947 and 4949-8376 |
| 4949 | 1-4948 and 4950-8376 |
| 4950 | 1-4949 and 4951-8376 |
| 4951 | 1-4950 and 4952-8376 |
| 4952 | 1-4951 and 4953-8376 |
| 4953 | 1-4952 and 4954-8376 |
| 4954 | 1-4953 and 4955-8376 |
| 4955 | 1-4954 and 4956-8376 |
| 4956 | 1-4955 and 4957-8376 |
| 4957 | 1-4956 and 4958-8376 |
| 4958 | 1-4957 and 4959-8376 |
| 4959 | 1-4958 and 4960-8376 |
| 4960 | 1-4959 and 4961-8376 |
| 4961 | 1-4960 and 4962-8376 |
| 4962 | 1-4961 and 4963-8376 |
| 4963 | 1-4962 and 4964-8376 |
| 4964 | 1-4963 and 4965-8376 |
| 4965 | 1-4964 and 4966-8376 |
| 4966 | 1-4965 and 4967-8376 |
| 4967 | 1-4966 and 4968-8376 |
| 4968 | 1-4967 and 4969-8376 |
| 4969 | 1-4968 and 4970-8376 |
| 4970 | 1-4969 and 4971-8376 |
| 4971 | 1-4970 and 4972-8376 |
| 4972 | 1-4971 and 4973-8376 |
| 4973 | 1-4972 and 4974-8376 |
| 4974 | 1-4973 and 4975-8376 |
| 4975 | 1-4974 and 4976-8376 |
| 4976 | 1-4975 and 4977-8376 |
| 4977 | 1-4976 and 4978-8376 |
| 4978 | 1-4977 and 4979-8376 |
| 4979 | 1-4978 and 4980-8376 |
| 4980 | 1-4979 and 4981-8376 |
| 4981 | 1-4980 and 4982-8376 |
| 4982 | 1-4981 and 4983-8376 |
| 4983 | 1-4982 and 4984-8376 |
| 4984 | 1-4983 and 4985-8376 |
| 4985 | 1-4984 and 4986-8376 |
| 4986 | 1-4985 and 4987-8376 |
| 4987 | 1-4986 and 4988-8376 |
| 4988 | 1-4987 and 4989-8376 |
| 4989 | 1-4988 and 4990-8376 |
| 4990 | 1-4989 and 4991-8376 |
| 4991 | 1-4990 and 4992-8376 |
| 4992 | 1-4991 and 4993-8376 |
| 4993 | 1-4992 and 4994-8376 |
| 4994 | 1-4993 and 4995-8376 |
| 4995 | 1-4994 and 4996-8376 |
| 4996 | 1-4995 and 4997-8376 |
| 4997 | 1-4996 and 4998-8376 |
| 4998 | 1-4997 and 4999-8376 |
| 4999 | 1-4998 and 5000-8376 |
| 5000 | 1-4999 and 5001-8376 |
| 5001 | 1-5000 and 5002-8376 |
| 5002 | 1-5001 and 5003-8376 |
| 5003 | 1-5002 and 5004-8376 |
| 5004 | 1-5003 and 5005-8376 |
| 5005 | 1-5004 and 5006-8376 |
| 5006 | 1-5005 and 5007-8376 |
| 5007 | 1-5006 and 5008-8376 |
| 5008 | 1-5007 and 5009-8376 |
| 5009 | 1-5008 and 5010-8376 |
| 5010 | 1-5009 and 5011-8376 |
| 5011 | 1-5010 and 5012-8376 |
| 5012 | 1-5011 and 5013-8376 |
| 5013 | 1-5012 and 5014-8376 |
| 5014 | 1-5013 and 5015-8376 |
| 5015 | 1-5014 and 5016-8376 |
| 5016 | 1-5015 and 5017-8376 |
| 5017 | 1-5016 and 5018-8376 |
| 5018 | 1-5017 and 5019-8376 |
| 5019 | 1-5018 and 5020-8376 |
| 5020 | 1-5019 and 5021-8376 |
| 5021 | 1-5020 and 5022-8376 |
| 5022 | 1-5021 and 5023-8376 |
| 5023 | 1-5022 and 5024-8376 |
| 5024 | 1-5023 and 5025-8376 |
| 5025 | 1-5024 and 5026-8376 |
| 5026 | 1-5025 and 5027-8376 |
| 5027 | 1-5026 and 5028-8376 |
| 5028 | 1-5027 and 5029-8376 |
| 5029 | 1-5028 and 5030-8376 |
| 5030 | 1-5029 and 5031-8376 |
| 5031 | 1-5030 and 5032-8376 |
| 5032 | 1-5031 and 5033-8376 |
| 5033 | 1-5032 and 5034-8376 |
| 5034 | 1-5033 and 5035-8376 |
| 5035 | 1-5034 and 5036-8376 |
| 5036 | 1-5035 and 5037-8376 |
| 5037 | 1-5036 and 5038-8376 |
| 5038 | 1-5037 and 5039-8376 |
| 5039 | 1-5038 and 5040-8376 |
| 5040 | 1-5039 and 5041-8376 |
| 5041 | 1-5040 and 5042-8376 |
| 5042 | 1-5041 and 5043-8376 |
| 5043 | 1-5042 and 5044-8376 |
| 5044 | 1-5043 and 5045-8376 |
| 5045 | 1-5044 and 5046-8376 |
| 5046 | 1-5045 and 5047-8376 |
| 5047 | 1-5046 and 5048-8376 |
| 5048 | 1-5047 and 5049-8376 |
| 5049 | 1-5048 and 5050-8376 |
| 5050 | 1-5049 and 5051-8376 |
| 5051 | 1-5050 and 5052-8376 |
| 5052 | 1-5051 and 5053-8376 |
| 5053 | 1-5052 and 5054-8376 |
| 5054 | 1-5053 and 5055-8376 |
| 5055 | 1-5054 and 5056-8376 |
| 5056 | 1-5055 and 5057-8376 |
| 5057 | 1-5056 and 5058-8376 |
| 5058 | 1-5057 and 5059-8376 |
| 5059 | 1-5058 and 5060-8376 |
| 5060 | 1-5059 and 5061-8376 |
| 5061 | 1-5060 and 5062-8376 |
| 5062 | 1-5061 and 5063-8376 |
| 5063 | 1-5062 and 5064-8376 |

| First | Second |
|---|---|
| 5064 | 1-5063 and 5065-8376 |
| 5065 | 1-5064 and 5066-8376 |
| 5066 | 1-5065 and 5067-8376 |
| 5067 | 1-5066 and 5068-8376 |
| 5068 | 1-5067 and 5069-8376 |
| 5069 | 1-5068 and 5070-8376 |
| 5070 | 1-5069 and 5071-8376 |
| 5071 | 1-5070 and 5072-8376 |
| 5072 | 1-5071 and 5073-8376 |
| 5073 | 1-5072 and 5074-8376 |
| 5074 | 1-5073 and 5075-8376 |
| 5075 | 1-5074 and 5076-8376 |
| 5076 | 1-5075 and 5077-8376 |
| 5077 | 1-5076 and 5078-8376 |
| 5078 | 1-5077 and 5079-8376 |
| 5079 | 1-5078 and 5080-8376 |
| 5080 | 1-5079 and 5081-8376 |
| 5081 | 1-5080 and 5082-8376 |
| 5082 | 1-5081 and 5083-8376 |
| 5083 | 1-5082 and 5084-8376 |
| 5084 | 1-5083 and 5085-8376 |
| 5085 | 1-5084 and 5086-8376 |
| 5086 | 1-5085 and 5087-8376 |
| 5087 | 1-5086 and 5088-8376 |
| 5088 | 1-5087 and 5089-8376 |
| 5089 | 1-5088 and 5090-8376 |
| 5090 | 1-5089 and 5091-8376 |
| 5091 | 1-5090 and 5092-8376 |
| 5092 | 1-5091 and 5093-8376 |
| 5093 | 1-5092 and 5094-8376 |
| 5094 | 1-5093 and 5095-8376 |
| 5095 | 1-5094 and 5096-8376 |
| 5096 | 1-5095 and 5097-8376 |
| 5097 | 1-5096 and 5098-8376 |
| 5098 | 1-5097 and 5099-8376 |
| 5099 | 1-5098 and 5100-8376 |
| 5100 | 1-5099 and 5101-8376 |
| 5101 | 1-5100 and 5102-8376 |
| 5102 | 1-5101 and 5103-8376 |
| 5103 | 1-5102 and 5104-8376 |
| 5104 | 1-5103 and 5105-8376 |
| 5105 | 1-5104 and 5106-8376 |
| 5106 | 1-5105 and 5107-8376 |
| 5107 | 1-5106 and 5108-8376 |
| 5108 | 1-5107 and 5109-8376 |
| 5109 | 1-5108 and 5110-8376 |
| 5110 | 1-5109 and 5111-8376 |
| 5111 | 1-5110 and 5112-8376 |
| 5112 | 1-5111 and 5113-8376 |
| 5113 | 1-5112 and 5114-8376 |
| 5114 | 1-5113 and 5115-8376 |
| 5115 | 1-5114 and 5116-8376 |
| 5116 | 1-5115 and 5117-8376 |
| 5117 | 1-5116 and 5118-8376 |
| 5118 | 1-5117 and 5119-8376 |
| 5119 | 1-5118 and 5120-8376 |
| 5120 | 1-5119 and 5121-8376 |
| 5121 | 1-5120 and 5122-8376 |
| 5122 | 1-5121 and 5123-8376 |
| 5123 | 1-5122 and 5124-8376 |
| 5124 | 1-5123 and 5125-8376 |
| 5125 | 1-5124 and 5126-8376 |
| 5126 | 1-5125 and 5127-8376 |
| 5127 | 1-5126 and 5128-8376 |
| 5128 | 1-5127 and 5129-8376 |
| 5129 | 1-5128 and 5130-8376 |
| 5130 | 1-5129 and 5131-8376 |
| 5131 | 1-5130 and 5132-8376 |
| 5132 | 1-5131 and 5133-8376 |
| 5133 | 1-5132 and 5134-8376 |
| 5134 | 1-5133 and 5135-8376 |
| 5135 | 1-5134 and 5136-8376 |
| 5136 | 1-5135 and 5137-8376 |
| 5137 | 1-5136 and 5138-8376 |
| 5138 | 1-5137 and 5139-8376 |
| 5139 | 1-5138 and 5140-8376 |
| 5140 | 1-5139 and 5141-8376 |
| 5141 | 1-5140 and 5142-8376 |
| 5142 | 1-5141 and 5143-8376 |
| 5143 | 1-5142 and 5144-8376 |
| 5144 | 1-5143 and 5145-8376 |
| 5145 | 1-5144 and 5146-8376 |
| 5146 | 1-5145 and 5147-8376 |
| 5147 | 1-5146 and 5148-8376 |
| 5148 | 1-5147 and 5149-8376 |
| 5149 | 1-5148 and 5150-8376 |
| 5150 | 1-5149 and 5151-8376 |
| 5151 | 1-5150 and 5152-8376 |
| 5152 | 1-5151 and 5153-8376 |
| 5153 | 1-5152 and 5154-8376 |
| 5154 | 1-5153 and 5155-8376 |
| 5155 | 1-5154 and 5156-8376 |
| 5156 | 1-5155 and 5157-8376 |
| 5157 | 1-5156 and 5158-8376 |
| 5158 | 1-5157 and 5159-8376 |
| 5159 | 1-5158 and 5160-8376 |
| 5160 | 1-5159 and 5161-8376 |
| 5161 | 1-5160 and 5162-8376 |
| 5162 | 1-5161 and 5163-8376 |
| 5163 | 1-5162 and 5164-8376 |
| 5164 | 1-5163 and 5165-8376 |
| 5165 | 1-5164 and 5166-8376 |
| 5166 | 1-5165 and 5167-8376 |
| 5167 | 1-5166 and 5168-8376 |
| 5168 | 1-5167 and 5169-8376 |
| 5169 | 1-5168 and 5170-8376 |
| 5170 | 1-5169 and 5171-8376 |
| 5171 | 1-5170 and 5172-8376 |
| 5172 | 1-5171 and 5173-8376 |
| 5173 | 1-5172 and 5174-8376 |
| 5174 | 1-5173 and 5175-8376 |
| 5175 | 1-5174 and 5176-8376 |
| 5176 | 1-5175 and 5177-8376 |
| 5177 | 1-5176 and 5178-8376 |
| 5178 | 1-5177 and 5179-8376 |
| 5179 | 1-5178 and 5180-8376 |
| 5180 | 1-5179 and 5181-8376 |
| 5181 | 1-5180 and 5182-8376 |
| 5182 | 1-5181 and 5183-8376 |
| 5183 | 1-5182 and 5184-8376 |
| 5184 | 1-5183 and 5185-8376 |
| 5185 | 1-5184 and 5186-8376 |
| 5186 | 1-5185 and 5187-8376 |
| 5187 | 1-5186 and 5188-8376 |
| 5188 | 1-5187 and 5189-8376 |
| 5189 | 1-5188 and 5190-8376 |
| 5190 | 1-5189 and 5191-8376 |
| 5191 | 1-5190 and 5192-8376 |
| 5192 | 1-5191 and 5193-8376 |
| 5193 | 1-5192 and 5194-8376 |
| 5194 | 1-5193 and 5195-8376 |
| 5195 | 1-5194 and 5196-8376 |
| 5196 | 1-5195 and 5197-8376 |
| 5197 | 1-5196 and 5198-8376 |
| 5198 | 1-5197 and 5199-8376 |
| 5199 | 1-5198 and 5200-8376 |
| 5200 | 1-5199 and 5201-8376 |
| 5201 | 1-5200 and 5202-8376 |
| 5202 | 1-5201 and 5203-8376 |
| 5203 | 1-5202 and 5204-8376 |
| 5204 | 1-5203 and 5205-8376 |
| 5205 | 1-5204 and 5206-8376 |
| 5206 | 1-5205 and 5207-8376 |
| 5207 | 1-5206 and 5208-8376 |
| 5208 | 1-5207 and 5209-8376 |
| 5209 | 1-5208 and 5210-8376 |
| 5210 | 1-5209 and 5211-8376 |
| 5211 | 1-5210 and 5212-8376 |
| 5212 | 1-5211 and 5213-8376 |
| 5213 | 1-5212 and 5214-8376 |
| 5214 | 1-5213 and 5215-8376 |
| 5215 | 1-5214 and 5216-8376 |
| 5216 | 1-5215 and 5217-8376 |
| 5217 | 1-5216 and 5218-8376 |

| First | Second |
|---|---|
| 5218 | 1-5217 and 5219-8376 |
| 5219 | 1-5218 and 5220-8376 |
| 5220 | 1-5219 and 5221-8376 |
| 5221 | 1-5220 and 5222-8376 |
| 5222 | 1-5221 and 5223-8376 |
| 5223 | 1-5222 and 5224-8376 |
| 5224 | 1-5223 and 5225-8376 |
| 5225 | 1-5224 and 5226-8376 |
| 5226 | 1-5225 and 5227-8376 |
| 5227 | 1-5226 and 5228-8376 |
| 5228 | 1-5227 and 5229-8376 |
| 5229 | 1-5228 and 5230-8376 |
| 5230 | 1-5229 and 5231-8376 |
| 5231 | 1-5230 and 5232-8376 |
| 5232 | 1-5231 and 5233-8376 |
| 5233 | 1-5232 and 5234-8376 |
| 5234 | 1-5233 and 5235-8376 |
| 5235 | 1-5234 and 5236-8376 |
| 5236 | 1-5235 and 5237-8376 |
| 5237 | 1-5236 and 5238-8376 |
| 5238 | 1-5237 and 5239-8376 |
| 5239 | 1-5238 and 5240-8376 |
| 5240 | 1-5239 and 5241-8376 |
| 5241 | 1-5240 and 5242-8376 |
| 5242 | 1-5241 and 5243-8376 |
| 5243 | 1-5242 and 5244-8376 |
| 5244 | 1-5243 and 5245-8376 |
| 5245 | 1-5244 and 5246-8376 |
| 5246 | 1-5245 and 5247-8376 |
| 5247 | 1-5246 and 5248-8376 |
| 5248 | 1-5247 and 5249-8376 |
| 5249 | 1-5248 and 5250-8376 |
| 5250 | 1-5249 and 5251-8376 |
| 5251 | 1-5250 and 5252-8376 |
| 5252 | 1-5251 and 5253-8376 |
| 5253 | 1-5252 and 5254-8376 |
| 5254 | 1-5253 and 5255-8376 |
| 5255 | 1-5254 and 5256-8376 |
| 5256 | 1-5255 and 5257-8376 |
| 5257 | 1-5256 and 5258-8376 |
| 5258 | 1-5257 and 5259-8376 |
| 5259 | 1-5258 and 5260-8376 |
| 5260 | 1-5259 and 5261-8376 |
| 5261 | 1-5260 and 5262-8376 |
| 5262 | 1-5261 and 5263-8376 |
| 5263 | 1-5262 and 5264-8376 |
| 5264 | 1-5263 and 5265-8376 |
| 5265 | 1-5264 and 5266-8376 |
| 5266 | 1-5265 and 5267-8376 |
| 5267 | 1-5266 and 5268-8376 |
| 5268 | 1-5267 and 5269-8376 |
| 5269 | 1-5268 and 5270-8376 |
| 5270 | 1-5269 and 5271-8376 |
| 5271 | 1-5270 and 5272-8376 |
| 5272 | 1-5271 and 5273-8376 |
| 5273 | 1-5272 and 5274-8376 |
| 5274 | 1-5273 and 5275-8376 |
| 5275 | 1-5274 and 5276-8376 |
| 5276 | 1-5275 and 5277-8376 |
| 5277 | 1-5276 and 5278-8376 |
| 5278 | 1-5277 and 5279-8376 |
| 5279 | 1-5278 and 5280-8376 |
| 5280 | 1-5279 and 5281-8376 |
| 5281 | 1-5280 and 5282-8376 |
| 5282 | 1-5281 and 5283-8376 |
| 5283 | 1-5282 and 5284-8376 |
| 5284 | 1-5283 and 5285-8376 |
| 5285 | 1-5284 and 5286-8376 |
| 5286 | 1-5285 and 5287-8376 |
| 5287 | 1-5286 and 5288-8376 |
| 5288 | 1-5287 and 5289-8376 |
| 5289 | 1-5288 and 5290-8376 |
| 5290 | 1-5289 and 5291-8376 |
| 5291 | 1-5290 and 5292-8376 |
| 5292 | 1-5291 and 5293-8376 |
| 5293 | 1-5292 and 5294-8376 |
| 5294 | 1-5293 and 5295-8376 |
| 5295 | 1-5294 and 5296-8376 |
| 5296 | 1-5295 and 5297-8376 |
| 5297 | 1-5296 and 5298-8376 |
| 5298 | 1-5297 and 5299-8376 |
| 5299 | 1-5298 and 5300-8376 |
| 5300 | 1-5299 and 5301-8376 |
| 5301 | 1-5300 and 5302-8376 |
| 5302 | 1-5301 and 5303-8376 |
| 5303 | 1-5302 and 5304-8376 |
| 5304 | 1-5303 and 5305-8376 |
| 5305 | 1-5304 and 5306-8376 |
| 5306 | 1-5305 and 5307-8376 |
| 5307 | 1-5306 and 5308-8376 |
| 5308 | 1-5307 and 5309-8376 |
| 5309 | 1-5308 and 5310-8376 |
| 5310 | 1-5309 and 5311-8376 |
| 5311 | 1-5310 and 5312-8376 |
| 5312 | 1-5311 and 5313-8376 |
| 5313 | 1-5312 and 5314-8376 |
| 5314 | 1-5313 and 5315-8376 |
| 5315 | 1-5314 and 5316-8376 |
| 5316 | 1-5315 and 5317-8376 |
| 5317 | 1-5316 and 5318-8376 |
| 5318 | 1-5317 and 5319-8376 |
| 5319 | 1-5318 and 5320-8376 |
| 5320 | 1-5319 and 5321-8376 |
| 5321 | 1-5320 and 5322-8376 |
| 5322 | 1-5321 and 5323-8376 |
| 5323 | 1-5322 and 5324-8376 |
| 5324 | 1-5323 and 5325-8376 |
| 5325 | 1-5324 and 5326-8376 |
| 5326 | 1-5325 and 5327-8376 |
| 5327 | 1-5326 and 5328-8376 |
| 5328 | 1-5327 and 5329-8376 |
| 5329 | 1-5328 and 5330-8376 |
| 5330 | 1-5329 and 5331-8376 |
| 5331 | 1-5330 and 5332-8376 |
| 5332 | 1-5331 and 5333-8376 |
| 5333 | 1-5332 and 5334-8376 |
| 5334 | 1-5333 and 5335-8376 |
| 5335 | 1-5334 and 5336-8376 |
| 5336 | 1-5335 and 5337-8376 |
| 5337 | 1-5336 and 5338-8376 |
| 5338 | 1-5337 and 5339-8376 |
| 5339 | 1-5338 and 5340-8376 |
| 5340 | 1-5339 and 5341-8376 |
| 5341 | 1-5340 and 5342-8376 |
| 5342 | 1-5341 and 5343-8376 |
| 5343 | 1-5342 and 5344-8376 |
| 5344 | 1-5343 and 5345-8376 |
| 5345 | 1-5344 and 5346-8376 |
| 5346 | 1-5345 and 5347-8376 |
| 5347 | 1-5346 and 5348-8376 |
| 5348 | 1-5347 and 5349-8376 |
| 5349 | 1-5348 and 5350-8376 |
| 5350 | 1-5349 and 5351-8376 |
| 5351 | 1-5350 and 5352-8376 |
| 5352 | 1-5351 and 5353-8376 |
| 5353 | 1-5352 and 5354-8376 |
| 5354 | 1-5353 and 5355-8376 |
| 5355 | 1-5354 and 5356-8376 |
| 5356 | 1-5355 and 5357-8376 |
| 5357 | 1-5356 and 5358-8376 |
| 5358 | 1-5357 and 5359-8376 |
| 5359 | 1-5358 and 5360-8376 |
| 5360 | 1-5359 and 5361-8376 |
| 5361 | 1-5360 and 5362-8376 |
| 5362 | 1-5361 and 5363-8376 |
| 5363 | 1-5362 and 5364-8376 |
| 5364 | 1-5363 and 5365-8376 |
| 5365 | 1-5364 and 5366-8376 |
| 5366 | 1-5365 and 5367-8376 |
| 5367 | 1-5366 and 5368-8376 |
| 5368 | 1-5367 and 5369-8376 |
| 5369 | 1-5368 and 5370-8376 |
| 5370 | 1-5369 and 5371-8376 |
| 5371 | 1-5370 and 5372-8376 |

| First | Second |
|---|---|
| 5372 | 1-5371 and 5373-8376 |
| 5373 | 1-5372 and 5374-8376 |
| 5374 | 1-5373 and 5375-8376 |
| 5375 | 1-5374 and 5376-8376 |
| 5376 | 1-5375 and 5377-8376 |
| 5377 | 1-5376 and 5378-8376 |
| 5378 | 1-5377 and 5379-8376 |
| 5379 | 1-5378 and 5380-8376 |
| 5380 | 1-5379 and 5381-8376 |
| 5381 | 1-5380 and 5382-8376 |
| 5382 | 1-5381 and 5383-8376 |
| 5383 | 1-5382 and 5384-8376 |
| 5384 | 1-5383 and 5385-8376 |
| 5385 | 1-5384 and 5386-8376 |
| 5386 | 1-5385 and 5387-8376 |
| 5387 | 1-5386 and 5388-8376 |
| 5388 | 1-5387 and 5389-8376 |
| 5389 | 1-5388 and 5390-8376 |
| 5390 | 1-5389 and 5391-8376 |
| 5391 | 1-5390 and 5392-8376 |
| 5392 | 1-5391 and 5393-8376 |
| 5393 | 1-5392 and 5394-8376 |
| 5394 | 1-5393 and 5395-8376 |
| 5395 | 1-5394 and 5396-8376 |
| 5396 | 1-5395 and 5397-8376 |
| 5397 | 1-5396 and 5398-8376 |
| 5398 | 1-5397 and 5399-8376 |
| 5399 | 1-5398 and 5400-8376 |
| 5400 | 1-5399 and 5401-8376 |
| 5401 | 1-5400 and 5402-8376 |
| 5402 | 1-5401 and 5403-8376 |
| 5403 | 1-5402 and 5404-8376 |
| 5404 | 1-5403 and 5405-8376 |
| 5405 | 1-5404 and 5406-8376 |
| 5406 | 1-5405 and 5407-8376 |
| 5407 | 1-5406 and 5408-8376 |
| 5408 | 1-5407 and 5409-8376 |
| 5409 | 1-5408 and 5410-8376 |
| 5410 | 1-5409 and 5411-8376 |
| 5411 | 1-5410 and 5412-8376 |
| 5412 | 1-5411 and 5413-8376 |
| 5413 | 1-5412 and 5414-8376 |
| 5414 | 1-5413 and 5415-8376 |
| 5415 | 1-5414 and 5416-8376 |
| 5416 | 1-5415 and 5417-8376 |
| 5417 | 1-5416 and 5418-8376 |
| 5418 | 1-5417 and 5419-8376 |
| 5419 | 1-5418 and 5420-8376 |
| 5420 | 1-5419 and 5421-8376 |
| 5421 | 1-5420 and 5422-8376 |
| 5422 | 1-5421 and 5423-8376 |
| 5423 | 1-5422 and 5424-8376 |
| 5424 | 1-5423 and 5425-8376 |
| 5425 | 1-5424 and 5426-8376 |
| 5426 | 1-5425 and 5427-8376 |
| 5427 | 1-5426 and 5428-8376 |
| 5428 | 1-5427 and 5429-8376 |
| 5429 | 1-5428 and 5430-8376 |
| 5430 | 1-5429 and 5431-8376 |
| 5431 | 1-5430 and 5432-8376 |
| 5432 | 1-5431 and 5433-8376 |
| 5433 | 1-5432 and 5434-8376 |
| 5434 | 1-5433 and 5435-8376 |
| 5435 | 1-5434 and 5436-8376 |
| 5436 | 1-5435 and 5437-8376 |
| 5437 | 1-5436 and 5438-8376 |
| 5438 | 1-5437 and 5439-8376 |
| 5439 | 1-5438 and 5440-8376 |
| 5440 | 1-5439 and 5441-8376 |
| 5441 | 1-5440 and 5442-8376 |
| 5442 | 1-5441 and 5443-8376 |
| 5443 | 1-5442 and 5444-8376 |
| 5444 | 1-5443 and 5445-8376 |
| 5445 | 1-5444 and 5446-8376 |
| 5446 | 1-5445 and 5447-8376 |
| 5447 | 1-5446 and 5448-8376 |
| 5448 | 1-5447 and 5449-8376 |
| 5449 | 1-5448 and 5450-8376 |
| 5450 | 1-5449 and 5451-8376 |
| 5451 | 1-5450 and 5452-8376 |
| 5452 | 1-5451 and 5453-8376 |
| 5453 | 1-5452 and 5454-8376 |
| 5454 | 1-5453 and 5455-8376 |
| 5455 | 1-5454 and 5456-8376 |
| 5456 | 1-5455 and 5457-8376 |
| 5457 | 1-5456 and 5458-8376 |
| 5458 | 1-5457 and 5459-8376 |
| 5459 | 1-5458 and 5460-8376 |
| 5460 | 1-5459 and 5461-8376 |
| 5461 | 1-5460 and 5462-8376 |
| 5462 | 1-5461 and 5463-8376 |
| 5463 | 1-5462 and 5464-8376 |
| 5464 | 1-5463 and 5465-8376 |
| 5465 | 1-5464 and 5466-8376 |
| 5466 | 1-5465 and 5467-8376 |
| 5467 | 1-5466 and 5468-8376 |
| 5468 | 1-5467 and 5469-8376 |
| 5469 | 1-5468 and 5470-8376 |
| 5470 | 1-5469 and 5471-8376 |
| 5471 | 1-5470 and 5472-8376 |
| 5472 | 1-5471 and 5473-8376 |
| 5473 | 1-5472 and 5474-8376 |
| 5474 | 1-5473 and 5475-8376 |
| 5475 | 1-5474 and 5476-8376 |
| 5476 | 1-5475 and 5477-8376 |
| 5477 | 1-5476 and 5478-8376 |
| 5478 | 1-5477 and 5479-8376 |
| 5479 | 1-5478 and 5480-8376 |
| 5480 | 1-5479 and 5481-8376 |
| 5481 | 1-5480 and 5482-8376 |
| 5482 | 1-5481 and 5483-8376 |
| 5483 | 1-5482 and 5484-8376 |
| 5484 | 1-5483 and 5485-8376 |
| 5485 | 1-5484 and 5486-8376 |
| 5486 | 1-5485 and 5487-8376 |
| 5487 | 1-5486 and 5488-8376 |
| 5488 | 1-5487 and 5489-8376 |
| 5489 | 1-5488 and 5490-8376 |
| 5490 | 1-5489 and 5491-8376 |
| 5491 | 1-5490 and 5492-8376 |
| 5492 | 1-5491 and 5493-8376 |
| 5493 | 1-5492 and 5494-8376 |
| 5494 | 1-5493 and 5495-8376 |
| 5495 | 1-5494 and 5496-8376 |
| 5496 | 1-5495 and 5497-8376 |
| 5497 | 1-5496 and 5498-8376 |
| 5498 | 1-5497 and 5499-8376 |
| 5499 | 1-5498 and 5500-8376 |
| 5500 | 1-5499 and 5501-8376 |
| 5501 | 1-5500 and 5502-8376 |
| 5502 | 1-5501 and 5503-8376 |
| 5503 | 1-5502 and 5504-8376 |
| 5504 | 1-5503 and 5505-8376 |
| 5505 | 1-5504 and 5506-8376 |
| 5506 | 1-5505 and 5507-8376 |
| 5507 | 1-5506 and 5508-8376 |
| 5508 | 1-5507 and 5509-8376 |
| 5509 | 1-5508 and 5510-8376 |
| 5510 | 1-5509 and 5511-8376 |
| 5511 | 1-5510 and 5512-8376 |
| 5512 | 1-5511 and 5513-8376 |
| 5513 | 1-5512 and 5514-8376 |
| 5514 | 1-5513 and 5515-8376 |
| 5515 | 1-5514 and 5516-8376 |
| 5516 | 1-5515 and 5517-8376 |
| 5517 | 1-5516 and 5518-8376 |
| 5518 | 1-5517 and 5519-8376 |
| 5519 | 1-5518 and 5520-8376 |
| 5520 | 1-5519 and 5521-8376 |
| 5521 | 1-5520 and 5522-8376 |
| 5522 | 1-5521 and 5523-8376 |
| 5523 | 1-5522 and 5524-8376 |
| 5524 | 1-5523 and 5525-8376 |
| 5525 | 1-5524 and 5526-8376 |

| First | Second |
|---|---|
| 5526 | 1-5525 and 5527-8376 |
| 5527 | 1-5526 and 5528-8376 |
| 5528 | 1-5527 and 5529-8376 |
| 5529 | 1-5528 and 5530-8376 |
| 5530 | 1-5529 and 5531-8376 |
| 5531 | 1-5530 and 5532-8376 |
| 5532 | 1-5531 and 5533-8376 |
| 5533 | 1-5532 and 5534-8376 |
| 5534 | 1-5533 and 5535-8376 |
| 5535 | 1-5534 and 5536-8376 |
| 5536 | 1-5535 and 5537-8376 |
| 5537 | 1-5536 and 5538-8376 |
| 5538 | 1-5537 and 5539-8376 |
| 5539 | 1-5538 and 5540-8376 |
| 5540 | 1-5539 and 5541-8376 |
| 5541 | 1-5540 and 5542-8376 |
| 5542 | 1-5541 and 5543-8376 |
| 5543 | 1-5542 and 5544-8376 |
| 5544 | 1-5543 and 5545-8376 |
| 5545 | 1-5544 and 5546-8376 |
| 5546 | 1-5545 and 5547-8376 |
| 5547 | 1-5546 and 5548-8376 |
| 5548 | 1-5547 and 5549-8376 |
| 5549 | 1-5548 and 5550-8376 |
| 5550 | 1-5549 and 5551-8376 |
| 5551 | 1-5550 and 5552-8376 |
| 5552 | 1-5551 and 5553-8376 |
| 5553 | 1-5552 and 5554-8376 |
| 5554 | 1-5553 and 5555-8376 |
| 5555 | 1-5554 and 5556-8376 |
| 5556 | 1-5555 and 5557-8376 |
| 5557 | 1-5556 and 5558-8376 |
| 5558 | 1-5557 and 5559-8376 |
| 5559 | 1-5558 and 5560-8376 |
| 5560 | 1-5559 and 5561-8376 |
| 5561 | 1-5560 and 5562-8376 |
| 5562 | 1-5561 and 5563-8376 |
| 5563 | 1-5562 and 5564-8376 |
| 5564 | 1-5563 and 5565-8376 |
| 5565 | 1-5564 and 5566-8376 |
| 5566 | 1-5565 and 5567-8376 |
| 5567 | 1-5566 and 5568-8376 |
| 5568 | 1-5567 and 5569-8376 |
| 5569 | 1-5568 and 5570-8376 |
| 5570 | 1-5569 and 5571-8376 |
| 5571 | 1-5570 and 5572-8376 |
| 5572 | 1-5571 and 5573-8376 |
| 5573 | 1-5572 and 5574-8376 |
| 5574 | 1-5573 and 5575-8376 |
| 5575 | 1-5574 and 5576-8376 |
| 5576 | 1-5575 and 5577-8376 |
| 5577 | 1-5576 and 5578-8376 |
| 5578 | 1-5577 and 5579-8376 |
| 5579 | 1-5578 and 5580-8376 |
| 5580 | 1-5579 and 5581-8376 |
| 5581 | 1-5580 and 5582-8376 |
| 5582 | 1-5581 and 5583-8376 |
| 5583 | 1-5582 and 5584-8376 |
| 5584 | 1-5583 and 5585-8376 |
| 5585 | 1-5584 and 5586-8376 |
| 5586 | 1-5585 and 5587-8376 |
| 5587 | 1-5586 and 5588-8376 |
| 5588 | 1-5587 and 5589-8376 |
| 5589 | 1-5588 and 5590-8376 |
| 5590 | 1-5589 and 5591-8376 |
| 5591 | 1-5590 and 5592-8376 |
| 5592 | 1-5591 and 5593-8376 |
| 5593 | 1-5592 and 5594-8376 |
| 5594 | 1-5593 and 5595-8376 |
| 5595 | 1-5594 and 5596-8376 |
| 5596 | 1-5595 and 5597-8376 |
| 5597 | 1-5596 and 5598-8376 |
| 5598 | 1-5597 and 5599-8376 |
| 5599 | 1-5598 and 5600-8376 |
| 5600 | 1-5599 and 5601-8376 |
| 5601 | 1-5600 and 5602-8376 |
| 5602 | 1-5601 and 5603-8376 |
| 5603 | 1-5602 and 5604-8376 |
| 5604 | 1-5603 and 5605-8376 |
| 5605 | 1-5604 and 5606-8376 |
| 5606 | 1-5605 and 5607-8376 |
| 5607 | 1-5606 and 5608-8376 |
| 5608 | 1-5607 and 5609-8376 |
| 5609 | 1-5608 and 5610-8376 |
| 5610 | 1-5609 and 5611-8376 |
| 5611 | 1-5610 and 5612-8376 |
| 5612 | 1-5611 and 5613-8376 |
| 5613 | 1-5612 and 5614-8376 |
| 5614 | 1-5613 and 5615-8376 |
| 5615 | 1-5614 and 5616-8376 |
| 5616 | 1-5615 and 5617-8376 |
| 5617 | 1-5616 and 5618-8376 |
| 5618 | 1-5617 and 5619-8376 |
| 5619 | 1-5618 and 5620-8376 |
| 5620 | 1-5619 and 5621-8376 |
| 5621 | 1-5620 and 5622-8376 |
| 5622 | 1-5621 and 5623-8376 |
| 5623 | 1-5622 and 5624-8376 |
| 5624 | 1-5623 and 5625-8376 |
| 5625 | 1-5624 and 5626-8376 |
| 5626 | 1-5625 and 5627-8376 |
| 5627 | 1-5626 and 5628-8376 |
| 5628 | 1-5627 and 5629-8376 |
| 5629 | 1-5628 and 5630-8376 |
| 5630 | 1-5629 and 5631-8376 |
| 5631 | 1-5630 and 5632-8376 |
| 5632 | 1-5631 and 5633-8376 |
| 5633 | 1-5632 and 5634-8376 |
| 5634 | 1-5633 and 5635-8376 |
| 5635 | 1-5634 and 5636-8376 |
| 5636 | 1-5635 and 5637-8376 |
| 5637 | 1-5636 and 5638-8376 |
| 5638 | 1-5637 and 5639-8376 |
| 5639 | 1-5638 and 5640-8376 |
| 5640 | 1-5639 and 5641-8376 |
| 5641 | 1-5640 and 5642-8376 |
| 5642 | 1-5641 and 5643-8376 |
| 5643 | 1-5642 and 5644-8376 |
| 5644 | 1-5643 and 5645-8376 |
| 5645 | 1-5644 and 5646-8376 |
| 5646 | 1-5645 and 5647-8376 |
| 5647 | 1-5646 and 5648-8376 |
| 5648 | 1-5647 and 5649-8376 |
| 5649 | 1-5648 and 5650-8376 |
| 5650 | 1-5649 and 5651-8376 |
| 5651 | 1-5650 and 5652-8376 |
| 5652 | 1-5651 and 5653-8376 |
| 5653 | 1-5652 and 5654-8376 |
| 5654 | 1-5653 and 5655-8376 |
| 5655 | 1-5654 and 5656-8376 |
| 5656 | 1-5655 and 5657-8376 |
| 5657 | 1-5656 and 5658-8376 |
| 5658 | 1-5657 and 5659-8376 |
| 5659 | 1-5658 and 5660-8376 |
| 5660 | 1-5659 and 5661-8376 |
| 5661 | 1-5660 and 5662-8376 |
| 5662 | 1-5661 and 5663-8376 |
| 5663 | 1-5662 and 5664-8376 |
| 5664 | 1-5663 and 5665-8376 |
| 5665 | 1-5664 and 5666-8376 |
| 5666 | 1-5665 and 5667-8376 |
| 5667 | 1-5666 and 5668-8376 |
| 5668 | 1-5667 and 5669-8376 |
| 5669 | 1-5668 and 5670-8376 |
| 5670 | 1-5669 and 5671-8376 |
| 5671 | 1-5670 and 5672-8376 |
| 5672 | 1-5671 and 5673-8376 |
| 5673 | 1-5672 and 5674-8376 |
| 5674 | 1-5673 and 5675-8376 |
| 5675 | 1-5674 and 5676-8376 |
| 5676 | 1-5675 and 5677-8376 |
| 5677 | 1-5676 and 5678-8376 |
| 5678 | 1-5677 and 5679-8376 |
| 5679 | 1-5678 and 5680-8376 |

| First | Second |
|---|---|
| 5680 | 1-5679 and 5681-8376 |
| 5681 | 1-5680 and 5682-8376 |
| 5682 | 1-5681 and 5683-8376 |
| 5683 | 1-5682 and 5684-8376 |
| 5684 | 1-5683 and 5685-8376 |
| 5685 | 1-5684 and 5686-8376 |
| 5686 | 1-5685 and 5687-8376 |
| 5687 | 1-5686 and 5688-8376 |
| 5688 | 1-5687 and 5689-8376 |
| 5689 | 1-5688 and 5690-8376 |
| 5690 | 1-5689 and 5691-8376 |
| 5691 | 1-5690 and 5692-8376 |
| 5692 | 1-5691 and 5693-8376 |
| 5693 | 1-5692 and 5694-8376 |
| 5694 | 1-5693 and 5695-8376 |
| 5695 | 1-5694 and 5696-8376 |
| 5696 | 1-5695 and 5697-8376 |
| 5697 | 1-5696 and 5698-8376 |
| 5698 | 1-5697 and 5699-8376 |
| 5699 | 1-5698 and 5700-8376 |
| 5700 | 1-5699 and 5701-8376 |
| 5701 | 1-5700 and 5702-8376 |
| 5702 | 1-5701 and 5703-8376 |
| 5703 | 1-5702 and 5704-8376 |
| 5704 | 1-5703 and 5705-8376 |
| 5705 | 1-5704 and 5706-8376 |
| 5706 | 1-5705 and 5707-8376 |
| 5707 | 1-5706 and 5708-8376 |
| 5708 | 1-5707 and 5709-8376 |
| 5709 | 1-5708 and 5710-8376 |
| 5710 | 1-5709 and 5711-8376 |
| 5711 | 1-5710 and 5712-8376 |
| 5712 | 1-5711 and 5713-8376 |
| 5713 | 1-5712 and 5714-8376 |
| 5714 | 1-5713 and 5715-8376 |
| 5715 | 1-5714 and 5716-8376 |
| 5716 | 1-5715 and 5717-8376 |
| 5717 | 1-5716 and 5718-8376 |
| 5718 | 1-5717 and 5719-8376 |
| 5719 | 1-5718 and 5720-8376 |
| 5720 | 1-5719 and 5721-8376 |
| 5721 | 1-5720 and 5722-8376 |
| 5722 | 1-5721 and 5723-8376 |
| 5723 | 1-5722 and 5724-8376 |
| 5724 | 1-5723 and 5725-8376 |
| 5725 | 1-5724 and 5726-8376 |
| 5726 | 1-5725 and 5727-8376 |
| 5727 | 1-5726 and 5728-8376 |
| 5728 | 1-5727 and 5729-8376 |
| 5729 | 1-5728 and 5730-8376 |
| 5730 | 1-5729 and 5731-8376 |
| 5731 | 1-5730 and 5732-8376 |
| 5732 | 1-5731 and 5733-8376 |
| 5733 | 1-5732 and 5734-8376 |
| 5734 | 1-5733 and 5735-8376 |
| 5735 | 1-5734 and 5736-8376 |
| 5736 | 1-5735 and 5737-8376 |
| 5737 | 1-5736 and 5738-8376 |
| 5738 | 1-5737 and 5739-8376 |
| 5739 | 1-5738 and 5740-8376 |
| 5740 | 1-5739 and 5741-8376 |
| 5741 | 1-5740 and 5742-8376 |
| 5742 | 1-5741 and 5743-8376 |
| 5743 | 1-5742 and 5744-8376 |
| 5744 | 1-5743 and 5745-8376 |
| 5745 | 1-5744 and 5746-8376 |
| 5746 | 1-5745 and 5747-8376 |
| 5747 | 1-5746 and 5748-8376 |
| 5748 | 1-5747 and 5749-8376 |
| 5749 | 1-5748 and 5750-8376 |
| 5750 | 1-5749 and 5751-8376 |
| 5751 | 1-5750 and 5752-8376 |
| 5752 | 1-5751 and 5753-8376 |
| 5753 | 1-5752 and 5754-8376 |
| 5754 | 1-5753 and 5755-8376 |
| 5755 | 1-5754 and 5756-8376 |
| 5756 | 1-5755 and 5757-8376 |
| 5757 | 1-5756 and 5758-8376 |
| 5758 | 1-5757 and 5759-8376 |
| 5759 | 1-5758 and 5760-8376 |
| 5760 | 1-5759 and 5761-8376 |
| 5761 | 1-5760 and 5762-8376 |
| 5762 | 1-5761 and 5763-8376 |
| 5763 | 1-5762 and 5764-8376 |
| 5764 | 1-5763 and 5765-8376 |
| 5765 | 1-5764 and 5766-8376 |
| 5766 | 1-5765 and 5767-8376 |
| 5767 | 1-5766 and 5768-8376 |
| 5768 | 1-5767 and 5769-8376 |
| 5769 | 1-5768 and 5770-8376 |
| 5770 | 1-5769 and 5771-8376 |
| 5771 | 1-5770 and 5772-8376 |
| 5772 | 1-5771 and 5773-8376 |
| 5773 | 1-5772 and 5774-8376 |
| 5774 | 1-5773 and 5775-8376 |
| 5775 | 1-5774 and 5776-8376 |
| 5776 | 1-5775 and 5777-8376 |
| 5777 | 1-5776 and 5778-8376 |
| 5778 | 1-5777 and 5779-8376 |
| 5779 | 1-5778 and 5780-8376 |
| 5780 | 1-5779 and 5781-8376 |
| 5781 | 1-5780 and 5782-8376 |
| 5782 | 1-5781 and 5783-8376 |
| 5783 | 1-5782 and 5784-8376 |
| 5784 | 1-5783 and 5785-8376 |
| 5785 | 1-5784 and 5786-8376 |
| 5786 | 1-5785 and 5787-8376 |
| 5787 | 1-5786 and 5788-8376 |
| 5788 | 1-5787 and 5789-8376 |
| 5789 | 1-5788 and 5790-8376 |
| 5790 | 1-5789 and 5791-8376 |
| 5791 | 1-5790 and 5792-8376 |
| 5792 | 1-5791 and 5793-8376 |
| 5793 | 1-5792 and 5794-8376 |
| 5794 | 1-5793 and 5795-8376 |
| 5795 | 1-5794 and 5796-8376 |
| 5796 | 1-5795 and 5797-8376 |
| 5797 | 1-5796 and 5798-8376 |
| 5798 | 1-5797 and 5799-8376 |
| 5799 | 1-5798 and 5800-8376 |
| 5800 | 1-5799 and 5801-8376 |
| 5801 | 1-5800 and 5802-8376 |
| 5802 | 1-5801 and 5803-8376 |
| 5803 | 1-5802 and 5804-8376 |
| 5804 | 1-5803 and 5805-8376 |
| 5805 | 1-5804 and 5806-8376 |
| 5806 | 1-5805 and 5807-8376 |
| 5807 | 1-5806 and 5808-8376 |
| 5808 | 1-5807 and 5809-8376 |
| 5809 | 1-5808 and 5810-8376 |
| 5810 | 1-5809 and 5811-8376 |
| 5811 | 1-5810 and 5812-8376 |
| 5812 | 1-5811 and 5813-8376 |
| 5813 | 1-5812 and 5814-8376 |
| 5814 | 1-5813 and 5815-8376 |
| 5815 | 1-5814 and 5816-8376 |
| 5816 | 1-5815 and 5817-8376 |
| 5817 | 1-5816 and 5818-8376 |
| 5818 | 1-5817 and 5819-8376 |
| 5819 | 1-5818 and 5820-8376 |
| 5820 | 1-5819 and 5821-8376 |
| 5821 | 1-5820 and 5822-8376 |
| 5822 | 1-5821 and 5823-8376 |
| 5823 | 1-5822 and 5824-8376 |
| 5824 | 1-5823 and 5825-8376 |
| 5825 | 1-5824 and 5826-8376 |
| 5826 | 1-5825 and 5827-8376 |
| 5827 | 1-5826 and 5828-8376 |
| 5828 | 1-5827 and 5829-8376 |
| 5829 | 1-5828 and 5830-8376 |
| 5830 | 1-5829 and 5831-8376 |
| 5831 | 1-5830 and 5832-8376 |
| 5832 | 1-5831 and 5833-8376 |
| 5833 | 1-5832 and 5834-8376 |

| First | Second |
|---|---|
| 5834 | 1-5833 and 5835-8376 |
| 5835 | 1-5834 and 5836-8376 |
| 5836 | 1-5835 and 5837-8376 |
| 5837 | 1-5836 and 5838-8376 |
| 5838 | 1-5837 and 5839-8376 |
| 5839 | 1-5838 and 5840-8376 |
| 5840 | 1-5839 and 5841-8376 |
| 5841 | 1-5840 and 5842-8376 |
| 5842 | 1-5841 and 5843-8376 |
| 5843 | 1-5842 and 5844-8376 |
| 5844 | 1-5843 and 5845-8376 |
| 5845 | 1-5844 and 5846-8376 |
| 5846 | 1-5845 and 5847-8376 |
| 5847 | 1-5846 and 5848-8376 |
| 5848 | 1-5847 and 5849-8376 |
| 5849 | 1-5848 and 5850-8376 |
| 5850 | 1-5849 and 5851-8376 |
| 5851 | 1-5850 and 5852-8376 |
| 5852 | 1-5851 and 5853-8376 |
| 5853 | 1-5852 and 5854-8376 |
| 5854 | 1-5853 and 5855-8376 |
| 5855 | 1-5854 and 5856-8376 |
| 5856 | 1-5855 and 5857-8376 |
| 5857 | 1-5856 and 5858-8376 |
| 5858 | 1-5857 and 5859-8376 |
| 5859 | 1-5858 and 5860-8376 |
| 5860 | 1-5859 and 5861-8376 |
| 5861 | 1-5860 and 5862-8376 |
| 5862 | 1-5861 and 5863-8376 |
| 5863 | 1-5862 and 5864-8376 |
| 5864 | 1-5863 and 5865-8376 |
| 5865 | 1-5864 and 5866-8376 |
| 5866 | 1-5865 and 5867-8376 |
| 5867 | 1-5866 and 5868-8376 |
| 5868 | 1-5867 and 5869-8376 |
| 5869 | 1-5868 and 5870-8376 |
| 5870 | 1-5869 and 5871-8376 |
| 5871 | 1-5870 and 5872-8376 |
| 5872 | 1-5871 and 5873-8376 |
| 5873 | 1-5872 and 5874-8376 |
| 5874 | 1-5873 and 5875-8376 |
| 5875 | 1-5874 and 5876-8376 |
| 5876 | 1-5875 and 5877-8376 |
| 5877 | 1-5876 and 5878-8376 |
| 5878 | 1-5877 and 5879-8376 |
| 5879 | 1-5878 and 5880-8376 |
| 5880 | 1-5879 and 5881-8376 |
| 5881 | 1-5880 and 5882-8376 |
| 5882 | 1-5881 and 5883-8376 |
| 5883 | 1-5882 and 5884-8376 |
| 5884 | 1-5883 and 5885-8376 |
| 5885 | 1-5884 and 5886-8376 |
| 5886 | 1-5885 and 5887-8376 |
| 5887 | 1-5886 and 5888-8376 |
| 5888 | 1-5887 and 5889-8376 |
| 5889 | 1-5888 and 5890-8376 |
| 5890 | 1-5889 and 5891-8376 |
| 5891 | 1-5890 and 5892-8376 |
| 5892 | 1-5891 and 5893-8376 |
| 5893 | 1-5892 and 5894-8376 |
| 5894 | 1-5893 and 5895-8376 |
| 5895 | 1-5894 and 5896-8376 |
| 5896 | 1-5895 and 5897-8376 |
| 5897 | 1-5896 and 5898-8376 |
| 5898 | 1-5897 and 5899-8376 |
| 5899 | 1-5898 and 5900-8376 |
| 5900 | 1-5899 and 5901-8376 |
| 5901 | 1-5900 and 5902-8376 |
| 5902 | 1-5901 and 5903-8376 |
| 5903 | 1-5902 and 5904-8376 |
| 5904 | 1-5903 and 5905-8376 |
| 5905 | 1-5904 and 5906-8376 |
| 5906 | 1-5905 and 5907-8376 |
| 5907 | 1-5906 and 5908-8376 |
| 5908 | 1-5907 and 5909-8376 |
| 5909 | 1-5908 and 5910-8376 |
| 5910 | 1-5909 and 5911-8376 |
| 5911 | 1-5910 and 5912-8376 |
| 5912 | 1-5911 and 5913-8376 |
| 5913 | 1-5912 and 5914-8376 |
| 5914 | 1-5913 and 5915-8376 |
| 5915 | 1-5914 and 5916-8376 |
| 5916 | 1-5915 and 5917-8376 |
| 5917 | 1-5916 and 5918-8376 |
| 5918 | 1-5917 and 5919-8376 |
| 5919 | 1-5918 and 5920-8376 |
| 5920 | 1-5919 and 5921-8376 |
| 5921 | 1-5920 and 5922-8376 |
| 5922 | 1-5921 and 5923-8376 |
| 5923 | 1-5922 and 5924-8376 |
| 5924 | 1-5923 and 5925-8376 |
| 5925 | 1-5924 and 5926-8376 |
| 5926 | 1-5925 and 5927-8376 |
| 5927 | 1-5926 and 5928-8376 |
| 5928 | 1-5927 and 5929-8376 |
| 5929 | 1-5928 and 5930-8376 |
| 5930 | 1-5929 and 5931-8376 |
| 5931 | 1-5930 and 5932-8376 |
| 5932 | 1-5931 and 5933-8376 |
| 5933 | 1-5932 and 5934-8376 |
| 5934 | 1-5933 and 5935-8376 |
| 5935 | 1-5934 and 5936-8376 |
| 5936 | 1-5935 and 5937-8376 |
| 5937 | 1-5936 and 5938-8376 |
| 5938 | 1-5937 and 5939-8376 |
| 5939 | 1-5938 and 5940-8376 |
| 5940 | 1-5939 and 5941-8376 |
| 5941 | 1-5940 and 5942-8376 |
| 5942 | 1-5941 and 5943-8376 |
| 5943 | 1-5942 and 5944-8376 |
| 5944 | 1-5943 and 5945-8376 |
| 5945 | 1-5944 and 5946-8376 |
| 5946 | 1-5945 and 5947-8376 |
| 5947 | 1-5946 and 5948-8376 |
| 5948 | 1-5947 and 5949-8376 |
| 5949 | 1-5948 and 5950-8376 |
| 5950 | 1-5949 and 5951-8376 |
| 5951 | 1-5950 and 5952-8376 |
| 5952 | 1-5951 and 5953-8376 |
| 5953 | 1-5952 and 5954-8376 |
| 5954 | 1-5953 and 5955-8376 |
| 5955 | 1-5954 and 5956-8376 |
| 5956 | 1-5955 and 5957-8376 |
| 5957 | 1-5956 and 5958-8376 |
| 5958 | 1-5957 and 5959-8376 |
| 5959 | 1-5958 and 5960-8376 |
| 5960 | 1-5959 and 5961-8376 |
| 5961 | 1-5960 and 5962-8376 |
| 5962 | 1-5961 and 5963-8376 |
| 5963 | 1-5962 and 5964-8376 |
| 5964 | 1-5963 and 5965-8376 |
| 5965 | 1-5964 and 5966-8376 |
| 5966 | 1-5965 and 5967-8376 |
| 5967 | 1-5966 and 5968-8376 |
| 5968 | 1-5967 and 5969-8376 |
| 5969 | 1-5968 and 5970-8376 |
| 5970 | 1-5969 and 5971-8376 |
| 5971 | 1-5970 and 5972-8376 |
| 5972 | 1-5971 and 5973-8376 |
| 5973 | 1-5972 and 5974-8376 |
| 5974 | 1-5973 and 5975-8376 |
| 5975 | 1-5974 and 5976-8376 |
| 5976 | 1-5975 and 5977-8376 |
| 5977 | 1-5976 and 5978-8376 |
| 5978 | 1-5977 and 5979-8376 |
| 5979 | 1-5978 and 5980-8376 |
| 5980 | 1-5979 and 5981-8376 |
| 5981 | 1-5980 and 5982-8376 |
| 5982 | 1-5981 and 5983-8376 |
| 5983 | 1-5982 and 5984-8376 |
| 5984 | 1-5983 and 5985-8376 |
| 5985 | 1-5984 and 5986-8376 |
| 5986 | 1-5985 and 5987-8376 |
| 5987 | 1-5986 and 5988-8376 |

| First | Second |
|---|---|
| 5988 | 1-5987 and 5989-8376 |
| 5989 | 1-5988 and 5990-8376 |
| 5990 | 1-5989 and 5991-8376 |
| 5991 | 1-5990 and 5992-8376 |
| 5992 | 1-5991 and 5993-8376 |
| 5993 | 1-5992 and 5994-8376 |
| 5994 | 1-5993 and 5995-8376 |
| 5995 | 1-5994 and 5996-8376 |
| 5996 | 1-5995 and 5997-8376 |
| 5997 | 1-5996 and 5998-8376 |
| 5998 | 1-5997 and 5999-8376 |
| 5999 | 1-5998 and 6000-8376 |
| 6000 | 1-5999 and 6001-8376 |
| 6001 | 1-6000 and 6002-8376 |
| 6002 | 1-6001 and 6003-8376 |
| 6003 | 1-6002 and 6004-8376 |
| 6004 | 1-6003 and 6005-8376 |
| 6005 | 1-6004 and 6006-8376 |
| 6006 | 1-6005 and 6007-8376 |
| 6007 | 1-6006 and 6008-8376 |
| 6008 | 1-6007 and 6009-8376 |
| 6009 | 1-6008 and 6010-8376 |
| 6010 | 1-6009 and 6011-8376 |
| 6011 | 1-6010 and 6012-8376 |
| 6012 | 1-6011 and 6013-8376 |
| 6013 | 1-6012 and 6014-8376 |
| 6014 | 1-6013 and 6015-8376 |
| 6015 | 1-6014 and 6016-8376 |
| 6016 | 1-6015 and 6017-8376 |
| 6017 | 1-6016 and 6018-8376 |
| 6018 | 1-6017 and 6019-8376 |
| 6019 | 1-6018 and 6020-8376 |
| 6020 | 1-6019 and 6021-8376 |
| 6021 | 1-6020 and 6022-8376 |
| 6022 | 1-6021 and 6023-8376 |
| 6023 | 1-6022 and 6024-8376 |
| 6024 | 1-6023 and 6025-8376 |
| 6025 | 1-6024 and 6026-8376 |
| 6026 | 1-6025 and 6027-8376 |
| 6027 | 1-6026 and 6028-8376 |
| 6028 | 1-6027 and 6029-8376 |
| 6029 | 1-6028 and 6030-8376 |
| 6030 | 1-6029 and 6031-8376 |
| 6031 | 1-6030 and 6032-8376 |
| 6032 | 1-6031 and 6033-8376 |
| 6033 | 1-6032 and 6034-8376 |
| 6034 | 1-6033 and 6035-8376 |
| 6035 | 1-6034 and 6036-8376 |
| 6036 | 1-6035 and 6037-8376 |
| 6037 | 1-6036 and 6038-8376 |
| 6038 | 1-6037 and 6039-8376 |
| 6039 | 1-6038 and 6040-8376 |
| 6040 | 1-6039 and 6041-8376 |
| 6041 | 1-6040 and 6042-8376 |
| 6042 | 1-6041 and 6043-8376 |
| 6043 | 1-6042 and 6044-8376 |
| 6044 | 1-6043 and 6045-8376 |
| 6045 | 1-6044 and 6046-8376 |
| 6046 | 1-6045 and 6047-8376 |
| 6047 | 1-6046 and 6048-8376 |
| 6048 | 1-6047 and 6049-8376 |
| 6049 | 1-6048 and 6050-8376 |
| 6050 | 1-6049 and 6051-8376 |
| 6051 | 1-6050 and 6052-8376 |
| 6052 | 1-6051 and 6053-8376 |
| 6053 | 1-6052 and 6054-8376 |
| 6054 | 1-6053 and 6055-8376 |
| 6055 | 1-6054 and 6056-8376 |
| 6056 | 1-6055 and 6057-8376 |
| 6057 | 1-6056 and 6058-8376 |
| 6058 | 1-6057 and 6059-8376 |
| 6059 | 1-6058 and 6060-8376 |
| 6060 | 1-6059 and 6061-8376 |
| 6061 | 1-6060 and 6062-8376 |
| 6062 | 1-6061 and 6063-8376 |
| 6063 | 1-6062 and 6064-8376 |
| 6064 | 1-6063 and 6065-8376 |
| 6065 | 1-6064 and 6066-8376 |
| 6066 | 1-6065 and 6067-8376 |
| 6067 | 1-6066 and 6068-8376 |
| 6068 | 1-6067 and 6069-8376 |
| 6069 | 1-6068 and 6070-8376 |
| 6070 | 1-6069 and 6071-8376 |
| 6071 | 1-6070 and 6072-8376 |
| 6072 | 1-6071 and 6073-8376 |
| 6073 | 1-6072 and 6074-8376 |
| 6074 | 1-6073 and 6075-8376 |
| 6075 | 1-6074 and 6076-8376 |
| 6076 | 1-6075 and 6077-8376 |
| 6077 | 1-6076 and 6078-8376 |
| 6078 | 1-6077 and 6079-8376 |
| 6079 | 1-6078 and 6080-8376 |
| 6080 | 1-6079 and 6081-8376 |
| 6081 | 1-6080 and 6082-8376 |
| 6082 | 1-6081 and 6083-8376 |
| 6083 | 1-6082 and 6084-8376 |
| 6084 | 1-6083 and 6085-8376 |
| 6085 | 1-6084 and 6086-8376 |
| 6086 | 1-6085 and 6087-8376 |
| 6087 | 1-6086 and 6088-8376 |
| 6088 | 1-6087 and 6089-8376 |
| 6089 | 1-6088 and 6090-8376 |
| 6090 | 1-6089 and 6091-8376 |
| 6091 | 1-6090 and 6092-8376 |
| 6092 | 1-6091 and 6093-8376 |
| 6093 | 1-6092 and 6094-8376 |
| 6094 | 1-6093 and 6095-8376 |
| 6095 | 1-6094 and 6096-8376 |
| 6096 | 1-6095 and 6097-8376 |
| 6097 | 1-6096 and 6098-8376 |
| 6098 | 1-6097 and 6099-8376 |
| 6099 | 1-6098 and 6100-8376 |
| 6100 | 1-6099 and 6101-8376 |
| 6101 | 1-6100 and 6102-8376 |
| 6102 | 1-6101 and 6103-8376 |
| 6103 | 1-6102 and 6104-8376 |
| 6104 | 1-6103 and 6105-8376 |
| 6105 | 1-6104 and 6106-8376 |
| 6106 | 1-6105 and 6107-8376 |
| 6107 | 1-6106 and 6108-8376 |
| 6108 | 1-6107 and 6109-8376 |
| 6109 | 1-6108 and 6110-8376 |
| 6110 | 1-6109 and 6111-8376 |
| 6111 | 1-6110 and 6112-8376 |
| 6112 | 1-6111 and 6113-8376 |
| 6113 | 1-6112 and 6114-8376 |
| 6114 | 1-6113 and 6115-8376 |
| 6115 | 1-6114 and 6116-8376 |
| 6116 | 1-6115 and 6117-8376 |
| 6117 | 1-6116 and 6118-8376 |
| 6118 | 1-6117 and 6119-8376 |
| 6119 | 1-6118 and 6120-8376 |
| 6120 | 1-6119 and 6121-8376 |
| 6121 | 1-6120 and 6122-8376 |
| 6122 | 1-6121 and 6123-8376 |
| 6123 | 1-6122 and 6124-8376 |
| 6124 | 1-6123 and 6125-8376 |
| 6125 | 1-6124 and 6126-8376 |
| 6126 | 1-6125 and 6127-8376 |
| 6127 | 1-6126 and 6128-8376 |
| 6128 | 1-6127 and 6129-8376 |
| 6129 | 1-6128 and 6130-8376 |
| 6130 | 1-6129 and 6131-8376 |
| 6131 | 1-6130 and 6132-8376 |
| 6132 | 1-6131 and 6133-8376 |
| 6133 | 1-6132 and 6134-8376 |
| 6134 | 1-6133 and 6135-8376 |
| 6135 | 1-6134 and 6136-8376 |
| 6136 | 1-6135 and 6137-8376 |
| 6137 | 1-6136 and 6138-8376 |
| 6138 | 1-6137 and 6139-8376 |
| 6139 | 1-6138 and 6140-8376 |
| 6140 | 1-6139 and 6141-8376 |
| 6141 | 1-6140 and 6142-8376 |

| First | Second |
|---|---|
| 6142 | 1-6141 and 6143-8376 |
| 6143 | 1-6142 and 6144-8376 |
| 6144 | 1-6143 and 6145-8376 |
| 6145 | 1-6144 and 6146-8376 |
| 6146 | 1-6145 and 6147-8376 |
| 6147 | 1-6146 and 6148-8376 |
| 6148 | 1-6147 and 6149-8376 |
| 6149 | 1-6148 and 6150-8376 |
| 6150 | 1-6149 and 6151-8376 |
| 6151 | 1-6150 and 6152-8376 |
| 6152 | 1-6151 and 6153-8376 |
| 6153 | 1-6152 and 6154-8376 |
| 6154 | 1-6153 and 6155-8376 |
| 6155 | 1-6154 and 6156-8376 |
| 6156 | 1-6155 and 6157-8376 |
| 6157 | 1-6156 and 6158-8376 |
| 6158 | 1-6157 and 6159-8376 |
| 6159 | 1-6158 and 6160-8376 |
| 6160 | 1-6159 and 6161-8376 |
| 6161 | 1-6160 and 6162-8376 |
| 6162 | 1-6161 and 6163-8376 |
| 6163 | 1-6162 and 6164-8376 |
| 6164 | 1-6163 and 6165-8376 |
| 6165 | 1-6164 and 6166-8376 |
| 6166 | 1-6165 and 6167-8376 |
| 6167 | 1-6166 and 6168-8376 |
| 6168 | 1-6167 and 6169-8376 |
| 6169 | 1-6168 and 6170-8376 |
| 6170 | 1-6169 and 6171-8376 |
| 6171 | 1-6170 and 6172-8376 |
| 6172 | 1-6171 and 6173-8376 |
| 6173 | 1-6172 and 6174-8376 |
| 6174 | 1-6173 and 6175-8376 |
| 6175 | 1-6174 and 6176-8376 |
| 6176 | 1-6175 and 6177-8376 |
| 6177 | 1-6176 and 6178-8376 |
| 6178 | 1-6177 and 6179-8376 |
| 6179 | 1-6178 and 6180-8376 |
| 6180 | 1-6179 and 6181-8376 |
| 6181 | 1-6180 and 6182-8376 |
| 6182 | 1-6181 and 6183-8376 |
| 6183 | 1-6182 and 6184-8376 |
| 6184 | 1-6183 and 6185-8376 |
| 6185 | 1-6184 and 6186-8376 |
| 6186 | 1-6185 and 6187-8376 |
| 6187 | 1-6186 and 6188-8376 |
| 6188 | 1-6187 and 6189-8376 |
| 6189 | 1-6188 and 6190-8376 |
| 6190 | 1-6189 and 6191-8376 |
| 6191 | 1-6190 and 6192-8376 |
| 6192 | 1-6191 and 6193-8376 |
| 6193 | 1-6192 and 6194-8376 |
| 6194 | 1-6193 and 6195-8376 |
| 6195 | 1-6194 and 6196-8376 |
| 6196 | 1-6195 and 6197-8376 |
| 6197 | 1-6196 and 6198-8376 |
| 6198 | 1-6197 and 6199-8376 |
| 6199 | 1-6198 and 6200-8376 |
| 6200 | 1-6199 and 6201-8376 |
| 6201 | 1-6200 and 6202-8376 |
| 6202 | 1-6201 and 6203-8376 |
| 6203 | 1-6202 and 6204-8376 |
| 6204 | 1-6203 and 6205-8376 |
| 6205 | 1-6204 and 6206-8376 |
| 6206 | 1-6205 and 6207-8376 |
| 6207 | 1-6206 and 6208-8376 |
| 6208 | 1-6207 and 6209-8376 |
| 6209 | 1-6208 and 6210-8376 |
| 6210 | 1-6209 and 6211-8376 |
| 6211 | 1-6210 and 6212-8376 |
| 6212 | 1-6211 and 6213-8376 |
| 6213 | 1-6212 and 6214-8376 |
| 6214 | 1-6213 and 6215-8376 |
| 6215 | 1-6214 and 6216-8376 |
| 6216 | 1-6215 and 6217-8376 |
| 6217 | 1-6216 and 6218-8376 |
| 6218 | 1-6217 and 6219-8376 |
| 6219 | 1-6218 and 6220-8376 |
| 6220 | 1-6219 and 6221-8376 |
| 6221 | 1-6220 and 6222-8376 |
| 6222 | 1-6221 and 6223-8376 |
| 6223 | 1-6222 and 6224-8376 |
| 6224 | 1-6223 and 6225-8376 |
| 6225 | 1-6224 and 6226-8376 |
| 6226 | 1-6225 and 6227-8376 |
| 6227 | 1-6226 and 6228-8376 |
| 6228 | 1-6227 and 6229-8376 |
| 6229 | 1-6228 and 6230-8376 |
| 6230 | 1-6229 and 6231-8376 |
| 6231 | 1-6230 and 6232-8376 |
| 6232 | 1-6231 and 6233-8376 |
| 6233 | 1-6232 and 6234-8376 |
| 6234 | 1-6233 and 6235-8376 |
| 6235 | 1-6234 and 6236-8376 |
| 6236 | 1-6235 and 6237-8376 |
| 6237 | 1-6236 and 6238-8376 |
| 6238 | 1-6237 and 6239-8376 |
| 6239 | 1-6238 and 6240-8376 |
| 6240 | 1-6239 and 6241-8376 |
| 6241 | 1-6240 and 6242-8376 |
| 6242 | 1-6241 and 6243-8376 |
| 6243 | 1-6242 and 6244-8376 |
| 6244 | 1-6243 and 6245-8376 |
| 6245 | 1-6244 and 6246-8376 |
| 6246 | 1-6245 and 6247-8376 |
| 6247 | 1-6246 and 6248-8376 |
| 6248 | 1-6247 and 6249-8376 |
| 6249 | 1-6248 and 6250-8376 |
| 6250 | 1-6249 and 6251-8376 |
| 6251 | 1-6250 and 6252-8376 |
| 6252 | 1-6251 and 6253-8376 |
| 6253 | 1-6252 and 6254-8376 |
| 6254 | 1-6253 and 6255-8376 |
| 6255 | 1-6254 and 6256-8376 |
| 6256 | 1-6255 and 6257-8376 |
| 6257 | 1-6256 and 6258-8376 |
| 6258 | 1-6257 and 6259-8376 |
| 6259 | 1-6258 and 6260-8376 |
| 6260 | 1-6259 and 6261-8376 |
| 6261 | 1-6260 and 6262-8376 |
| 6262 | 1-6261 and 6263-8376 |
| 6263 | 1-6262 and 6264-8376 |
| 6264 | 1-6263 and 6265-8376 |
| 6265 | 1-6264 and 6266-8376 |
| 6266 | 1-6265 and 6267-8376 |
| 6267 | 1-6266 and 6268-8376 |
| 6268 | 1-6267 and 6269-8376 |
| 6269 | 1-6268 and 6270-8376 |
| 6270 | 1-6269 and 6271-8376 |
| 6271 | 1-6270 and 6272-8376 |
| 6272 | 1-6271 and 6273-8376 |
| 6273 | 1-6272 and 6274-8376 |
| 6274 | 1-6273 and 6275-8376 |
| 6275 | 1-6274 and 6276-8376 |
| 6276 | 1-6275 and 6277-8376 |
| 6277 | 1-6276 and 6278-8376 |
| 6278 | 1-6277 and 6279-8376 |
| 6279 | 1-6278 and 6280-8376 |
| 6280 | 1-6279 and 6281-8376 |
| 6281 | 1-6280 and 6282-8376 |
| 6282 | 1-6281 and 6283-8376 |
| 6283 | 1-6282 and 6284-8376 |
| 6284 | 1-6283 and 6285-8376 |
| 6285 | 1-6284 and 6286-8376 |
| 6286 | 1-6285 and 6287-8376 |
| 6287 | 1-6286 and 6288-8376 |
| 6288 | 1-6287 and 6289-8376 |
| 6289 | 1-6288 and 6290-8376 |
| 6290 | 1-6289 and 6291-8376 |
| 6291 | 1-6290 and 6292-8376 |
| 6292 | 1-6291 and 6293-8376 |
| 6293 | 1-6292 and 6294-8376 |
| 6294 | 1-6293 and 6295-8376 |
| 6295 | 1-6294 and 6296-8376 |

| First | Second |
|---|---|
| 6296 | 1-6295 and 6297-8376 |
| 6297 | 1-6296 and 6298-8376 |
| 6298 | 1-6297 and 6299-8376 |
| 6299 | 1-6298 and 6300-8376 |
| 6300 | 1-6299 and 6301-8376 |
| 6301 | 1-6300 and 6302-8376 |
| 6302 | 1-6301 and 6303-8376 |
| 6303 | 1-6302 and 6304-8376 |
| 6304 | 1-6303 and 6305-8376 |
| 6305 | 1-6304 and 6306-8376 |
| 6306 | 1-6305 and 6307-8376 |
| 6307 | 1-6306 and 6308-8376 |
| 6308 | 1-6307 and 6309-8376 |
| 6309 | 1-6308 and 6310-8376 |
| 6310 | 1-6309 and 6311-8376 |
| 6311 | 1-6310 and 6312-8376 |
| 6312 | 1-6311 and 6313-8376 |
| 6313 | 1-6312 and 6314-8376 |
| 6314 | 1-6313 and 6315-8376 |
| 6315 | 1-6314 and 6316-8376 |
| 6316 | 1-6315 and 6317-8376 |
| 6317 | 1-6316 and 6318-8376 |
| 6318 | 1-6317 and 6319-8376 |
| 6319 | 1-6318 and 6320-8376 |
| 6320 | 1-6319 and 6321-8376 |
| 6321 | 1-6320 and 6322-8376 |
| 6322 | 1-6321 and 6323-8376 |
| 6323 | 1-6322 and 6324-8376 |
| 6324 | 1-6323 and 6325-8376 |
| 6325 | 1-6324 and 6326-8376 |
| 6326 | 1-6325 and 6327-8376 |
| 6327 | 1-6326 and 6328-8376 |
| 6328 | 1-6327 and 6329-8376 |
| 6329 | 1-6328 and 6330-8376 |
| 6330 | 1-6329 and 6331-8376 |
| 6331 | 1-6330 and 6332-8376 |
| 6332 | 1-6331 and 6333-8376 |
| 6333 | 1-6332 and 6334-8376 |
| 6334 | 1-6333 and 6335-8376 |
| 6335 | 1-6334 and 6336-8376 |
| 6336 | 1-6335 and 6337-8376 |
| 6337 | 1-6336 and 6338-8376 |
| 6338 | 1-6337 and 6339-8376 |
| 6339 | 1-6338 and 6340-8376 |
| 6340 | 1-6339 and 6341-8376 |
| 6341 | 1-6340 and 6342-8376 |
| 6342 | 1-6341 and 6343-8376 |
| 6343 | 1-6342 and 6344-8376 |
| 6344 | 1-6343 and 6345-8376 |
| 6345 | 1-6344 and 6346-8376 |
| 6346 | 1-6345 and 6347-8376 |
| 6347 | 1-6346 and 6348-8376 |
| 6348 | 1-6347 and 6349-8376 |
| 6349 | 1-6348 and 6350-8376 |
| 6350 | 1-6349 and 6351-8376 |
| 6351 | 1-6350 and 6352-8376 |
| 6352 | 1-6351 and 6353-8376 |
| 6353 | 1-6352 and 6354-8376 |
| 6354 | 1-6353 and 6355-8376 |
| 6355 | 1-6354 and 6356-8376 |
| 6356 | 1-6355 and 6357-8376 |
| 6357 | 1-6356 and 6358-8376 |
| 6358 | 1-6357 and 6359-8376 |
| 6359 | 1-6358 and 6360-8376 |
| 6360 | 1-6359 and 6361-8376 |
| 6361 | 1-6360 and 6362-8376 |
| 6362 | 1-6361 and 6363-8376 |
| 6363 | 1-6362 and 6364-8376 |
| 6364 | 1-6363 and 6365-8376 |
| 6365 | 1-6364 and 6366-8376 |
| 6366 | 1-6365 and 6367-8376 |
| 6367 | 1-6366 and 6368-8376 |
| 6368 | 1-6367 and 6369-8376 |
| 6369 | 1-6368 and 6370-8376 |
| 6370 | 1-6369 and 6371-8376 |
| 6371 | 1-6370 and 6372-8376 |
| 6372 | 1-6371 and 6373-8376 |
| 6373 | 1-6372 and 6374-8376 |
| 6374 | 1-6373 and 6375-8376 |
| 6375 | 1-6374 and 6376-8376 |
| 6376 | 1-6375 and 6377-8376 |
| 6377 | 1-6376 and 6378-8376 |
| 6378 | 1-6377 and 6379-8376 |
| 6379 | 1-6378 and 6380-8376 |
| 6380 | 1-6379 and 6381-8376 |
| 6381 | 1-6380 and 6382-8376 |
| 6382 | 1-6381 and 6383-8376 |
| 6383 | 1-6382 and 6384-8376 |
| 6384 | 1-6383 and 6385-8376 |
| 6385 | 1-6384 and 6386-8376 |
| 6386 | 1-6385 and 6387-8376 |
| 6387 | 1-6386 and 6388-8376 |
| 6388 | 1-6387 and 6389-8376 |
| 6389 | 1-6388 and 6390-8376 |
| 6390 | 1-6389 and 6391-8376 |
| 6391 | 1-6390 and 6392-8376 |
| 6392 | 1-6391 and 6393-8376 |
| 6393 | 1-6392 and 6394-8376 |
| 6394 | 1-6393 and 6395-8376 |
| 6395 | 1-6394 and 6396-8376 |
| 6396 | 1-6395 and 6397-8376 |
| 6397 | 1-6396 and 6398-8376 |
| 6398 | 1-6397 and 6399-8376 |
| 6399 | 1-6398 and 6400-8376 |
| 6400 | 1-6399 and 6401-8376 |
| 6401 | 1-6400 and 6402-8376 |
| 6402 | 1-6401 and 6403-8376 |
| 6403 | 1-6402 and 6404-8376 |
| 6404 | 1-6403 and 6405-8376 |
| 6405 | 1-6404 and 6406-8376 |
| 6406 | 1-6405 and 6407-8376 |
| 6407 | 1-6406 and 6408-8376 |
| 6408 | 1-6407 and 6409-8376 |
| 6409 | 1-6408 and 6410-8376 |
| 6410 | 1-6409 and 6411-8376 |
| 6411 | 1-6410 and 6412-8376 |
| 6412 | 1-6411 and 6413-8376 |
| 6413 | 1-6412 and 6414-8376 |
| 6414 | 1-6413 and 6415-8376 |
| 6415 | 1-6414 and 6416-8376 |
| 6416 | 1-6415 and 6417-8376 |
| 6417 | 1-6416 and 6418-8376 |
| 6418 | 1-6417 and 6419-8376 |
| 6419 | 1-6418 and 6420-8376 |
| 6420 | 1-6419 and 6421-8376 |
| 6421 | 1-6420 and 6422-8376 |
| 6422 | 1-6421 and 6423-8376 |
| 6423 | 1-6422 and 6424-8376 |
| 6424 | 1-6423 and 6425-8376 |
| 6425 | 1-6424 and 6426-8376 |
| 6426 | 1-6425 and 6427-8376 |
| 6427 | 1-6426 and 6428-8376 |
| 6428 | 1-6427 and 6429-8376 |
| 6429 | 1-6428 and 6430-8376 |
| 6430 | 1-6429 and 6431-8376 |
| 6431 | 1-6430 and 6432-8376 |
| 6432 | 1-6431 and 6433-8376 |
| 6433 | 1-6432 and 6434-8376 |
| 6434 | 1-6433 and 6435-8376 |
| 6435 | 1-6434 and 6436-8376 |
| 6436 | 1-6435 and 6437-8376 |
| 6437 | 1-6436 and 6438-8376 |
| 6438 | 1-6437 and 6439-8376 |
| 6439 | 1-6438 and 6440-8376 |
| 6440 | 1-6439 and 6441-8376 |
| 6441 | 1-6440 and 6442-8376 |
| 6442 | 1-6441 and 6443-8376 |
| 6443 | 1-6442 and 6444-8376 |
| 6444 | 1-6443 and 6445-8376 |
| 6445 | 1-6444 and 6446-8376 |
| 6446 | 1-6445 and 6447-8376 |
| 6447 | 1-6446 and 6448-8376 |
| 6448 | 1-6447 and 6449-8376 |
| 6449 | 1-6448 and 6450-8376 |

| First | Second |
|---|---|
| 6450 | 1-6449 and 6451-8376 |
| 6451 | 1-6450 and 6452-8376 |
| 6452 | 1-6451 and 6453-8376 |
| 6453 | 1-6452 and 6454-8376 |
| 6454 | 1-6453 and 6455-8376 |
| 6455 | 1-6454 and 6456-8376 |
| 6456 | 1-6455 and 6457-8376 |
| 6457 | 1-6456 and 6458-8376 |
| 6458 | 1-6457 and 6459-8376 |
| 6459 | 1-6458 and 6460-8376 |
| 6460 | 1-6459 and 6461-8376 |
| 6461 | 1-6460 and 6462-8376 |
| 6462 | 1-6461 and 6463-8376 |
| 6463 | 1-6462 and 6464-8376 |
| 6464 | 1-6463 and 6465-8376 |
| 6465 | 1-6464 and 6466-8376 |
| 6466 | 1-6465 and 6467-8376 |
| 6467 | 1-6466 and 6468-8376 |
| 6468 | 1-6467 and 6469-8376 |
| 6469 | 1-6468 and 6470-8376 |
| 6470 | 1-6469 and 6471-8376 |
| 6471 | 1-6470 and 6472-8376 |
| 6472 | 1-6471 and 6473-8376 |
| 6473 | 1-6472 and 6474-8376 |
| 6474 | 1-6473 and 6475-8376 |
| 6475 | 1-6474 and 6476-8376 |
| 6476 | 1-6475 and 6477-8376 |
| 6477 | 1-6476 and 6478-8376 |
| 6478 | 1-6477 and 6479-8376 |
| 6479 | 1-6478 and 6480-8376 |
| 6480 | 1-6479 and 6481-8376 |
| 6481 | 1-6480 and 6482-8376 |
| 6482 | 1-6481 and 6483-8376 |
| 6483 | 1-6482 and 6484-8376 |
| 6484 | 1-6483 and 6485-8376 |
| 6485 | 1-6484 and 6486-8376 |
| 6486 | 1-6485 and 6487-8376 |
| 6487 | 1-6486 and 6488-8376 |
| 6488 | 1-6487 and 6489-8376 |
| 6489 | 1-6488 and 6490-8376 |
| 6490 | 1-6489 and 6491-8376 |
| 6491 | 1-6490 and 6492-8376 |
| 6492 | 1-6491 and 6493-8376 |
| 6493 | 1-6492 and 6494-8376 |
| 6494 | 1-6493 and 6495-8376 |
| 6495 | 1-6494 and 6496-8376 |
| 6496 | 1-6495 and 6497-8376 |
| 6497 | 1-6496 and 6498-8376 |
| 6498 | 1-6497 and 6499-8376 |
| 6499 | 1-6498 and 6500-8376 |
| 6500 | 1-6499 and 6501-8376 |
| 6501 | 1-6500 and 6502-8376 |
| 6502 | 1-6501 and 6503-8376 |
| 6503 | 1-6502 and 6504-8376 |
| 6504 | 1-6503 and 6505-8376 |
| 6505 | 1-6504 and 6506-8376 |
| 6506 | 1-6505 and 6507-8376 |
| 6507 | 1-6506 and 6508-8376 |
| 6508 | 1-6507 and 6509-8376 |
| 6509 | 1-6508 and 6510-8376 |
| 6510 | 1-6509 and 6511-8376 |
| 6511 | 1-6510 and 6512-8376 |
| 6512 | 1-6511 and 6513-8376 |
| 6513 | 1-6512 and 6514-8376 |
| 6514 | 1-6513 and 6515-8376 |
| 6515 | 1-6514 and 6516-8376 |
| 6516 | 1-6515 and 6517-8376 |
| 6517 | 1-6516 and 6518-8376 |
| 6518 | 1-6517 and 6519-8376 |
| 6519 | 1-6518 and 6520-8376 |
| 6520 | 1-6519 and 6521-8376 |
| 6521 | 1-6520 and 6522-8376 |
| 6522 | 1-6521 and 6523-8376 |
| 6523 | 1-6522 and 6524-8376 |
| 6524 | 1-6523 and 6525-8376 |
| 6525 | 1-6524 and 6526-8376 |
| 6526 | 1-6525 and 6527-8376 |
| 6527 | 1-6526 and 6528-8376 |
| 6528 | 1-6527 and 6529-8376 |
| 6529 | 1-6528 and 6530-8376 |
| 6530 | 1-6529 and 6531-8376 |
| 6531 | 1-6530 and 6532-8376 |
| 6532 | 1-6531 and 6533-8376 |
| 6533 | 1-6532 and 6534-8376 |
| 6534 | 1-6533 and 6535-8376 |
| 6535 | 1-6534 and 6536-8376 |
| 6536 | 1-6535 and 6537-8376 |
| 6537 | 1-6536 and 6538-8376 |
| 6538 | 1-6537 and 6539-8376 |
| 6539 | 1-6538 and 6540-8376 |
| 6540 | 1-6539 and 6541-8376 |
| 6541 | 1-6540 and 6542-8376 |
| 6542 | 1-6541 and 6543-8376 |
| 6543 | 1-6542 and 6544-8376 |
| 6544 | 1-6543 and 6545-8376 |
| 6545 | 1-6544 and 6546-8376 |
| 6546 | 1-6545 and 6547-8376 |
| 6547 | 1-6546 and 6548-8376 |
| 6548 | 1-6547 and 6549-8376 |
| 6549 | 1-6548 and 6550-8376 |
| 6550 | 1-6549 and 6551-8376 |
| 6551 | 1-6550 and 6552-8376 |
| 6552 | 1-6551 and 6553-8376 |
| 6553 | 1-6552 and 6554-8376 |
| 6554 | 1-6553 and 6555-8376 |
| 6555 | 1-6554 and 6556-8376 |
| 6556 | 1-6555 and 6557-8376 |
| 6557 | 1-6556 and 6558-8376 |
| 6558 | 1-6557 and 6559-8376 |
| 6559 | 1-6558 and 6560-8376 |
| 6560 | 1-6559 and 6561-8376 |
| 6561 | 1-6560 and 6562-8376 |
| 6562 | 1-6561 and 6563-8376 |
| 6563 | 1-6562 and 6564-8376 |
| 6564 | 1-6563 and 6565-8376 |
| 6565 | 1-6564 and 6566-8376 |
| 6566 | 1-6565 and 6567-8376 |
| 6567 | 1-6566 and 6568-8376 |
| 6568 | 1-6567 and 6569-8376 |
| 6569 | 1-6568 and 6570-8376 |
| 6570 | 1-6569 and 6571-8376 |
| 6571 | 1-6570 and 6572-8376 |
| 6572 | 1-6571 and 6573-8376 |
| 6573 | 1-6572 and 6574-8376 |
| 6574 | 1-6573 and 6575-8376 |
| 6575 | 1-6574 and 6576-8376 |
| 6576 | 1-6575 and 6577-8376 |
| 6577 | 1-6576 and 6578-8376 |
| 6578 | 1-6577 and 6579-8376 |
| 6579 | 1-6578 and 6580-8376 |
| 6580 | 1-6579 and 6581-8376 |
| 6581 | 1-6580 and 6582-8376 |
| 6582 | 1-6581 and 6583-8376 |
| 6583 | 1-6582 and 6584-8376 |
| 6584 | 1-6583 and 6585-8376 |
| 6585 | 1-6584 and 6586-8376 |
| 6586 | 1-6585 and 6587-8376 |
| 6587 | 1-6586 and 6588-8376 |
| 6588 | 1-6587 and 6589-8376 |
| 6589 | 1-6588 and 6590-8376 |
| 6590 | 1-6589 and 6591-8376 |
| 6591 | 1-6590 and 6592-8376 |
| 6592 | 1-6591 and 6593-8376 |
| 6593 | 1-6592 and 6594-8376 |
| 6594 | 1-6593 and 6595-8376 |
| 6595 | 1-6594 and 6596-8376 |
| 6596 | 1-6595 and 6597-8376 |
| 6597 | 1-6596 and 6598-8376 |
| 6598 | 1-6597 and 6599-8376 |
| 6599 | 1-6598 and 6600-8376 |
| 6600 | 1-6599 and 6601-8376 |
| 6601 | 1-6600 and 6602-8376 |
| 6602 | 1-6601 and 6603-8376 |
| 6603 | 1-6602 and 6604-8376 |

| First | Second |
|---|---|
| 6604 | 1-6603 and 6605-8376 |
| 6605 | 1-6604 and 6606-8376 |
| 6606 | 1-6605 and 6607-8376 |
| 6607 | 1-6606 and 6608-8376 |
| 6608 | 1-6607 and 6609-8376 |
| 6609 | 1-6608 and 6610-8376 |
| 6610 | 1-6609 and 6611-8376 |
| 6611 | 1-6610 and 6612-8376 |
| 6612 | 1-6611 and 6613-8376 |
| 6613 | 1-6612 and 6614-8376 |
| 6614 | 1-6613 and 6615-8376 |
| 6615 | 1-6614 and 6616-8376 |
| 6616 | 1-6615 and 6617-8376 |
| 6617 | 1-6616 and 6618-8376 |
| 6618 | 1-6617 and 6619-8376 |
| 6619 | 1-6618 and 6620-8376 |
| 6620 | 1-6619 and 6621-8376 |
| 6621 | 1-6620 and 6622-8376 |
| 6622 | 1-6621 and 6623-8376 |
| 6623 | 1-6622 and 6624-8376 |
| 6624 | 1-6623 and 6625-8376 |
| 6625 | 1-6624 and 6626-8376 |
| 6626 | 1-6625 and 6627-8376 |
| 6627 | 1-6626 and 6628-8376 |
| 6628 | 1-6627 and 6629-8376 |
| 6629 | 1-6628 and 6630-8376 |
| 6630 | 1-6629 and 6631-8376 |
| 6631 | 1-6630 and 6632-8376 |
| 6632 | 1-6631 and 6633-8376 |
| 6633 | 1-6632 and 6634-8376 |
| 6634 | 1-6633 and 6635-8376 |
| 6635 | 1-6634 and 6636-8376 |
| 6636 | 1-6635 and 6637-8376 |
| 6637 | 1-6636 and 6638-8376 |
| 6638 | 1-6637 and 6639-8376 |
| 6639 | 1-6638 and 6640-8376 |
| 6640 | 1-6639 and 6641-8376 |
| 6641 | 1-6640 and 6642-8376 |
| 6642 | 1-6641 and 6643-8376 |
| 6643 | 1-6642 and 6644-8376 |
| 6644 | 1-6643 and 6645-8376 |
| 6645 | 1-6644 and 6646-8376 |
| 6646 | 1-6645 and 6647-8376 |
| 6647 | 1-6646 and 6648-8376 |
| 6648 | 1-6647 and 6649-8376 |
| 6649 | 1-6648 and 6650-8376 |
| 6650 | 1-6649 and 6651-8376 |
| 6651 | 1-6650 and 6652-8376 |
| 6652 | 1-6651 and 6653-8376 |
| 6653 | 1-6652 and 6654-8376 |
| 6654 | 1-6653 and 6655-8376 |
| 6655 | 1-6654 and 6656-8376 |
| 6656 | 1-6655 and 6657-8376 |
| 6657 | 1-6656 and 6658-8376 |
| 6658 | 1-6657 and 6659-8376 |
| 6659 | 1-6658 and 6660-8376 |
| 6660 | 1-6659 and 6661-8376 |
| 6661 | 1-6660 and 6662-8376 |
| 6662 | 1-6661 and 6663-8376 |
| 6663 | 1-6662 and 6664-8376 |
| 6664 | 1-6663 and 6665-8376 |
| 6665 | 1-6664 and 6666-8376 |
| 6666 | 1-6665 and 6667-8376 |
| 6667 | 1-6666 and 6668-8376 |
| 6668 | 1-6667 and 6669-8376 |
| 6669 | 1-6668 and 6670-8376 |
| 6670 | 1-6669 and 6671-8376 |
| 6671 | 1-6670 and 6672-8376 |
| 6672 | 1-6671 and 6673-8376 |
| 6673 | 1-6672 and 6674-8376 |
| 6674 | 1-6673 and 6675-8376 |
| 6675 | 1-6674 and 6676-8376 |
| 6676 | 1-6675 and 6677-8376 |
| 6677 | 1-6676 and 6678-8376 |
| 6678 | 1-6677 and 6679-8376 |
| 6679 | 1-6678 and 6680-8376 |
| 6680 | 1-6679 and 6681-8376 |
| 6681 | 1-6680 and 6682-8376 |
| 6682 | 1-6681 and 6683-8376 |
| 6683 | 1-6682 and 6684-8376 |
| 6684 | 1-6683 and 6685-8376 |
| 6685 | 1-6684 and 6686-8376 |
| 6686 | 1-6685 and 6687-8376 |
| 6687 | 1-6686 and 6688-8376 |
| 6688 | 1-6687 and 6689-8376 |
| 6689 | 1-6688 and 6690-8376 |
| 6690 | 1-6689 and 6691-8376 |
| 6691 | 1-6690 and 6692-8376 |
| 6692 | 1-6691 and 6693-8376 |
| 6693 | 1-6692 and 6694-8376 |
| 6694 | 1-6693 and 6695-8376 |
| 6695 | 1-6694 and 6696-8376 |
| 6696 | 1-6695 and 6697-8376 |
| 6697 | 1-6696 and 6698-8376 |
| 6698 | 1-6697 and 6699-8376 |
| 6699 | 1-6698 and 6700-8376 |
| 6700 | 1-6699 and 6701-8376 |
| 6701 | 1-6700 and 6702-8376 |
| 6702 | 1-6701 and 6703-8376 |
| 6703 | 1-6702 and 6704-8376 |
| 6704 | 1-6703 and 6705-8376 |
| 6705 | 1-6704 and 6706-8376 |
| 6706 | 1-6705 and 6707-8376 |
| 6707 | 1-6706 and 6708-8376 |
| 6708 | 1-6707 and 6709-8376 |
| 6709 | 1-6708 and 6710-8376 |
| 6710 | 1-6709 and 6711-8376 |
| 6711 | 1-6710 and 6712-8376 |
| 6712 | 1-6711 and 6713-8376 |
| 6713 | 1-6712 and 6714-8376 |
| 6714 | 1-6713 and 6715-8376 |
| 6715 | 1-6714 and 6716-8376 |
| 6716 | 1-6715 and 6717-8376 |
| 6717 | 1-6716 and 6718-8376 |
| 6718 | 1-6717 and 6719-8376 |
| 6719 | 1-6718 and 6720-8376 |
| 6720 | 1-6719 and 6721-8376 |
| 6721 | 1-6720 and 6722-8376 |
| 6722 | 1-6721 and 6723-8376 |
| 6723 | 1-6722 and 6724-8376 |
| 6724 | 1-6723 and 6725-8376 |
| 6725 | 1-6724 and 6726-8376 |
| 6726 | 1-6725 and 6727-8376 |
| 6727 | 1-6726 and 6728-8376 |
| 6728 | 1-6727 and 6729-8376 |
| 6729 | 1-6728 and 6730-8376 |
| 6730 | 1-6729 and 6731-8376 |
| 6731 | 1-6730 and 6732-8376 |
| 6732 | 1-6731 and 6733-8376 |
| 6733 | 1-6732 and 6734-8376 |
| 6734 | 1-6733 and 6735-8376 |
| 6735 | 1-6734 and 6736-8376 |
| 6736 | 1-6735 and 6737-8376 |
| 6737 | 1-6736 and 6738-8376 |
| 6738 | 1-6737 and 6739-8376 |
| 6739 | 1-6738 and 6740-8376 |
| 6740 | 1-6739 and 6741-8376 |
| 6741 | 1-6740 and 6742-8376 |
| 6742 | 1-6741 and 6743-8376 |
| 6743 | 1-6742 and 6744-8376 |
| 6744 | 1-6743 and 6745-8376 |
| 6745 | 1-6744 and 6746-8376 |
| 6746 | 1-6745 and 6747-8376 |
| 6747 | 1-6746 and 6748-8376 |
| 6748 | 1-6747 and 6749-8376 |
| 6749 | 1-6748 and 6750-8376 |
| 6750 | 1-6749 and 6751-8376 |
| 6751 | 1-6750 and 6752-8376 |
| 6752 | 1-6751 and 6753-8376 |
| 6753 | 1-6752 and 6754-8376 |
| 6754 | 1-6753 and 6755-8376 |
| 6755 | 1-6754 and 6756-8376 |
| 6756 | 1-6755 and 6757-8376 |
| 6757 | 1-6756 and 6758-8376 |

-continued

| First | Second |
|---|---|
| 6758 | 1-6757 and 6759-8376 |
| 6759 | 1-6758 and 6760-8376 |
| 6760 | 1-6759 and 6761-8376 |
| 6761 | 1-6760 and 6762-8376 |
| 6762 | 1-6761 and 6763-8376 |
| 6763 | 1-6762 and 6764-8376 |
| 6764 | 1-6763 and 6765-8376 |
| 6765 | 1-6764 and 6766-8376 |
| 6766 | 1-6765 and 6767-8376 |
| 6767 | 1-6766 and 6768-8376 |
| 6768 | 1-6767 and 6769-8376 |
| 6769 | 1-6768 and 6770-8376 |
| 6770 | 1-6769 and 6771-8376 |
| 6771 | 1-6770 and 6772-8376 |
| 6772 | 1-6771 and 6773-8376 |
| 6773 | 1-6772 and 6774-8376 |
| 6774 | 1-6773 and 6775-8376 |
| 6775 | 1-6774 and 6776-8376 |
| 6776 | 1-6775 and 6777-8376 |
| 6777 | 1-6776 and 6778-8376 |
| 6778 | 1-6777 and 6779-8376 |
| 6779 | 1-6778 and 6780-8376 |
| 6780 | 1-6779 and 6781-8376 |
| 6781 | 1-6780 and 6782-8376 |
| 6782 | 1-6781 and 6783-8376 |
| 6783 | 1-6782 and 6784-8376 |
| 6784 | 1-6783 and 6785-8376 |
| 6785 | 1-6784 and 6786-8376 |
| 6786 | 1-6785 and 6787-8376 |
| 6787 | 1-6786 and 6788-8376 |
| 6788 | 1-6787 and 6789-8376 |
| 6789 | 1-6788 and 6790-8376 |
| 6790 | 1-6789 and 6791-8376 |
| 6791 | 1-6790 and 6792-8376 |
| 6792 | 1-6791 and 6793-8376 |
| 6793 | 1-6792 and 6794-8376 |
| 6794 | 1-6793 and 6795-8376 |
| 6795 | 1-6794 and 6796-8376 |
| 6796 | 1-6795 and 6797-8376 |
| 6797 | 1-6796 and 6798-8376 |
| 6798 | 1-6797 and 6799-8376 |
| 6799 | 1-6798 and 6800-8376 |
| 6800 | 1-6799 and 6801-8376 |
| 6801 | 1-6800 and 6802-8376 |
| 6802 | 1-6801 and 6803-8376 |
| 6803 | 1-6802 and 6804-8376 |
| 6804 | 1-6803 and 6805-8376 |
| 6805 | 1-6804 and 6806-8376 |
| 6806 | 1-6805 and 6807-8376 |
| 6807 | 1-6806 and 6808-8376 |
| 6808 | 1-6807 and 6809-8376 |
| 6809 | 1-6808 and 6810-8376 |
| 6810 | 1-6809 and 6811-8376 |
| 6811 | 1-6810 and 6812-8376 |
| 6812 | 1-6811 and 6813-8376 |
| 6813 | 1-6812 and 6814-8376 |
| 6814 | 1-6813 and 6815-8376 |
| 6815 | 1-6814 and 6816-8376 |
| 6816 | 1-6815 and 6817-8376 |
| 6817 | 1-6816 and 6818-8376 |
| 6818 | 1-6817 and 6819-8376 |
| 6819 | 1-6818 and 6820-8376 |
| 6820 | 1-6819 and 6821-8376 |
| 6821 | 1-6820 and 6822-8376 |
| 6822 | 1-6821 and 6823-8376 |
| 6823 | 1-6822 and 6824-8376 |
| 6824 | 1-6823 and 6825-8376 |
| 6825 | 1-6824 and 6826-8376 |
| 6826 | 1-6825 and 6827-8376 |
| 6827 | 1-6826 and 6828-8376 |
| 6828 | 1-6827 and 6829-8376 |
| 6829 | 1-6828 and 6830-8376 |
| 6830 | 1-6829 and 6831-8376 |
| 6831 | 1-6830 and 6832-8376 |
| 6832 | 1-6831 and 6833-8376 |
| 6833 | 1-6832 and 6834-8376 |
| 6834 | 1-6833 and 6835-8376 |

-continued

| First | Second |
|---|---|
| 6835 | 1-6834 and 6836-8376 |
| 6836 | 1-6835 and 6837-8376 |
| 6837 | 1-6836 and 6838-8376 |
| 6838 | 1-6837 and 6839-8376 |
| 6839 | 1-6838 and 6840-8376 |
| 6840 | 1-6839 and 6841-8376 |
| 6841 | 1-6840 and 6842-8376 |
| 6842 | 1-6841 and 6843-8376 |
| 6843 | 1-6842 and 6844-8376 |
| 6844 | 1-6843 and 6845-8376 |
| 6845 | 1-6844 and 6846-8376 |
| 6846 | 1-6845 and 6847-8376 |
| 6847 | 1-6846 and 6848-8376 |
| 6848 | 1-6847 and 6849-8376 |
| 6849 | 1-6848 and 6850-8376 |
| 6850 | 1-6849 and 6851-8376 |
| 6851 | 1-6850 and 6852-8376 |
| 6852 | 1-6851 and 6853-8376 |
| 6853 | 1-6852 and 6854-8376 |
| 6854 | 1-6853 and 6855-8376 |
| 6855 | 1-6854 and 6856-8376 |
| 6856 | 1-6855 and 6857-8376 |
| 6857 | 1-6856 and 6858-8376 |
| 6858 | 1-6857 and 6859-8376 |
| 6859 | 1-6858 and 6860-8376 |
| 6860 | 1-6859 and 6861-8376 |
| 6861 | 1-6860 and 6862-8376 |
| 6862 | 1-6861 and 6863-8376 |
| 6863 | 1-6862 and 6864-8376 |
| 6864 | 1-6863 and 6865-8376 |
| 6865 | 1-6864 and 6866-8376 |
| 6866 | 1-6865 and 6867-8376 |
| 6867 | 1-6866 and 6868-8376 |
| 6868 | 1-6867 and 6869-8376 |
| 6869 | 1-6868 and 6870-8376 |
| 6870 | 1-6869 and 6871-8376 |
| 6871 | 1-6870 and 6872-8376 |
| 6872 | 1-6871 and 6873-8376 |
| 6873 | 1-6872 and 6874-8376 |
| 6874 | 1-6873 and 6875-8376 |
| 6875 | 1-6874 and 6876-8376 |
| 6876 | 1-6875 and 6877-8376 |
| 6877 | 1-6876 and 6878-8376 |
| 6878 | 1-6877 and 6879-8376 |
| 6879 | 1-6878 and 6880-8376 |
| 6880 | 1-6879 and 6881-8376 |
| 6881 | 1-6880 and 6882-8376 |
| 6882 | 1-6881 and 6883-8376 |
| 6883 | 1-6882 and 6884-8376 |
| 6884 | 1-6883 and 6885-8376 |
| 6885 | 1-6884 and 6886-8376 |
| 6886 | 1-6885 and 6887-8376 |
| 6887 | 1-6886 and 6888-8376 |
| 6888 | 1-6887 and 6889-8376 |
| 6889 | 1-6888 and 6890-8376 |
| 6890 | 1-6889 and 6891-8376 |
| 6891 | 1-6890 and 6892-8376 |
| 6892 | 1-6891 and 6893-8376 |
| 6893 | 1-6892 and 6894-8376 |
| 6894 | 1-6893 and 6895-8376 |
| 6895 | 1-6894 and 6896-8376 |
| 6896 | 1-6895 and 6897-8376 |
| 6897 | 1-6896 and 6898-8376 |
| 6898 | 1-6897 and 6899-8376 |
| 6899 | 1-6898 and 6900-8376 |
| 6900 | 1-6899 and 6901-8376 |
| 6901 | 1-6900 and 6902-8376 |
| 6902 | 1-6901 and 6903-8376 |
| 6903 | 1-6902 and 6904-8376 |
| 6904 | 1-6903 and 6905-8376 |
| 6905 | 1-6904 and 6906-8376 |
| 6906 | 1-6905 and 6907-8376 |
| 6907 | 1-6906 and 6908-8376 |
| 6908 | 1-6907 and 6909-8376 |
| 6909 | 1-6908 and 6910-8376 |
| 6910 | 1-6909 and 6911-8376 |
| 6911 | 1-6910 and 6912-8376 |

-continued

| First | Second |
|---|---|
| 6912 | 1-6911 and 6913-8376 |
| 6913 | 1-6912 and 6914-8376 |
| 6914 | 1-6913 and 6915-8376 |
| 6915 | 1-6914 and 6916-8376 |
| 6916 | 1-6915 and 6917-8376 |
| 6917 | 1-6916 and 6918-8376 |
| 6918 | 1-6917 and 6919-8376 |
| 6919 | 1-6918 and 6920-8376 |
| 6920 | 1-6919 and 6921-8376 |
| 6921 | 1-6920 and 6922-8376 |
| 6922 | 1-6921 and 6923-8376 |
| 6923 | 1-6922 and 6924-8376 |
| 6924 | 1-6923 and 6925-8376 |
| 6925 | 1-6924 and 6926-8376 |
| 6926 | 1-6925 and 6927-8376 |
| 6927 | 1-6926 and 6928-8376 |
| 6928 | 1-6927 and 6929-8376 |
| 6929 | 1-6928 and 6930-8376 |
| 6930 | 1-6929 and 6931-8376 |
| 6931 | 1-6930 and 6932-8376 |
| 6932 | 1-6931 and 6933-8376 |
| 6933 | 1-6932 and 6934-8376 |
| 6934 | 1-6933 and 6935-8376 |
| 6935 | 1-6934 and 6936-8376 |
| 6936 | 1-6935 and 6937-8376 |
| 6937 | 1-6936 and 6938-8376 |
| 6938 | 1-6937 and 6939-8376 |
| 6939 | 1-6938 and 6940-8376 |
| 6940 | 1-6939 and 6941-8376 |
| 6941 | 1-6940 and 6942-8376 |
| 6942 | 1-6941 and 6943-8376 |
| 6943 | 1-6942 and 6944-8376 |
| 6944 | 1-6943 and 6945-8376 |
| 6945 | 1-6944 and 6946-8376 |
| 6946 | 1-6945 and 6947-8376 |
| 6947 | 1-6946 and 6948-8376 |
| 6948 | 1-6947 and 6949-8376 |
| 6949 | 1-6948 and 6950-8376 |
| 6950 | 1-6949 and 6951-8376 |
| 6951 | 1-6950 and 6952-8376 |
| 6952 | 1-6951 and 6953-8376 |
| 6953 | 1-6952 and 6954-8376 |
| 6954 | 1-6953 and 6955-8376 |
| 6955 | 1-6954 and 6956-8376 |
| 6956 | 1-6955 and 6957-8376 |
| 6957 | 1-6956 and 6958-8376 |
| 6958 | 1-6957 and 6959-8376 |
| 6959 | 1-6958 and 6960-8376 |
| 6960 | 1-6959 and 6961-8376 |
| 6961 | 1-6960 and 6962-8376 |
| 6962 | 1-6961 and 6963-8376 |
| 6963 | 1-6962 and 6964-8376 |
| 6964 | 1-6963 and 6965-8376 |
| 6965 | 1-6964 and 6966-8376 |
| 6966 | 1-6965 and 6967-8376 |
| 6967 | 1-6966 and 6968-8376 |
| 6968 | 1-6967 and 6969-8376 |
| 6969 | 1-6968 and 6970-8376 |
| 6970 | 1-6969 and 6971-8376 |
| 6971 | 1-6970 and 6972-8376 |
| 6972 | 1-6971 and 6973-8376 |
| 6973 | 1-6972 and 6974-8376 |
| 6974 | 1-6973 and 6975-8376 |
| 6975 | 1-6974 and 6976-8376 |
| 6976 | 1-6975 and 6977-8376 |
| 6977 | 1-6976 and 6978-8376 |
| 6978 | 1-6977 and 6979-8376 |
| 6979 | 1-6978 and 6980-8376 |
| 6980 | 1-6979 and 6981-8376 |
| 6981 | 1-6980 and 6982-8376 |
| 6982 | 1-6981 and 6983-8376 |
| 6983 | 1-6982 and 6984-8376 |
| 6984 | 1-6983 and 6985-8376 |
| 6985 | 1-6984 and 6986-8376 |
| 6986 | 1-6985 and 6987-8376 |
| 6987 | 1-6986 and 6988-8376 |
| 6988 | 1-6987 and 6989-8376 |

-continued

| First | Second |
|---|---|
| 6989 | 1-6988 and 6990-8376 |
| 6990 | 1-6989 and 6991-8376 |
| 6991 | 1-6990 and 6992-8376 |
| 6992 | 1-6991 and 6993-8376 |
| 6993 | 1-6992 and 6994-8376 |
| 6994 | 1-6993 and 6995-8376 |
| 6995 | 1-6994 and 6996-8376 |
| 6996 | 1-6995 and 6997-8376 |
| 6997 | 1-6996 and 6998-8376 |
| 6998 | 1-6997 and 6999-8376 |
| 6999 | 1-6998 and 7000-8376 |
| 7000 | 1-6999 and 7001-8376 |
| 7001 | 1-7000 and 7002-8376 |
| 7002 | 1-7001 and 7003-8376 |
| 7003 | 1-7002 and 7004-8376 |
| 7004 | 1-7003 and 7005-8376 |
| 7005 | 1-7004 and 7006-8376 |
| 7006 | 1-7005 and 7007-8376 |
| 7007 | 1-7006 and 7008-8376 |
| 7008 | 1-7007 and 7009-8376 |
| 7009 | 1-7008 and 7010-8376 |
| 7010 | 1-7009 and 7011-8376 |
| 7011 | 1-7010 and 7012-8376 |
| 7012 | 1-7011 and 7013-8376 |
| 7013 | 1-7012 and 7014-8376 |
| 7014 | 1-7013 and 7015-8376 |
| 7015 | 1-7014 and 7016-8376 |
| 7016 | 1-7015 and 7017-8376 |
| 7017 | 1-7016 and 7018-8376 |
| 7018 | 1-7017 and 7019-8376 |
| 7019 | 1-7018 and 7020-8376 |
| 7020 | 1-7019 and 7021-8376 |
| 7021 | 1-7020 and 7022-8376 |
| 7022 | 1-7021 and 7023-8376 |
| 7023 | 1-7022 and 7024-8376 |
| 7024 | 1-7023 and 7025-8376 |
| 7025 | 1-7024 and 7026-8376 |
| 7026 | 1-7025 and 7027-8376 |
| 7027 | 1-7026 and 7028-8376 |
| 7028 | 1-7027 and 7029-8376 |
| 7029 | 1-7028 and 7030-8376 |
| 7030 | 1-7029 and 7031-8376 |
| 7031 | 1-7030 and 7032-8376 |
| 7032 | 1-7031 and 7033-8376 |
| 7033 | 1-7032 and 7034-8376 |
| 7034 | 1-7033 and 7035-8376 |
| 7035 | 1-7034 and 7036-8376 |
| 7036 | 1-7035 and 7037-8376 |
| 7037 | 1-7036 and 7038-8376 |
| 7038 | 1-7037 and 7039-8376 |
| 7039 | 1-7038 and 7040-8376 |
| 7040 | 1-7039 and 7041-8376 |
| 7041 | 1-7040 and 7042-8376 |
| 7042 | 1-7041 and 7043-8376 |
| 7043 | 1-7042 and 7044-8376 |
| 7044 | 1-7043 and 7045-8376 |
| 7045 | 1-7044 and 7046-8376 |
| 7046 | 1-7045 and 7047-8376 |
| 7047 | 1-7046 and 7048-8376 |
| 7048 | 1-7047 and 7049-8376 |
| 7049 | 1-7048 and 7050-8376 |
| 7050 | 1-7049 and 7051-8376 |
| 7051 | 1-7050 and 7052-8376 |
| 7052 | 1-7051 and 7053-8376 |
| 7053 | 1-7052 and 7054-8376 |
| 7054 | 1-7053 and 7055-8376 |
| 7055 | 1-7054 and 7056-8376 |
| 7056 | 1-7055 and 7057-8376 |
| 7057 | 1-7056 and 7058-8376 |
| 7058 | 1-7057 and 7059-8376 |
| 7059 | 1-7058 and 7060-8376 |
| 7060 | 1-7059 and 7061-8376 |
| 7061 | 1-7060 and 7062-8376 |
| 7062 | 1-7061 and 7063-8376 |
| 7063 | 1-7062 and 7064-8376 |
| 7064 | 1-7063 and 7065-8376 |
| 7065 | 1-7064 and 7066-8376 |

| First | Second |
|---|---|
| 7066 | 1-7065 and 7067-8376 |
| 7067 | 1-7066 and 7068-8376 |
| 7068 | 1-7067 and 7069-8376 |
| 7069 | 1-7068 and 7070-8376 |
| 7070 | 1-7069 and 7071-8376 |
| 7071 | 1-7070 and 7072-8376 |
| 7072 | 1-7071 and 7073-8376 |
| 7073 | 1-7072 and 7074-8376 |
| 7074 | 1-7073 and 7075-8376 |
| 7075 | 1-7074 and 7076-8376 |
| 7076 | 1-7075 and 7077-8376 |
| 7077 | 1-7076 and 7078-8376 |
| 7078 | 1-7077 and 7079-8376 |
| 7079 | 1-7078 and 7080-8376 |
| 7080 | 1-7079 and 7081-8376 |
| 7081 | 1-7080 and 7082-8376 |
| 7082 | 1-7081 and 7083-8376 |
| 7083 | 1-7082 and 7084-8376 |
| 7084 | 1-7083 and 7085-8376 |
| 7085 | 1-7084 and 7086-8376 |
| 7086 | 1-7085 and 7087-8376 |
| 7087 | 1-7086 and 7088-8376 |
| 7088 | 1-7087 and 7089-8376 |
| 7089 | 1-7088 and 7090-8376 |
| 7090 | 1-7089 and 7091-8376 |
| 7091 | 1-7090 and 7092-8376 |
| 7092 | 1-7091 and 7093-8376 |
| 7093 | 1-7092 and 7094-8376 |
| 7094 | 1-7093 and 7095-8376 |
| 7095 | 1-7094 and 7096-8376 |
| 7096 | 1-7095 and 7097-8376 |
| 7097 | 1-7096 and 7098-8376 |
| 7098 | 1-7097 and 7099-8376 |
| 7099 | 1-7098 and 7100-8376 |
| 7100 | 1-7099 and 7101-8376 |
| 7101 | 1-7100 and 7102-8376 |
| 7102 | 1-7101 and 7103-8376 |
| 7103 | 1-7102 and 7104-8376 |
| 7104 | 1-7103 and 7105-8376 |
| 7105 | 1-7104 and 7106-8376 |
| 7106 | 1-7105 and 7107-8376 |
| 7107 | 1-7106 and 7108-8376 |
| 7108 | 1-7107 and 7109-8376 |
| 7109 | 1-7108 and 7110-8376 |
| 7110 | 1-7109 and 7111-8376 |
| 7111 | 1-7110 and 7112-8376 |
| 7112 | 1-7111 and 7113-8376 |
| 7113 | 1-7112 and 7114-8376 |
| 7114 | 1-7113 and 7115-8376 |
| 7115 | 1-7114 and 7116-8376 |
| 7116 | 1-7115 and 7117-8376 |
| 7117 | 1-7116 and 7118-8376 |
| 7118 | 1-7117 and 7119-8376 |
| 7119 | 1-7118 and 7120-8376 |
| 7120 | 1-7119 and 7121-8376 |
| 7121 | 1-7120 and 7122-8376 |
| 7122 | 1-7121 and 7123-8376 |
| 7123 | 1-7122 and 7124-8376 |
| 7124 | 1-7123 and 7125-8376 |
| 7125 | 1-7124 and 7126-8376 |
| 7126 | 1-7125 and 7127-8376 |
| 7127 | 1-7126 and 7128-8376 |
| 7128 | 1-7127 and 7129-8376 |
| 7129 | 1-7128 and 7130-8376 |
| 7130 | 1-7129 and 7131-8376 |
| 7131 | 1-7130 and 7132-8376 |
| 7132 | 1-7131 and 7133-8376 |
| 7133 | 1-7132 and 7134-8376 |
| 7134 | 1-7133 and 7135-8376 |
| 7135 | 1-7134 and 7136-8376 |
| 7136 | 1-7135 and 7137-8376 |
| 7137 | 1-7136 and 7138-8376 |
| 7138 | 1-7137 and 7139-8376 |
| 7139 | 1-7138 and 7140-8376 |
| 7140 | 1-7139 and 7141-8376 |
| 7141 | 1-7140 and 7142-8376 |
| 7142 | 1-7141 and 7143-8376 |
| 7143 | 1-7142 and 7144-8376 |
| 7144 | 1-7143 and 7145-8376 |
| 7145 | 1-7144 and 7146-8376 |
| 7146 | 1-7145 and 7147-8376 |
| 7147 | 1-7146 and 7148-8376 |
| 7148 | 1-7147 and 7149-8376 |
| 7149 | 1-7148 and 7150-8376 |
| 7150 | 1-7149 and 7151-8376 |
| 7151 | 1-7150 and 7152-8376 |
| 7152 | 1-7151 and 7153-8376 |
| 7153 | 1-7152 and 7154-8376 |
| 7154 | 1-7153 and 7155-8376 |
| 7155 | 1-7154 and 7156-8376 |
| 7156 | 1-7155 and 7157-8376 |
| 7157 | 1-7156 and 7158-8376 |
| 7158 | 1-7157 and 7159-8376 |
| 7159 | 1-7158 and 7160-8376 |
| 7160 | 1-7159 and 7161-8376 |
| 7161 | 1-7160 and 7162-8376 |
| 7162 | 1-7161 and 7163-8376 |
| 7163 | 1-7162 and 7164-8376 |
| 7164 | 1-7163 and 7165-8376 |
| 7165 | 1-7164 and 7166-8376 |
| 7166 | 1-7165 and 7167-8376 |
| 7167 | 1-7166 and 7168-8376 |
| 7168 | 1-7167 and 7169-8376 |
| 7169 | 1-7168 and 7170-8376 |
| 7170 | 1-7169 and 7171-8376 |
| 7171 | 1-7170 and 7172-8376 |
| 7172 | 1-7171 and 7173-8376 |
| 7173 | 1-7172 and 7174-8376 |
| 7174 | 1-7173 and 7175-8376 |
| 7175 | 1-7174 and 7176-8376 |
| 7176 | 1-7175 and 7177-8376 |
| 7177 | 1-7176 and 7178-8376 |
| 7178 | 1-7177 and 7179-8376 |
| 7179 | 1-7178 and 7180-8376 |
| 7180 | 1-7179 and 7181-8376 |
| 7181 | 1-7180 and 7182-8376 |
| 7182 | 1-7181 and 7183-8376 |
| 7183 | 1-7182 and 7184-8376 |
| 7184 | 1-7183 and 7185-8376 |
| 7185 | 1-7184 and 7186-8376 |
| 7186 | 1-7185 and 7187-8376 |
| 7187 | 1-7186 and 7188-8376 |
| 7188 | 1-7187 and 7189-8376 |
| 7189 | 1-7188 and 7190-8376 |
| 7190 | 1-7189 and 7191-8376 |
| 7191 | 1-7190 and 7192-8376 |
| 7192 | 1-7191 and 7193-8376 |
| 7193 | 1-7192 and 7194-8376 |
| 7194 | 1-7193 and 7195-8376 |
| 7195 | 1-7194 and 7196-8376 |
| 7196 | 1-7195 and 7197-8376 |
| 7197 | 1-7196 and 7198-8376 |
| 7198 | 1-7197 and 7199-8376 |
| 7199 | 1-7198 and 7200-8376 |
| 7200 | 1-7199 and 7201-8376 |
| 7201 | 1-7200 and 7202-8376 |
| 7202 | 1-7201 and 7203-8376 |
| 7203 | 1-7202 and 7204-8376 |
| 7204 | 1-7203 and 7205-8376 |
| 7205 | 1-7204 and 7206-8376 |
| 7206 | 1-7205 and 7207-8376 |
| 7207 | 1-7206 and 7208-8376 |
| 7208 | 1-7207 and 7209-8376 |
| 7209 | 1-7208 and 7210-8376 |
| 7210 | 1-7209 and 7211-8376 |
| 7211 | 1-7210 and 7212-8376 |
| 7212 | 1-7211 and 7213-8376 |
| 7213 | 1-7212 and 7214-8376 |
| 7214 | 1-7213 and 7215-8376 |
| 7215 | 1-7214 and 7216-8376 |
| 7216 | 1-7215 and 7217-8376 |
| 7217 | 1-7216 and 7218-8376 |
| 7218 | 1-7217 and 7219-8376 |
| 7219 | 1-7218 and 7220-8376 |

| First | Second |
|---|---|
| 7220 | 1-7219 and 7221-8376 |
| 7221 | 1-7220 and 7222-8376 |
| 7222 | 1-7221 and 7223-8376 |
| 7223 | 1-7222 and 7224-8376 |
| 7224 | 1-7223 and 7225-8376 |
| 7225 | 1-7224 and 7226-8376 |
| 7226 | 1-7225 and 7227-8376 |
| 7227 | 1-7226 and 7228-8376 |
| 7228 | 1-7227 and 7229-8376 |
| 7229 | 1-7228 and 7230-8376 |
| 7230 | 1-7229 and 7231-8376 |
| 7231 | 1-7230 and 7232-8376 |
| 7232 | 1-7231 and 7233-8376 |
| 7233 | 1-7232 and 7234-8376 |
| 7234 | 1-7233 and 7235-8376 |
| 7235 | 1-7234 and 7236-8376 |
| 7236 | 1-7235 and 7237-8376 |
| 7237 | 1-7236 and 7238-8376 |
| 7238 | 1-7237 and 7239-8376 |
| 7239 | 1-7238 and 7240-8376 |
| 7240 | 1-7239 and 7241-8376 |
| 7241 | 1-7240 and 7242-8376 |
| 7242 | 1-7241 and 7243-8376 |
| 7243 | 1-7242 and 7244-8376 |
| 7244 | 1-7243 and 7245-8376 |
| 7245 | 1-7244 and 7246-8376 |
| 7246 | 1-7245 and 7247-8376 |
| 7247 | 1-7246 and 7248-8376 |
| 7248 | 1-7247 and 7249-8376 |
| 7249 | 1-7248 and 7250-8376 |
| 7250 | 1-7249 and 7251-8376 |
| 7251 | 1-7250 and 7252-8376 |
| 7252 | 1-7251 and 7253-8376 |
| 7253 | 1-7252 and 7254-8376 |
| 7254 | 1-7253 and 7255-8376 |
| 7255 | 1-7254 and 7256-8376 |
| 7256 | 1-7255 and 7257-8376 |
| 7257 | 1-7256 and 7258-8376 |
| 7258 | 1-7257 and 7259-8376 |
| 7259 | 1-7258 and 7260-8376 |
| 7260 | 1-7259 and 7261-8376 |
| 7261 | 1-7260 and 7262-8376 |
| 7262 | 1-7261 and 7263-8376 |
| 7263 | 1-7262 and 7264-8376 |
| 7264 | 1-7263 and 7265-8376 |
| 7265 | 1-7264 and 7266-8376 |
| 7266 | 1-7265 and 7267-8376 |
| 7267 | 1-7266 and 7268-8376 |
| 7268 | 1-7267 and 7269-8376 |
| 7269 | 1-7268 and 7270-8376 |
| 7270 | 1-7269 and 7271-8376 |
| 7271 | 1-7270 and 7272-8376 |
| 7272 | 1-7271 and 7273-8376 |
| 7273 | 1-7272 and 7274-8376 |
| 7274 | 1-7273 and 7275-8376 |
| 7275 | 1-7274 and 7276-8376 |
| 7276 | 1-7275 and 7277-8376 |
| 7277 | 1-7276 and 7278-8376 |
| 7278 | 1-7277 and 7279-8376 |
| 7279 | 1-7278 and 7280-8376 |
| 7280 | 1-7279 and 7281-8376 |
| 7281 | 1-7280 and 7282-8376 |
| 7282 | 1-7281 and 7283-8376 |
| 7283 | 1-7282 and 7284-8376 |
| 7284 | 1-7283 and 7285-8376 |
| 7285 | 1-7284 and 7286-8376 |
| 7286 | 1-7285 and 7287-8376 |
| 7287 | 1-7286 and 7288-8376 |
| 7288 | 1-7287 and 7289-8376 |
| 7289 | 1-7288 and 7290-8376 |
| 7290 | 1-7289 and 7291-8376 |
| 7291 | 1-7290 and 7292-8376 |
| 7292 | 1-7291 and 7293-8376 |
| 7293 | 1-7292 and 7294-8376 |
| 7294 | 1-7293 and 7295-8376 |
| 7295 | 1-7294 and 7296-8376 |
| 7296 | 1-7295 and 7297-8376 |
| 7297 | 1-7296 and 7298-8376 |
| 7298 | 1-7297 and 7299-8376 |
| 7299 | 1-7298 and 7300-8376 |
| 7300 | 1-7299 and 7301-8376 |
| 7301 | 1-7300 and 7302-8376 |
| 7302 | 1-7301 and 7303-8376 |
| 7303 | 1-7302 and 7304-8376 |
| 7304 | 1-7303 and 7305-8376 |
| 7305 | 1-7304 and 7306-8376 |
| 7306 | 1-7305 and 7307-8376 |
| 7307 | 1-7306 and 7308-8376 |
| 7308 | 1-7307 and 7309-8376 |
| 7309 | 1-7308 and 7310-8376 |
| 7310 | 1-7309 and 7311-8376 |
| 7311 | 1-7310 and 7312-8376 |
| 7312 | 1-7311 and 7313-8376 |
| 7313 | 1-7312 and 7314-8376 |
| 7314 | 1-7313 and 7315-8376 |
| 7315 | 1-7314 and 7316-8376 |
| 7316 | 1-7315 and 7317-8376 |
| 7317 | 1-7316 and 7318-8376 |
| 7318 | 1-7317 and 7319-8376 |
| 7319 | 1-7318 and 7320-8376 |
| 7320 | 1-7319 and 7321-8376 |
| 7321 | 1-7320 and 7322-8376 |
| 7322 | 1-7321 and 7323-8376 |
| 7323 | 1-7322 and 7324-8376 |
| 7324 | 1-7323 and 7325-8376 |
| 7325 | 1-7324 and 7326-8376 |
| 7326 | 1-7325 and 7327-8376 |
| 7327 | 1-7326 and 7328-8376 |
| 7328 | 1-7327 and 7329-8376 |
| 7329 | 1-7328 and 7330-8376 |
| 7330 | 1-7329 and 7331-8376 |
| 7331 | 1-7330 and 7332-8376 |
| 7332 | 1-7331 and 7333-8376 |
| 7333 | 1-7332 and 7334-8376 |
| 7334 | 1-7333 and 7335-8376 |
| 7335 | 1-7334 and 7336-8376 |
| 7336 | 1-7335 and 7337-8376 |
| 7337 | 1-7336 and 7338-8376 |
| 7338 | 1-7337 and 7339-8376 |
| 7339 | 1-7338 and 7340-8376 |
| 7340 | 1-7339 and 7341-8376 |
| 7341 | 1-7340 and 7342-8376 |
| 7342 | 1-7341 and 7343-8376 |
| 7343 | 1-7342 and 7344-8376 |
| 7344 | 1-7343 and 7345-8376 |
| 7345 | 1-7344 and 7346-8376 |
| 7346 | 1-7345 and 7347-8376 |
| 7347 | 1-7346 and 7348-8376 |
| 7348 | 1-7347 and 7349-8376 |
| 7349 | 1-7348 and 7350-8376 |
| 7350 | 1-7349 and 7351-8376 |
| 7351 | 1-7350 and 7352-8376 |
| 7352 | 1-7351 and 7353-8376 |
| 7353 | 1-7352 and 7354-8376 |
| 7354 | 1-7353 and 7355-8376 |
| 7355 | 1-7354 and 7356-8376 |
| 7356 | 1-7355 and 7357-8376 |
| 7357 | 1-7356 and 7358-8376 |
| 7358 | 1-7357 and 7359-8376 |
| 7359 | 1-7358 and 7360-8376 |
| 7360 | 1-7359 and 7361-8376 |
| 7361 | 1-7360 and 7362-8376 |
| 7362 | 1-7361 and 7363-8376 |
| 7363 | 1-7362 and 7364-8376 |
| 7364 | 1-7363 and 7365-8376 |
| 7365 | 1-7364 and 7366-8376 |
| 7366 | 1-7365 and 7367-8376 |
| 7367 | 1-7366 and 7368-8376 |
| 7368 | 1-7367 and 7369-8376 |
| 7369 | 1-7368 and 7370-8376 |
| 7370 | 1-7369 and 7371-8376 |
| 7371 | 1-7370 and 7372-8376 |
| 7372 | 1-7371 and 7373-8376 |
| 7373 | 1-7372 and 7374-8376 |

| First | Second |
|---|---|
| 7374 | 1-7373 and 7375-8376 |
| 7375 | 1-7374 and 7376-8376 |
| 7376 | 1-7375 and 7377-8376 |
| 7377 | 1-7376 and 7378-8376 |
| 7378 | 1-7377 and 7379-8376 |
| 7379 | 1-7378 and 7380-8376 |
| 7380 | 1-7379 and 7381-8376 |
| 7381 | 1-7380 and 7382-8376 |
| 7382 | 1-7381 and 7383-8376 |
| 7383 | 1-7382 and 7384-8376 |
| 7384 | 1-7383 and 7385-8376 |
| 7385 | 1-7384 and 7386-8376 |
| 7386 | 1-7385 and 7387-8376 |
| 7387 | 1-7386 and 7388-8376 |
| 7388 | 1-7387 and 7389-8376 |
| 7389 | 1-7388 and 7390-8376 |
| 7390 | 1-7389 and 7391-8376 |
| 7391 | 1-7390 and 7392-8376 |
| 7392 | 1-7391 and 7393-8376 |
| 7393 | 1-7392 and 7394-8376 |
| 7394 | 1-7393 and 7395-8376 |
| 7395 | 1-7394 and 7396-8376 |
| 7396 | 1-7395 and 7397-8376 |
| 7397 | 1-7396 and 7398-8376 |
| 7398 | 1-7397 and 7399-8376 |
| 7399 | 1-7398 and 7400-8376 |
| 7400 | 1-7399 and 7401-8376 |
| 7401 | 1-7400 and 7402-8376 |
| 7402 | 1-7401 and 7403-8376 |
| 7403 | 1-7402 and 7404-8376 |
| 7404 | 1-7403 and 7405-8376 |
| 7405 | 1-7404 and 7406-8376 |
| 7406 | 1-7405 and 7407-8376 |
| 7407 | 1-7406 and 7408-8376 |
| 7408 | 1-7407 and 7409-8376 |
| 7409 | 1-7408 and 7410-8376 |
| 7410 | 1-7409 and 7411-8376 |
| 7411 | 1-7410 and 7412-8376 |
| 7412 | 1-7411 and 7413-8376 |
| 7413 | 1-7412 and 7414-8376 |
| 7414 | 1-7413 and 7415-8376 |
| 7415 | 1-7414 and 7416-8376 |
| 7416 | 1-7415 and 7417-8376 |
| 7417 | 1-7416 and 7418-8376 |
| 7418 | 1-7417 and 7419-8376 |
| 7419 | 1-7418 and 7420-8376 |
| 7420 | 1-7419 and 7421-8376 |
| 7421 | 1-7420 and 7422-8376 |
| 7422 | 1-7421 and 7423-8376 |
| 7423 | 1-7422 and 7424-8376 |
| 7424 | 1-7423 and 7425-8376 |
| 7425 | 1-7424 and 7426-8376 |
| 7426 | 1-7425 and 7427-8376 |
| 7427 | 1-7426 and 7428-8376 |
| 7428 | 1-7427 and 7429-8376 |
| 7429 | 1-7428 and 7430-8376 |
| 7430 | 1-7429 and 7431-8376 |
| 7431 | 1-7430 and 7432-8376 |
| 7432 | 1-7431 and 7433-8376 |
| 7433 | 1-7432 and 7434-8376 |
| 7434 | 1-7433 and 7435-8376 |
| 7435 | 1-7434 and 7436-8376 |
| 7436 | 1-7435 and 7437-8376 |
| 7437 | 1-7436 and 7438-8376 |
| 7438 | 1-7437 and 7439-8376 |
| 7439 | 1-7438 and 7440-8376 |
| 7440 | 1-7439 and 7441-8376 |
| 7441 | 1-7440 and 7442-8376 |
| 7442 | 1-7441 and 7443-8376 |
| 7443 | 1-7442 and 7444-8376 |
| 7444 | 1-7443 and 7445-8376 |
| 7445 | 1-7444 and 7446-8376 |
| 7446 | 1-7445 and 7447-8376 |
| 7447 | 1-7446 and 7448-8376 |
| 7448 | 1-7447 and 7449-8376 |
| 7449 | 1-7448 and 7450-8376 |
| 7450 | 1-7449 and 7451-8376 |
| 7451 | 1-7450 and 7452-8376 |
| 7452 | 1-7451 and 7453-8376 |
| 7453 | 1-7452 and 7454-8376 |
| 7454 | 1-7453 and 7455-8376 |
| 7455 | 1-7454 and 7456-8376 |
| 7456 | 1-7455 and 7457-8376 |
| 7457 | 1-7456 and 7458-8376 |
| 7458 | 1-7457 and 7459-8376 |
| 7459 | 1-7458 and 7460-8376 |
| 7460 | 1-7459 and 7461-8376 |
| 7461 | 1-7460 and 7462-8376 |
| 7462 | 1-7461 and 7463-8376 |
| 7463 | 1-7462 and 7464-8376 |
| 7464 | 1-7463 and 7465-8376 |
| 7465 | 1-7464 and 7466-8376 |
| 7466 | 1-7465 and 7467-8376 |
| 7467 | 1-7466 and 7468-8376 |
| 7468 | 1-7467 and 7469-8376 |
| 7469 | 1-7468 and 7470-8376 |
| 7470 | 1-7469 and 7471-8376 |
| 7471 | 1-7470 and 7472-8376 |
| 7472 | 1-7471 and 7473-8376 |
| 7473 | 1-7472 and 7474-8376 |
| 7474 | 1-7473 and 7475-8376 |
| 7475 | 1-7474 and 7476-8376 |
| 7476 | 1-7475 and 7477-8376 |
| 7477 | 1-7476 and 7478-8376 |
| 7478 | 1-7477 and 7479-8376 |
| 7479 | 1-7478 and 7480-8376 |
| 7480 | 1-7479 and 7481-8376 |
| 7481 | 1-7480 and 7482-8376 |
| 7482 | 1-7481 and 7483-8376 |
| 7483 | 1-7482 and 7484-8376 |
| 7484 | 1-7483 and 7485-8376 |
| 7485 | 1-7484 and 7486-8376 |
| 7486 | 1-7485 and 7487-8376 |
| 7487 | 1-7486 and 7488-8376 |
| 7488 | 1-7487 and 7489-8376 |
| 7489 | 1-7488 and 7490-8376 |
| 7490 | 1-7489 and 7491-8376 |
| 7491 | 1-7490 and 7492-8376 |
| 7492 | 1-7491 and 7493-8376 |
| 7493 | 1-7492 and 7494-8376 |
| 7494 | 1-7493 and 7495-8376 |
| 7495 | 1-7494 and 7496-8376 |
| 7496 | 1-7495 and 7497-8376 |
| 7497 | 1-7496 and 7498-8376 |
| 7498 | 1-7497 and 7499-8376 |
| 7499 | 1-7498 and 7500-8376 |
| 7500 | 1-7499 and 7501-8376 |
| 7501 | 1-7500 and 7502-8376 |
| 7502 | 1-7501 and 7503-8376 |
| 7503 | 1-7502 and 7504-8376 |
| 7504 | 1-7503 and 7505-8376 |
| 7505 | 1-7504 and 7506-8376 |
| 7506 | 1-7505 and 7507-8376 |
| 7507 | 1-7506 and 7508-8376 |
| 7508 | 1-7507 and 7509-8376 |
| 7509 | 1-7508 and 7510-8376 |
| 7510 | 1-7509 and 7511-8376 |
| 7511 | 1-7510 and 7512-8376 |
| 7512 | 1-7511 and 7513-8376 |
| 7513 | 1-7512 and 7514-8376 |
| 7514 | 1-7513 and 7515-8376 |
| 7515 | 1-7514 and 7516-8376 |
| 7516 | 1-7515 and 7517-8376 |
| 7517 | 1-7516 and 7518-8376 |
| 7518 | 1-7517 and 7519-8376 |
| 7519 | 1-7518 and 7520-8376 |
| 7520 | 1-7519 and 7521-8376 |
| 7521 | 1-7520 and 7522-8376 |
| 7522 | 1-7521 and 7523-8376 |
| 7523 | 1-7522 and 7524-8376 |
| 7524 | 1-7523 and 7525-8376 |
| 7525 | 1-7524 and 7526-8376 |
| 7526 | 1-7525 and 7527-8376 |
| 7527 | 1-7526 and 7528-8376 |

101
-continued

| First | Second |
|---|---|
| 7528 | 1-7527 and 7529-8376 |
| 7529 | 1-7528 and 7530-8376 |
| 7530 | 1-7529 and 7531-8376 |
| 7531 | 1-7530 and 7532-8376 |
| 7532 | 1-7531 and 7533-8376 |
| 7533 | 1-7532 and 7534-8376 |
| 7534 | 1-7533 and 7535-8376 |
| 7535 | 1-7534 and 7536-8376 |
| 7536 | 1-7535 and 7537-8376 |
| 7537 | 1-7536 and 7538-8376 |
| 7538 | 1-7537 and 7539-8376 |
| 7539 | 1-7538 and 7540-8376 |
| 7540 | 1-7539 and 7541-8376 |
| 7541 | 1-7540 and 7542-8376 |
| 7542 | 1-7541 and 7543-8376 |
| 7543 | 1-7542 and 7544-8376 |
| 7544 | 1-7543 and 7545-8376 |
| 7545 | 1-7544 and 7546-8376 |
| 7546 | 1-7545 and 7547-8376 |
| 7547 | 1-7546 and 7548-8376 |
| 7548 | 1-7547 and 7549-8376 |
| 7549 | 1-7548 and 7550-8376 |
| 7550 | 1-7549 and 7551-8376 |
| 7551 | 1-7550 and 7552-8376 |
| 7552 | 1-7551 and 7553-8376 |
| 7553 | 1-7552 and 7554-8376 |
| 7554 | 1-7553 and 7555-8376 |
| 7555 | 1-7554 and 7556-8376 |
| 7556 | 1-7555 and 7557-8376 |
| 7557 | 1-7556 and 7558-8376 |
| 7558 | 1-7557 and 7559-8376 |
| 7559 | 1-7558 and 7560-8376 |
| 7560 | 1-7559 and 7561-8376 |
| 7561 | 1-7560 and 7562-8376 |
| 7562 | 1-7561 and 7563-8376 |
| 7563 | 1-7562 and 7564-8376 |
| 7564 | 1-7563 and 7565-8376 |
| 7565 | 1-7564 and 7566-8376 |
| 7566 | 1-7565 and 7567-8376 |
| 7567 | 1-7566 and 7568-8376 |
| 7568 | 1-7567 and 7569-8376 |
| 7569 | 1-7568 and 7570-8376 |
| 7570 | 1-7569 and 7571-8376 |
| 7571 | 1-7570 and 7572-8376 |
| 7572 | 1-7571 and 7573-8376 |
| 7573 | 1-7572 and 7574-8376 |
| 7574 | 1-7573 and 7575-8376 |
| 7575 | 1-7574 and 7576-8376 |
| 7576 | 1-7575 and 7577-8376 |
| 7577 | 1-7576 and 7578-8376 |
| 7578 | 1-7577 and 7579-8376 |
| 7579 | 1-7578 and 7580-8376 |
| 7580 | 1-7579 and 7581-8376 |
| 7581 | 1-7580 and 7582-8376 |
| 7582 | 1-7581 and 7583-8376 |
| 7583 | 1-7582 and 7584-8376 |
| 7584 | 1-7583 and 7585-8376 |
| 7585 | 1-7584 and 7586-8376 |
| 7586 | 1-7585 and 7587-8376 |
| 7587 | 1-7586 and 7588-8376 |
| 7588 | 1-7587 and 7589-8376 |
| 7589 | 1-7588 and 7590-8376 |
| 7590 | 1-7589 and 7591-8376 |
| 7591 | 1-7590 and 7592-8376 |
| 7592 | 1-7591 and 7593-8376 |
| 7593 | 1-7592 and 7594-8376 |
| 7594 | 1-7593 and 7595-8376 |
| 7595 | 1-7594 and 7596-8376 |
| 7596 | 1-7595 and 7597-8376 |
| 7597 | 1-7596 and 7598-8376 |
| 7598 | 1-7597 and 7599-8376 |
| 7599 | 1-7598 and 7600-8376 |
| 7600 | 1-7599 and 7601-8376 |
| 7601 | 1-7600 and 7602-8376 |
| 7602 | 1-7601 and 7603-8376 |
| 7603 | 1-7602 and 7604-8376 |
| 7604 | 1-7603 and 7605-8376 |

102
-continued

| First | Second |
|---|---|
| 7605 | 1-7604 and 7606-8376 |
| 7606 | 1-7605 and 7607-8376 |
| 7607 | 1-7606 and 7608-8376 |
| 7608 | 1-7607 and 7609-8376 |
| 7609 | 1-7608 and 7610-8376 |
| 7610 | 1-7609 and 7611-8376 |
| 7611 | 1-7610 and 7612-8376 |
| 7612 | 1-7611 and 7613-8376 |
| 7613 | 1-7612 and 7614-8376 |
| 7614 | 1-7613 and 7615-8376 |
| 7615 | 1-7614 and 7616-8376 |
| 7616 | 1-7615 and 7617-8376 |
| 7617 | 1-7616 and 7618-8376 |
| 7618 | 1-7617 and 7619-8376 |
| 7619 | 1-7618 and 7620-8376 |
| 7620 | 1-7619 and 7621-8376 |
| 7621 | 1-7620 and 7622-8376 |
| 7622 | 1-7621 and 7623-8376 |
| 7623 | 1-7622 and 7624-8376 |
| 7624 | 1-7623 and 7625-8376 |
| 7625 | 1-7624 and 7626-8376 |
| 7626 | 1-7625 and 7627-8376 |
| 7627 | 1-7626 and 7628-8376 |
| 7628 | 1-7627 and 7629-8376 |
| 7629 | 1-7628 and 7630-8376 |
| 7630 | 1-7629 and 7631-8376 |
| 7631 | 1-7630 and 7632-8376 |
| 7632 | 1-7631 and 7633-8376 |
| 7633 | 1-7632 and 7634-8376 |
| 7634 | 1-7633 and 7635-8376 |
| 7635 | 1-7634 and 7636-8376 |
| 7636 | 1-7635 and 7637-8376 |
| 7637 | 1-7636 and 7638-8376 |
| 7638 | 1-7637 and 7639-8376 |
| 7639 | 1-7638 and 7640-8376 |
| 7640 | 1-7639 and 7641-8376 |
| 7641 | 1-7640 and 7642-8376 |
| 7642 | 1-7641 and 7643-8376 |
| 7643 | 1-7642 and 7644-8376 |
| 7644 | 1-7643 and 7645-8376 |
| 7645 | 1-7644 and 7646-8376 |
| 7646 | 1-7645 and 7647-8376 |
| 7647 | 1-7646 and 7648-8376 |
| 7648 | 1-7647 and 7649-8376 |
| 7649 | 1-7648 and 7650-8376 |
| 7650 | 1-7649 and 7651-8376 |
| 7651 | 1-7650 and 7652-8376 |
| 7652 | 1-7651 and 7653-8376 |
| 7653 | 1-7652 and 7654-8376 |
| 7654 | 1-7653 and 7655-8376 |
| 7655 | 1-7654 and 7656-8376 |
| 7656 | 1-7655 and 7657-8376 |
| 7657 | 1-7656 and 7658-8376 |
| 7658 | 1-7657 and 7659-8376 |
| 7659 | 1-7658 and 7660-8376 |
| 7660 | 1-7659 and 7661-8376 |
| 7661 | 1-7660 and 7662-8376 |
| 7662 | 1-7661 and 7663-8376 |
| 7663 | 1-7662 and 7664-8376 |
| 7664 | 1-7663 and 7665-8376 |
| 7665 | 1-7664 and 7666-8376 |
| 7666 | 1-7665 and 7667-8376 |
| 7667 | 1-7666 and 7668-8376 |
| 7668 | 1-7667 and 7669-8376 |
| 7669 | 1-7668 and 7670-8376 |
| 7670 | 1-7669 and 7671-8376 |
| 7671 | 1-7670 and 7672-8376 |
| 7672 | 1-7671 and 7673-8376 |
| 7673 | 1-7672 and 7674-8376 |
| 7674 | 1-7673 and 7675-8376 |
| 7675 | 1-7674 and 7676-8376 |
| 7676 | 1-7675 and 7677-8376 |
| 7677 | 1-7676 and 7678-8376 |
| 7678 | 1-7677 and 7679-8376 |
| 7679 | 1-7678 and 7680-8376 |
| 7680 | 1-7679 and 7681-8376 |
| 7681 | 1-7680 and 7682-8376 |

| First | Second |
|---|---|
| 7682 | 1-7681 and 7683-8376 |
| 7683 | 1-7682 and 7684-8376 |
| 7684 | 1-7683 and 7685-8376 |
| 7685 | 1-7684 and 7686-8376 |
| 7686 | 1-7685 and 7687-8376 |
| 7687 | 1-7686 and 7688-8376 |
| 7688 | 1-7687 and 7689-8376 |
| 7689 | 1-7688 and 7690-8376 |
| 7690 | 1-7689 and 7691-8376 |
| 7691 | 1-7690 and 7692-8376 |
| 7692 | 1-7691 and 7693-8376 |
| 7693 | 1-7692 and 7694-8376 |
| 7694 | 1-7693 and 7695-8376 |
| 7695 | 1-7694 and 7696-8376 |
| 7696 | 1-7695 and 7697-8376 |
| 7697 | 1-7696 and 7698-8376 |
| 7698 | 1-7697 and 7699-8376 |
| 7699 | 1-7698 and 7700-8376 |
| 7700 | 1-7699 and 7701-8376 |
| 7701 | 1-7700 and 7702-8376 |
| 7702 | 1-7701 and 7703-8376 |
| 7703 | 1-7702 and 7704-8376 |
| 7704 | 1-7703 and 7705-8376 |
| 7705 | 1-7704 and 7706-8376 |
| 7706 | 1-7705 and 7707-8376 |
| 7707 | 1-7706 and 7708-8376 |
| 7708 | 1-7707 and 7709-8376 |
| 7709 | 1-7708 and 7710-8376 |
| 7710 | 1-7709 and 7711-8376 |
| 7711 | 1-7710 and 7712-8376 |
| 7712 | 1-7711 and 7713-8376 |
| 7713 | 1-7712 and 7714-8376 |
| 7714 | 1-7713 and 7715-8376 |
| 7715 | 1-7714 and 7716-8376 |
| 7716 | 1-7715 and 7717-8376 |
| 7717 | 1-7716 and 7718-8376 |
| 7718 | 1-7717 and 7719-8376 |
| 7719 | 1-7718 and 7720-8376 |
| 7720 | 1-7719 and 7721-8376 |
| 7721 | 1-7720 and 7722-8376 |
| 7722 | 1-7721 and 7723-8376 |
| 7723 | 1-7722 and 7724-8376 |
| 7724 | 1-7723 and 7725-8376 |
| 7725 | 1-7724 and 7726-8376 |
| 7726 | 1-7725 and 7727-8376 |
| 7727 | 1-7726 and 7728-8376 |
| 7728 | 1-7727 and 7729-8376 |
| 7729 | 1-7728 and 7730-8376 |
| 7730 | 1-7729 and 7731-8376 |
| 7731 | 1-7730 and 7732-8376 |
| 7732 | 1-7731 and 7733-8376 |
| 7733 | 1-7732 and 7734-8376 |
| 7734 | 1-7733 and 7735-8376 |
| 7735 | 1-7734 and 7736-8376 |
| 7736 | 1-7735 and 7737-8376 |
| 7737 | 1-7736 and 7738-8376 |
| 7738 | 1-7737 and 7739-8376 |
| 7739 | 1-7738 and 7740-8376 |
| 7740 | 1-7739 and 7741-8376 |
| 7741 | 1-7740 and 7742-8376 |
| 7742 | 1-7741 and 7743-8376 |
| 7743 | 1-7742 and 7744-8376 |
| 7744 | 1-7743 and 7745-8376 |
| 7745 | 1-7744 and 7746-8376 |
| 7746 | 1-7745 and 7747-8376 |
| 7747 | 1-7746 and 7748-8376 |
| 7748 | 1-7747 and 7749-8376 |
| 7749 | 1-7748 and 7750-8376 |
| 7750 | 1-7749 and 7751-8376 |
| 7751 | 1-7750 and 7752-8376 |
| 7752 | 1-7751 and 7753-8376 |
| 7753 | 1-7752 and 7754-8376 |
| 7754 | 1-7753 and 7755-8376 |
| 7755 | 1-7754 and 7756-8376 |
| 7756 | 1-7755 and 7757-8376 |
| 7757 | 1-7756 and 7758-8376 |
| 7758 | 1-7757 and 7759-8376 |
| 7759 | 1-7758 and 7760-8376 |
| 7760 | 1-7759 and 7761-8376 |
| 7761 | 1-7760 and 7762-8376 |
| 7762 | 1-7761 and 7763-8376 |
| 7763 | 1-7762 and 7764-8376 |
| 7764 | 1-7763 and 7765-8376 |
| 7765 | 1-7764 and 7766-8376 |
| 7766 | 1-7765 and 7767-8376 |
| 7767 | 1-7766 and 7768-8376 |
| 7768 | 1-7767 and 7769-8376 |
| 7769 | 1-7768 and 7770-8376 |
| 7770 | 1-7769 and 7771-8376 |
| 7771 | 1-7770 and 7772-8376 |
| 7772 | 1-7771 and 7773-8376 |
| 7773 | 1-7772 and 7774-8376 |
| 7774 | 1-7773 and 7775-8376 |
| 7775 | 1-7774 and 7776-8376 |
| 7776 | 1-7775 and 7777-8376 |
| 7777 | 1-7776 and 7778-8376 |
| 7778 | 1-7777 and 7779-8376 |
| 7779 | 1-7778 and 7780-8376 |
| 7780 | 1-7779 and 7781-8376 |
| 7781 | 1-7780 and 7782-8376 |
| 7782 | 1-7781 and 7783-8376 |
| 7783 | 1-7782 and 7784-8376 |
| 7784 | 1-7783 and 7785-8376 |
| 7785 | 1-7784 and 7786-8376 |
| 7786 | 1-7785 and 7787-8376 |
| 7787 | 1-7786 and 7788-8376 |
| 7788 | 1-7787 and 7789-8376 |
| 7789 | 1-7788 and 7790-8376 |
| 7790 | 1-7789 and 7791-8376 |
| 7791 | 1-7790 and 7792-8376 |
| 7792 | 1-7791 and 7793-8376 |
| 7793 | 1-7792 and 7794-8376 |
| 7794 | 1-7793 and 7795-8376 |
| 7795 | 1-7794 and 7796-8376 |
| 7796 | 1-7795 and 7797-8376 |
| 7797 | 1-7796 and 7798-8376 |
| 7798 | 1-7797 and 7799-8376 |
| 7799 | 1-7798 and 7800-8376 |
| 7800 | 1-7799 and 7801-8376 |
| 7801 | 1-7800 and 7802-8376 |
| 7802 | 1-7801 and 7803-8376 |
| 7803 | 1-7802 and 7804-8376 |
| 7804 | 1-7803 and 7805-8376 |
| 7805 | 1-7804 and 7806-8376 |
| 7806 | 1-7805 and 7807-8376 |
| 7807 | 1-7806 and 7808-8376 |
| 7808 | 1-7807 and 7809-8376 |
| 7809 | 1-7808 and 7810-8376 |
| 7810 | 1-7809 and 7811-8376 |
| 7811 | 1-7810 and 7812-8376 |
| 7812 | 1-7811 and 7813-8376 |
| 7813 | 1-7812 and 7814-8376 |
| 7814 | 1-7813 and 7815-8376 |
| 7815 | 1-7814 and 7816-8376 |
| 7816 | 1-7815 and 7817-8376 |
| 7817 | 1-7816 and 7818-8376 |
| 7818 | 1-7817 and 7819-8376 |
| 7819 | 1-7818 and 7820-8376 |
| 7820 | 1-7819 and 7821-8376 |
| 7821 | 1-7820 and 7822-8376 |
| 7822 | 1-7821 and 7823-8376 |
| 7823 | 1-7822 and 7824-8376 |
| 7824 | 1-7823 and 7825-8376 |
| 7825 | 1-7824 and 7826-8376 |
| 7826 | 1-7825 and 7827-8376 |
| 7827 | 1-7826 and 7828-8376 |
| 7828 | 1-7827 and 7829-8376 |
| 7829 | 1-7828 and 7830-8376 |
| 7830 | 1-7829 and 7831-8376 |
| 7831 | 1-7830 and 7832-8376 |
| 7832 | 1-7831 and 7833-8376 |
| 7833 | 1-7832 and 7834-8376 |
| 7834 | 1-7833 and 7835-8376 |
| 7835 | 1-7834 and 7836-8376 |

| First | Second |
|---|---|
| 7836 | 1-7835 and 7837-8376 |
| 7837 | 1-7836 and 7838-8376 |
| 7838 | 1-7837 and 7839-8376 |
| 7839 | 1-7838 and 7840-8376 |
| 7840 | 1-7839 and 7841-8376 |
| 7841 | 1-7840 and 7842-8376 |
| 7842 | 1-7841 and 7843-8376 |
| 7843 | 1-7842 and 7844-8376 |
| 7844 | 1-7843 and 7845-8376 |
| 7845 | 1-7844 and 7846-8376 |
| 7846 | 1-7845 and 7847-8376 |
| 7847 | 1-7846 and 7848-8376 |
| 7848 | 1-7847 and 7849-8376 |
| 7849 | 1-7848 and 7850-8376 |
| 7850 | 1-7849 and 7851-8376 |
| 7851 | 1-7850 and 7852-8376 |
| 7852 | 1-7851 and 7853-8376 |
| 7853 | 1-7852 and 7854-8376 |
| 7854 | 1-7853 and 7855-8376 |
| 7855 | 1-7854 and 7856-8376 |
| 7856 | 1-7855 and 7857-8376 |
| 7857 | 1-7856 and 7858-8376 |
| 7858 | 1-7857 and 7859-8376 |
| 7859 | 1-7858 and 7860-8376 |
| 7860 | 1-7859 and 7861-8376 |
| 7861 | 1-7860 and 7862-8376 |
| 7862 | 1-7861 and 7863-8376 |
| 7863 | 1-7862 and 7864-8376 |
| 7864 | 1-7863 and 7865-8376 |
| 7865 | 1-7864 and 7866-8376 |
| 7866 | 1-7865 and 7867-8376 |
| 7867 | 1-7866 and 7868-8376 |
| 7868 | 1-7867 and 7869-8376 |
| 7869 | 1-7868 and 7870-8376 |
| 7870 | 1-7869 and 7871-8376 |
| 7871 | 1-7870 and 7872-8376 |
| 7872 | 1-7871 and 7873-8376 |
| 7873 | 1-7872 and 7874-8376 |
| 7874 | 1-7873 and 7875-8376 |
| 7875 | 1-7874 and 7876-8376 |
| 7876 | 1-7875 and 7877-8376 |
| 7877 | 1-7876 and 7878-8376 |
| 7878 | 1-7877 and 7879-8376 |
| 7879 | 1-7878 and 7880-8376 |
| 7880 | 1-7879 and 7881-8376 |
| 7881 | 1-7880 and 7882-8376 |
| 7882 | 1-7881 and 7883-8376 |
| 7883 | 1-7882 and 7884-8376 |
| 7884 | 1-7883 and 7885-8376 |
| 7885 | 1-7884 and 7886-8376 |
| 7886 | 1-7885 and 7887-8376 |
| 7887 | 1-7886 and 7888-8376 |
| 7888 | 1-7887 and 7889-8376 |
| 7889 | 1-7888 and 7890-8376 |
| 7890 | 1-7889 and 7891-8376 |
| 7891 | 1-7890 and 7892-8376 |
| 7892 | 1-7891 and 7893-8376 |
| 7893 | 1-7892 and 7894-8376 |
| 7894 | 1-7893 and 7895-8376 |
| 7895 | 1-7894 and 7896-8376 |
| 7896 | 1-7895 and 7897-8376 |
| 7897 | 1-7896 and 7898-8376 |
| 7898 | 1-7897 and 7899-8376 |
| 7899 | 1-7898 and 7900-8376 |
| 7900 | 1-7899 and 7901-8376 |
| 7901 | 1-7900 and 7902-8376 |
| 7902 | 1-7901 and 7903-8376 |
| 7903 | 1-7902 and 7904-8376 |
| 7904 | 1-7903 and 7905-8376 |
| 7905 | 1-7904 and 7906-8376 |
| 7906 | 1-7905 and 7907-8376 |
| 7907 | 1-7906 and 7908-8376 |
| 7908 | 1-7907 and 7909-8376 |
| 7909 | 1-7908 and 7910-8376 |
| 7910 | 1-7909 and 7911-8376 |
| 7911 | 1-7910 and 7912-8376 |
| 7912 | 1-7911 and 7913-8376 |
| 7913 | 1-7912 and 7914-8376 |
| 7914 | 1-7913 and 7915-8376 |
| 7915 | 1-7914 and 7916-8376 |
| 7916 | 1-7915 and 7917-8376 |
| 7917 | 1-7916 and 7918-8376 |
| 7918 | 1-7917 and 7919-8376 |
| 7919 | 1-7918 and 7920-8376 |
| 7920 | 1-7919 and 7921-8376 |
| 7921 | 1-7920 and 7922-8376 |
| 7922 | 1-7921 and 7923-8376 |
| 7923 | 1-7922 and 7924-8376 |
| 7924 | 1-7923 and 7925-8376 |
| 7925 | 1-7924 and 7926-8376 |
| 7926 | 1-7925 and 7927-8376 |
| 7927 | 1-7926 and 7928-8376 |
| 7928 | 1-7927 and 7929-8376 |
| 7929 | 1-7928 and 7930-8376 |
| 7930 | 1-7929 and 7931-8376 |
| 7931 | 1-7930 and 7932-8376 |
| 7932 | 1-7931 and 7933-8376 |
| 7933 | 1-7932 and 7934-8376 |
| 7934 | 1-7933 and 7935-8376 |
| 7935 | 1-7934 and 7936-8376 |
| 7936 | 1-7935 and 7937-8376 |
| 7937 | 1-7936 and 7938-8376 |
| 7938 | 1-7937 and 7939-8376 |
| 7939 | 1-7938 and 7940-8376 |
| 7940 | 1-7939 and 7941-8376 |
| 7941 | 1-7940 and 7942-8376 |
| 7942 | 1-7941 and 7943-8376 |
| 7943 | 1-7942 and 7944-8376 |
| 7944 | 1-7943 and 7945-8376 |
| 7945 | 1-7944 and 7946-8376 |
| 7946 | 1-7945 and 7947-8376 |
| 7947 | 1-7946 and 7948-8376 |
| 7948 | 1-7947 and 7949-8376 |
| 7949 | 1-7948 and 7950-8376 |
| 7950 | 1-7949 and 7951-8376 |
| 7951 | 1-7950 and 7952-8376 |
| 7952 | 1-7951 and 7953-8376 |
| 7953 | 1-7952 and 7954-8376 |
| 7954 | 1-7953 and 7955-8376 |
| 7955 | 1-7954 and 7956-8376 |
| 7956 | 1-7955 and 7957-8376 |
| 7957 | 1-7956 and 7958-8376 |
| 7958 | 1-7957 and 7959-8376 |
| 7959 | 1-7958 and 7960-8376 |
| 7960 | 1-7959 and 7961-8376 |
| 7961 | 1-7960 and 7962-8376 |
| 7962 | 1-7961 and 7963-8376 |
| 7963 | 1-7962 and 7964-8376 |
| 7964 | 1-7963 and 7965-8376 |
| 7965 | 1-7964 and 7966-8376 |
| 7966 | 1-7965 and 7967-8376 |
| 7967 | 1-7966 and 7968-8376 |
| 7968 | 1-7967 and 7969-8376 |
| 7969 | 1-7968 and 7970-8376 |
| 7970 | 1-7969 and 7971-8376 |
| 7971 | 1-7970 and 7972-8376 |
| 7972 | 1-7971 and 7973-8376 |
| 7973 | 1-7972 and 7974-8376 |
| 7974 | 1-7973 and 7975-8376 |
| 7975 | 1-7974 and 7976-8376 |
| 7976 | 1-7975 and 7977-8376 |
| 7977 | 1-7976 and 7978-8376 |
| 7978 | 1-7977 and 7979-8376 |
| 7979 | 1-7978 and 7980-8376 |
| 7980 | 1-7979 and 7981-8376 |
| 7981 | 1-7980 and 7982-8376 |
| 7982 | 1-7981 and 7983-8376 |
| 7983 | 1-7982 and 7984-8376 |
| 7984 | 1-7983 and 7985-8376 |
| 7985 | 1-7984 and 7986-8376 |
| 7986 | 1-7985 and 7987-8376 |
| 7987 | 1-7986 and 7988-8376 |
| 7988 | 1-7987 and 7989-8376 |
| 7989 | 1-7988 and 7990-8376 |

| First | Second |
|---|---|
| 7990 | 1-7989 and 7991-8376 |
| 7991 | 1-7990 and 7992-8376 |
| 7992 | 1-7991 and 7993-8376 |
| 7993 | 1-7992 and 7994-8376 |
| 7994 | 1-7993 and 7995-8376 |
| 7995 | 1-7994 and 7996-8376 |
| 7996 | 1-7995 and 7997-8376 |
| 7997 | 1-7996 and 7998-8376 |
| 7998 | 1-7997 and 7999-8376 |
| 7999 | 1-7998 and 8000-8376 |
| 8000 | 1-7999 and 8001-8376 |
| 8001 | 1-8000 and 8002-8376 |
| 8002 | 1-8001 and 8003-8376 |
| 8003 | 1-8002 and 8004-8376 |
| 8004 | 1-8003 and 8005-8376 |
| 8005 | 1-8004 and 8006-8376 |
| 8006 | 1-8005 and 8007-8376 |
| 8007 | 1-8006 and 8008-8376 |
| 8008 | 1-8007 and 8009-8376 |
| 8009 | 1-8008 and 8010-8376 |
| 8010 | 1-8009 and 8011-8376 |
| 8011 | 1-8010 and 8012-8376 |
| 8012 | 1-8011 and 8013-8376 |
| 8013 | 1-8012 and 8014-8376 |
| 8014 | 1-8013 and 8015-8376 |
| 8015 | 1-8014 and 8016-8376 |
| 8016 | 1-8015 and 8017-8376 |
| 8017 | 1-8016 and 8018-8376 |
| 8018 | 1-8017 and 8019-8376 |
| 8019 | 1-8018 and 8020-8376 |
| 8020 | 1-8019 and 8021-8376 |
| 8021 | 1-8020 and 8022-8376 |
| 8022 | 1-8021 and 8023-8376 |
| 8023 | 1-8022 and 8024-8376 |
| 8024 | 1-8023 and 8025-8376 |
| 8025 | 1-8024 and 8026-8376 |
| 8026 | 1-8025 and 8027-8376 |
| 8027 | 1-8026 and 8028-8376 |
| 8028 | 1-8027 and 8029-8376 |
| 8029 | 1-8028 and 8030-8376 |
| 8030 | 1-8029 and 8031-8376 |
| 8031 | 1-8030 and 8032-8376 |
| 8032 | 1-8031 and 8033-8376 |
| 8033 | 1-8032 and 8034-8376 |
| 8034 | 1-8033 and 8035-8376 |
| 8035 | 1-8034 and 8036-8376 |
| 8036 | 1-8035 and 8037-8376 |
| 8037 | 1-8036 and 8038-8376 |
| 8038 | 1-8037 and 8039-8376 |
| 8039 | 1-8038 and 8040-8376 |
| 8040 | 1-8039 and 8041-8376 |
| 8041 | 1-8040 and 8042-8376 |
| 8042 | 1-8041 and 8043-8376 |
| 8043 | 1-8042 and 8044-8376 |
| 8044 | 1-8043 and 8045-8376 |
| 8045 | 1-8044 and 8046-8376 |
| 8046 | 1-8045 and 8047-8376 |
| 8047 | 1-8046 and 8048-8376 |
| 8048 | 1-8047 and 8049-8376 |
| 8049 | 1-8048 and 8050-8376 |
| 8050 | 1-8049 and 8051-8376 |
| 8051 | 1-8050 and 8052-8376 |
| 8052 | 1-8051 and 8053-8376 |
| 8053 | 1-8052 and 8054-8376 |
| 8054 | 1-8053 and 8055-8376 |
| 8055 | 1-8054 and 8056-8376 |
| 8056 | 1-8055 and 8057-8376 |
| 8057 | 1-8056 and 8058-8376 |
| 8058 | 1-8057 and 8059-8376 |
| 8059 | 1-8058 and 8060-8376 |
| 8060 | 1-8059 and 8061-8376 |
| 8061 | 1-8060 and 8062-8376 |
| 8062 | 1-8061 and 8063-8376 |
| 8063 | 1-8062 and 8064-8376 |
| 8064 | 1-8063 and 8065-8376 |
| 8065 | 1-8064 and 8066-8376 |
| 8066 | 1-8065 and 8067-8376 |
| 8067 | 1-8066 and 8068-8376 |
| 8068 | 1-8067 and 8069-8376 |
| 8069 | 1-8068 and 8070-8376 |
| 8070 | 1-8069 and 8071-8376 |
| 8071 | 1-8070 and 8072-8376 |
| 8072 | 1-8071 and 8073-8376 |
| 8073 | 1-8072 and 8074-8376 |
| 8074 | 1-8073 and 8075-8376 |
| 8075 | 1-8074 and 8076-8376 |
| 8076 | 1-8075 and 8077-8376 |
| 8077 | 1-8076 and 8078-8376 |
| 8078 | 1-8077 and 8079-8376 |
| 8079 | 1-8078 and 8080-8376 |
| 8080 | 1-8079 and 8081-8376 |
| 8081 | 1-8080 and 8082-8376 |
| 8082 | 1-8081 and 8083-8376 |
| 8083 | 1-8082 and 8084-8376 |
| 8084 | 1-8083 and 8085-8376 |
| 8085 | 1-8084 and 8086-8376 |
| 8086 | 1-8085 and 8087-8376 |
| 8087 | 1-8086 and 8088-8376 |
| 8088 | 1-8087 and 8089-8376 |
| 8089 | 1-8088 and 8090-8376 |
| 8090 | 1-8089 and 8091-8376 |
| 8091 | 1-8090 and 8092-8376 |
| 8092 | 1-8091 and 8093-8376 |
| 8093 | 1-8092 and 8094-8376 |
| 8094 | 1-8093 and 8095-8376 |
| 8095 | 1-8094 and 8096-8376 |
| 8096 | 1-8095 and 8097-8376 |
| 8097 | 1-8096 and 8098-8376 |
| 8098 | 1-8097 and 8099-8376 |
| 8099 | 1-8098 and 8100-8376 |
| 8100 | 1-8099 and 8101-8376 |
| 8101 | 1-8100 and 8102-8376 |
| 8102 | 1-8101 and 8103-8376 |
| 8103 | 1-8102 and 8104-8376 |
| 8104 | 1-8103 and 8105-8376 |
| 8105 | 1-8104 and 8106-8376 |
| 8106 | 1-8105 and 8107-8376 |
| 8107 | 1-8106 and 8108-8376 |
| 8108 | 1-8107 and 8109-8376 |
| 8109 | 1-8108 and 8110-8376 |
| 8110 | 1-8109 and 8111-8376 |
| 8111 | 1-8110 and 8112-8376 |
| 8112 | 1-8111 and 8113-8376 |
| 8113 | 1-8112 and 8114-8376 |
| 8114 | 1-8113 and 8115-8376 |
| 8115 | 1-8114 and 8116-8376 |
| 8116 | 1-8115 and 8117-8376 |
| 8117 | 1-8116 and 8118-8376 |
| 8118 | 1-8117 and 8119-8376 |
| 8119 | 1-8118 and 8120-8376 |
| 8120 | 1-8119 and 8121-8376 |
| 8121 | 1-8120 and 8122-8376 |
| 8122 | 1-8121 and 8123-8376 |
| 8123 | 1-8122 and 8124-8376 |
| 8124 | 1-8123 and 8125-8376 |
| 8125 | 1-8124 and 8126-8376 |
| 8126 | 1-8125 and 8127-8376 |
| 8127 | 1-8126 and 8128-8376 |
| 8128 | 1-8127 and 8129-8376 |
| 8129 | 1-8128 and 8130-8376 |
| 8130 | 1-8129 and 8131-8376 |
| 8131 | 1-8130 and 8132-8376 |
| 8132 | 1-8131 and 8133-8376 |
| 8133 | 1-8132 and 8134-8376 |
| 8134 | 1-8133 and 8135-8376 |
| 8135 | 1-8134 and 8136-8376 |
| 8136 | 1-8135 and 8137-8376 |
| 8137 | 1-8136 and 8138-8376 |
| 8138 | 1-8137 and 8139-8376 |
| 8139 | 1-8138 and 8140-8376 |
| 8140 | 1-8139 and 8141-8376 |
| 8141 | 1-8140 and 8142-8376 |
| 8142 | 1-8141 and 8143-8376 |
| 8143 | 1-8142 and 8144-8376 |

| First | Second |
|---|---|
| 8144 | 1-8143 and 8145-8376 |
| 8145 | 1-8144 and 8146-8376 |
| 8146 | 1-8145 and 8147-8376 |
| 8147 | 1-8146 and 8148-8376 |
| 8148 | 1-8147 and 8149-8376 |
| 8149 | 1-8148 and 8150-8376 |
| 8150 | 1-8149 and 8151-8376 |
| 8151 | 1-8150 and 8152-8376 |
| 8152 | 1-8151 and 8153-8376 |
| 8153 | 1-8152 and 8154-8376 |
| 8154 | 1-8153 and 8155-8376 |
| 8155 | 1-8154 and 8156-8376 |
| 8156 | 1-8155 and 8157-8376 |
| 8157 | 1-8156 and 8158-8376 |
| 8158 | 1-8157 and 8159-8376 |
| 8159 | 1-8158 and 8160-8376 |
| 8160 | 1-8159 and 8161-8376 |
| 8161 | 1-8160 and 8162-8376 |
| 8162 | 1-8161 and 8163-8376 |
| 8163 | 1-8162 and 8164-8376 |
| 8164 | 1-8163 and 8165-8376 |
| 8165 | 1-8164 and 8166-8376 |
| 8166 | 1-8165 and 8167-8376 |
| 8167 | 1-8166 and 8168-8376 |
| 8168 | 1-8167 and 8169-8376 |
| 8169 | 1-8168 and 8170-8376 |
| 8170 | 1-8169 and 8171-8376 |
| 8171 | 1-8170 and 8172-8376 |
| 8172 | 1-8171 and 8173-8376 |
| 8173 | 1-8172 and 8174-8376 |
| 8174 | 1-8173 and 8175-8376 |
| 8175 | 1-8174 and 8176-8376 |
| 8176 | 1-8175 and 8177-8376 |
| 8177 | 1-8176 and 8178-8376 |
| 8178 | 1-8177 and 8179-8376 |
| 8179 | 1-8178 and 8180-8376 |
| 8180 | 1-8179 and 8181-8376 |
| 8181 | 1-8180 and 8182-8376 |
| 8182 | 1-8181 and 8183-8376 |
| 8183 | 1-8182 and 8184-8376 |
| 8184 | 1-8183 and 8185-8376 |
| 8185 | 1-8184 and 8186-8376 |
| 8186 | 1-8185 and 8187-8376 |
| 8187 | 1-8186 and 8188-8376 |
| 8188 | 1-8187 and 8189-8376 |
| 8189 | 1-8188 and 8190-8376 |
| 8190 | 1-8189 and 8191-8376 |
| 8191 | 1-8190 and 8192-8376 |
| 8192 | 1-8191 and 8193-8376 |
| 8193 | 1-8192 and 8194-8376 |
| 8194 | 1-8193 and 8195-8376 |
| 8195 | 1-8194 and 8196-8376 |
| 8196 | 1-8195 and 8197-8376 |
| 8197 | 1-8196 and 8198-8376 |
| 8198 | 1-8197 and 8199-8376 |
| 8199 | 1-8198 and 8200-8376 |
| 8200 | 1-8199 and 8201-8376 |
| 8201 | 1-8200 and 8202-8376 |
| 8202 | 1-8201 and 8203-8376 |
| 8203 | 1-8202 and 8204-8376 |
| 8204 | 1-8203 and 8205-8376 |
| 8205 | 1-8204 and 8206-8376 |
| 8206 | 1-8205 and 8207-8376 |
| 8207 | 1-8206 and 8208-8376 |
| 8208 | 1-8207 and 8209-8376 |
| 8209 | 1-8208 and 8210-8376 |
| 8210 | 1-8209 and 8211-8376 |
| 8211 | 1-8210 and 8212-8376 |
| 8212 | 1-8211 and 8213-8376 |
| 8213 | 1-8212 and 8214-8376 |
| 8214 | 1-8213 and 8215-8376 |
| 8215 | 1-8214 and 8216-8376 |
| 8216 | 1-8215 and 8217-8376 |
| 8217 | 1-8216 and 8218-8376 |
| 8218 | 1-8217 and 8219-8376 |
| 8219 | 1-8218 and 8220-8376 |
| 8220 | 1-8219 and 8221-8376 |
| 8221 | 1-8220 and 8222-8376 |
| 8222 | 1-8221 and 8223-8376 |
| 8223 | 1-8222 and 8224-8376 |
| 8224 | 1-8223 and 8225-8376 |
| 8225 | 1-8224 and 8226-8376 |
| 8226 | 1-8225 and 8227-8376 |
| 8227 | 1-8226 and 8228-8376 |
| 8228 | 1-8227 and 8229-8376 |
| 8229 | 1-8228 and 8230-8376 |
| 8230 | 1-8229 and 8231-8376 |
| 8231 | 1-8230 and 8232-8376 |
| 8232 | 1-8231 and 8233-8376 |
| 8233 | 1-8232 and 8234-8376 |
| 8234 | 1-8233 and 8235-8376 |
| 8235 | 1-8234 and 8236-8376 |
| 8236 | 1-8235 and 8237-8376 |
| 8237 | 1-8236 and 8238-8376 |
| 8238 | 1-8237 and 8239-8376 |
| 8239 | 1-8238 and 8240-8376 |
| 8240 | 1-8239 and 8241-8376 |
| 8241 | 1-8240 and 8242-8376 |
| 8242 | 1-8241 and 8243-8376 |
| 8243 | 1-8242 and 8244-8376 |
| 8244 | 1-8243 and 8245-8376 |
| 8245 | 1-8244 and 8246-8376 |
| 8246 | 1-8245 and 8247-8376 |
| 8247 | 1-8246 and 8248-8376 |
| 8248 | 1-8247 and 8249-8376 |
| 8249 | 1-8248 and 8250-8376 |
| 8250 | 1-8249 and 8251-8376 |
| 8251 | 1-8250 and 8252-8376 |
| 8252 | 1-8251 and 8253-8376 |
| 8253 | 1-8252 and 8254-8376 |
| 8254 | 1-8253 and 8255-8376 |
| 8255 | 1-8254 and 8256-8376 |
| 8256 | 1-8255 and 8257-8376 |
| 8257 | 1-8256 and 8258-8376 |
| 8258 | 1-8257 and 8259-8376 |
| 8259 | 1-8258 and 8260-8376 |
| 8260 | 1-8259 and 8261-8376 |
| 8261 | 1-8260 and 8262-8376 |
| 8262 | 1-8261 and 8263-8376 |
| 8263 | 1-8262 and 8264-8376 |
| 8264 | 1-8263 and 8265-8376 |
| 8265 | 1-8264 and 8266-8376 |
| 8266 | 1-8265 and 8267-8376 |
| 8267 | 1-8266 and 8268-8376 |
| 8268 | 1-8267 and 8269-8376 |
| 8269 | 1-8268 and 8270-8376 |
| 8270 | 1-8269 and 8271-8376 |
| 8271 | 1-8270 and 8272-8376 |
| 8272 | 1-8271 and 8273-8376 |
| 8273 | 1-8272 and 8274-8376 |
| 8274 | 1-8273 and 8275-8376 |
| 8275 | 1-8274 and 8276-8376 |
| 8276 | 1-8275 and 8277-8376 |
| 8277 | 1-8276 and 8278-8376 |
| 8278 | 1-8277 and 8279-8376 |
| 8279 | 1-8278 and 8280-8376 |
| 8280 | 1-8279 and 8281-8376 |
| 8281 | 1-8280 and 8282-8376 |
| 8282 | 1-8281 and 8283-8376 |
| 8283 | 1-8282 and 8284-8376 |
| 8284 | 1-8283 and 8285-8376 |
| 8285 | 1-8284 and 8286-8376 |
| 8286 | 1-8285 and 8287-8376 |
| 8287 | 1-8286 and 8288-8376 |
| 8288 | 1-8287 and 8289-8376 |
| 8289 | 1-8288 and 8290-8376 |
| 8290 | 1-8289 and 8291-8376 |
| 8291 | 1-8290 and 8292-8376 |
| 8292 | 1-8291 and 8293-8376 |
| 8293 | 1-8292 and 8294-8376 |
| 8294 | 1-8293 and 8295-8376 |
| 8295 | 1-8294 and 8296-8376 |
| 8296 | 1-8295 and 8297-8376 |
| 8297 | 1-8296 and 8298-8376 |

| First | Second |
| --- | --- |
| 8298 | 1-8297 and 8299-8376 |
| 8299 | 1-8298 and 8300-8376 |
| 8300 | 1-8299 and 8301-8376 |
| 8301 | 1-8300 and 8302-8376 |
| 8302 | 1-8301 and 8303-8376 |
| 8303 | 1-8302 and 8304-8376 |
| 8304 | 1-8303 and 8305-8376 |
| 8305 | 1-8304 and 8306-8376 |
| 8306 | 1-8305 and 8307-8376 |
| 8307 | 1-8306 and 8308-8376 |
| 8308 | 1-8307 and 8309-8376 |
| 8309 | 1-8308 and 8310-8376 |
| 8310 | 1-8309 and 8311-8376 |
| 8311 | 1-8310 and 8312-8376 |
| 8312 | 1-8311 and 8313-8376 |
| 8313 | 1-8312 and 8314-8376 |
| 8314 | 1-8313 and 8315-8376 |
| 8315 | 1-8314 and 8316-8376 |
| 8316 | 1-8315 and 8317-8376 |
| 8317 | 1-8316 and 8318-8376 |
| 8318 | 1-8317 and 8319-8376 |
| 8319 | 1-8318 and 8320-8376 |
| 8320 | 1-8319 and 8321-8376 |
| 8321 | 1-8320 and 8322-8376 |
| 8322 | 1-8321 and 8323-8376 |
| 8323 | 1-8322 and 8324-8376 |
| 8324 | 1-8323 and 8325-8376 |
| 8325 | 1-8324 and 8326-8376 |
| 8326 | 1-8325 and 8327-8376 |
| 8327 | 1-8326 and 8328-8376 |
| 8328 | 1-8327 and 8329-8376 |
| 8329 | 1-8328 and 8330-8376 |
| 8330 | 1-8329 and 8331-8376 |
| 8331 | 1-8330 and 8332-8376 |
| 8332 | 1-8331 and 8333-8376 |
| 8333 | 1-8332 and 8334-8376 |
| 8334 | 1-8333 and 8335-8376 |
| 8335 | 1-8334 and 8336-8376 |
| 8336 | 1-8335 and 8337-8376 |
| 8337 | 1-8336 and 8338-8376 |
| 8338 | 1-8337 and 8339-8376 |
| 8339 | 1-8338 and 8340-8376 |
| 8340 | 1-8339 and 8341-8376 |
| 8341 | 1-8340 and 8342-8376 |
| 8342 | 1-8341 and 8343-8376 |
| 8343 | 1-8342 and 8344-8376 |
| 8344 | 1-8343 and 8345-8376 |
| 8345 | 1-8344 and 8346-8376 |
| 8346 | 1-8345 and 8347-8376 |
| 8347 | 1-8346 and 8348-8376 |
| 8348 | 1-8347 and 8349-8376 |
| 8349 | 1-8348 and 8350-8376 |
| 8350 | 1-8349 and 8351-8376 |
| 8351 | 1-8350 and 8352-8376 |
| 8352 | 1-8351 and 8353-8376 |
| 8353 | 1-8352 and 8354-8376 |
| 8354 | 1-8353 and 8355-8376 |
| 8355 | 1-8354 and 8356-8376 |
| 8356 | 1-8355 and 8357-8376 |
| 8357 | 1-8356 and 8358-8376 |
| 8358 | 1-8357 and 8359-8376 |
| 8359 | 1-8358 and 8360-8376 |
| 8360 | 1-8359 and 8361-8376 |
| 8361 | 1-8360 and 8362-8376 |
| 8362 | 1-8361 and 8363-8376 |
| 8363 | 1-8362 and 8364-8376 |
| 8364 | 1-8363 and 8365-8376 |
| 8365 | 1-8364 and 8366-8376 |
| 8366 | 1-8365 and 8367-8376 |
| 8367 | 1-8366 and 8368-8376 |
| 8368 | 1-8367 and 8369-8376 |
| 8369 | 1-8368 and 8370-8376 |
| 8370 | 1-8369 and 8371-8376 |
| 8371 | 1-8370 and 8372-8376 |
| 8372 | 1-8371 and 8373-8376 |
| 8373 | 1-8372 and 8374-8376 |
| 8374 | 1-8373 and 8375-8376 |
| 8375 | 1-8374 and 8376 |
| 8376 | 1-8375 |

Thus the invention includes each of the 35074500 possible pairs of SEQ IDs 1-8376 (1&2, 1&3, 1&4, 1&5 ... 1&8375, 1&8376, 2&3, 2&4, 2&5 ... 2&8375, 2&8376, 3&4 ... 1000&1001, 1000&1002 ... 1000&8376 ... 8374&8375, 8374&8376, 8373&8376) although, for reasons of space, these are not listed in full here.

Details as to how the molecules which make up the SEQ IDs 1-4056 can be produced and used can be found from the relevant international applications and these details need not be repeated here. Similar principles apply to SEQ IDs 4057-8376.

SEQ IDs 1-8376 in the compositions of the invention may be supplemented or substituted with molecules comprising sequences homologous (ie. having sequence identity) to SEQ IDs 1-8376. Depending on the particular sequence, the degree of identity is preferably greater than 50% (eg. 65%, 80%, 90%, or more), and include mutants and allelic variants. Sequence identity between the proteins is preferably determined by the Smith-Waterman homology search algorithm as implemented in the MPSRCH program (Oxford Molecular), using an affine gap search with parameters gap open penalty=12 and gap extension penalty=1.

SEQ IDs 1-8376 in the compositions of the invention may be supplemented or substituted with molecules comprising fragments of SEQ IDs 1-8376. Such fragments should comprise at least n consecutive monomers from the molecules and, depending on the particular sequence, n is either (i) 7 or more for protein molecules (eg. 8, 10, 12, 14, 16, 18, 20 or more), preferably such that the fragment comprises an epitope from the sequence, or (ii) 10 or more for nucleic acid molecules (eg 12, 14, 15, 18, 20, 25, 30, 35, 40 or more).

Where the composition includes a protein that exists in different nascent and mature forms, the mature form of the protein is preferably used. For example, the mature form of the NspA protein (SEQ IDs 4008-4033: WO96/29412: FIG. 29) lacking the signal peptide may be used.

In the case of protein molecules. SEQ IDs 1-8376 in the compositions of the invention may be supplemented or substituted with an antibody that binds to the protein. This antibody may be monoclonal or polyclonal.

In the case of nucleic acid molecules. SEQ IDs 1-8376 in the compositions of the invention may be supplemented or substituted with nucleic acid which can hybridise to the Neisserial nucleic acid, preferably under "high stringency" conditions (eg. 65° C. in a 0.1×SSC. 0.5% SDS solution).

It will be appreciated that any nucleic acid in the compositions can take various forms (eg. single stranded, double stranded, vectors, probes etc.). In addition, the term "nucleic acid" includes DNA and RNA, and also their analogues, such as those containing modified backbones, and also peptide nucleic acids (PNA) etc.

In certain embodiments, the composition comprises molecules from different *Neisseria* species, such as one or more *N. meningitidis* molecule and one or more *N. gonorrhoeae* molecule. In some embodiments, the composition may comprise molecules from different serogroups and/or strains of the same species, such as strains A and B of *N. meningitidis*. Further embodiments comprise mixtures of one or more *N. meningitidis* molecules from different strains and also one or more *N. gonorrhoeae* molecules.

Many proteins are relatively conserved between different species, serogroups and strains of *N. meningitidis* and *N. gonorrhoeae* (eg. SEQ IDs 52, 54, 58). PCT/IB00/00642 includes a more detailed experimental analysis of conserved regions in these proteins. To ensure maximum cross-strain recognition and reactivity, regions of proteins that are conserved between different Neisserial species, serogroups and strains can be used in the compositions of the present invention. The invention therefore provides proteins which comprise stretches of amino acid sequence that are shared across the majority of *Neisseria*, particularly *N. meningitidis* and *N. gonorrhoeae*. Preferably, therefore, the composition comprises a protein comprising a fragment of a Neisserial protein (preferably a protein from SEQ IDs 1-8376, or more preferably SEQ IDs 1-4002), wherein said fragment consists of n consecutive conserved amino acids. Depending on the particular protein, n is 7 or more (eg. 8, 10, 12, 14, 16, 18, 20 or more). The fragment preferably comprises an antigenic or immunogenic region of the Neisserial protein. A "conserved" amino acid is one that is present in a particular Neisserial protein in at least x % of *Neisseria* (or, preferably, in at least of combined *N. meningitidis* and *N. gonorrhoeae* strains). The value of x may be 50% or more eg. 66%, 75%, 80%, 90%, 95% or even 100% (ie. the amino acid is found in the protein in question in all *Neisseria*). In order to determine whether an amino acid is "conserved" in a particular Neisserial protein, it is necessary to compare that amino acid residue in the sequences of the protein in question from a plurality of different *Neisseria* (a "reference population"). Suitable definitions of "reference populations" can be found in PCT/IB00/00642. Amino acid sequences of different *Neissieriae* can easily be compared using computers. This will typically involve the alignment of a number of sequences using an algorithm such as CLUSTAL [Thompson et al. (1994) *Nucleic Acids Res* 22:4673-4680: *Trends Biochem Sci* (1998) 23:403-405] or, preferably. PILEUP [part of the GCG Wisconsin package, preferably version 9.0]. Conserved amino acids are readily apparent in a multiple sequence alignment—at the amino acid position in question a majority of the aligned sequences will contain a particular amino acid. Conserved amino acids can be made more visually apparent by using a program such as BOXSHADE [available, for instance, at the NIH on-line], PRETTYBOX [GCG Wisconsin, version 10] or JALVIEW [available on-line at EBI].

Specific compositions according to the invention therefore include those comprising:
  two or more biological molecules selected from SEQ IDs 1-4002:
  one or more biological molecules selected from SEQ IDs 1-4002 combined with one or more biological molecules selected from SEQ IDs 4003-8376:
  one or more biological molecules selected from SEQ IDs 1-4002 combined with the NspA protein as disclosed in WO96/29412: see also FIG. 29 herein), preferably in mature form:
  one or more biological molecules selected from SEQ IDs 1-8376 (preferably SEQ IDs 1-4002) combined with transferring binding protein A (TbpA) and/or B (TbpB), such as the TbpA and TbpB disclosed in WO00/25811 (or immunogenic fragments thereof).
  one or more fragments of proteins selected from SEQ IDs 1-4002, with the fragment preferably comprising a stretch of conserved amino acids;
  a combination of different proteins, wherein the combination as a whole includes one or more proteins that is recognised by each strain in a reference population, although each individual protein in the combination may not itself be recognised by each strain in the reference population ie. each member of a reference population recognises at least one protein in the combination.

The invention also provides the compositions of the invention for use as medicaments (eg. as immunogenic compositions or vaccines) or as diagnostic reagents. It also provides the use of the compositions in the manufacture of: (i) a medicament for treating or preventing infection due to Neisserial bacteria: (ii) a diagnostic reagent for detecting the presence of Neisserial bacteria or of antibodies raised against Neisserial bacteria; and/or (iii) a reagent which can raise antibodies against Neisserial bacteria.

The invention also provides a method of treating a patient, comprising administering to the patient a therapeutically effective amount of a composition according to the invention.

The invention further provides a process for producing a composition according to the invention, comprising the step of bringing one or more of SEQ IDs 1-8376 into combination with one or more other of SEQ IDs 1-8376.

BRIEF DESCRIPTION OF THE DRAWINGS

FIGS. 1A-1B shows SDS-PAGE results for the expression of ORFs 6, 7, 13, 65-1, 72, 73-1, 105-1, 137-1, 143-1 and 147-1. The left-hand lanes show molecular weight markers (set M1).

FIG. 3 shows SDS-PAGE results for the expression of ORFs 2-1, 5-1, 22-1, 132-1 and 4. The left-hand lanes show molecular weight markers (set M1).

FIG. 29A, FIG. 29B, and FIG. 29C shows sequence variability of NspA from various strains of meningococcus B and gonococcus: NM 608 B (SEQ ID NO: 4009), NM NG6/88+ (SEQ ID NO: 4009), NM CU385+ (SEQ ID NO: 8422), NM 8047+ (SEQ ID NO: 8423), NM NGP165– (SEQ ID NO: 4009), NM MC58– (SEQ ID NO: 8422), NM M986– (SEQ ID NO: 4009), NM BZ232– (SEQ ID NO: 8424), NM M136– (SEQ ID NO: 8425), NM NG3/88– (SEQ ID NO: 8426), NG FA1090 (SEQ ID NO: 8429), and NG B2 (SEQ ID NO: 8428). These sequences may be used as alternatives to the NspA of WO 96/29412 (SEQ IDs 4008-4033).

FIGS. 31A-31E shows similar data for encapsulated strains 8047. CU385 & M986 (FIGS. 31A-31B) and non-encapsulated strains BZ232. MC58, NG3/88 & NGB 165 (FIGS. 31C-E).

FIGS. 33A-33I shows FACS analysis of non-encapsulated strain M7 (FIG. 33A) ethanol-treated (to disrupt the capsule) strains 2996, N44776, MC58, 1000, BZ232, BZ133, NG6/88, BZ198, NG3/88, 297-0, BZ147 and BZ169 (FIGS. 33B-33I).

EXAMPLES

Example 1

Expression and Purification Experiments

Figure 2A:
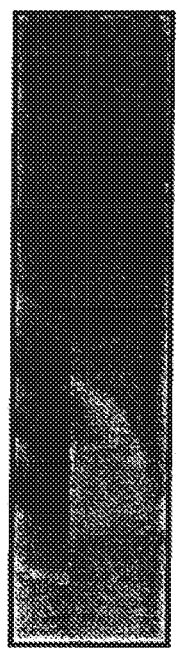
FIGS. 2A-2C shows (FIG. 2A) SDS-PAGE results for ORF9 (FIG. 2B) the positions of the *N. meningitidis* immunoreactive band in a Western blot against a *N. meningitidis* outer membrane vesicle preparation (FIG. 2C) FACS analysis.

ORFs 6, 7, 13, 65-1, 72, 73-1, 105-1, 137-1, 143-1 and 147-1 disclosed in WO99/24578 were expressed in *E. coli* and purified, as set out in the following table:

| ORF | His-fusion | GST-fusion | Purification | MW (kDa) |
|---|---|---|---|---|
| 6 | | + | GST-fusion | 23 |
| 7 | + | + | GST-fusion | 28 |
| 13 | | + | GST-fusion | 10 |
| 65-1 | | + | UST-fusion | 32 |
| 72 | + | | His-fusion | 13.5 |
| 73-1 | | + | GST-fusion | 13 |
| 105-1 | + | + | His-fusion | 32 |
| 137-1 | | + | GST-fusion | 31 |
| 143-1 | + | + | His-fusion | 23.5 |
| 147-1 | − | + | His-fusion | 32 |

NOTE:
ORF73-1 was expressed as a fragment (amino acids 41-161)

The protocols used to express these ten ORFs were essentially the same as those described in WO99/24578, using pGEX and pET vectors. Examples of the PCR primers used to amplify the ORFs are in the following table:

| ORF | Primer | Sequence | Restriction sites |
|---|---|---|---|
| ORF65-1 | Forward | CGCGGATCCCATATG-TTTATGAACAAATTTTCC (SEQ ID NO: 8430) | BamHI-NdeI |
| | Reverse | CCCGCTCGAG-TTTGCTTTCGATAGAACGG (SEQ ID NO: 8431) | XhoI |
| ORF73-1 | Forward | CGCGGATCCCATATG-GCCGGCGTGCTGATG (SEQ ID NO: 8432) | BamHI-NdeI |
| | Reverse | CCCGCTCGAG-TTCATCTTTTTCATGTTCG (SEQ ID NO: 8433) | XhoI |
| ORF105-1 | Forward | CGCGGATCCCATATG-CCGACCGTCCGTT (SEQ ID NO: 8434) | BamHI-NdeI |
| | Reverse | CCCGCTCGAG-TAAACGAATGCCGTCCAG (SEQ ID NO: 8435) | XhoI |
| ORF143-1 | Forward | CGCGGATCCCATATG-GAATCAACACTTTCAC (SEQ ID NO: 8436) | BamHI-NdeI |
| | Reverse | CCCGCTCGAG-CACGCGGTTGCTGTAAC (SEQ ID NO: 8437) | XhoI |
| ORF147-1 | Forward | CCGGAATTCTACATATG-TTTCAGAAACATTTGCAG (SEQ ID NO: 8438) | EcoRI-NdeI |
| | Reverse | CCCGCTCGAG-TTTGTTTTTCCAAGACAGAG (SEQ ID NO: 8439) | XhoI |

SDS-PAGE results for the ten expressed ORFs are shown in FIG. 1.

The ORF7-His fusion was used to immunise mice. The sera were used in an ELISA assay, essentially as described in WO99/24578, and gave positive results.

The following proteins were also expressed and purified results not shown:

| ORF | His-fusion expression | GST-fusion expression | Expressed as a fragment | Fragment amino acid positions |
|---|---|---|---|---|
| orf1 (s) | − | − | − | 43-1087 |
| orf1 (β) | n.d. | − | − | 1051-1457 |
| orf35-1 | − | − | − | |
| orf41 | n.d. | n.d. | − | 25-619 |
| orf46 | − | − | − | 25-433 |
| orf61 | n.d. | n.d. | − | 1-575 |
| orf83-1 | − | − | − | 15-313 |
| orf100-1 | n.d. | − | − | 21-376 |
| orf114-1 | n.d. | − | − | 1-1423 |
| orf124-1 | n.d. | n.d. | − | |
| orf131-1 | n.d. | − | − | 22-135 |

The following PCR primers were used to amplify these ORFs:

| ORF | Primer | Sequence | Restriction sites |
|---|---|---|---|
| ORF1 (s) | Forward | CGCGGATCCGCTAGC-GGACACACTTATTTCGG (SEQ ID NO: 8440) | BamHI-NheI |
| | Reverse | CCCGCTCGAG-CAGCGCGTCAAGGCTT (SEQ ID NO: 8441) | XhoI |
| ORF1 (β) | Forward | CGCGGATCCGCTAGC-GAGTTCCGCCTGCATAA (SEQ ID NO: 8442) | BamHI-NheI |
| | Reverse | CCCGCTCGAG-CCAGCGGTAGCCTAATT (SEQ ID NO: 8443) | XhoI |
| ORF35-1 | Forward | CGCGGATCCGCTAGC-AGGGGCGACGACGTG (SEQ ID NO: 8444) | BamHI-NheI |
| | Reverse | CCCGCTCGAG-AAACAGCCATTTGAGCGA (SEQ ID NO: 8445) | XhoI |
| ORF41 | Forward | CGCGGATCCCATATG-TATTTGAAACAGCTCCAAG (SEQ ID NO: 8446) | BamHI-NdeI |
| | Reverse | CCCGCTCGAG-TTCTGGGTGAATGTTA (SEQ ID NO: 8447) | XhoI |
| ORF46 | Forward | CGCGGATCCCATATG-TCAGATTTGGCAAACATC (SEQ ID NO: 8448) | BamHI-NdeI |
| | Reverse | CCCGCTCGAG-CGTATCATATTTCACGTGC (SEQ ID NO: 8449) | XhoI |

-continued

| ORF | Primer | Sequence | Restriction sites |
|---|---|---|---|
| ORF61 | Forward | CGCGGATCCGCTAGC-ACGGTTTTGAAGCTTT CGC (SEQ ID NO: 8450) | BamHI-NheI |
|  | Reverse | CCCGCTCGAG-AATGA CGAGGTTGTCCG (SEQ ID NO: 8451) | XhoI |
| ORF83-1 | Forward | CGCGGATCCCATATG-TGCGGCACACTGACCG (SEQ ID NO: 8452) | BamHI-NdeI |
|  | Reverse | CCCGCTCGAG-GCCGC CTTTGCGGC (SEQ ID NO: 8453) | XhoI |
| ORF100-1 | Forward | CGCGGATCCCATATG-TCGGGCATTTACACCG G (SEQ ID NO: 8454) | BamHI-NdeI |
|  | Reverse | CCCGCTCGAG-TTCGT CGAAAACCTTTGC (SEQ ID NO: 8455) | XhoI |
| ORF114-1 | Forward | CGCGGATCCCATATG-AATAAAGGTTTACATC GCAT (SEQ ID NO: 8456) | BamHI-NdeI |
|  | Reverse | CCCGCTCGAG-AATCG CTGCACCGGCT (SEQ ID NO: 8457) | XhoI |
| ORF124-1 | Forward | CGCGGATCCCATATG-ACTGCCTTTTCGACA (SEQ ID NO: 8458) | BamHI-NdeI |
|  | Reverse | CCCGCTCGAG-GCGTG AAGCGTCAGGA (SEQ ID NO: 8459) | XhoI |
| ORF131-1 | Forward | CGCGGATCCCATATG-TGCCGGCTGGCGGG (SEQ ID NO: 8460) | BamHI-NdeI |
|  | Reverse | CCCGCTCGAG-CCAGC GGACGCGTTC (SEQ ID NO: 8461) | XhoI |

Each of these ORFs can be combined with one or more of SEQ IDs 1-8376.

Example 2

ORF9 Expression and Purification

Figure 2B:
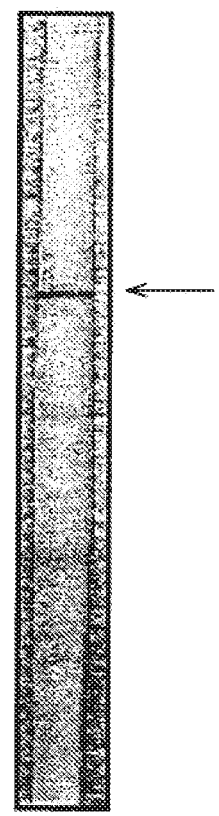
Figure 2C:
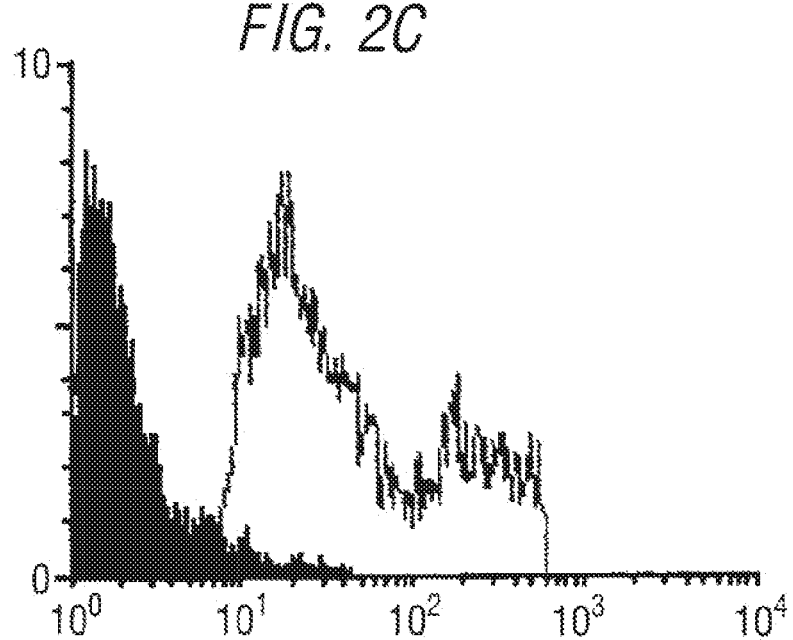
Figure 4:
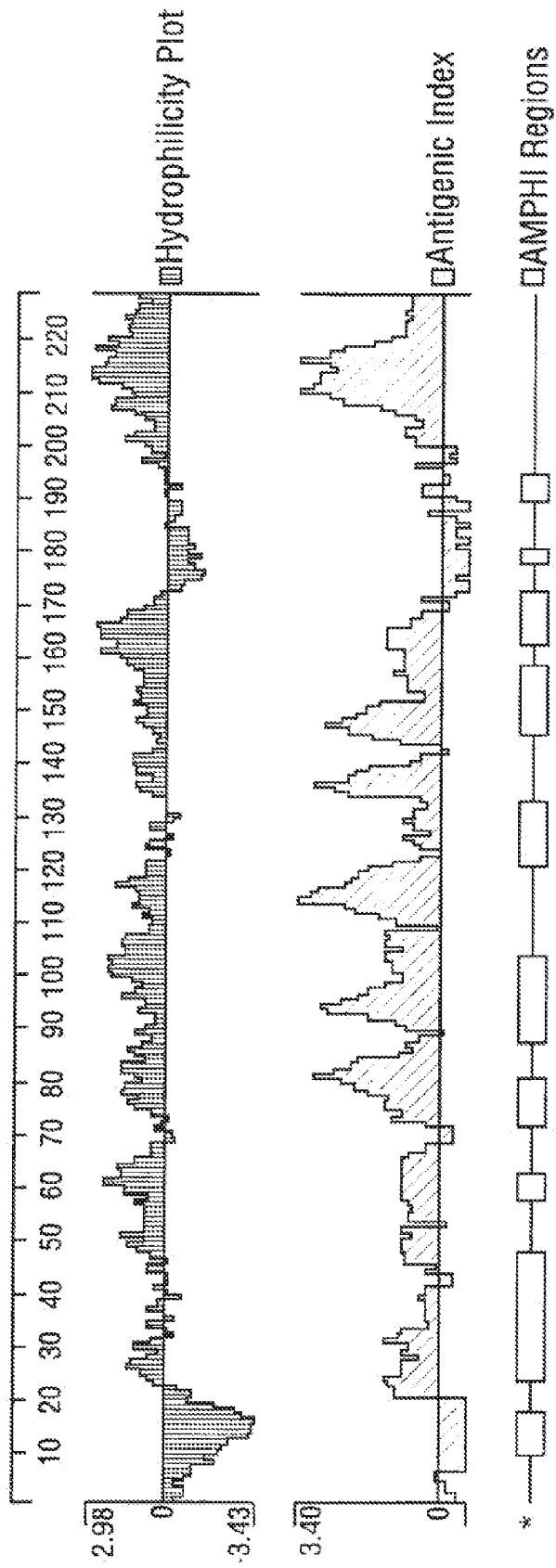
FIGS. 4 to 28 show a hydrophilicity plot (upper), antigenic index (middle), and AMPHI regions (lower) for ORFs 2, 5, 6, 7, 9, 13a, 15, 22, 23, 27, 28, 32, 65, 72, 73, 76, 79, 89, 105, 106-1, 132, 137, 138, 143 and 147.
Figure 5:
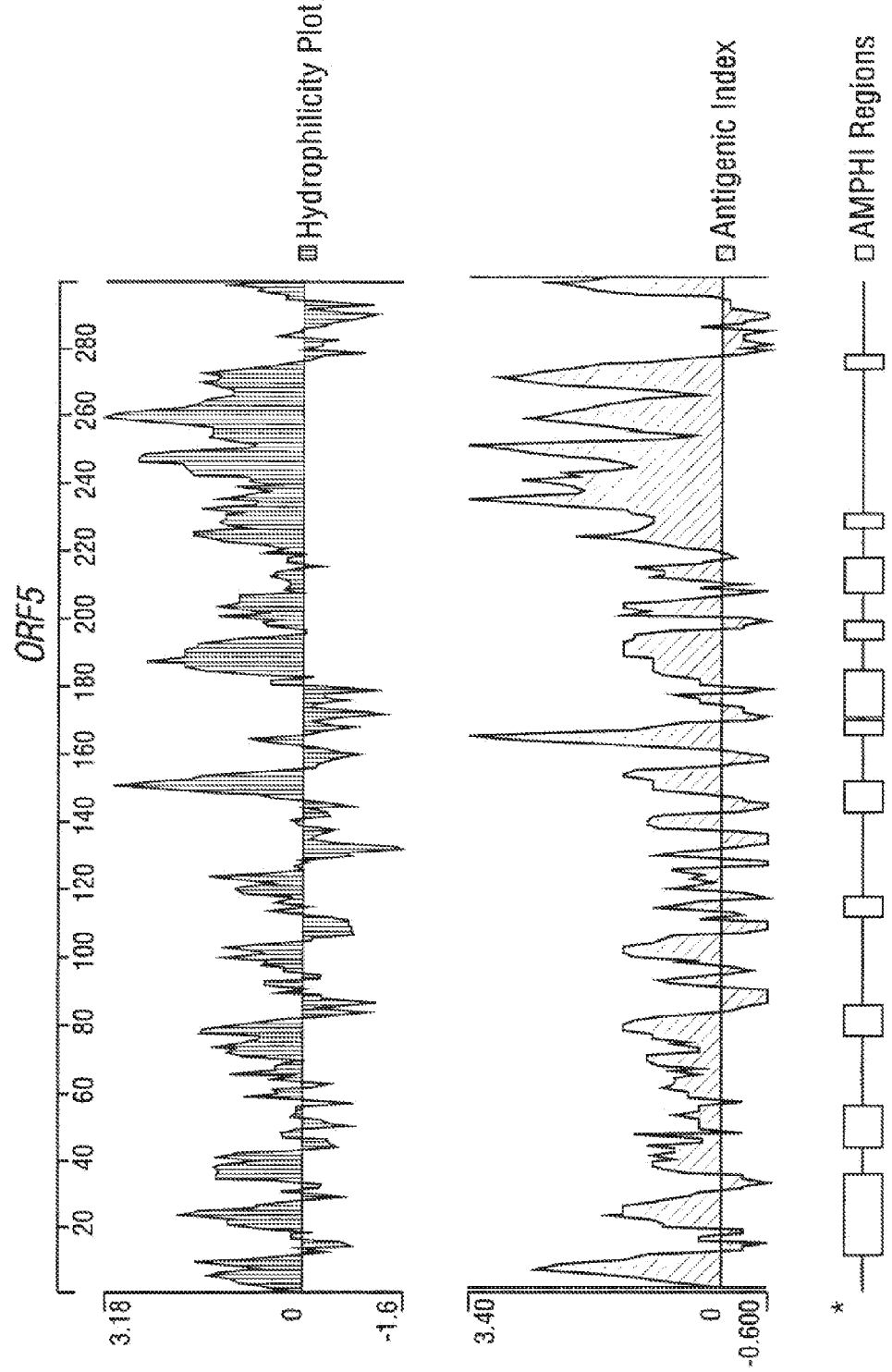
Figure 6:
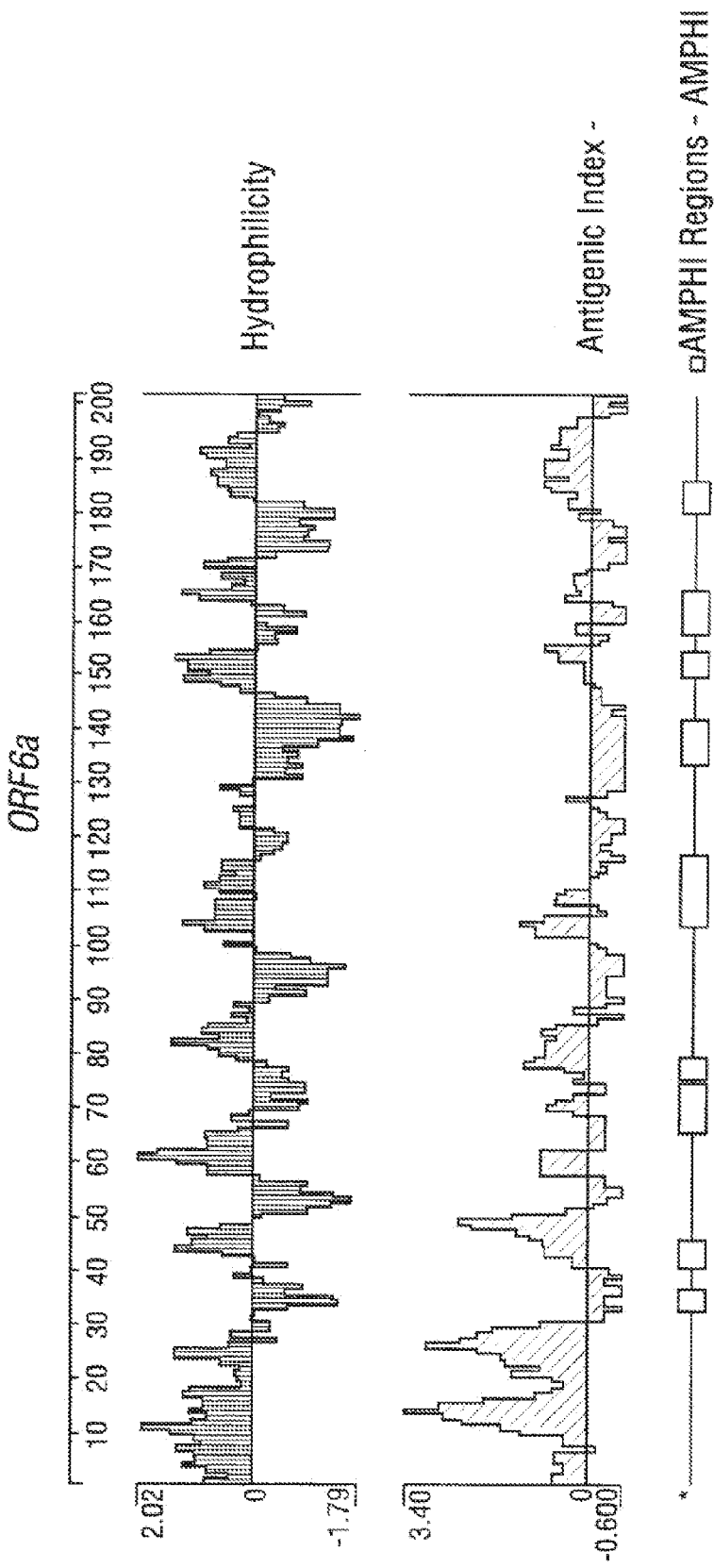
Figure 7:
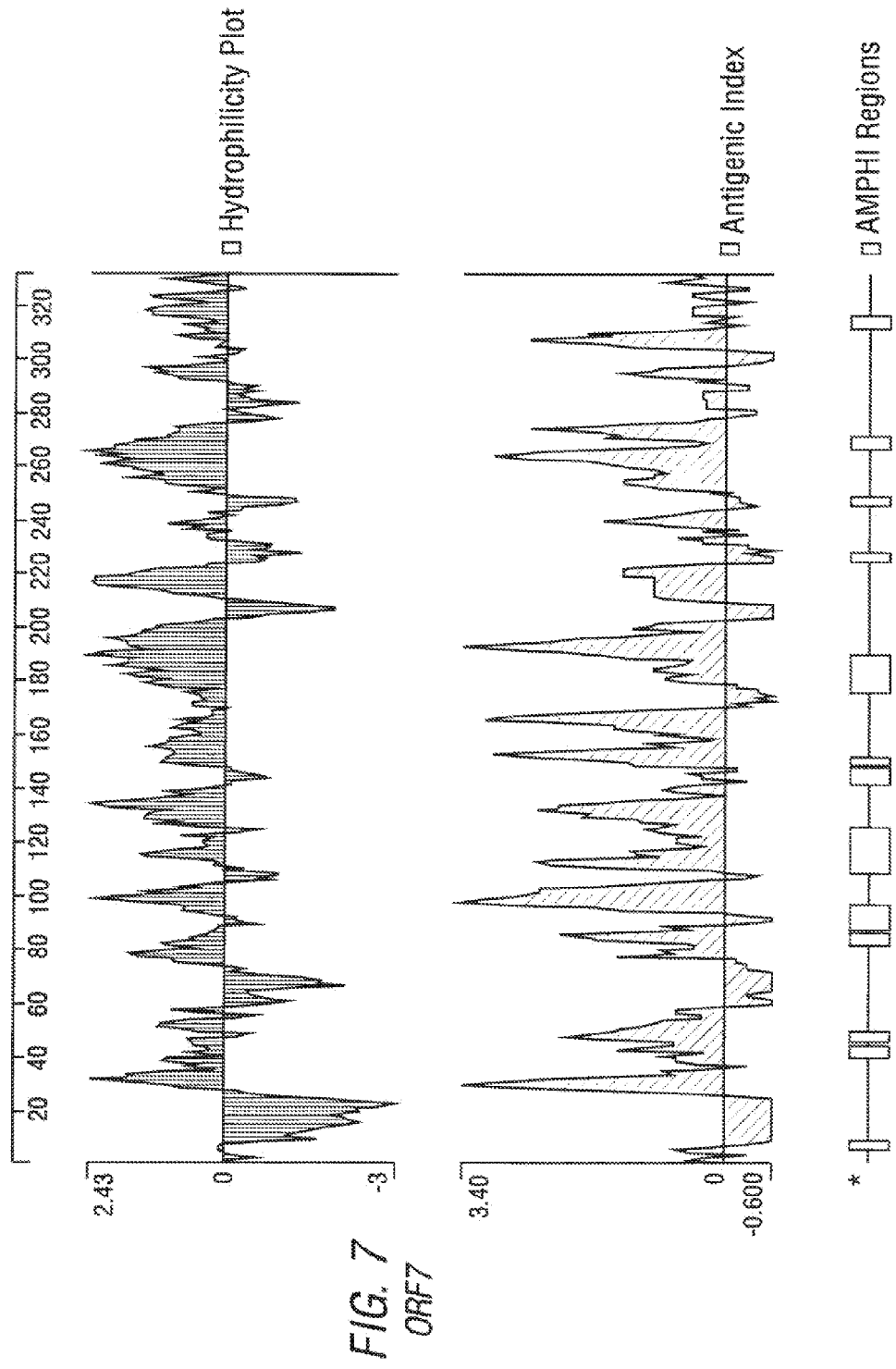
Figure 8:
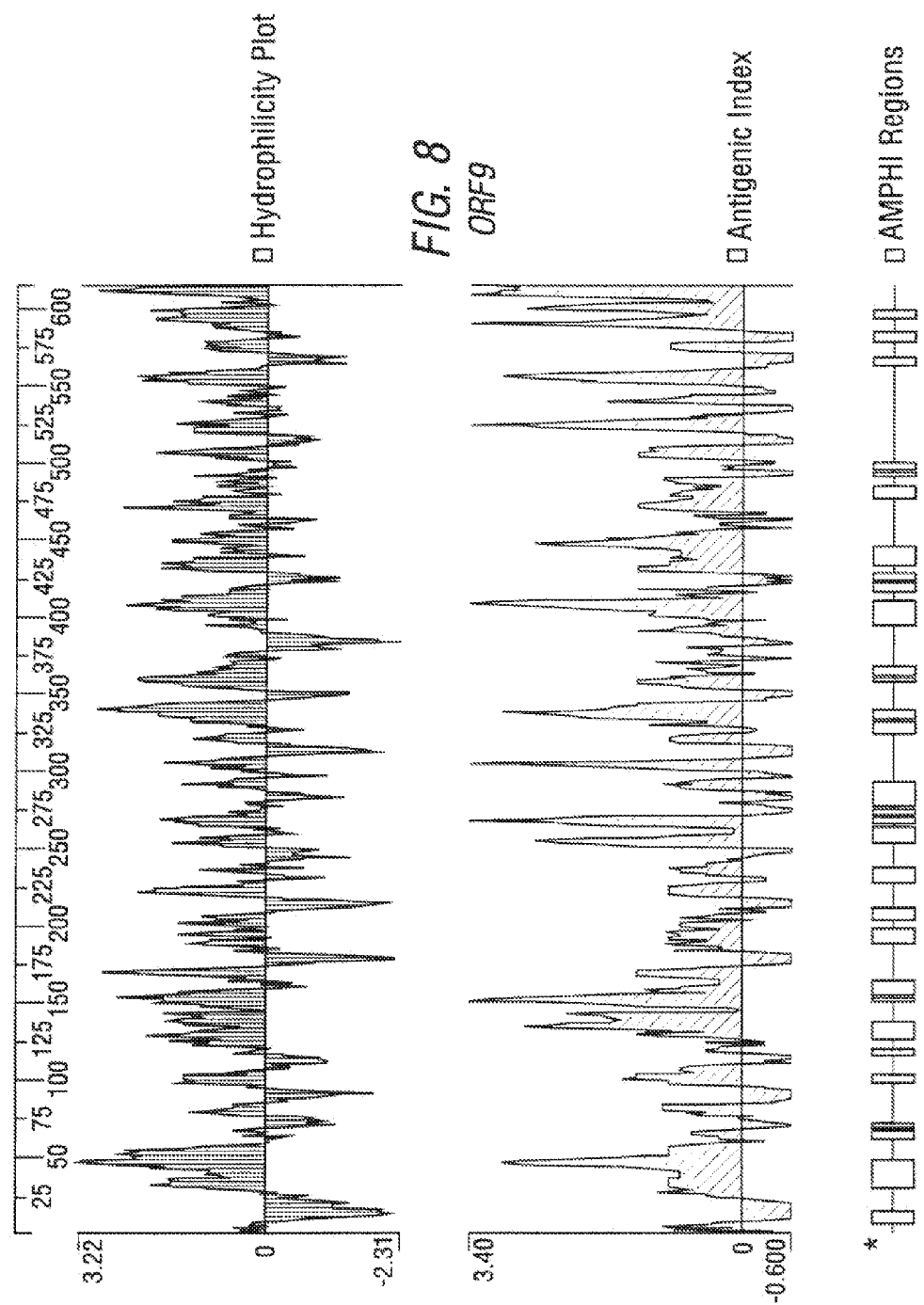
Figure 9:
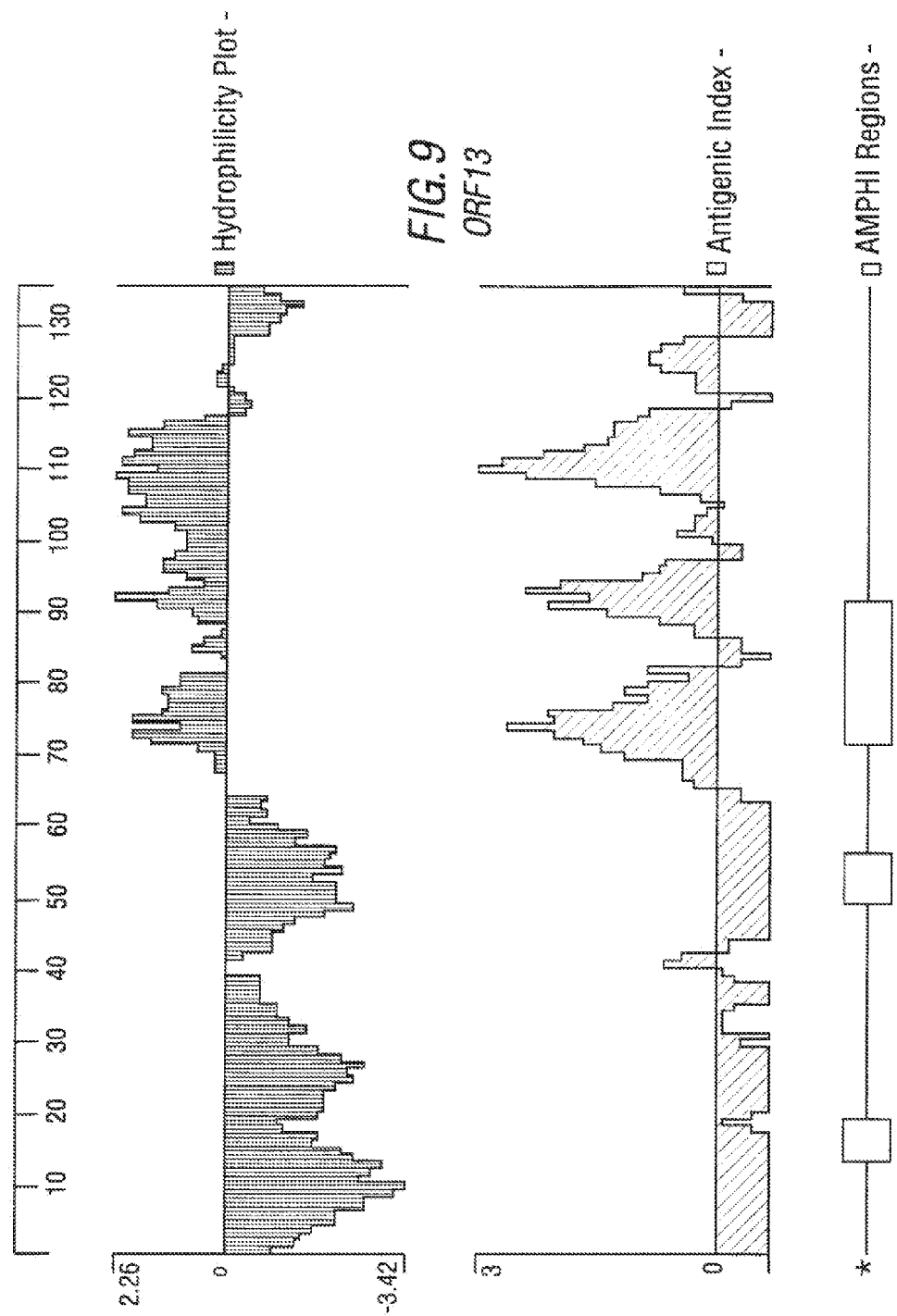
Figure 10:
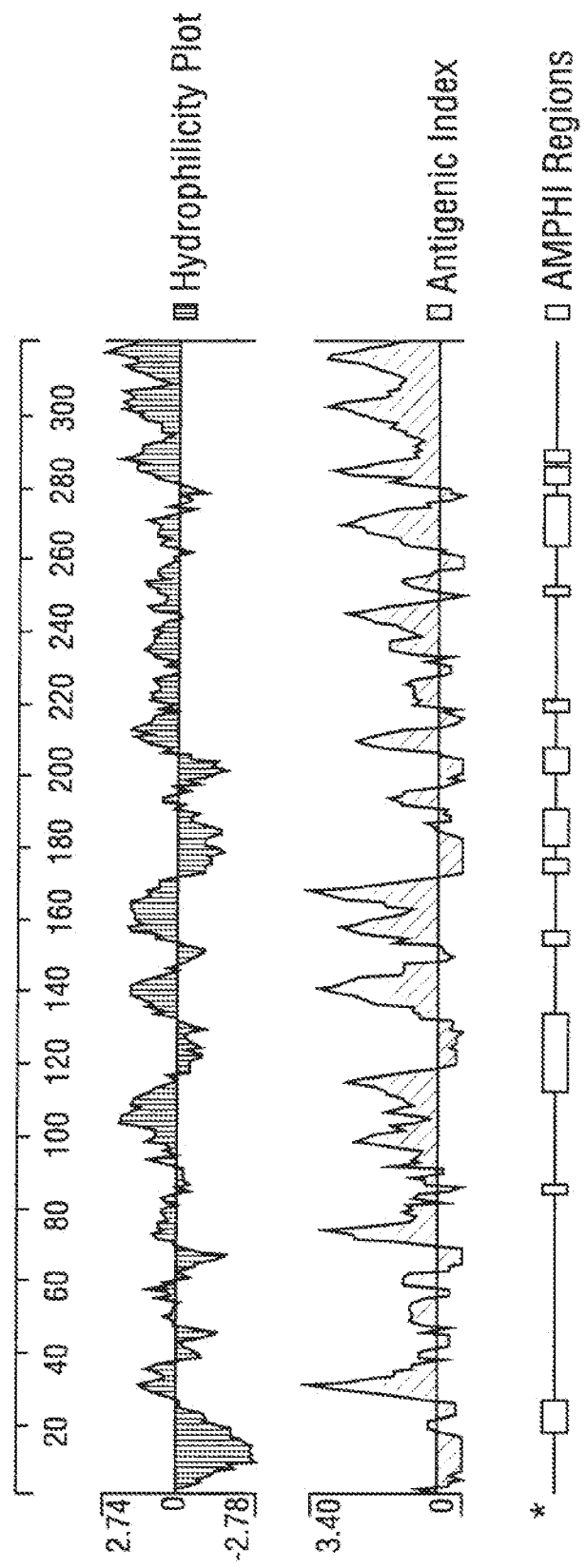
Figure 11:
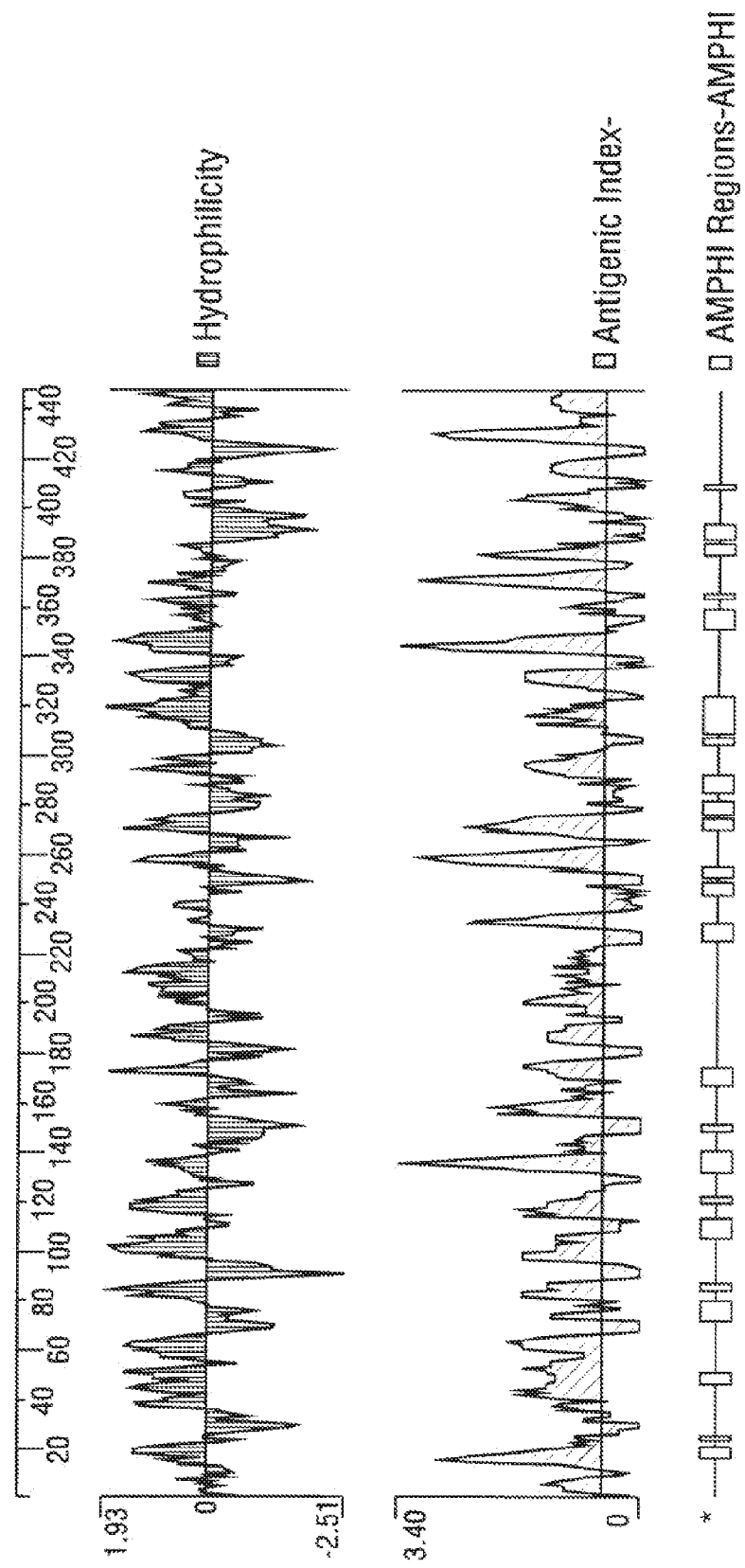
Figure 12:
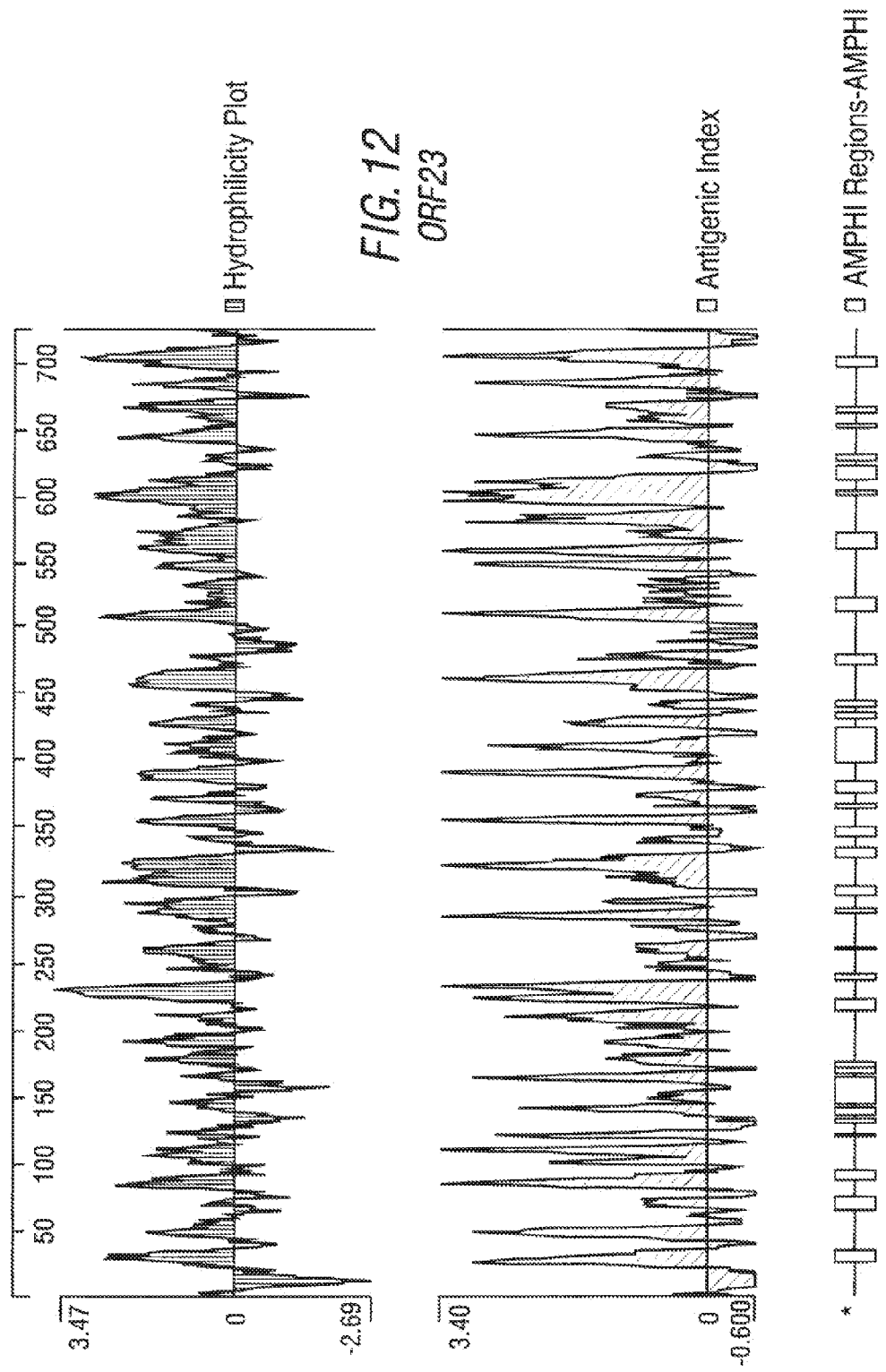
Figure 13:
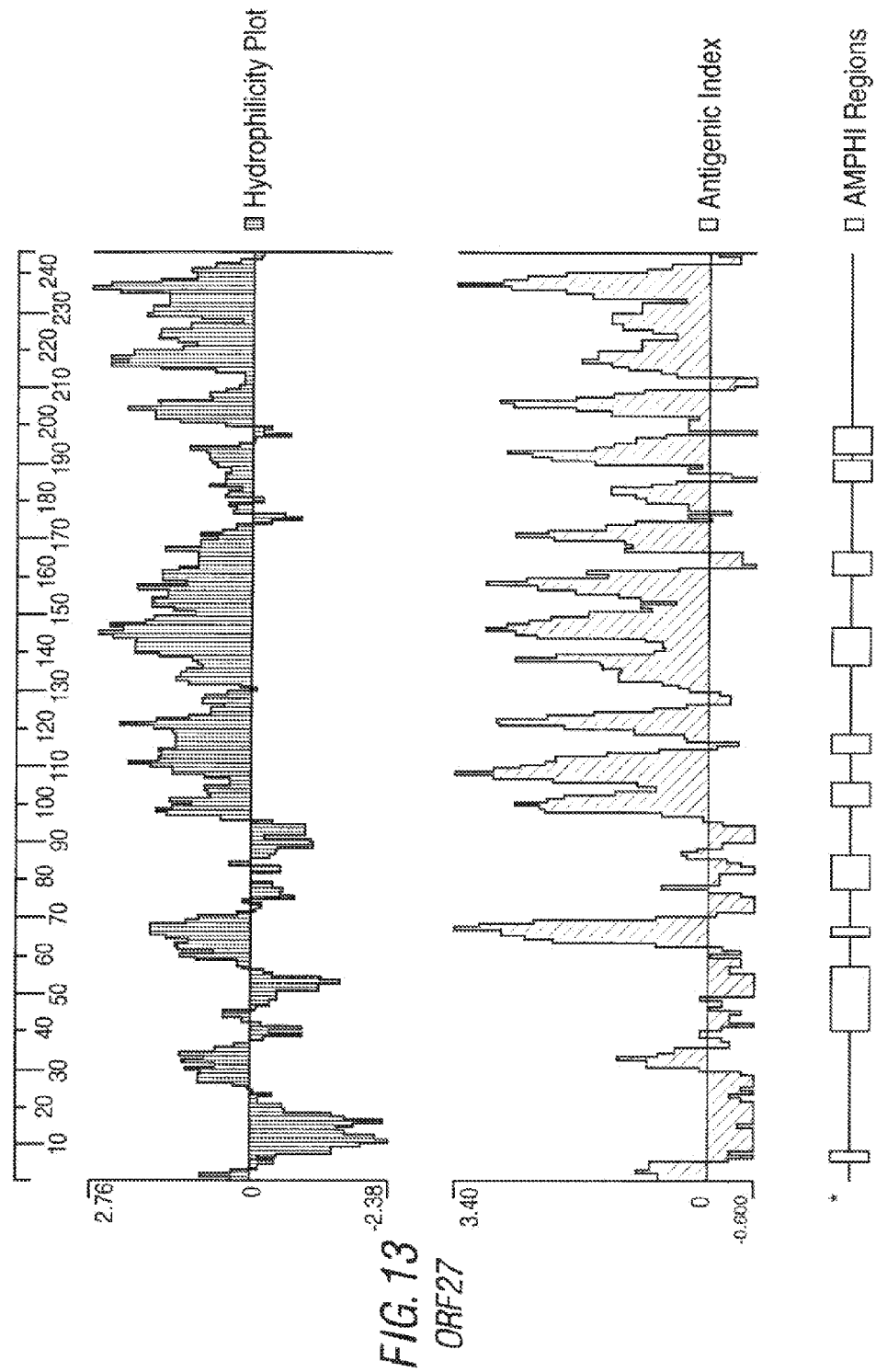
Figure 14:
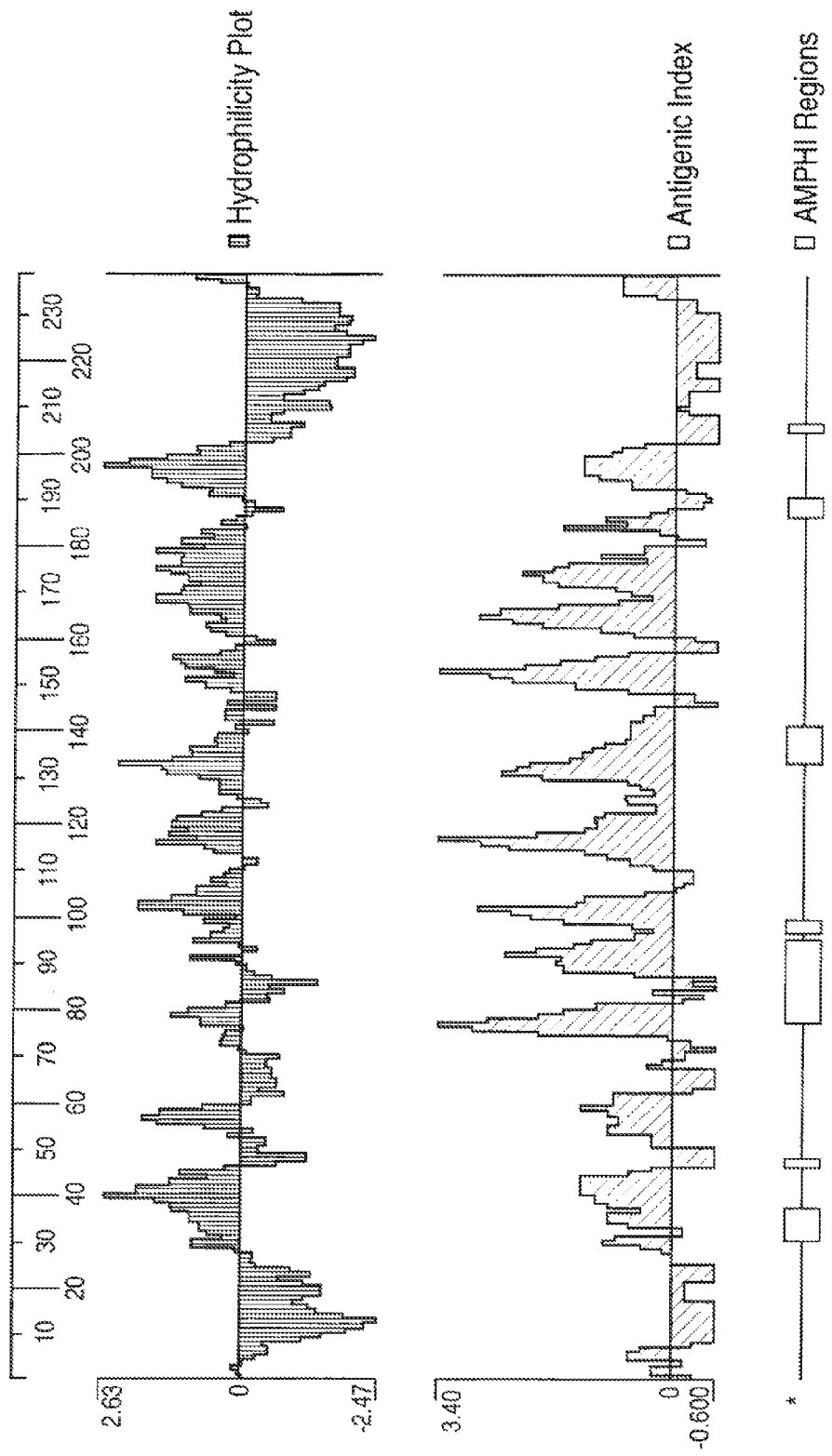
Figure 15:
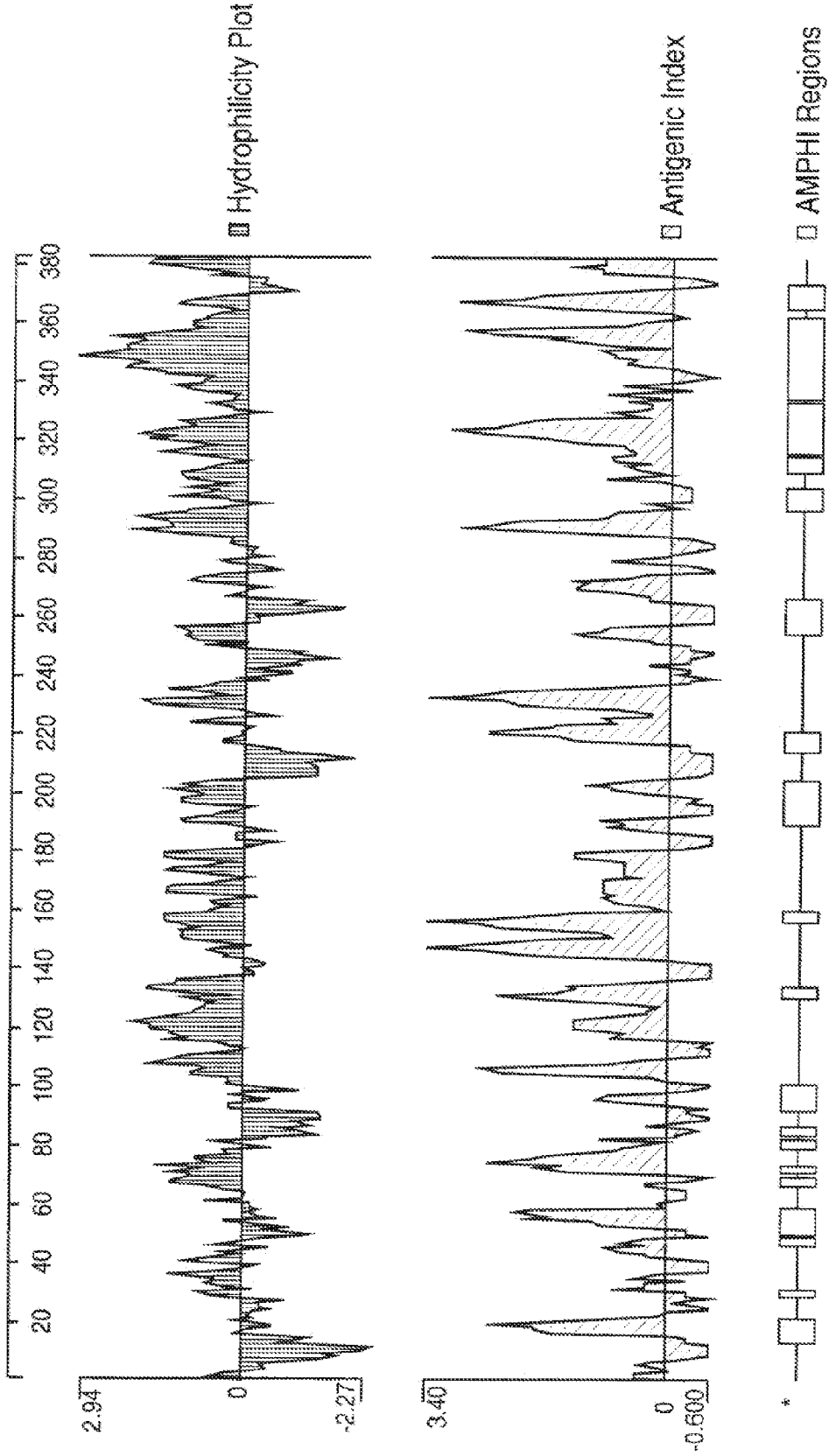
Figure 16:
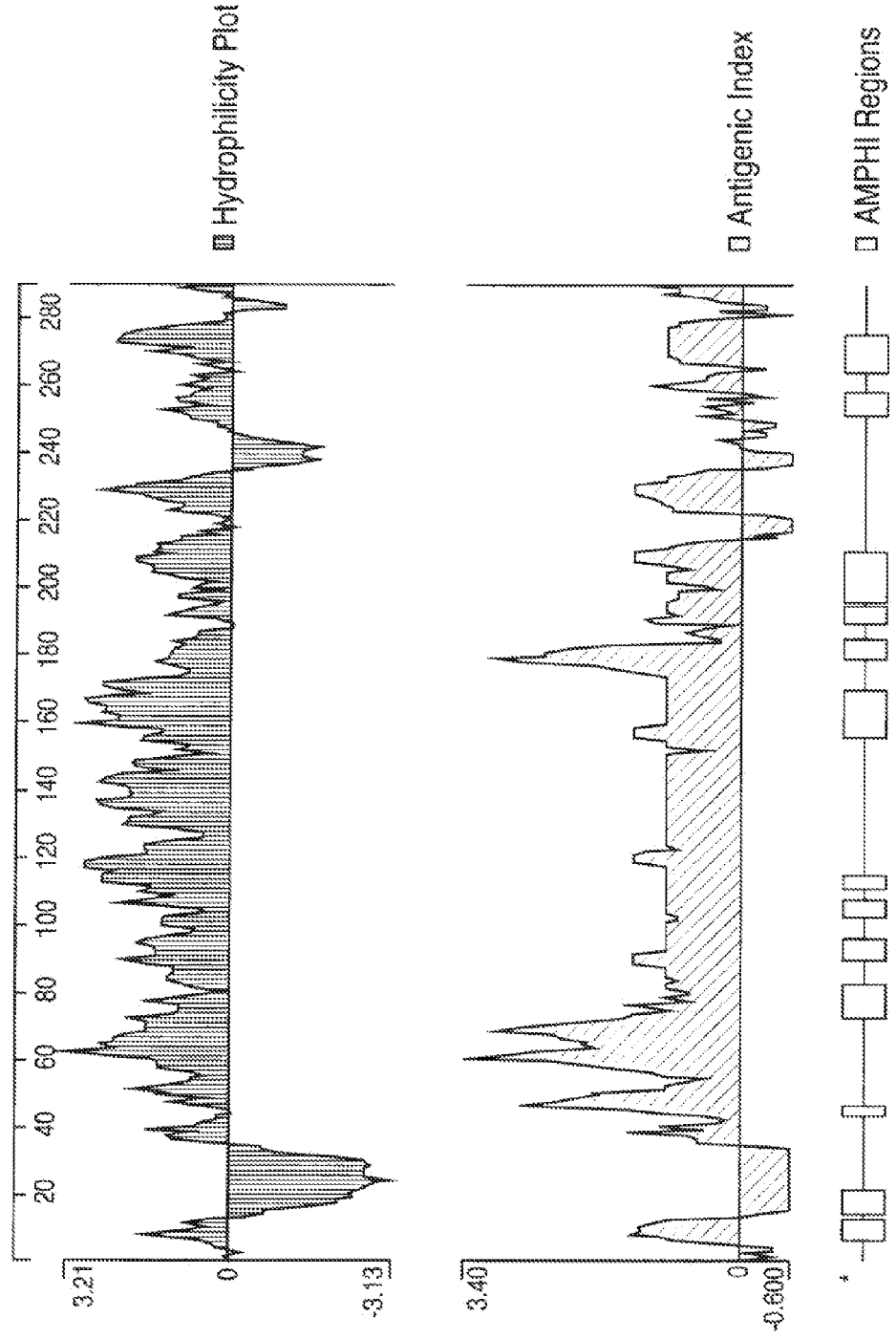
Figure 17:
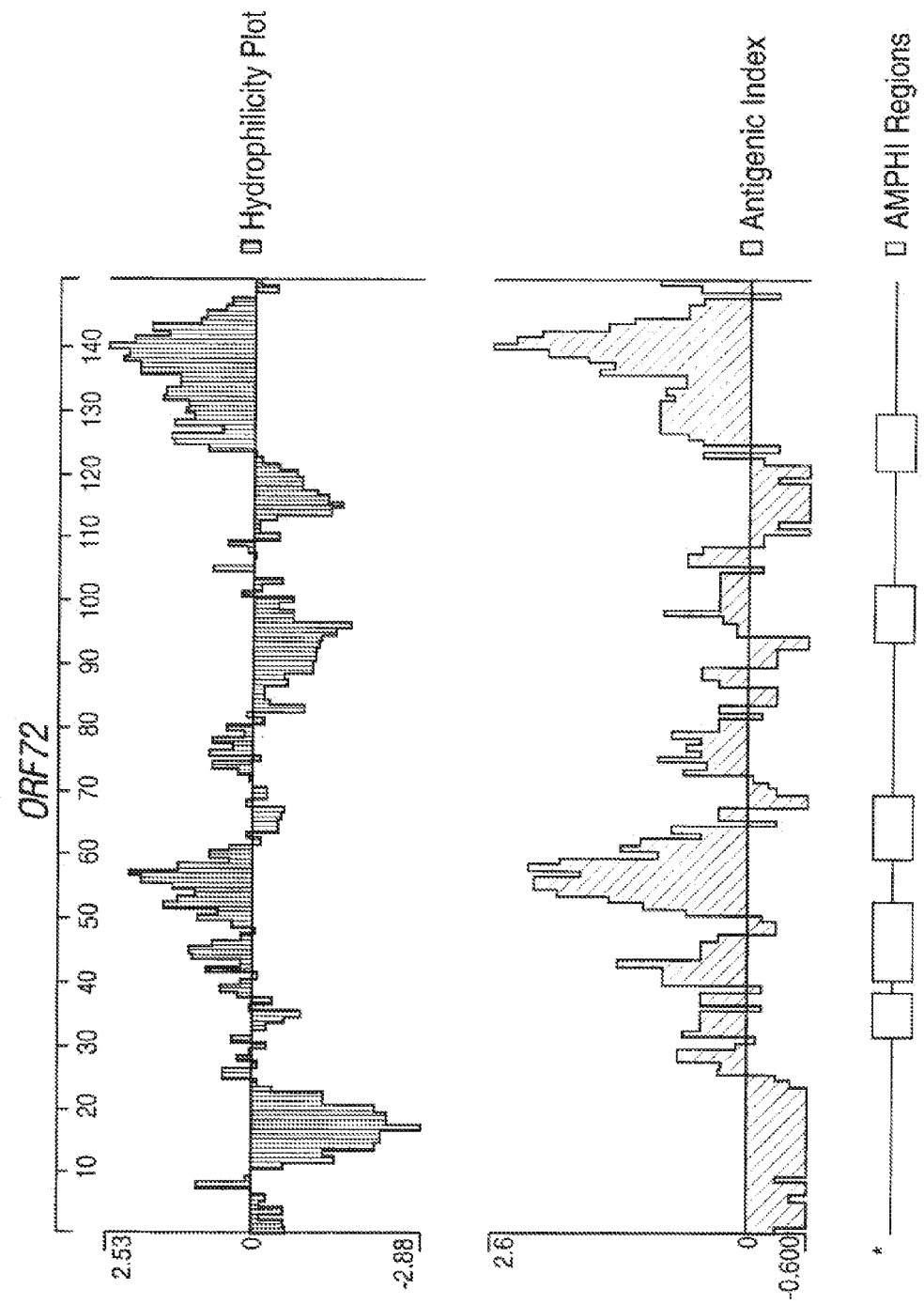
Figure 18:
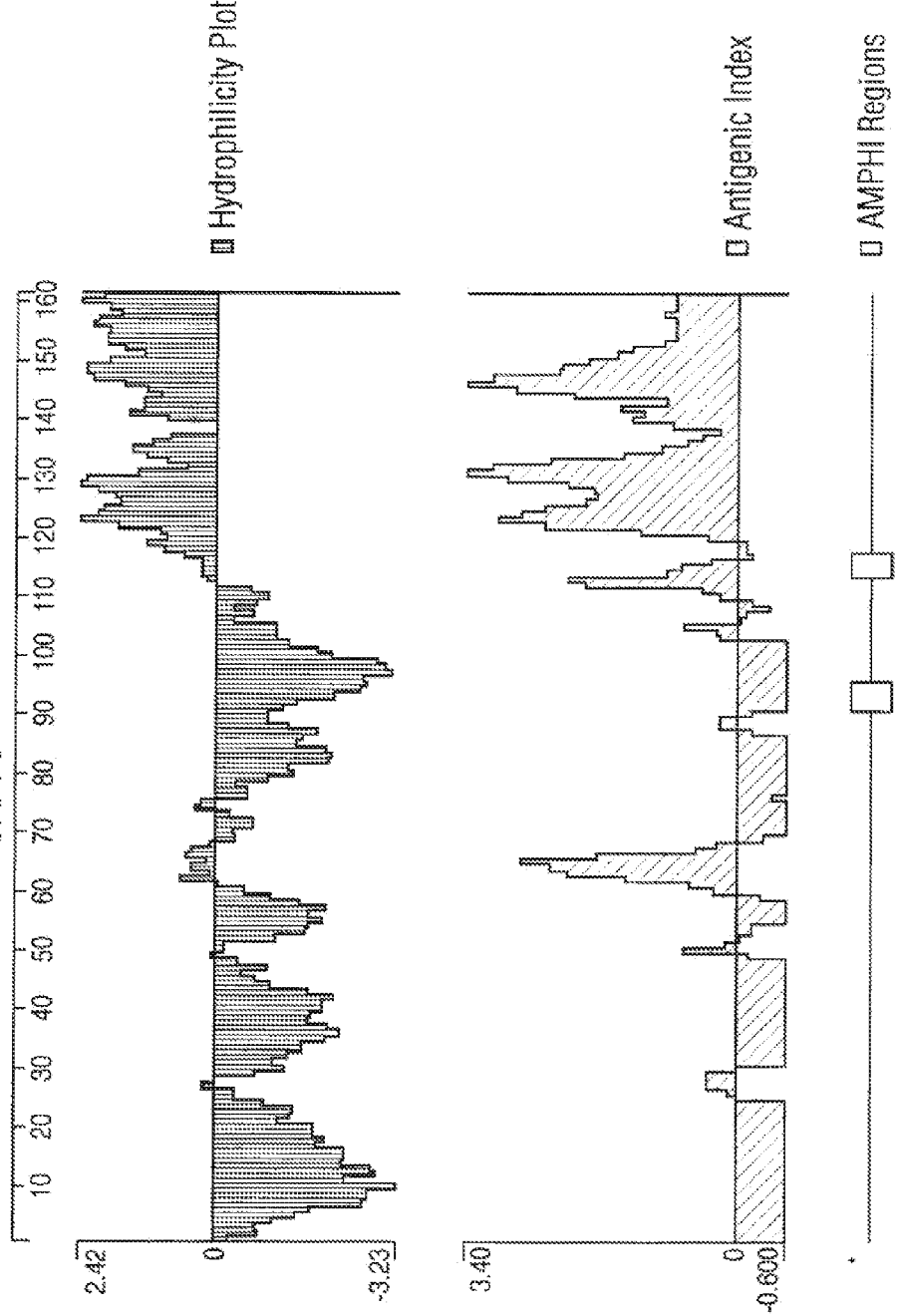
Figure 19:
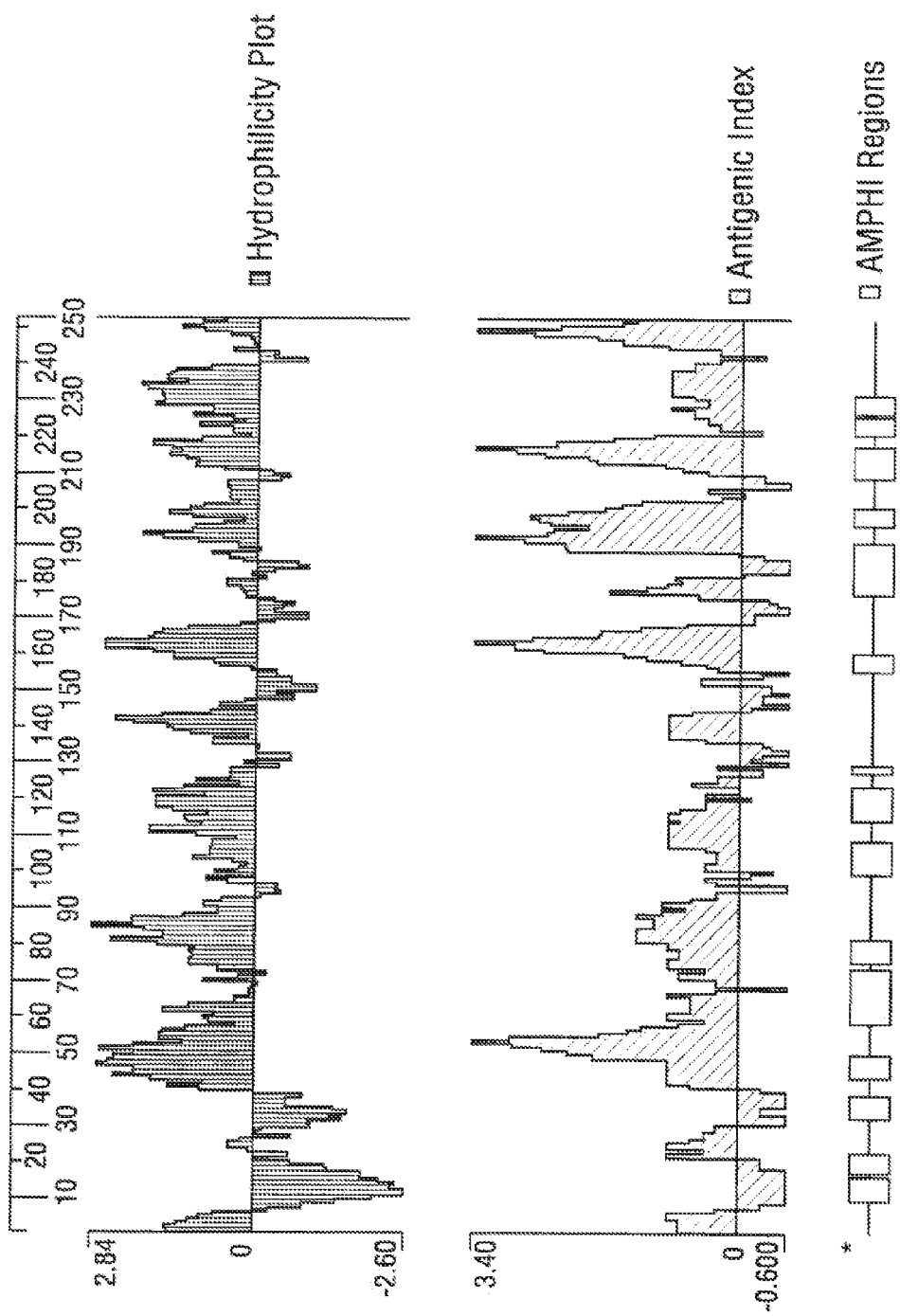
Figure 20:
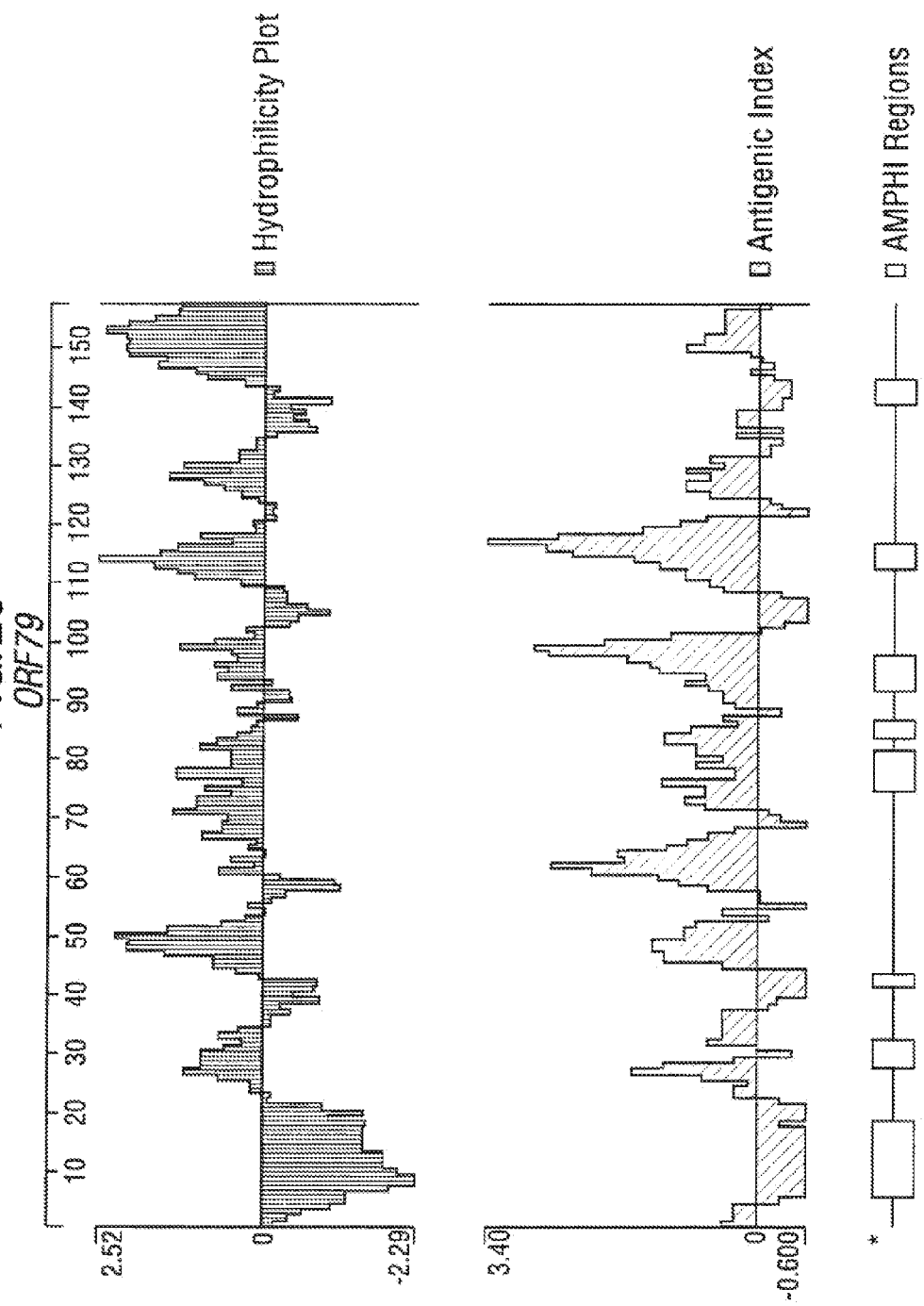
Figure 21:
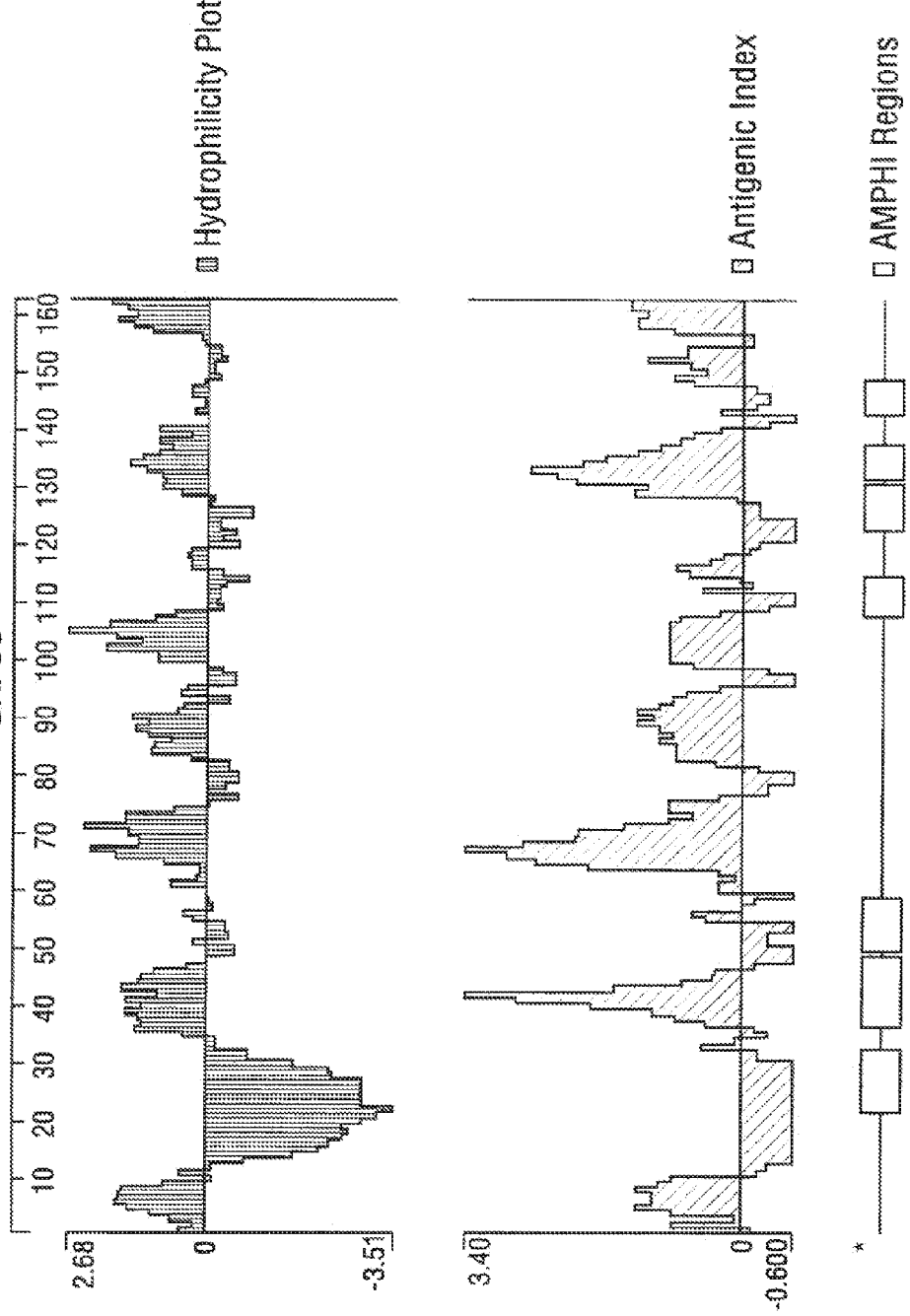
Figure 22:
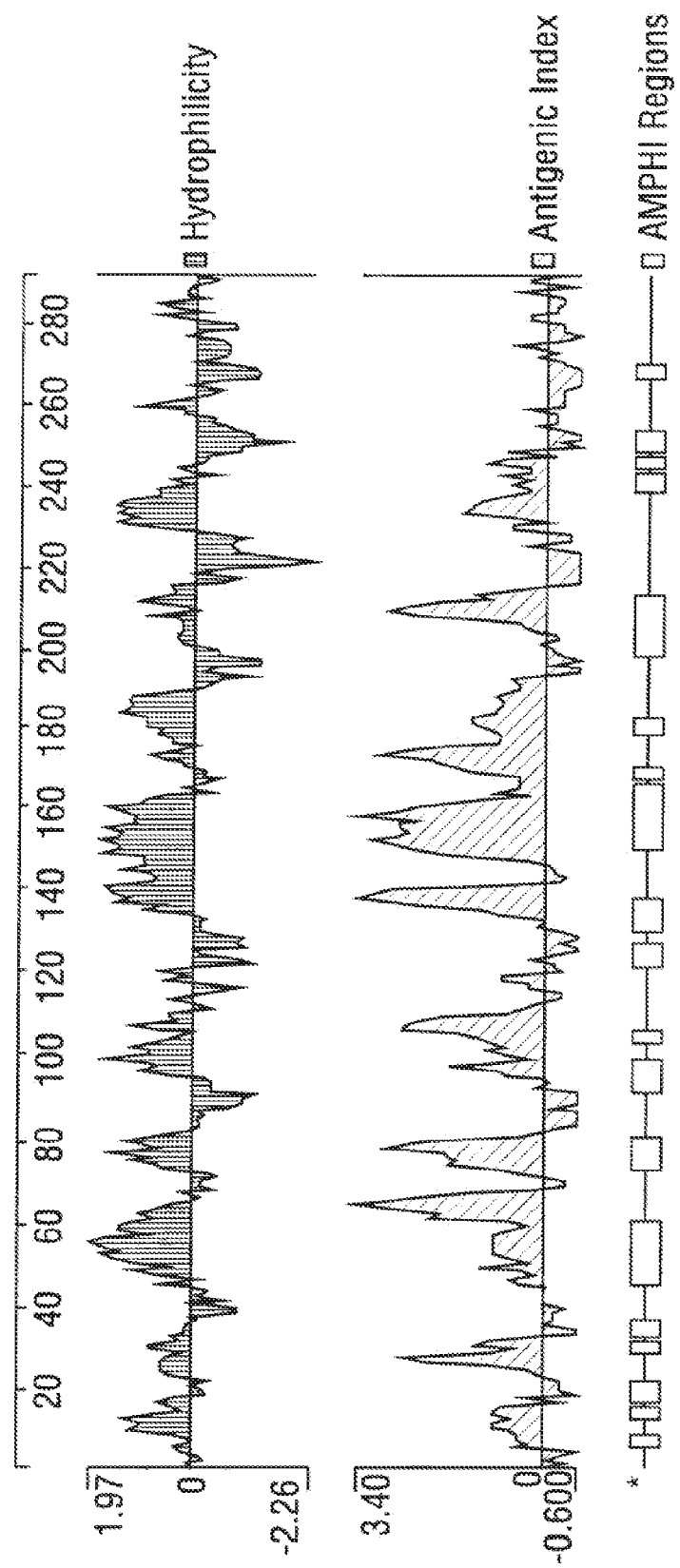
Figure 23:
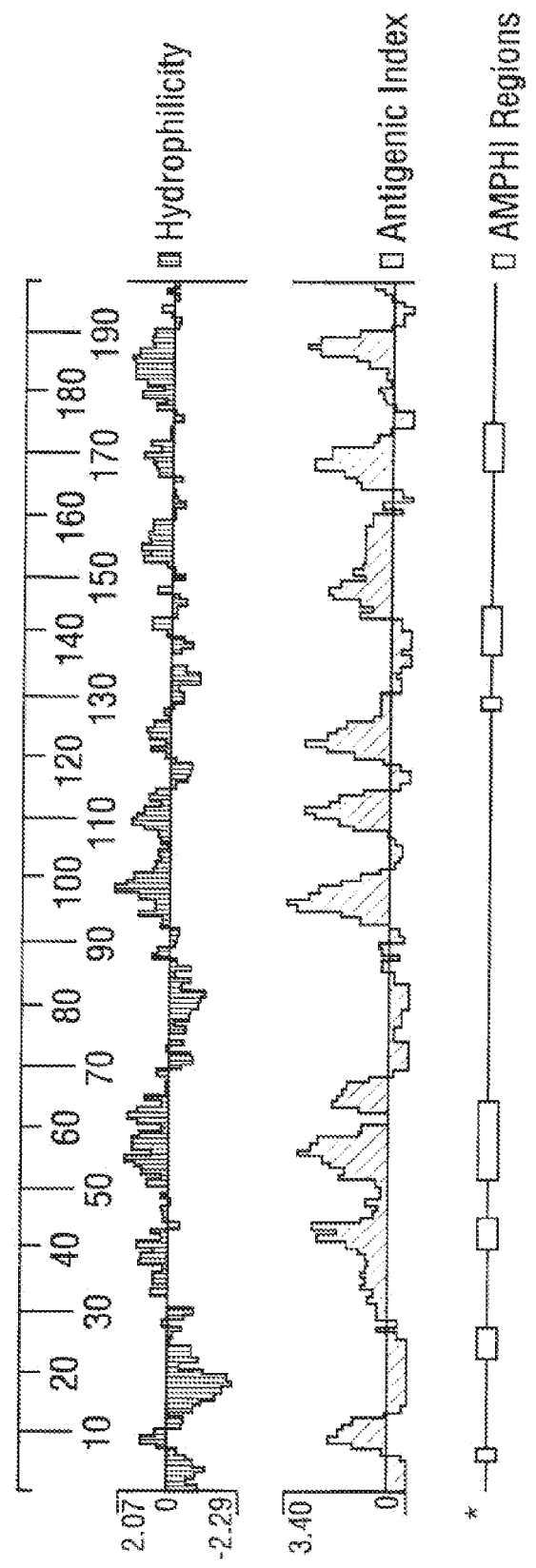
Figure 24:
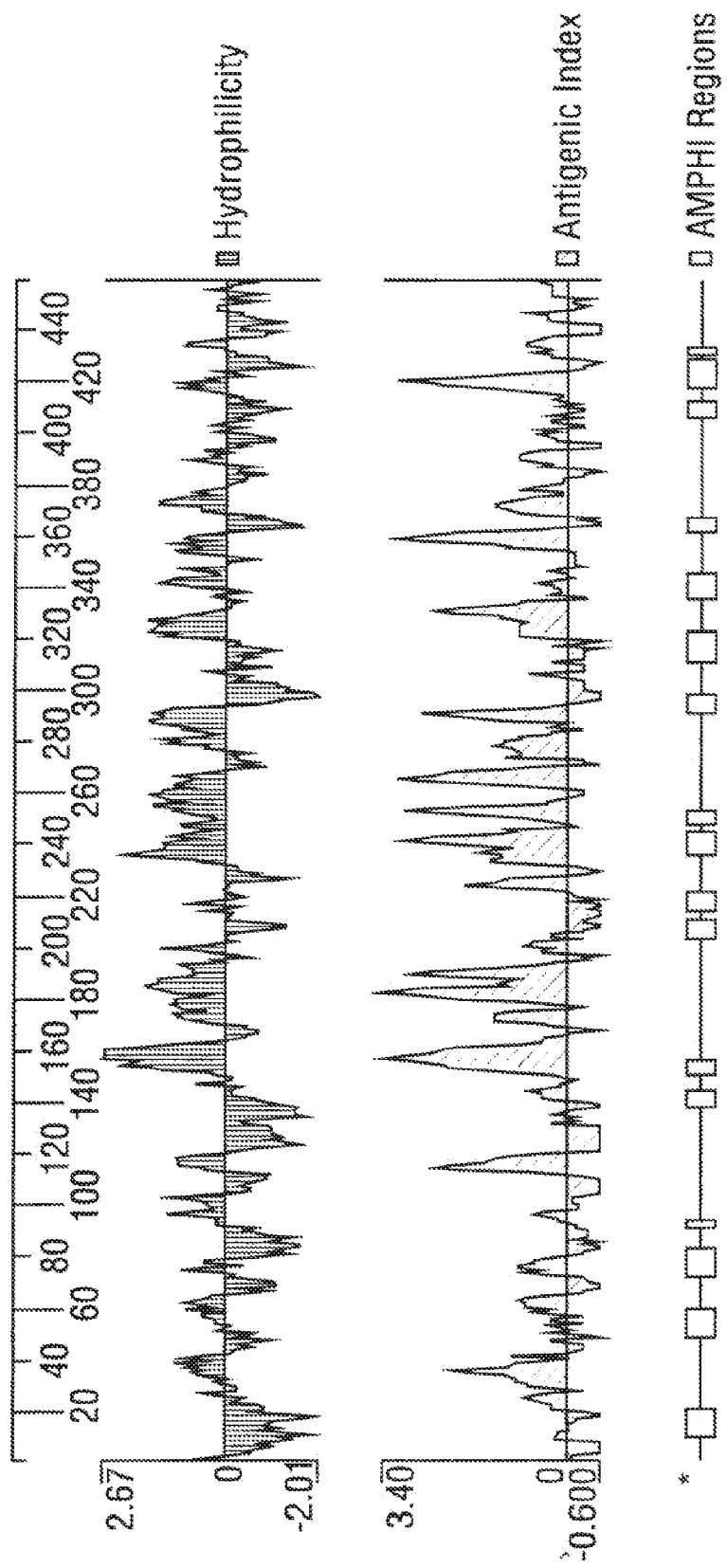
Figure 25:
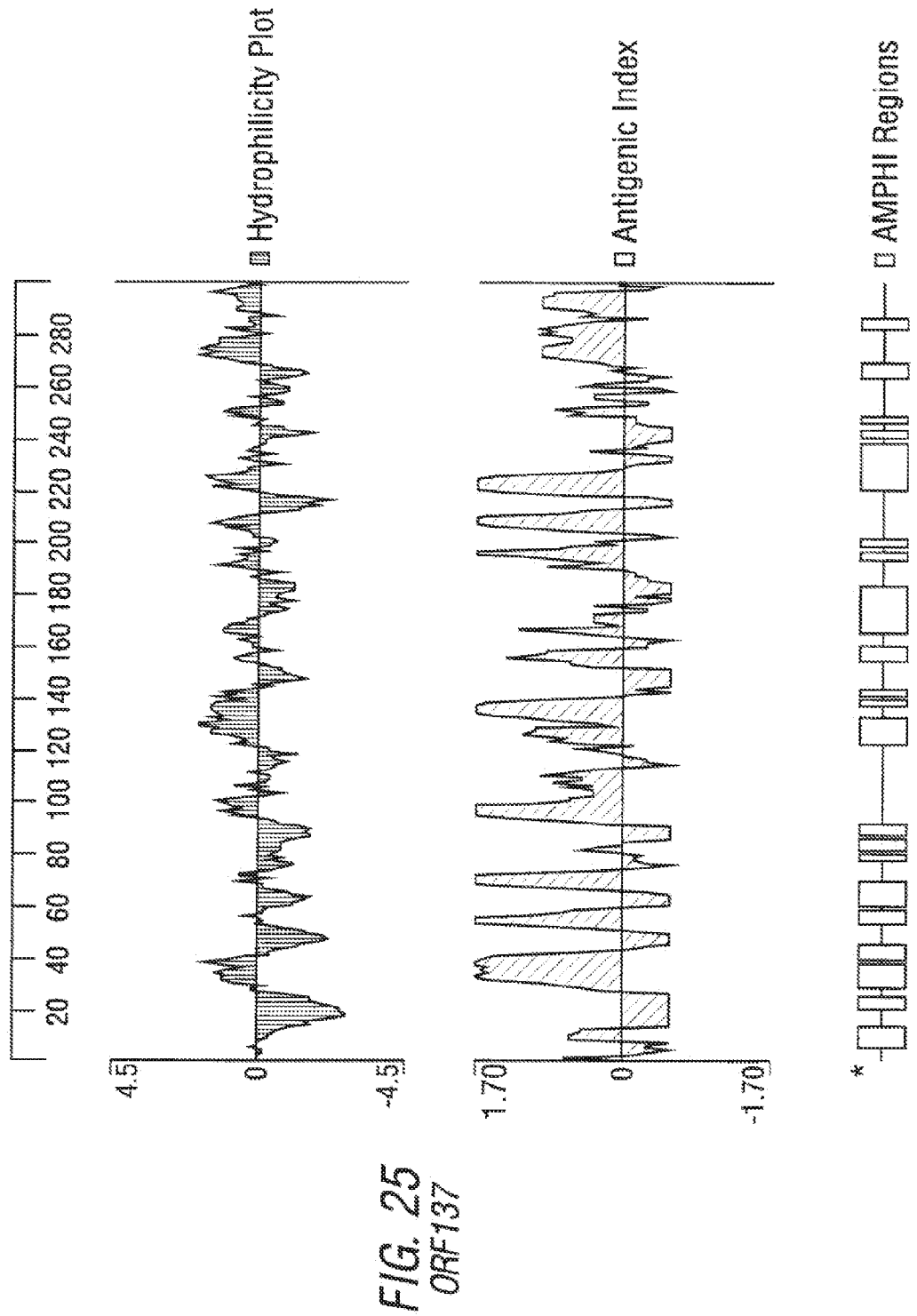
Figure 26:
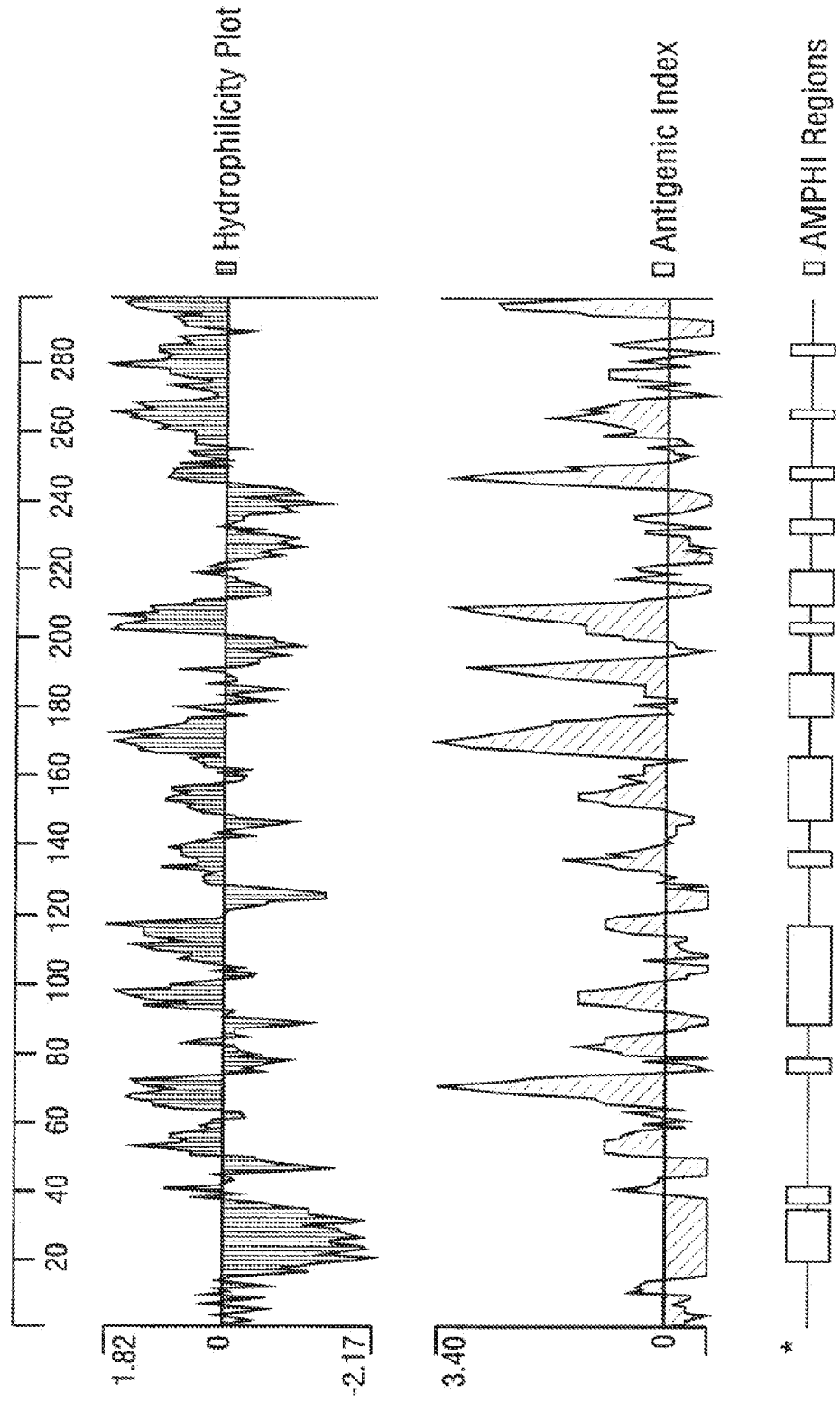
Figure 27:
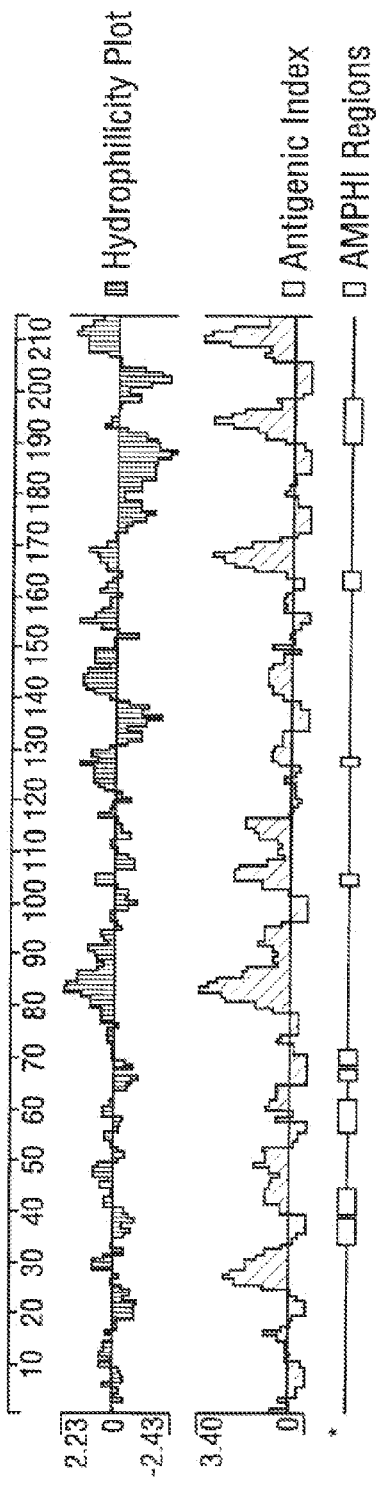
Figure 28:
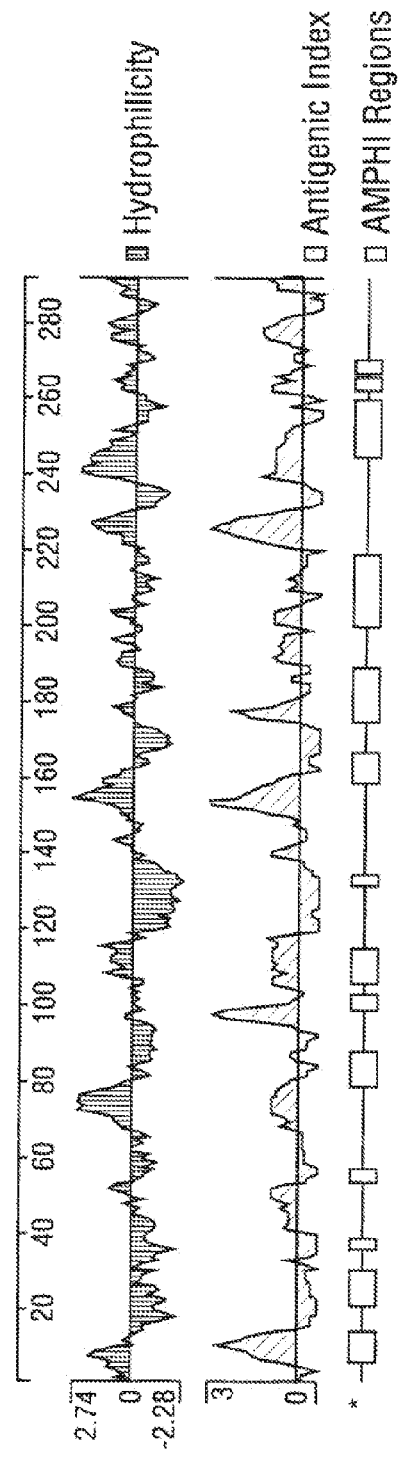

ORF9 disclosed in WO99/24578 was cloned in the pET vector and expressed in *E. coli*. The purified ORF-His fusion protein was analysed by SDS-PAGE, as shown in FIG. 2A. Mice were immunised with the purified ORF9-His and sera were used for Western blot analysis (FIG. 2B). FACS analysis (FIG. 2C), and ELISA assay. The protocols used were essentially the same as those set out in WO99/24578.

The results confirm that ORF9 is a surface-exposed protein. ORF9 is suitable for combining with one or more other of SEQ IDs 1-8376.

Example 3

Further Expression Experiments

Further expression and purification experiments were carried out in *E. coli* for ORFs 2-1, 5-1, 22-1 and 132-1 disclosed in WO99/24578, as set out in the following table:

| ORF | His-fusion | GST-fusion | Purification | MW (kDa) |
|---|---|---|---|---|
| 2-1 |  | + | GST-fusion | 26 |
| 5-1 | + | + | GST-fusion | 33 |
| 22-1 | + | + | GST-fusion | 49 |
| 132-1 | + | + | GST-fusion | 48 |

The protocols used to express these four ORFs were essentially the same as those described in WO99/24578, using pGEX and pET vectors. Examples of the PCR primers used to amplify the ORFs are in the following table:

| ORF | Printer | Sequence | Restriction sites |
|---|---|---|---|
| ORF5-1 | Forward | CGCGGATCCGCTAGC-GACGGCGCACAACCGA (SEQ ID NO: 8462) | BamHI-NheI |
|  | Reverse | CCCGCTCGAG-TGTTT GGCGGATGGGG (SEQ ID NO: 8463) | XhoI |
| ORF22-1 | Forward | CGCGGATCCCATATG-ATTAAAATCAAAAAG GTC (SEQ ID NO: 8464) | BamHI-NdeI |
|  | Reverse | CCCGCTCGAG-GCCTT CCTTCTCAATGG (SEQ ID NO: 8465) | XhoI |
| ORF132-1 | Forward | CGCGGATCCCATATG-AAAGAAGCGGGGTTTG AA (SEQ ID NO: 8466) | BamHI-NdeI |
|  | Reverse | CCCGCTCGAG-TCTCA AAGCTTCCAGCAG (SEQ ID NO: 8467) | XhoI |

SDS-PAGE results for the four expressed ORFs are shown in FIG. 3.

Each of these ORFs can be combined with one or more of SEQ IDs 1-8376.

Example 4

ORF4 Lipoprotein Expression and Purification

ORF-4 is disclosed in WO99/24578 as containing a lipopeptide signal sequence (LPSS). The full length ORF was amplified using the following PCR primers:

```
orf4-L for
                                    (SEQ ID NO: 8468)
CGCGGATCCCATATGAAAACCTTCTTCAAAACC orf4-L rev
                                    (SEQ ID NO: 8469)
CCCGCTCGAGTTATTTGGCTGCGCCTTC
```

The amplified DNA fragment was cloned into the vector pET21b+ for expression as a C-terminus His-tagged fusion. A log phase culture of *E. coli* containing pET21b+orf4-LPSS was induced with 1.0 mM IPTF for 3 h at 30° C. collected by centrifugation for 10 min at 8000 g, and resuspended in PBS. The suspension was sonicated on ice and Triton X-114 added to a final concentration of 0.6% (v/v). The material was incubated on ice for 20 minutes then warmed to 37° C. until phase separation occurred (indicated by a high degree of cloudiness). After centrifugation for 10 min at 10,000 g at 20° C. the upper aqueous phase was discarded, and the lower detergent phase collected without disrupting the bacterial pellet. To the detergent phase was added 13 volumes of 20 mM Histidine, 2 mM EDTA, 30 mM NaCl (pH 5.8). This was centrifuged for 10 min at 4° C. and the supernatant combined batchwise at 4° C. for 30 min. with Q Sepharose Fast Flow resin (Pharmacia). The mixture was centrifuged, the supernatant retained and the resin washed with 20 mM Histidine, 2 mM EDTA, 30 mM NaCl (pH 5.8). Triton X-100 0.3% (v/v) and eluted with 1M NaCl in the same buffer. The majority of Orf4 lipoprotein was found in the supernatant obtained after binding. Final purification was accomplished by chromatography on Hi-Trap™ Q (Pharmacia). The binding-supernatant was adjusted to pH 7.0 by the addition of 0.1M HCl and applied to a Hi-Trap™ Q column equilibrated with 50 mM Tris-HCl (pH 7.0), 2 mM EDTA, 0.3% Triton X-100, 10 mM NaCl. The column was washed with 5.0 ml of the equilibration buffer and a NaCl gradient from 10 mM to 1M was applied. Two electrophoretically distinct forms of the protein eluted. One in the wash and the other in the NaCl gradient between 150 mM and 300 mM NaCl. The protein obtained in the wash was used for immunization of mice. This form of the protein probably represents the fully processed, lipidated molecule.

The 31 kDa purified lipoprotein can be seen in FIG. 3. ORF4 is suitable for combining with one or more other of SEQ IDs 1-8376.

Example 5

Computer Prediction

Computer analysis of ORFs 2, 5, 6a, 7, 9, 13a, 15, 22, 23, 27, 28, 32, 65, 72, 73, 76, 79, 89, 105, 106-1, 132, 137, 138, 143 and 147 as disclosed in WO99/24578) was performed. FIGS. 4 to 28 show, for each of these ORFs, a hydrophilicity plot (upper), an antigenic index plot (middle), and an AMPHI analysis (lower). The AMPHI program has been used to predict T-cell epitopes [Gao et al. (1989) *J. Immunol.* 143:3007; Roberts et al. (1996) *AIDS Res Hum Retrovir* 12:593; Quakyi et al. (1992) *Scand J Immunol* suppl. 11:9) and is available in the Protean package of DNASTAR. Inc. (1228 South Park Street. Madison, Wis. 53715 USA).

Each of these ORFs can be combined with one or more other of SEQ IDs 1-8376.

Example 6

Tetravalent Mixture

A mixture of proteins 919 (WO99/57280), 225 (WO99/57280), ORF4 (WO99/24578, example 26) and ORF40 (WO99/36544, example 1) was produced and assessed by ELISA and FACS. The ELISA titres against 13 test strains were as follows:

| Strain | M7 conF | 2996 | MC58 | BZ133 | BZ232 | H44/76 | 1000 |
|---|---|---|---|---|---|---|---|
| Titre | 38176 | 7892 | 17216 | 41488 | 17945 | 83990 | 6575 |
| Strain | BZ198 | NG6/88 | BZ169 | BZ147 | NG3/88 | 297-0 | |
| Titre | 3329 | 59275 | — | — | 12877 | 25640 | |

Figure 33H:
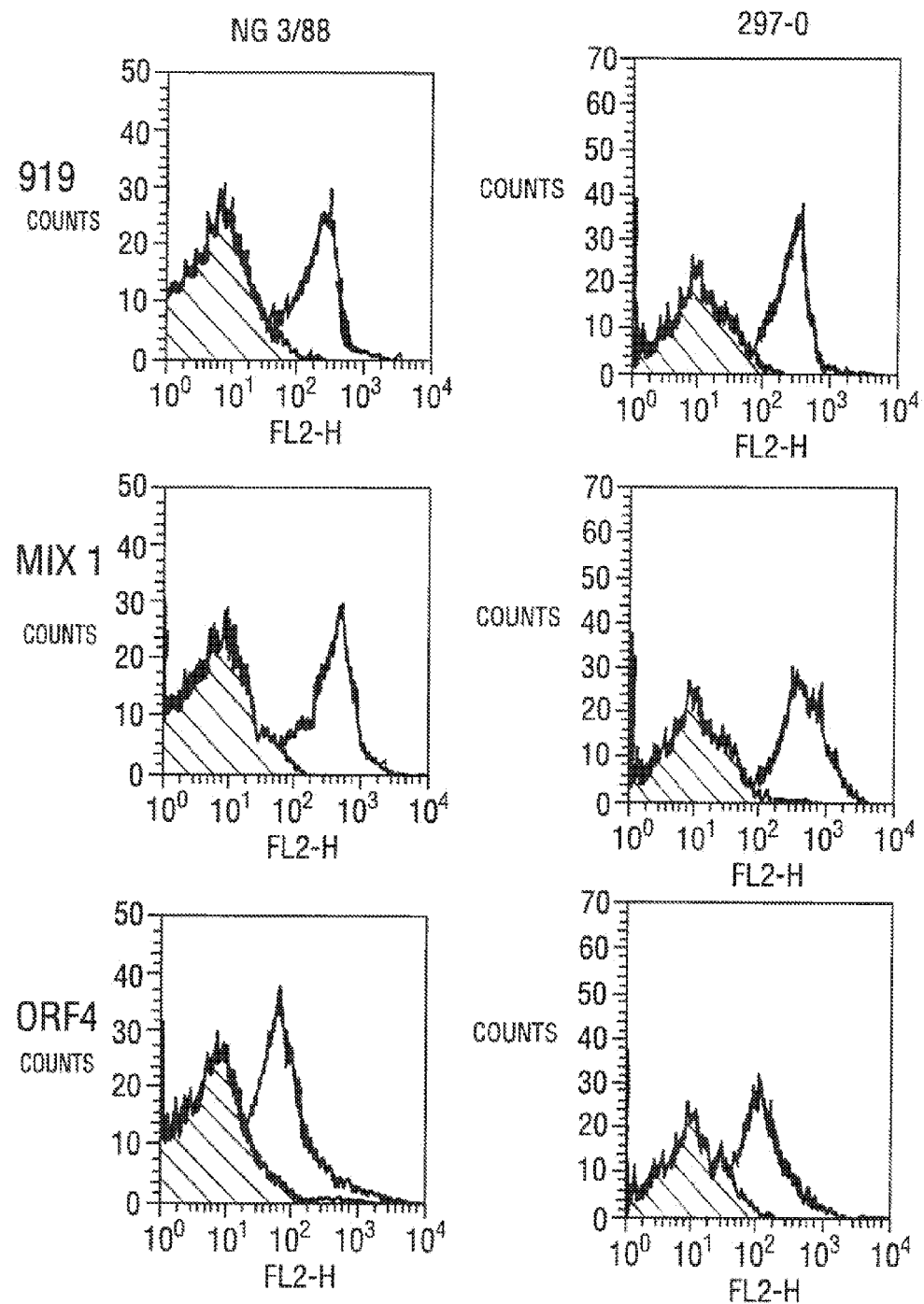
Figure 33I:
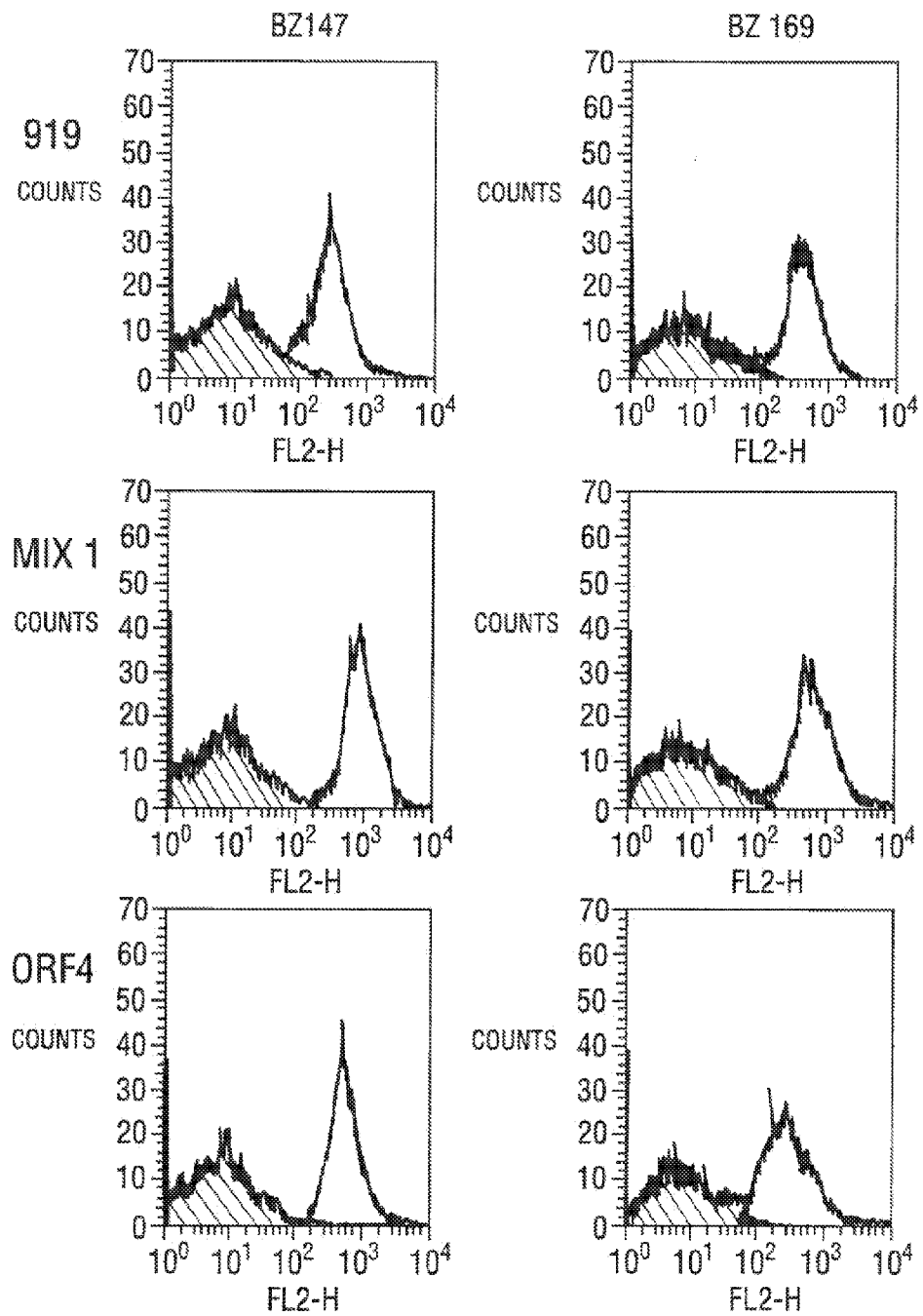

The FACS results are shown in FIG. 33. It is evident that the tetravalent mixture gives excellent results, regardless of the particular menB strain used. In addition, antisera raised against the mixture in strain 2996 is bactericidal at up to 1:2048 dilution.

Example 7

Pentavalent Mixture

A mixture of proteins ORF4-L (the lipidated protein—see example 4 above). ORF37 (WO99/24578, example 1). ORF40 (WO99/36544, example 1), 502 (WO99/57280, pages 687-690) and 8 (WO99/57280, pages 165-167) was produced. The ELISA titres against 13 test strains were as follows:

| Strain | M7 conF | 2996 | MC58 | BZ133 | BZ232 | H44/76 | 1000 |
|---|---|---|---|---|---|---|---|
| Titre | — | — | 25428 | — | 58300 | >109350 | >109350 |
| Strain | BZ198 | NG6/88 | BZ169 | BZ147 | NG3/88 | 297-0 | |
| Titre | 10999 | 109532 | 42888 | 28324 | 104212 | 33996 | |

Figure 34A:
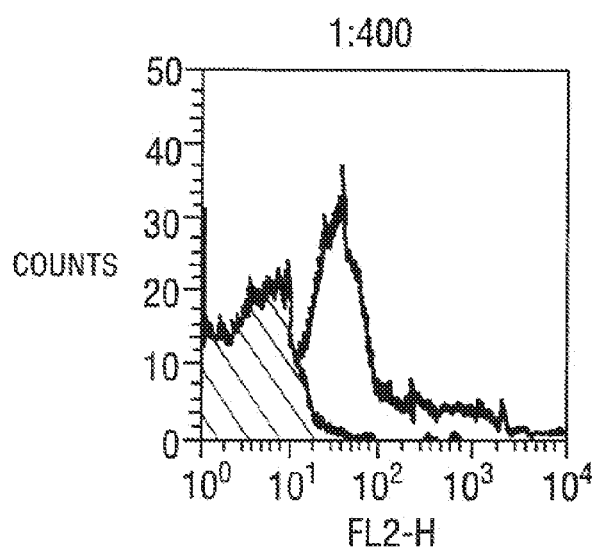
FIGS. 34A-34C shows FACS analysis of M7 strain using a pentavalent mixture at 1:400 (FIG. 34A), 1:200 (FIG. 34B), & 1:100 (FIG. 34C) dilutions.
Figure 34B:
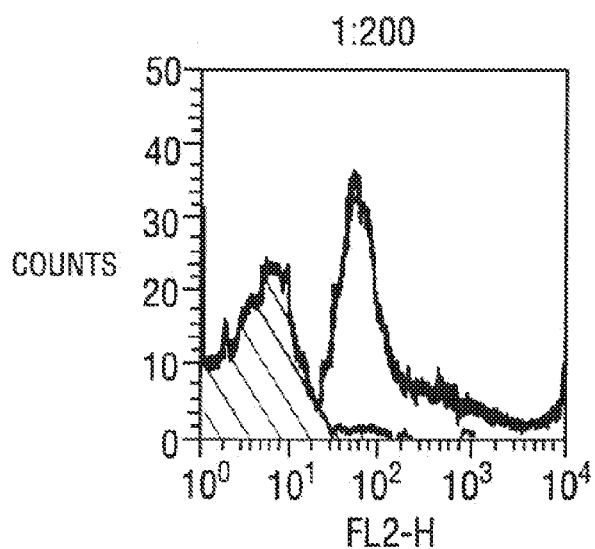
Figure 34C:
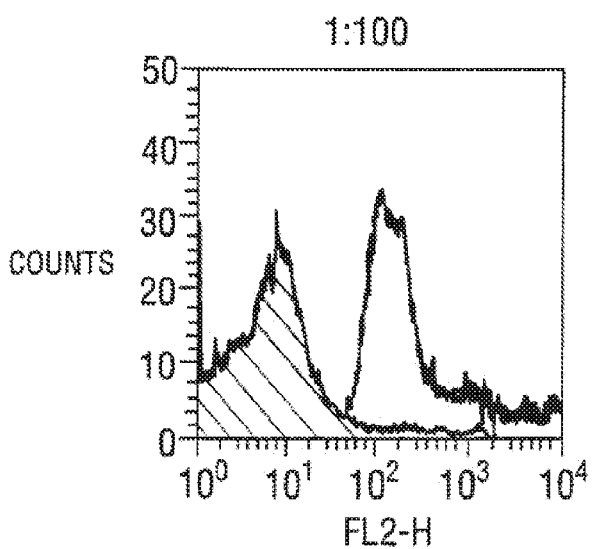

The FACS results are shown in FIG. 34. It is evident that the pentavalent mixture gives excellent results, regardless of the particular menB strain used. In addition, antisera raised against the mixture in strain 2996 is bacteriostatic.

Example 8

Trivalent Mixture

Proteins ORF1 (e.g. example 77 of WO99/24578: see also WO99/55873), '287' (e.g. FIG. 21 of WO99/57280; also SEQ IDs 3103-3108 therein) and '919' (e.g. WO99/57280 FIG. 23 and SEQ IDs 3069-3074 therein) were combined and adjuvanted with Al(OH)$_3$. The proteins were from the 2996 strain of MenB.

This mixture was also combined with a MenC polysaccharide conjugate antigen [e.g. Costantino et al. (1992) *Vaccine* 10:691-698]. OMVs were used as controls.

The mixture was used in a bactericidal assay against the homologous strain and also heterologous MenB strains. Titres were as follows:

| | 2996 | BZ133 | BZ232 | 1000 | MC58 | NGH38 |
|---|---|---|---|---|---|---|
| Trivalent | 2048 | 2048 | 4 | <4 | 64 | 4 |
| +MenC | 2048 | >32000 | 4 | 128 | 1024 | 128 |
| Control | 32765 | 4096 | 8192 | 16384 | 16384 | 8192 |

Example 9

Proteins 287, 919 and 953

Proteins 287, 919 and 953 are disclosed in WO99/57280. These proteins from *N. meningitidis* serogroup B strain 2996 were expressed and tested in a bactericidal assay against strain 2996, alone and in combinations. OMVs from 2996 were used as a positive control.

| Antigen | 287 | 919 | 953 | Control |
|---|---|---|---|---|
| Titre | 8192 | 2048 | 128 | 65536 |
| Combination | 287 + 919 | 287 + 953 | 919 + 953 | 287 + 919 + 953 |
| Titre | 32000 | 8192 | 8192 | 8192 |

Figure 35A:
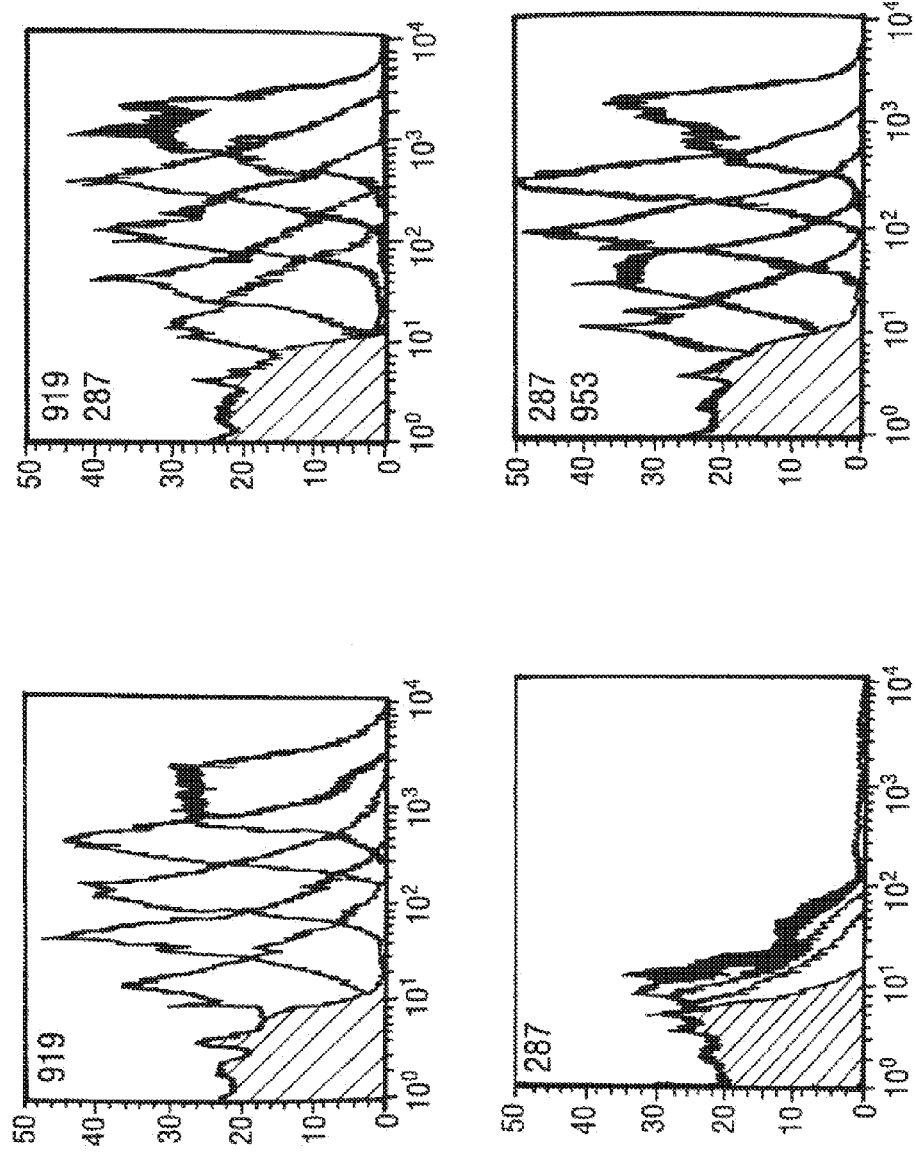
FIGS. 35A-35B show FACS for the individual antigens 287, 919, and 953 and combinations thereof.
Figure 35B:
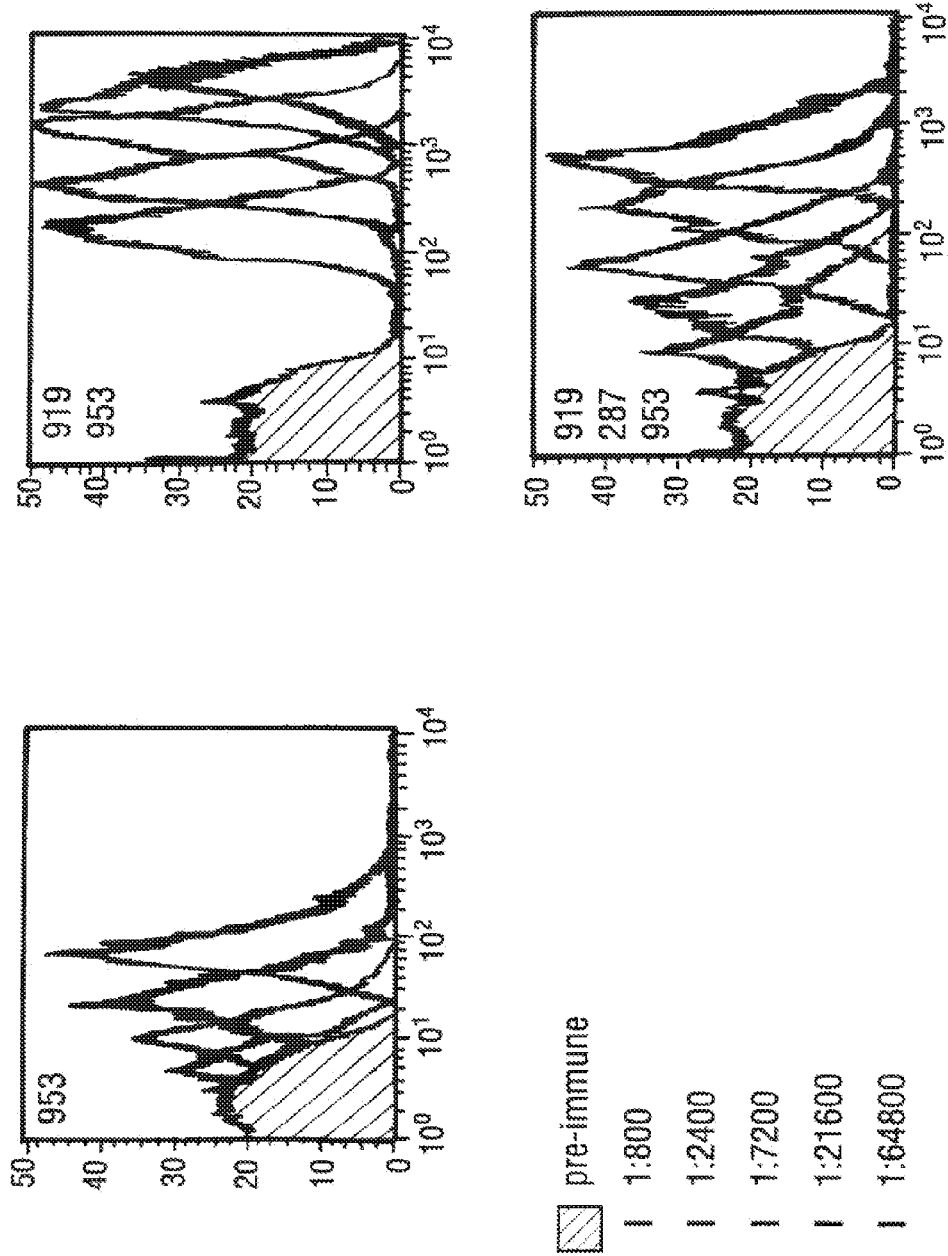

FIG. 35 shows FACS data for the individual antigens and for the four combinations.

It is evident that the antigen mixtures are more effective than the antigens in isolation on and, in particular, that combinations of 919+953 give surprisingly good results.

The individual antigens from 2996 and combinations were also tested against different serogroup A, B & C strains (i.e. heterologous challenge). Bactericidal titres were as follows:

| | Serogroup B (MenB) strains | | | | | MenA | MenC |
|---|---|---|---|---|---|---|---|
| Antigen | 2996 | BZ133 | BZ232 | MC58 | NGH38 | F6124 | C11 |
| 287 | 8192 | >4096 | 256 | 1024 | 2048 | 1024 | 2048 |
| 919 | 2048 | — | 1024 | — | — | — | — |
| 953 | 128 | — | — | — | — | — | — |
| 287 + 919 | 32000 | >4096 | 512 | 512 | 1024 | 512 | >2048 |
| 287 + 953 | 8192 | >4096 | 1024 | 512 | 2048 | 2048 | >2048 |
| 919 + 953 | 8192 | — | 8192 | — | — | — | — |
| Trivalent | 8192 | >2048 | 256 | — | 1024 | >2048 | >2048 |
| Control | 65536 | — | 8192 | 2048 | — | 2048 | 32768 |

It is apparent that the antigen mixtures are useful in conferring cross-strain activity.

In a second set of experiments, titres for the individual antigens were as follows:

| | Serogroup B (MenB) strains | | | | | MenA | MenC |
|---|---|---|---|---|---|---|---|
| Antigen | 2996 | BZ133 | BZ232 | MC58 | NGH38 | F6124 | C11 |
| 287 | 16000 | 2048 | 16 | 512 | >2048 | 64 | 1024 |
| 919 | 16000 | — | 2048 | — | — | — | — |
| 953 | 2048 | — | 16 | — | — | — | — |

The three proteins used in this example were expressed and used in the following forms:

(1) Protein 287 was expressed in *E. coli* as a GST fusion;
(2) Protein 919 was expressed in *E. coli* without its leader peptide, without its mature N-terminal cysteine, and without any fusion partners ("919-untag"); and
(3) Protein 953 was expressed using a histidine tag.

Three immunisations were administered with Freund's adjuvants—the first included CFA, and the final two included IFA.

Example 10

Further Polyvalent Combinations

Further combinations of antigens were tested in CD1 mice:

| Antigens * | Adjuvant | FACS | ELISA | Bactericidal acitivity |
|---|---|---|---|---|
| 919-his + Orf4-his + 225-his + Orf40-his | Freund | +++ | + | 8192 |
| Orf-4-L + Orf37-GST + Orf40-his + 502-his + 8-his | Freund | +++ | + | Bacteriostatic |
| 919-untag + 791-his + 792-his | Freund | +++ | + | 4096 |
| 919-untag + 287-GST + 953-his | Freund | +++ | + | 8192 |
| 919-untag + 287-GST | Freund | +++ | + | 32000 |
| 287-GST + 953-his | Freund | +++ | + | 8192 |
| 919-untag + 953-his | Freund | +++ | + | 8192 |
| 919-untag + Orf1-his + 287-GST | Al(OH)$_3$ | +++ | + | 2048 |
| 919-untag + Orf1-his + 287-GST + MenC glycoconj. | Al(OH)$_3$ | +++ | + | 2048 |
| Orf-46.1-his + 287-GST | Al(OH)$_3$ | n.d. | + | 128 |

* : "his" indicates expression and immunisation with a histidine-tagged protein;
"ORF4-L" is the lipidated form of ORF4;
"GST" indicates expression and immunisation with a GST fusion protein;
"919-untag" is as defined in Example 9;
"MenC glycoconj" is the MenC glycoconjugate described in Example 8.

Further combinations of antigens were tested in guinea pigs:

| Antigens | Adjuvant | FACS | ELISA | Bactericidal activity |
|---|---|---|---|---|
| 919-his + 287-GST + 953-his + Orf46.1-his | Freund | + | + | 4096 |
| 919-untage + 287-GST + 953-his | Freund | + | + | 4096 |
| 287-GST + 953-his | Al(OH)$_3$ | n.d. | + | 256 |

Evidently the combinations give excellent immunological results.

Example 11

NspA Combinations

NspA protein is disclosed in WO96/29412, and is represented herein as SEQ IDs 4008-4033. The academic literature disclosure of this protein [Martin et al. (1997) *J. Exp. Med* 185 1173-1183] reported the protein to be highly conserved between *Neisseria* strains (99% cross-reactivity of anti-NspA antibodies with 250 meningococcal A, B & C strains) and also efficient protection against deadly challenge with live bacteria. There have also been reports that NspA adsorbed on alum elicits serum meningococcal bactericidal antibody responses in rabbits and monkeys [Martin et al. (1998) *Abstracts of 11th International pathogenic Neisseria conference*, page 198]. On the basis of these data, rNspA (recombinant NspA) is being developed as a vaccine for the prevention of meningococcal disease caused by all serogroups.

Despite sequence conservation, however, it has surprisingly been discovered that rNspA cell surface epitopes are detected on only 65% of the serogroup B strains tested below, and susceptibility to anti-NspA bactericidal activity is also less than that reported by Martin et al. These results contrast with Martin et al., and suggest that a rNspA-based meningococcal B vaccines will need to be supplemented with additional antigens in order to be effective.

The *N. meningitidis* strains tested in this example were isolated from patients residing in different countries over a period of more than 30 years (see table on page 72). These strains were selected to be representative of widely divergent 'clonal' groups, as defined by multilocus isoenzyme typing [Seiler et al. (1996) *Mol. Microbiol.* 19:841-856] and/or multilocus sequence typing [Maiden et al. (1998) *PNAS USA* 95:3140-45]. Strain M7, which is derived from strain NMB, contains a transposon insertion that blocks capsular polysaccharide biosynthesis [Stephens et al. (1991) *Infect. Immun.* 59:4097-4102], but all the other strains are encapsulated.

Based on the nucleotide sequence in Martin et al. (1997), PCR primers were designed and the NspA gene from strain 8047 was amplified. The sequence, including the promoter region, was cloned into pSK+ plasmid (rNspA). A plasmid pTrc.NspA.1 encoding a protein in which a portion of the signal sequence has been replaced with a poly-histidine tag was also used. Both plasmids were expressed in *E. coli* strain BL21(DE3) and the proteins were purified. In *E. coli*, rNspA is secreted, rather than being associated with the outer membrane. The protein was partially purified from the culture medium by precipitation with 55% w/v ammonium sulphate, and had an apparent MW of 18.6 kDa, confirmed by Western Blot.

The two forms of NspA (rNspA and denature His-tage NspA) were injected into 6-week old female CD-1 mice to raise antisera. The ability of these to bind to the surface of *N. meningitidis* strain B was determined using flow cytometric detection of indirect fluorescence assay [Granoff et al. (1998) *J. Immunol.* 160:5028-36]. The results for strains NMB and M7 (an acapsulated mutant of NMB) are shown in FIG. 30. As expected, anti-group B polysaccharide mAb SEAM-3 [Granoff et al] only binds to the encapsulated strain, whereas the positive anti-P1.2 (PorA) control mAb binds to both strains. The antisera raised against rNspA is able to bind both strains. Antisera against the His-tag NspA gave negative results, however. These antisera were also negative for strains 8047. CU385 and M986 (FIG. 31A), but by Western Blot these antisera gave positive results.

These data suggest that antibodies prepared using His-tag NspA recognise epitopes that are present in denatured NspA, but not native NspA as found on the cell-surface in vivo. In contrast, antibodies prepared against rNspA seem to recognise conformational NspA epitopes.

The flow cytometric assay was applied to the strains shown in the table on page 72. FIG. 31A shows that murine antibodies raised against rNspA bind to the surface of strain 8047 (the strain from which the nspA gene was cloned) and strain CU385, but not to M986. FIG. 31B shows similar negative results for strains BZ232, MC58, NG3/88 and NGP165. In all of these negative cases, however, the anticapsular mAb control was positive.

The table on page 72 summarises the flow cytometry results. Although NspA is reported o be accessible at the surface of all intact *N. meningitidis* strains tested [Martin et al. (1997) *J. Exp. Med* 185 1173-1183: Plante et al. (1999) *Infect. Immun.* 67:2855-61], only 11 of the 17 test strains (65%) reacted with the anti-rNspA sera. There was no apparent relationship between cell-surface expression in a given strain and classification (by serotype, subtype, or electrophoretic type), or with year or country of isolation.

In an attempt to explain the differences in reactivity with the anti-rNspA sera, the nspA genes from five of the six negative strains (BX232, NG3/88, NGP165, M136 & M986) and from three of the positive strains (8047, CU385 & NG6/88) were sequenced. The sequence for the sixth negative strain (MC58) was already available from the complete genome sequence.

The nspA sequences for all ten strains were highly conserved, varying at most by 5 nucleotides from the prototype sequence of Martin et al. The most variant protein had only 3 amino acid differences (see FIG. 29). With one exception, all of the amino acid variants involved the same respective residues in discrete segments of the protein. These include the signal peptide, which is not present in the mature protein, and two short segments in the 50 C-terminal residues. These differences do not explain the antisera results, as there are examples of identical variant sequences in strains that were positive and those that were negative (compare M136 & 8047; NGP165 & NG6/88; MC58 & CU385).

As neither lack of the gene nor polymorphism explained the antiserum results, the amount of NspA protein in the outer membranes of five strains (8047, CU385 & NG6/88—all positive for anti-rNspA; M986 & M136—both negative) were tested. Bacterial cell pellets were extracted with lauryl sarcosinate, and the insoluble outer membrane fractions were analysed. An 18.6 kDa band was seen for all five strains, and this was cross-reactive with anti-His-tag-NspA by Western Blot. Thus strain differences in nspA expression also failed to explain the results.

The ability of anti-rNspA to bind to the bacterial cell surface could be influenced by the amount of polysaccharide capsule present. The quantity of capsular polysaccharide produced by the 17 test strains was therefore assessed by inhibition ELISA.

Extracts of capsular polysaccharide were prepared based on a method described by Corn et al. [*J. Infect. Dis.* (1993) 167:356-64]. Individual bacterial clones were grown to an $OD_{620}$ 0.5-0.7 in 7 mL of Mueller-Hinton broth. Bacteria were collected by centrifugation at 5000 g for 15 min, washed in 0.6 mL of 10 mM Hepes, pH 8.0, and then resuspended in 0.6 mL of the same buffer containing 10 mM EDTA and incubated at 37° C. for 1 hr. The cells were pelleted at 10,000 g for 1 minute and the relative amount of meningococcal B polysaccharide antigen released into the supernatant was determined by an inhibition ELISA, performed as described by Azmi et al. [*Infect. Immun.* (1995) 63:1906-13]. The solid phase antigen in the ELISA was meningococcal B polysaccharide-ADH-biotin absorbed to avidin-coated microtiter plates [Granoff et al.]. The meningococcal B polysaccharide-reactive human paraprotein LIP [Azmi et al.] was used as the primary antibody (0.2 µg/ml). In the absence of inhibitor, this concentration of antibody was sufficient to given an OD of ~0.7 to 1.0 after 30 minutes incubation with substrate [Azmi et al.]. The titre of polysaccharide released into the supernatant was measured by determining the dilution of supernatant that resulted in 50% inhibition of antibody binding. Controls in this assay included an EDTA extract prepared from the strain M7, which does not produce any capsular polysaccharide, and purified meningococal B polysaccharide. To ensure that all of the capsular polysaccharide was released by the EDTA treatment, the same inhibition ELISA was performed using the cell pellet resuspended in the same buffer and volume as the capsule extract. The observable inhibitory activity from the cell pellet was between 0 and 10% of the activity observed in the capsule extracts with the latter, higher percentage coming from cell pellets of strains that produce the largest amounts of capsule.

The results for each strain are shown in the table on page 72. On average, the six negative anti-rNspA, strains produced three-fold more capsular polysaccharide than the eleven positive strains (respective reciprocal geometric mean dilutions of 676 vs. 224, p<0.05). This may explain the results obtained with the antiserum—conceivably, the presence of larger amounts of capsule could interfere with the ability of the anti-rNspA antibody to bind to NspA epitopes which, in strains with lower amounts of capsule, are accessible.

The complement-dependent bactericidal activity of the anti-rNspA antisera were tested using an assay similar to that described by Mandrell et al. [*J. Infect. Dis.* (1995) 172:1279-89]. The complement source was human serum from a healthy adult with no detectable anti-capsular antibody to group B polysaccharide and no intrinsic bactericidal activity against the test strain. Serum bactericidal titres were defined as the serum dilution resulting in a 50% decrease in CFU/ml after 60 minutes incubation of bacteria in the reaction mixture, compared to the control CFU/ml at time zero.

Typically, bacteria incubated with a negative control antibody showed a 150-200% increase in CFU/ml during the 60 minutes of incubation. The positive control antibody [anti-capsular IgG2a mAb SEAM 12, Granoff et al.] showed complement-mediated bactericidal activity against all 17 strains. In contrast, the six strains that were negative for anti-rNspA antisera binding by flow assay were resistant, showing no bactericidal or bacteriostatic effects. Ten of the other eleven positive strains were either killed by complement and the antisera (SWZ107, J351, CU385, NG6/88, BZ198, H44/76, NMB & 8047) or were inhibited (H355 & S3446); strain 1000, however, was not affected.

The ability of the anti-rNspA antisera to confer passive protection against meningococcal B bacteremia was tested in infant rats using a method adapted from Saukkonen [*J. Infect. Dis.* (1988) 158:209-212]. Briefly, 6-7 day old rats were randomly distributed to nursing mothers. Groups of 5-6 animals were challenged IP with 100 µl of approximately 5000 CFU of *N. meningitidis* group B bacteria. One strain negative for NspA surface epitopes (M986) and one positive strain (8047) were tested, each of which having been passaged three times in infant rats. Immediately before administration, the bacterial suspension was mixed with different dilutions of test or control antibody (positive control: anticapsular mAb; negative control: anti-*E. coli*). 18 hours after challenge, blood specimens were obtained from the heart. Aliquots were plated onto chocolate agar, and CFU/ml was determined after overnight incubation at 37° C. in 5% $CO_2$.

The protective activities of the various co-administered antibodies were as follows:

| Antibody treatment | Dose per rat or serum dilution | Strain | Blood culture Positive/total | CFU/ml (mean × $10^{-3}$) | CFU/ml (% of control) |
|---|---|---|---|---|---|
| Anticapsular mAb | 2 µg | M986 | 0/6 | <1 | <1 |
| Anti-rNspA | 1:5 | M986 | 6/6 | $44^a$ | 45 |
| Anti-rNspA | 1:25 | M986 | 6/6 | $93^a$ | 95 |
| Anti-*E.coli* control | 1:5 | M986 | 6/6 | $98^a$ | — |
| Anticapsular mAb | 2 µg | 8047 | 0/5 | <1 | <1 |
| Anti-rNspA | 1:5 | 8047 | 1/6 | $0.2^b$ | 2 |
| Anti-rNspA | 1:25 | 8047 | 1/5 | $0.4^b$ | 4 |
| Anti-*E.coli* control | 1:5 | 8047 | 6/6 | $10^b$ | — |

$^a$p > 0.5, compared to geometric mean CFU/ml of control rats
$^b$p < 0.001, compared to geometric mean CFU/ml of control rats As can be seen, a dose of 2 µg per rat of the positive anticapsular control was protective against both strains. A 1:5 or 1:25 dilution of anti-rNspA antiserum protected against bacteremia caused by strain 8047. Neither dilution was effective in preventing M986 bacteremia, however.

Despite the positive conclusions of Martin et al., therefore, NspA does not seem to be effective in preventing meningococcal B infection. Approximately one third of strains have decreased cell-surface expression of NspA epitopes when grown in vitro, are resistant to anti-NspA induced complement-mediated bacteriolysis, and are resistant to passive antiserum immunisation. These strains produce large amounts of capsular polysaccharide, and would thus be expected to have the greatest virulence. The ability of a vaccine containing only NspA to confer broad protective immunity against meningococcal B thus has to be doubted.

Figure 29A:
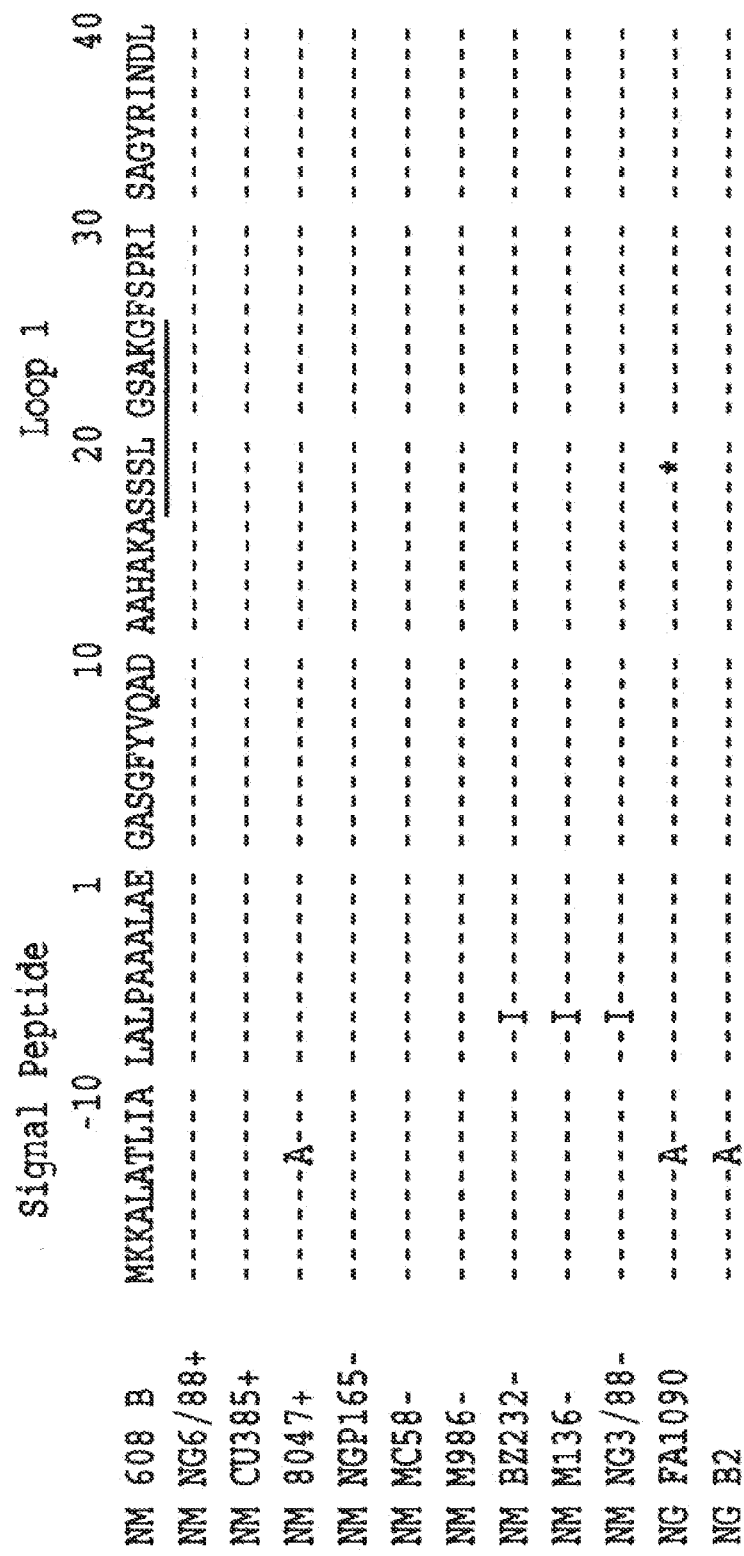
Figure 30A:
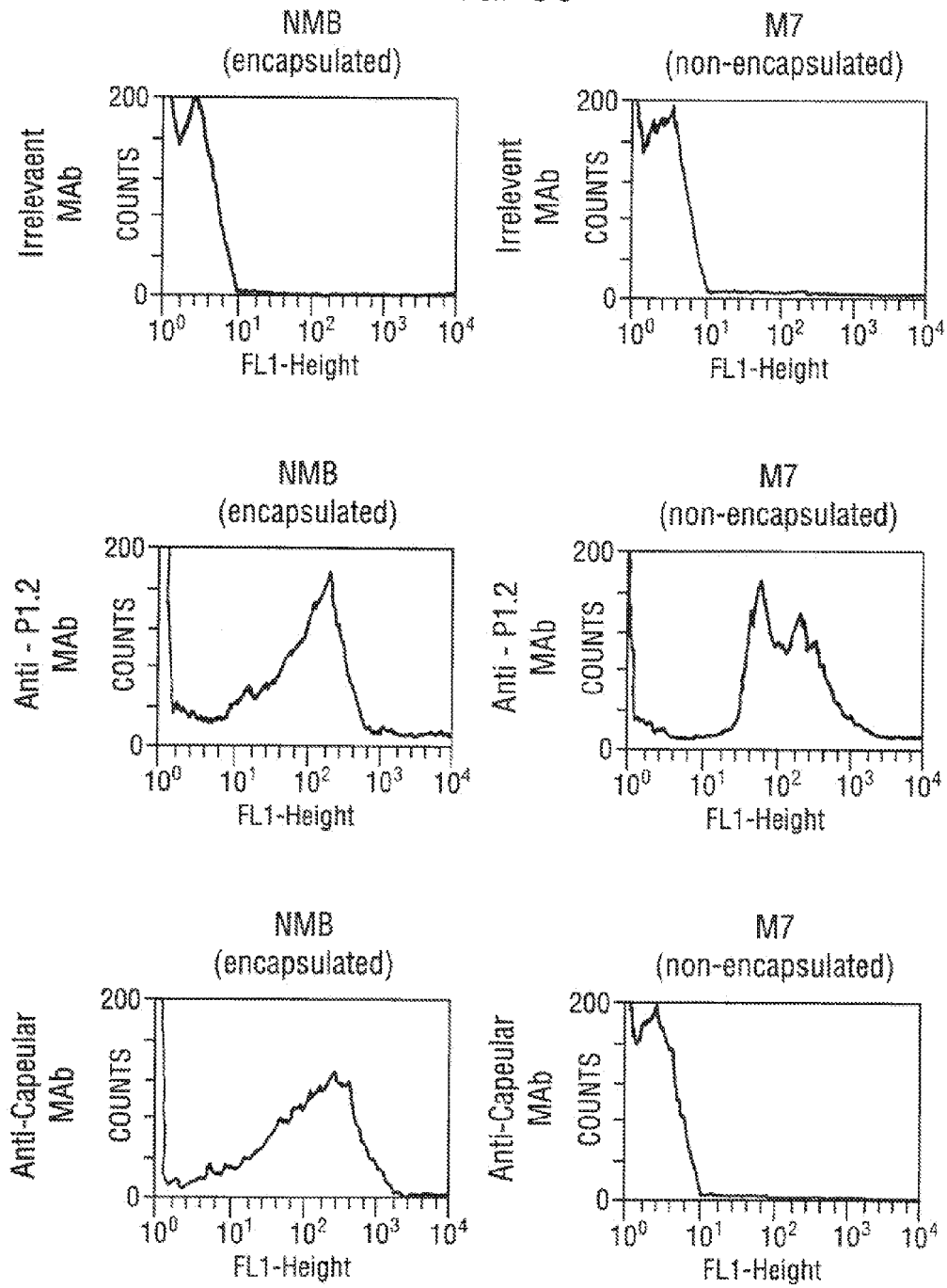
FIGS. 30A-30B shows the binding of polyclonal anti-rNspA by indirect fluorescence flow cytometry to encapsulated and non-encapsulated menB strains.
Figure 30B:
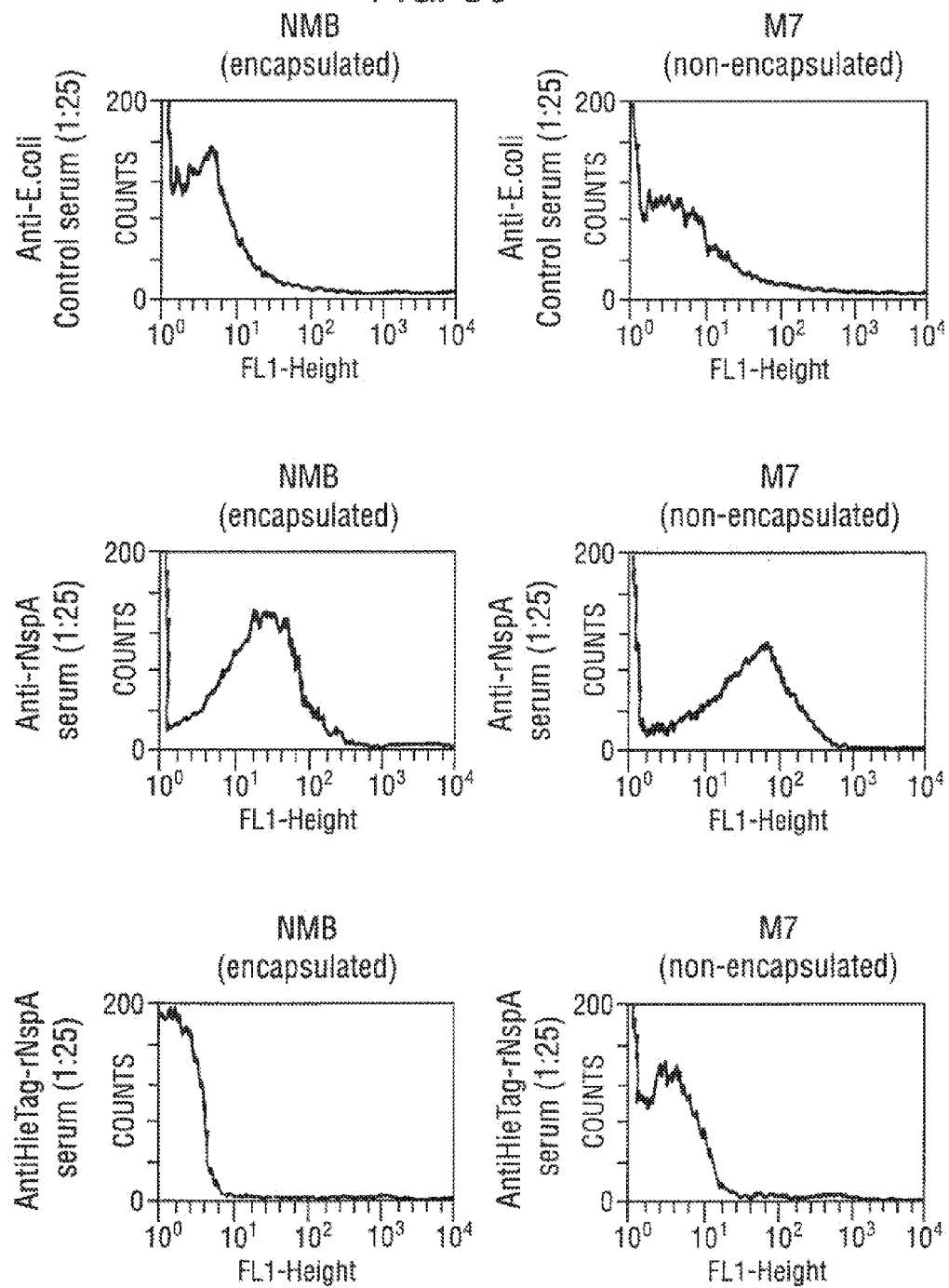
Figure 31A:
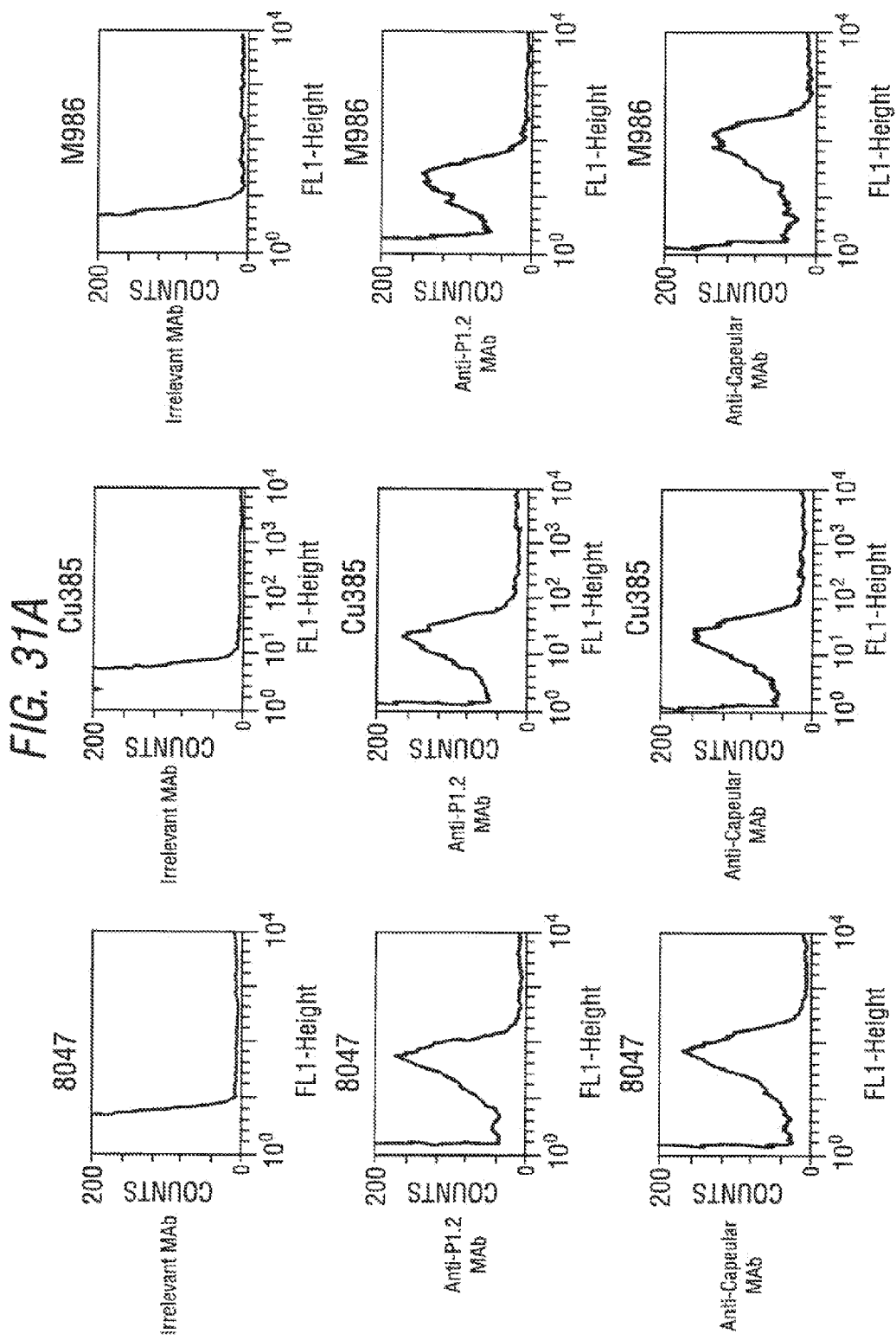
Figure 31D:
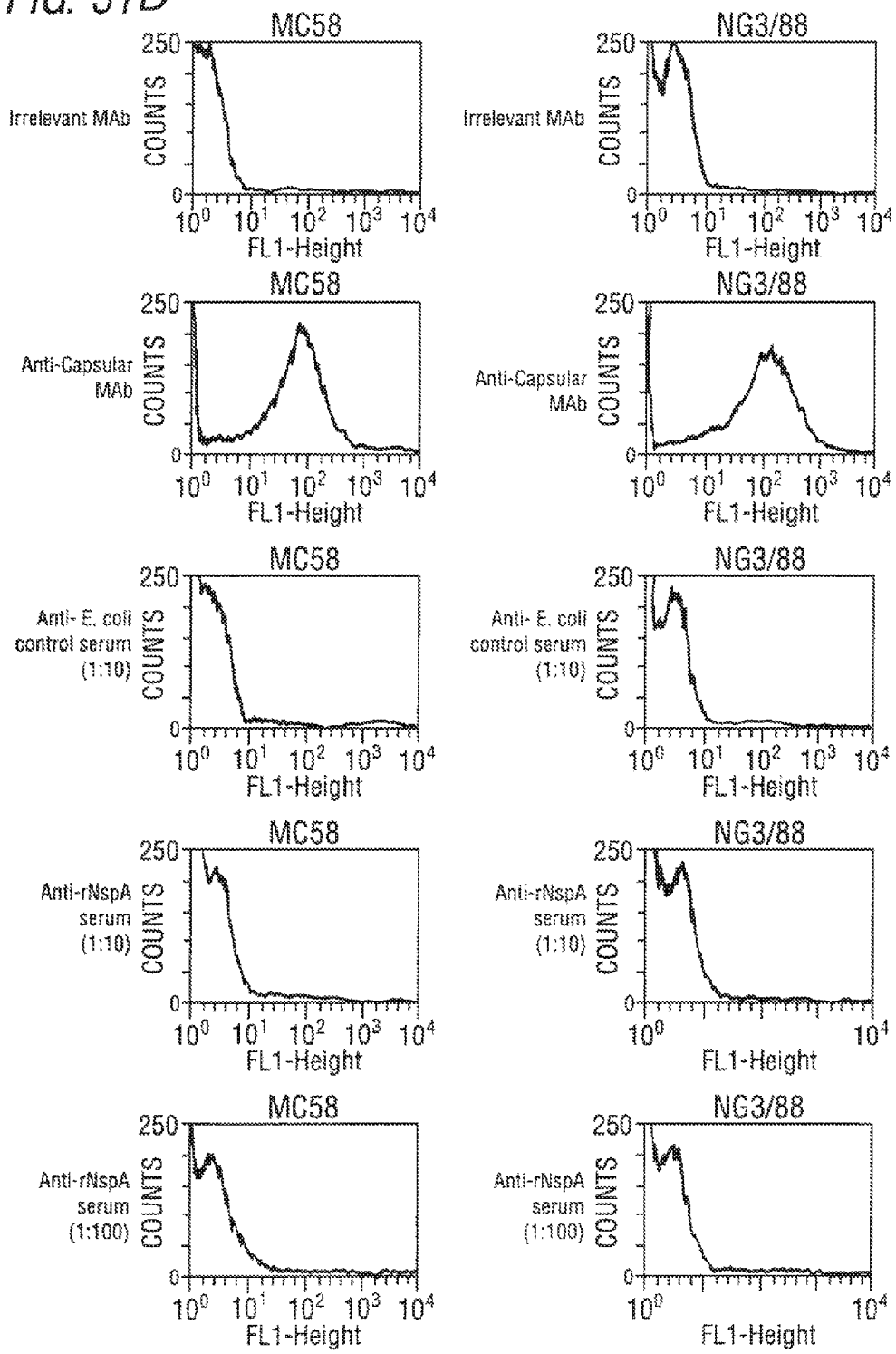
Figure 31E:
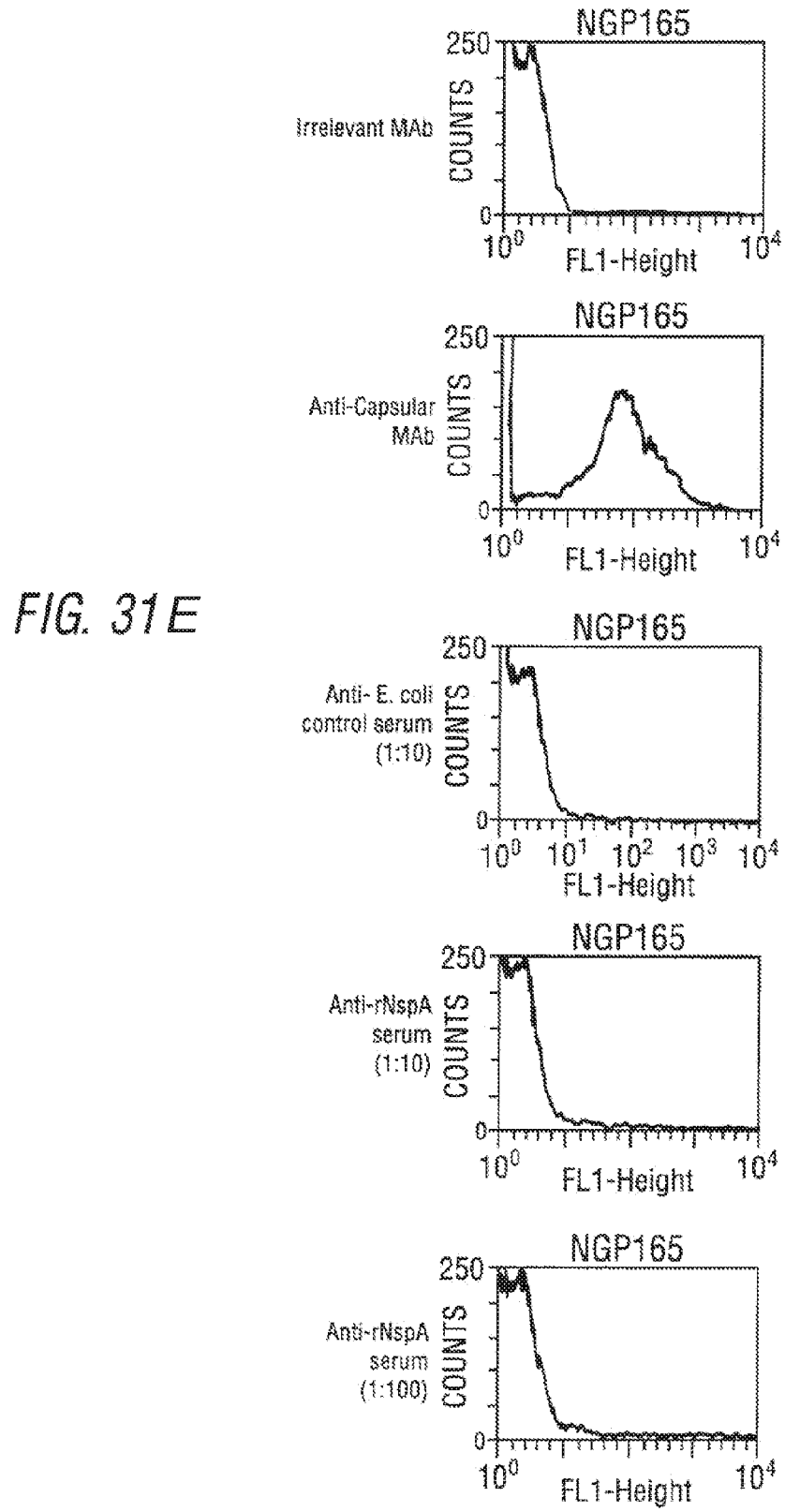

Compositions comprising NspA [SEC) IDs 4008-4033; FIG. 29] therefore advantageously comprise further antigens. A preferred aspect of the invention is thus a combination of NspA protein with one or more further Neisserial antigens.

Example 12

NspA Fragments

Figure 32:
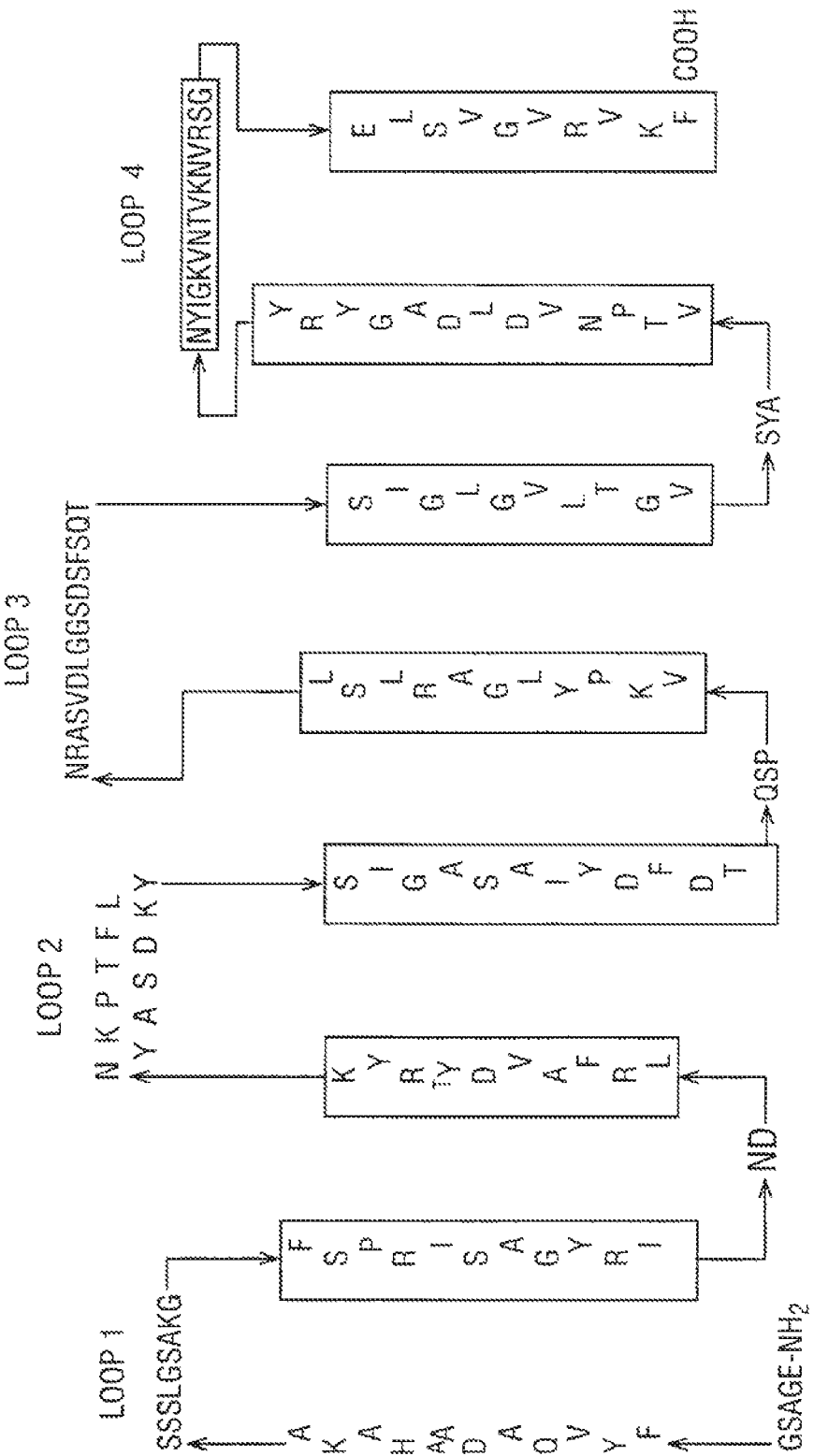
FIG. 32 shows a model of NspA secondary structure (SEQ ID NO: 4009).

A model of the secondary structure of NspA is shown in FIG. 32, containing eight transmembrane β-strands and 4 surface-exposed connecting loops. This fits the pattern of alternating hydrophobic and hydrophilic amino acids in NspA, which is characteristic of many β-barrel porins [Weiss et al. (1990) *FEBS Letts* 267:268-272]

The grey shaded areas in the model indicate segments that are >40% identical and >70% similar to encoded amino acid sequences of opacity proteins (Opa) from *N. meningitidis*, *N. gonorrhoeae*, *N. flavius*, *N. sicca*, and *H. influenzae* identified in a BLAST search of the non-redundant GenBank CDS. The alternating sequences are predicted amphiphilic β-strands; vertical segments correspond to transmembrane segments; the top of the figure corresponds to surface exposed segments, labelled as loops 1 to 4.

According to Martin et al., the only significant homology between the deduced amino acid sequence of NspA and those of other proteins are weak homologies with the *Neisseria* opacity protein (Opa) family in two small segments (~20 amino acids) near the C-terminal end of the protein. However, separate comparisons of the N- and C-termini of NspA with GenBank reveals a high degree of homology (>40% identity and >70% similarity) between NspA and Opa proteins from *N. meningitidis, N. gonorrhoeae, N. flavius, N. sicca*, and *H. influenzae*. The Opa proteins are thought to be integral membrane proteins that have eight transmembrane segments and a β-barrel topology in the membrane similar to that of porin [Merker et al. (1997) *Mol. Microbial.* 23:281-293]. The presence of NspA in detergent-insoluble membrane preparations indicate that NspA is located in the outer membrane, which would be consistent with the Opa-like membrane topology shown in the model. In addition, the segments of NspA that are most homologous to those of the Opa proteins are the putative transmembrane segments indicated in the shaded areas of FIG. 32.

The opacity proteins of *Neisseria* can, under certain circumstances, elicit protective antibody. However, problems with limited antibody accessibility of the opacity proteins in encapsulated bacteria, variability of amino acid sequences in exposed loop segments, and phase variation of protein expression during clinical infection, have limited the ability of Opa to elicit protective antibody consistently [Maloniy et al. (1998) *J. infect. Dis.* 172:1279-89]. In contrast, there appears to be little or no sequence variation in the surface exposed loops of NspA in FIG. 32. However, it was recently reported that a panel of anti-*N. meningitidis* NspA monoclonal antibodies that reacted with all meningococcal strains tested reacted with only a limited number of *N. gonorrhoeae* strains, even though the respective amino acid sequences in the two species are 92% identical. When the respective NspA sequences of the meningococcal and gonococcal strains are compared (FIG. 29), all of the respective amino acid differences result in changes in hydrophobicity or charge, and are located in the putative surface exposed connecting loops (FIG. 32). This finding suggests that the connecting loops in NspA, which are highly conserved in *N. meningitidis*, may be important epitopes for antibodies that bind to native NspA. These segments of the molecule, therefore, would appear to be of greatest interest with respect to interacting with protective antibody. However, the putative surface loops of NspA are relatively small (10-14 amino acids) compared to, for example, the highly immunogenic external loops of PorA and Opc (24 to 45 amino acids). The shorter length of the loops may limit the accessibility of NspA surface epitopes for binding interactions with serum antibody, especially in the presence of abundant capsular polysaccharide.

Accordingly, the invention provides the fragments of NspA that are exposed on the cell-surface in FIG. 32, namely SSSLGSAKG (SEQ ID NO: 8470), NYKAPSTDFKLY (SEQ ID NO: 8471), NRASVDLGGSDSFSQT (SEQ ID NO: 8472), and NYIGKVNTVKNVRSG (SEQ ID NO: 8473), and also provides corresponding fragments from allelic variants of NspA. In addition, the invention provides sub-sequences of these fragments, comprising 7 or more contiguous amino acids from the fragments. The invention further provides proteins comprising these fragments. Nucleic acid encoding these fragments and proteins is also provided.

These NspA fragments, proteins comprising the fragments, and nucleic acid, may be used in the compositions of the invention, in particular as substitutes for full-length NspA. In a further aspect, these fragments, proteins and nucleic acids may be used as products in isolation, that is to say they need not exclusively be used in combination with other biological molecules.

It will be appreciated that the invention has been described by means of example only, and that modifications may be made whilst remaining within the spirit and scope of the invention.

Reactivity of Anti-rNspA Polyclonal Antisera with Native NspA Exposed on the Surface of Live, Encapsulated, *Neisseria meningitidis* B Bacteria in Relation to Susceptibility to Bacteriolysis and Capsular Production.

| Meningococcal B Strains | | | | | NspA Cell | Anti-rNspA | Polysaccharide Capsule |
|---|---|---|---|---|---|---|---|
| Strain | Country | Year | Serologic Classification | ET Complex | Surface Reactivity [c] | Bactericidal Activity [d] (l/titer) | Production (l/titer ± SE) |
| SWZ107 [a] | Switzerland | 1980 | 4: P1.2 | 104 | Positive | ≥64 | 28 ± 4 |
| NG6/88 [a] | Norway | 1988 | NT: P1.1 | 173 | Positive | 4 | 115 ± 23 |
| CU385 [b] | Cuba | 1980 | 4: P1.15 | 5 | Positive | 4 | 116 ± 1 |
| IH5341 | Finland | 1985 | 15: P1.7.16 | ND | Positive | 16 | 176 ± 61 |
| BZ198 | Netherlands | 1986 | NT: P- | 154 | Positive | ≥64 | 362 ± 1 |
| NMB | US | 1968 | 2b: P1.2, 5 | ND | Positive | 16 | 244 ± 20 |
| 8047 | US | 1978 | 2b: P1.2 | ND | Positive | 16 | 1125 ± 50 |
| H44/76 | Norway | 1976 | 15: P1.7, 16 | 5 | Positive | 24 | 99 ± 16 |
| 1000 [d] | USSR | 1989 | NT: P1.5 | 61 | Positive | <4 | 287 ± 12 |
| S3446 [b] | US | 1972 | 14: P1.23, 14 | 11 (A1 cluster) | Positive | <4 (static = 16) | 585 ± 151 |
| H355 [b] | Norway | 1973 | 15: P1.15 | 11 cluster | Positive | <4 (static = 4) | 656 ± 141 |
| BZ232 [a] | Netherlands | 1964 | NT: P1.2 | 76 | Negative | <4 | 1493 ± 18 |
| NG3/88 [a] | Norway | 1988 | 8: P1.1 | A4 cluster | Negative | <4 | 498 ± 105 |
| MC58 | UK | 1985 | 15: P1.7, 16b | 5 | Negative | <4 | 627 ± 121 |
| M136 [b] | US | 1968 | 11: P1.15 | D1 cluster | Negative | <4 | 1056 ± 81 |
| M986 [b] | US | 1963 | 2a: P1.5, 2 | B2 cluster | Negative | <4 | 1442 ± 206 |
| NGP165 | Norway | 1974 | NT: P1.2 | 37 | Negative | <4 | 138 ± 6 |

[a] Denotes strains that have been characterized further by multilocus sequence typing [Maiden, 1998].

[b] Denotes strains obtained from the Frasch collection, US FDA. 8047 was obtained from W. Zollinger, Walter Reed Army Institute of Research, Washington, D.C. MC58 is the strain selected by TIGR for genomic sequencing. J351 was obtained from M. Sarvas, National Public Health Institute, Helsinki, Finland. The remaining strains are from the collection described by Seiler et al. [Seiler, 1996]. ET data are from Caugnant et al. [*j. Infect. Dis.* (1990) 162: 867-874], and Seiler et al.

[c] By indirect fluorescence flow cytometry with anti-rNspA antisera.

[d] Dilution of anti-rNspA antisera that when incubated for 60 min. with bacterial cells and 20% human complement yielded ≥50% decrease in CFU/ml, compared to that at time 0. "Static" refers to strains that were inhibited but not killed in the assay (≥50% but <100% survival at 60 mins).

[e] Titre defined as dilution of capsule extract giving 50% inhibition of antibody binding to meningococcal B polysaccharide antigen in an ELISA.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09364528B1). An electronic copy of the "Sequence Listing" will also be available from the USPTO upon request and payment of the fee set forth in 37 CFR 1.19(b)(3).

We claim:

1. A method of inducing a bactericidal immune response in an animal, comprising administering to the animal a composition which comprises
    (a) an immunologically effective amount of a protein lacking an N-terminal cysteine at position 20 of SEQ ID NO: 3518 having the amino acid sequence of the mature form of SEQ ID NO: 3518; and
    (b) an immunologically effective amount of an *N. meningitidis* protein comprising an amino acid sequence having at least 95% sequence identity to SEQ ID NO: 7645.

2. The method of claim 1, wherein the composition consists essentially of (a) and (b).

3. The method according to claim 1, wherein the protein lacking an N-terminal cysteine is a recombinant protein.

4. The method according to claim 1, wherein the protein lacking an N-terminal cysteine is expressed as a fusion protein.

5. The method according to claim 1, wherein the protein lacking the N-terminal cysteine is fused to a GST protein or a HIS-tag.

6. The method according to claim 1, wherein the protein lacking an N-terminal cysteine and the *N. meningitidis* protein are from different strains of *Neisseria meningitidis*.

7. The method according to claim 1, wherein the composition additionally comprises an adjuvant or buffer.

8. The method according to claim 1, wherein the composition additionally comprises an adjuvant.

9. The method according to claim 1, wherein the composition further comprises aluminum hydroxide.

10. The method according to claim 1, wherein the composition further comprises a third *Neisseria meningitidis* biological molecule different than (a) and (b).

11. The method according to claim 1, wherein the composition is administered by injection.

12. The method according to claim 1, wherein the animal is a human patient.

13. A method of eliciting antibodies against *N. meningitidis* bacteria in an animal, comprising administering to the animal a composition which comprises
    (a) an immunologically effective amount of a protein lacking an N-terminal cysteine at position 20 of SEQ ID NO: 3518 having the amino acid sequence of the mature form of SEQ ID NO: 3518; and
    (b) an immunologically effective amount of an *N. meningitidis* protein comprising an amino acid sequence having at least 95% sequence identity to SEQ ID NO: 7645.

14. The method according to claim 13, wherein the composition consists essentially of (a) and (b).

15. The method according to claim 13, wherein the protein lacking an N-terminal cysteine is expressed as a fusion protein.

16. The method according to claim 13, wherein the protein lacking an N-terminal cysteine and the *N. meningitidis* protein are from different strains of *Neisseria meningitidis*.

17. The method according to claim 13, wherein the composition additionally comprises an adjuvant or buffer.

18. The method according to claim 13, wherein the composition further comprises aluminum hydroxide.

19. The method according to claim 13, wherein the composition further comprises a third *Neisseria meningitidis* biological molecule different than (a) and (b).

20. The method according to claim 13, wherein the composition is administered by injection.

21. The method according to claim 13, wherein the animal is a human patient.

22. A method of eliciting antibodies against *N. meningitidis* bacteria in an animal, comprising administering by injection to the animal a composition which comprises
    (a) an immunologically effective amount of a protein lacking an N-terminal cysteine at position 20 of SEQ ID NO: 3518 having the amino acid sequence of the mature form of SEQ ID NO: 3518; and
    (b) an immunologically effective amount of an *N. meningitidis* protein comprising an amino acid sequence having at least 95% sequence identity to SEQ ID NO: 7645,
    (c) a buffer, and
    (d) aluminum hydroxide,
wherein the protein lacking an N-terminal cysteine and the *N. meningitidis* protein are from different strains of *Neisseria meningitidis*, thereby eliciting antibodies against *Neisseria meningitidis* bacteria in the animal.

23. The method of claim 22, wherein the immune response induced by the protein lacking an N-terminal cysteine is bactericidal against at least three strains of *Neisseria meningitidis* in the animal, thereby eliciting bactericidal antibodies against at least three strains of *Neisseria meningitidis* in the animal.

24. The method according to claim 22, wherein the composition consists essentially of (a) and (b).

* * * * *